US008106221B2

(12) United States Patent
Baldwin et al.

(10) Patent No.: US 8,106,221 B2
(45) Date of Patent: Jan. 31, 2012

(54) RENIN INHIBITORS

(75) Inventors: John J. Baldwin, Gwynedd Valley, PA (US); Salvacion Cacatian, Blue Bell, PA (US); David A. Claremon, Maple Glen, PA (US); Lawrence W. Dillard, Yardley, PA (US); Patrick T. Flaherty, Pittsburgh, PA (US); Alexey V. Ishchenko, Somerville, MA (US); Lanqi Jia, Horsham, PA (US); Gerard McGeehan, Garnet Valley, PA (US); Robert D. Simpson, Wilmington, DE (US); Suresh B. Singh, Kendall Park, NJ (US); Colin M. Tice, Ambler, PA (US); Zhenrong Xu, Horsham, PA (US); Jing Yuan, Lansdale, PA (US); Wei Zhao, Eagleville, PA (US); Linghang Zhuang, Chalfont, PA (US)

(73) Assignee: Vitae Pharmaceuticals, Inc., Fort Washington, PA (US)

( * ) Notice: Subject to any disclaimer, the term of this patent is extended or adjusted under 35 U.S.C. 154(b) by 0 days.

(21) Appl. No.: 12/665,219

(22) PCT Filed: Jun. 20, 2008

(86) PCT No.: PCT/US2008/007661
§ 371 (c)(1),
(2), (4) Date: Feb. 5, 2010

(87) PCT Pub. No.: WO2008/156816
PCT Pub. Date: Dec. 24, 2008

(65) Prior Publication Data
US 2010/0144825 A1 Jun. 10, 2010

Related U.S. Application Data

(60) Provisional application No. 60/936,397, filed on Jun. 20, 2007.

(51) Int. Cl.
*C07D 325/00* (2006.01)
*C07D 315/00* (2006.01)
*C07D 493/00* (2006.01)
*C07C 275/04* (2006.01)
*A61K 31/351* (2006.01)
*A61K 31/17* (2006.01)
*A01N 47/28* (2006.01)

(52) U.S. Cl. .......... 549/330; 549/347; 549/426; 564/47; 514/450; 514/451; 514/595

(58) Field of Classification Search .................. None
See application file for complete search history.

(56) References Cited

U.S. PATENT DOCUMENTS

2010/0168243 A1 7/2010 Baldwin et al.

FOREIGN PATENT DOCUMENTS

| EP | 0 066 987 A | 12/1982 |
| EP | 0 337 348 A | 10/1989 |
| EP | 1 172 358 A | 1/2002 |
| WO | WO 2006/042150 | 4/2006 |
| WO | WO 2006/083924 A | 8/2006 |

OTHER PUBLICATIONS

Corfield, G. C., et al., "N,N-Divinylureas: Further Polymerization Studies and Spectroscopic Investigation of Structure," *J. Macromol. Science A09*(7):1085-1111 (1975).
Mealy, N. E., et al., "Aliskiren Fumarate," *Drugs of the Future*, 26(12):1139-1148 (2001).
Rahuel, J., et al., "Structure-based Drug Design: The Discovery of Novel Nonpeptide Orally Active Inhibitors of Human Renin," *Chem Biol.*, 7(7):493-504 (2000).
Walsh, D. A., et al., "Synthesis and Antiallergy Activity of N-[2-(dimethylamino)ethyl]-4-aryl-1-piperazinecarboxamide Derivatives," *J. Med. Chem. 33*:2028-2032 (1990).
International Search Report from International Application No. PCT/US2008/007704, Date of Mailing: Apr. 21, 2009.
Written Opinion of the International Searching Authority from International Application No. PCT/US2008/007704, Date of Mailing: Apr. 21, 2009.
International Preliminary Report on Patentability from International Application No. PCT/US2008/007704, Date of Mailing: Jan. 7, 2010.
International Search Report from International Application No. PCT/US2008/007661, Date of Mailing: May 11, 2009.
Written Opinion of the International Searching Authority from International Application No. PCT/US2008/007661, Date of Mailing: May 11, 2009.
International Preliminary Report on Patentability from International Application No. PCT/US2008/007661, Date of Mailing: Jan. 7, 2010.

*Primary Examiner* — Kamal Saeed
*Assistant Examiner* — Nyeemah A Grazier
(74) *Attorney, Agent, or Firm* — Hamilton, Brook, Smith & Reynolds, P.C.

(57) ABSTRACT

The present invention is directed to aspartic protease inhibitors. The present invention is also directed to pharmaceutical compositions comprising the disclosed aspartic protease inhibitors. The present invention is further directed to methods of antagonizing one or more aspartic proteases in a subject in need thereof, and methods for treating an aspartic protease mediated disorder in a subject using the disclosed aspartic protease inhibitors.

26 Claims, No Drawings

RENIN INHIBITORS

RELATED APPLICATION

This application is the U.S. National Stage of International Application No. PCT/US2008/007661, filed Jun. 20, 2008, which designates the U.S., published in English, and claims the benefit of U.S. Provisional Application No. 60/936,397, filed Jun. 20, 2007. The entire teachings of the above application are incorporated herein by reference.

BACKGROUND OF THE INVENTION

Aspartic proteases, including renin, β-secretase (BACE), *Candida albicans* secreted aspartyl proteases, HIV protease, HTLV protease, and plasmepsins I and II, are implicated in a number of disease states. In hypertension, elevated levels of angiotensin I, the product of renin catalyzed cleavage of angioteninogen are present. Elevated levels of β-amyloid, the product of BACE activity on amyloid precursor protein, are widely believed to be responsible for the amyloid plaques present in the brains of Alzheimer's disease patients. Secreted aspartyl proteases play a role in the virulence of the pathogen *Candida albicans*. The viruses HIV and HTLV depend on their respective aspartic proteases for viral maturation. *Plasmodium falciparum* uses plasmepsins I and II to degrade hemoglobin.

In the renin-angiotensin-aldosterone system (RAAS), the biologically active peptide angiotensin II (Ang II) is generated by a two-step mechanism. The highly specific aspartic protease renin cleaves angiotensinogen to angiotensin I (Ang I), which is then further processed to Ang II by the less specific angiotensin-converting enzyme (ACE). Ang II is known to work on at least two receptor subtypes called $AT_1$ and $AT_2$. Whereas $AT_1$ seems to transmit most of the known functions of Ang II, the role of $AT_2$ is still unknown.

Modulation of the RAAS represents a major advance in the treatment of cardiovascular diseases (Zaman, M. A. et al *Nature Reviews Drug Discovery* 2002, 1, 621-636). ACE inhibitors and $AT_1$ blockers have been accepted as treatments of hypertension (Waeber B. et al., "The renin-angiotensin system: role in experimental and human hypertension", in Berkenhager W. H., Reid J. L. (eds): *Hypertension*, Amsterdam, Elsevier Science Publishing Co, 1996, 489-519; Weber M. A., *Am. J. Hypertens.*, 1992, 5, 247S). In addition, ACE inhibitors are used for renal protection (Rosenberg M. E. et al., *Kidney International*, 1994, 45, 403; Breyer J. A. et al., *Kidney International*, 1994, 45, S156), in the prevention of congestive heart failure (Vaughan D. E. et al., *Cardiovasc. Res.*, 1994, 28, 159; Fouad-Tarazi F. et al., *Am. J. Med.*, 1988, 84 (Suppl. 3A), 83) and myocardial infarction (Pfeffer M. A. et al., *N Engl. J: Med*, 1992, 327, 669).

Interest in the development of renin inhibitors stems from the specificity of renin (Kleinert H. D., *Cardiovasc. Drugs*, 1995, 9, 645). The only substrate known for renin is angiotensinogen, which can only be processed (under physiological conditions) by renin. In contrast, ACE can also cleave bradykinin besides Ang I and can be bypassed by chymase, a serine protease (Husain A., *J. Hypertens.*, 1993, 11, 1155). In patients, inhibition of ACE thus leads to bradykinin accumulation causing cough (5-20%) and potentially life-threatening angioneurotic edema (0.1-0.2%) (Israili Z. H. et al., *Annals of Internal Medicine*, 1992, 117, 234). Chymase is not inhibited by ACE inhibitors. Therefore, the formation of Ang II is still possible in patients treated with ACE inhibitors. Blockade of the ATI receptor (e.g., by losartan) on the other hand overexposes other AT-receptor subtypes to Ang II, whose concentration is dramatically increased by the blockade of ATI receptors. In summary, renin inhibitors are not only expected to be superior to ACE inhibitors and $AT_1$ blockers with regard to safety, but more importantly also with regard to their efficacy in blocking the RAAS.

Only limited clinical experience (Azizi M. et al., *J. Hypertens.*, 1994, 12, 419; Neutel J. M. et al., *Am. Heart*, 1991, 122, 1094) has been generated with renin inhibitors because their peptidomimetic character imparts insufficient oral activity (Kleinert H. D., *Cardiovasc. Drugs*, 1995, 9, 645). The clinical development of several compounds has been stopped because of this problem together with the high cost of goods. It appears as though only one compound has entered clinical trials (Rahuel J. et al., *Chem. Biol.*, 2000, 7, 493; Mealy N. E., *Drugs of the Future*, 2001, 26, 1139). Thus, metabolically stable, orally bioavailable and sufficiently soluble renin inhibitors that can be prepared on a large scale are not available. Recently, the first non-peptide renin inhibitors were described which show high in vitro activity (Oefner C. et al., *Chem. Biol.*, 1999, 6, 127; Patent Application WO 97/09311; Maerki H. P. et al., *Il Farmaco*, 2001, 56, 21). The present invention relates to the unexpected identification of renin inhibitors of a non-peptidic nature and of low molecular weight. Orally active renin inhibitors, which are active in indications beyond blood pressure regulation where the tissular renin-chymase system may be activated leading to pathophysiologically altered local functions such as renal, cardiac and vascular remodeling, atherosclerosis, and restenosis, are described.

All documents cited herein are incorporated by reference by its entirety.

SUMMARY OF THE INVENTION

One embodiment of the present invention is aspartic protease inhibitor represented by Structural Formula (I):

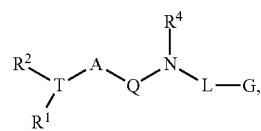

or an enantiomer, a diastereomer, or a pharmaceutically acceptable salt thereof, wherein:

$R^1$ is a) $(C_1-C_{12})$alkyl, $(C_3-C_7)$cycloalkyl, $(C_4-C_{12})$cycloalkylalkyl, halo$(C_1-C_{12})$alkyl, halo$(C_3-C_7)$-cycloalkyl, halo$(C_4-C_{12})$cycloalkylalkyl, saturated heterocyclyl optionally substituted with 1 to 5 groups independently selected from halogen, $(C_1-C_6)$alkyl, halo$(C_1-C_6)$alkyl, and oxo; or, b) phenyl, naphthyl, heteroaryl, or bicyclic heteroaryl each optionally substituted with 1 to 5 groups independently selected from:

1) fluorine, chlorine, bromine, iodine, cyano, nitro, amino, hydroxy, carboxy, $(C_1-C_8)$alkyl, $(C_3-C_8)$cycloalkyl, $(C_1-C_3)$alkyl$(C_3-C_8)$cycloalkyl, di$(C_1-C_3)$alkyl$(C_3-C_8)$cycloalkyl, $(C_4-C_8)$cycloalkylalkyl, $(C_2-C_6)$alkenyl, $(C_5-C_8)$cycloalkenyl, $(C_5-C_8)$cycloalkylalkenyl, $(C_2-C_8)$alkynyl, $(C_3-C_8)$cycloalkyl$(C_2-C_4)$alkynyl, halo$(C_1-C_8)$alkyl, halo$(C_3-C_6)$cycloalkyl, halo$(C_4-C_8)$cycloalkylalkyl, $(C_1-C_3)$alkyl$(C_4-C_8)$cycloalkylalkyl, di$(C_1-C_3)$allyl$(C_4-C_8)$cycloalkylalkyl, halo$(C_2-C_8)$alkenyl, halo$(C_5-C_8)$cycloalkenyl, halo$(C_6-C_8)$cycloalkenylalkyl, halo$(C_3-C_8)$alkynyl, halo$(C_5-C_8)$cycloalkylalkynyl, $(C_1-C_8)$alkoxy, $(C_3-C_8)$cycloalkoxy, $(C_4-C_8)$cycloalkylalkoxy, $(C_1-C_3)$alkyl$(C_3-C_8)$cycloalkoxy, $(C_1-C_3)$alkyl$(C_4-C_8)$cycloalkylalkoxy, di$(C_1-C_3)$alkyl$(C_3-C_8)$ cycloalkoxy, di($C_1$-$C_3$)alkyl($C_4$-$C_8$)cycloalkylalkoxy, halo($C_1$-$C_6$)alkoxy, halo($C_3$-$C_6$)cycloalkoxy, halo($C_4$-$C_8$)-cycloalkylalkoxy, ($C_1$-$C_3$)alkylthio, ($C_3$-$C_8$)cycloalkylthio, ($C_4$-$C_8$)cycloalkylalkylthio, ($C_1$-$C_3$)alkyl($C_3$-$C_8$)cycloalkylthio, ($C_1$-$C_3$)alkyl($C_4$-$C_8$)cycloalkylalkylthio, di($C_1$-$C_3$)alkyl($C_3$-$C_8$)cycloalkylthio, di($C_1$-$C_3$)alkyl($C_4$-$C_8$)cycloalkylalkylthio, halo($C_1$-$C_8$)alkylthio, halo($C_3$-$C_8$)cycloalkylthio, halo($C_4$-$C_8$)-cycloalkylalkylthio, ($C_1$-$C_8$)alkanesulfinyl, ($C_3$-$C_8$)-cycloalkanesulfinyl, ($C_4$-$C_8$)cycloalkyl-alkanesulfinyl, ($C_1$-$C_3$)alkyl($C_3$-$C_8$)cycloalkanesulfinyl, ($C_1$-$C_3$)alkyl ($C_4$-$C_8$)cycloalkyl-alkanesulfinyl, di($C_1$-$C_3$)alkyl($C_3$-$C_8$)cycloalkane-sulfinyl, di($C_1$-$C_3$)alkyl($C_4$-$C_8$)cycloalkyl-alkanesulfinyl, halo($C_1$-$C_8$)alkanesulfinyl, halo($C_3$-$C_8$)cycloalkanesulfinyl, halo($C_4$-$C_8$)cycloalkylalkanesulfinyl, ($C_1$-$C_8$)alkane-sulfonyl, ($C_3$-$C_8$)cycloalkanesulfonyl, ($C_4$-$C_8$) cycloalkylalkanesulfonyl, ($C_1$-$C_3$)alkyl($C_3$-$C_8$)cycloalkanesulfonyl, ($C_1$-$C_3$)alkyl ($C_4$-$C_8$)cycloalkyl-alkanesulfonyl, di($C_1$-$C_3$)alkyl($C_3$-$C_8$)cycloalkanesulfonyl, di($C_1$-$C_3$)alkyl ($C_4$-$C_8$)cycloalkylalkanesulfonyl, halo($C_1$-$C_8$)alkanesulfonyl, halo($C_3$-$C_8$)cycloalkanesulfonyl, halo($C_4$-$C_8$)cycloalkylalkanesulfonyl, ($C_1$-$C_8$)alkylamino, di($C_1$-$C_8$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_8$)alkoxycarbonyl, aminocarbonyl, ($C_1$-$C_8$)alkylaminocarbonyl, and di($C_1$-$C_8$)alkylaminocarbonyl, piperidino, pyrrolidino, cyano($C_1$-$C_6$)alkyl, hydroxy($C_1$-$C_6$)alkyl, carboxy($C_1$-$C_6$)alkyl, ($C_1$-$C_8$)alkoxy($C_1$-$C_6$)alkyl, ($C_3$-$C_8$)cycloalkoxy($C_1$-$C_6$)alkyl, ($C_4$-$C_8$)cycloalkylalkoxy($C_1$-$C_6$)alkyl, halo($C_1$-$C_6$)alkoxy($C_1$-$C_6$)alkyl, halo($C_3$-$C_6$)cycloalkoxy($C_1$-$C_6$)alkyl, halo($C_4$-$C_8$)-cycloalkylalkoxy($C_1$-$C_6$)alkyl, ($C_1$-$C_8$)alkylthio($C_1$-$C_6$)alkyl, ($C_3$-$C_8$)cycloalkylthio($C_1$-$C_6$)alkyl, ($C_4$-$C_8$)cycloalkylalkylthio($C_1$-$C_6$)alkyl, halo($C_1$-$C_8$)alkylthio($C_1$-$C_6$)alkyl, halo($C_3$-$C_8$)cycloalkylthio($C_1$-$C_6$)alkyl, halo($C_4$-$C_8$)-cycloalkylalkylthio($C_1$-$C_6$)alkyl, ($C_1$-$C_8$)alkanesulfinyl($C_1$-$C_6$)alkyl, ($C_3$-$C_8$)-cycloalkanesulfinyl($C_1$-$C_6$)alkyl, ($C_4$-$C_8$)cycloalkyl-alkanesulfinyl($C_1$-$C_6$)alkyl, halo($C_1$-$C_8$)alkanesulfinyl($C_1$-$C_6$)alkyl, halo($C_3$-$C_8$)cycloalkanesulfinyl($C_1$-$C_6$)alkyl, halo($C_4$-$C_8$)cycloalkylalkanesulfinyl($C_1$-$C_6$)alkyl, ($C_1$-$C_8$)alkanesulfonyl($C_1$-$C_6$)alkyl, ($C_3$-$C_8$)cycloalkanesulfonyl($C_1$-$C_6$)alkyl, ($C_4$-$C_8$)cycloalkylalkanesulfonyl($C_1$-$C_6$)allyl, halo($C_1$-$C_8$)alkanesulfonyl($C_1$-$C_6$)alkyl, halo($C_3$-$C_8$)cycloalkanesulfonyl($C_1$-$C_6$)alkyl, halo($C_4$-$C_8$)cycloalkylalkanesulfonyl($C_1$-$C_6$)alkyl, ($C_1$-$C_8$)alkylamino($C_1$-$C_6$)alkyl, di($C_1$-$C_8$)alkylamino($C_1$-$C_6$)alkyl, ($C_1$-$C_8$)alkoxycarbonyl($C_1$-$C_6$)alkyl, ($C_1$-$C_8$)acyloxy($C_1$-$C_6$)alkyl, aminocarbonyl($C_1$-$C_6$)alkyl, ($C_1$-$C_8$)alkylaminocarbonyl($C_1$-$C_6$)alkyl, di($C_1$-$C_8$)alkylaminocarbonyl($C_1$-$C_6$)alkyl, ($C_1$-$C_8$)acylamino($C_1$-$C_6$)alkyl, piperidino($C_1$-$C_6$)alkyl, pyrrolidino($C_1$-$C_6$)alkyl, ($C_1$-$C_8$)alkoxycarbonylamino, ($C_1$-$C_8$)alkoxycarbonylamino($C_1$-$C_6$)alkyl, aminocarboxy($C_1$-$C_6$)alkyl, ($C_1$-$C_8$)alkylaminocarboxy($C_1$-$C_6$)alkyl and, di($C_1$-$C_8$)alkylaminocarboxy($C_1$-$C_6$)alkyl; and 2) phenyl, naphthyl, heteroaryl, bicyclic heteroaryl, phenoxy, naphthyloxy, heteroaryloxy, bicyclic heteroaryloxy, phenylthio, naphthylthio, heteroarylthio, bicyclic heteroarylthio, phenylsulfinyl, naphthylsulfinyl, heteroarylsulfinyl, bicyclic heteroarylsulfinyl, phenylsulfonyl, naphthylsulfonyl, heteroarylsulfonyl, bicyclic heteroarylsulfonyl, phenyl($C_1$-$C_3$)alkyl, naphthyl($C_1$-$C_3$)alkyl, heteroaryl($C_1$-$C_3$)alkyl, bicyclic heteroaryl($C_1$-$C_3$)alkyl, phenyl($C_1$-$C_3$)alkoxy, naphthyl($C_1$-$C_3$)alkoxy, heteroaryl($C_1$-$C_3$)alkoxy, and bicyclic heteroaryl($C_1$-$C_3$)alkoxy, each optionally substituted with 1 to 5 groups independently selected from: fluorine, chlorine, cyano, ($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkanesulfonyl, ($C_1$-$C_6$)alkoxy-carbonyl, and aminocarbonyl;

$R^2$ is a ($C_1$-$C_{12}$)alkyl, ($C_2$-$C_{12}$)alkenyl, ($C_2$-$C_{12}$)alkynyl, ($C_1$-$C_{12}$)alkoxy, ($C_2$-$C_{12}$)alkenyloxy, ($C_1$-$C_{12}$)alkylthio, ($C_1$-$C_6$)alkoxy($C_1$-$C_6$)alkyl, ($C_1$-$C_6$)alkylthio-($C_1$-$C_6$)alkyl, ($C_1$-$C_6$)alkoxy($C_1$-$C_6$)alkoxy, ($C_1$-$C_6$)alkoxy($C_1$-$C_6$)alkylthio, ($C_1$-$C_6$)allylthio($C_1$-$C_6$)alkoxy, ($C_1$-$C_6$)alkylthio($C_1$-$C_6$)alkylthio, ($C_1$-$C_4$)alkoxy($C_1$-$C_4$)alkoxy($C_1$-$C_4$)alkyl, aminocarbonylamino($C_1$-$C_{12}$)alkyl, aminocarbonylamino($C_1$-$C_{12}$)alkoxy, aminocarbonylamino($C_1$-$C_{12}$)alkylthio, ($C_1$-$C_6$)alkanoylamino($C_1$-$C_6$)alkyl, ($C_1$-$C_6$)alkanoylamino($C_1$-$C_6$)alkoxy, ($C_1$-$C_6$)alkanoylamino($C_1$-$C_6$)alkylthio, ($C_3$-$C_4$)cycloalkylcarbonylamino($C_1$-$C_6$)alkyl, ($C_3$-$C_4$)cycloalkylcarbonylamino($C_1$-$C_6$)alkoxy, ($C_3$-$C_4$)cycloalkylcarbonylamino($C_1$-$C_6$)alkylthio, aminosulfonylamino($C_1$-$C_{12}$)alkyl, aminosulfonylamino($C_1$-$C_{12}$)alkoxy, aminosulfonylamino($C_1$-$C_{12}$)alkylthio, ($C_1$-$C_6$)alkanesulfonylamino($C_1$-$C_6$)alkyl, ($C_1$-$C_6$)alkanesulfonylamino($C_1$-$C_6$)alkoxy, ($C_1$-$C_6$)alkanesulfonylamino($C_1$-$C_6$)alkylthio, formylamino($C_1$-$C_6$)alkyl, formylamino($C_1$-$C_6$)alkoxy, formylamino($C_1$-$C_6$)alkylthio, ($C_1$-$C_6$)alkoxycarbonylamino($C_1$-$C_6$)alkyl, ($C_1$-$C_6$)alkoxycarbonylamino($C_1$-$C_6$)alkoxy, ($C_1$-$C_6$)alkoxycarbonylamino($C_1$-$C_6$)alkylthio, ($C_1$-$C_6$)alkylaminocarbonylamino($C_1$-$C_6$)alkyl, di($C_1$-$C_6$)alkylaminocarbonylamino($C_1$-$C_6$)alkyl, ($C_1$-$C_6$)alkylaminocarbonylamino($C_1$-$C_6$)alkoxy, $C_6$)alkylaminocarbonylamino($C_1$-$C_6$)alkoxy, ($C_1$-$C_6$)alkylaminocarbonylamino($C_1$-$C_6$)alkylthio, di($C_1$-$C_6$)alkylaminocarbonylamino($C_1$-$C_6$)alkylthio, aminocarbonyl($C_1$-$C_6$)alkyl, aminocarbonyl($C_1$-$C_6$)alkoxy, aminocarbonyl($C_1$-$C_6$)alkylthio, ($C_1$-$C_6$)allylaminocarbonyl($C_1$-$C_6$)alkyl, ($C_1$-$C_6$)alkylaminocarbonyl($C_1$-$C_6$)alkoxy, ($C_1$-$C_6$)alkylaminocarbonyl($C_1$-$C_6$)alkylthio, aminocarboxy($C_1$-$C_6$)alkyl, aminocarboxy($C_1$-$C_6$)alkoxy, aminocarboxy($C_1$-$C_6$)alkylthio, ($C_1$-$C_6$)alkylaminocarboxy($C_1$-$C_6$)alkyl, ($C_1$-$C_6$)alkylaminocarboxy($C_1$-$C_6$)alkoxy, ($C_1$-$C_6$)alkylaminocarboxy($C_1$-$C_6$)alkylthio, ($C_1$-$C_{12}$)alkoxycarbonylamino, ($C_1$-$C_{12}$)alkylaminocarbonylamino, ($C_1$-$C_8$)oxoalkyl, ($C_1$-$C_{12}$)alkanoylamino, ($C_3$-$C_7$)cycloalkoxycarbonylamino, aminocarbonyl, ($C_1$-$C_6$)alkylaminocarbonyl, ($C_3$-$C_7$)cycloalkylaminocarbonyl, aminocarboxy, ($C_1$-$C_6$)alkylaminocarboxy, ($C_3$-$C_7$)cycloalkylaminocarboxy, ($C_1$-$C_6$)alkylcarbonyl, ($C_3$-$C_7$)cycloalkylcarbonyl, —NHC(=NR$^{2e}$)(NHR$^{2a}$), or thiazolylamino, wherein R$^{2e}$ is H, ($C_1$-$C_6$)alkyl, phenyl, heteroaryl, cyano, nitro, —S(O)R$^{2a}$, —S(O$_2$)R$^{2a}$, —S(O$_2$)NHR$^{2a}$, —S(O$_2$)NR$^{2a}$R$^{2a}$, —C(O)R$^{2a}$, —C(S)R$^{2a}$, —C(O)OR$^{2a}$, —C(S)OR$^{2a}$, —C(O)(NH$_2$), —C(O)(NHR$^{2a}$) and R$^{2a}$ is straight or branched ($C_1$-$C_6$) alkyl, straight or branched ($C_1$-$C_6$) haloalkyl, ($C_3$-$C_7$) cycloalkyl or straight or branched $C_1$-$C_6$ alkoxyalkyl; and wherein each group represented by R$^2$ is substituted by 0 to 6 groups selected from:

halogen, cyano, hydroxyl, ($C_1$-$C_3$)alkoxy, ($C_3$-$C_6$)cycloalkyl, ($C_3$-$C_6$)cycloalkoxy, halo($C_1$-$C_3$)alkoxy, halo($C_3$-$C_6$)cycloalkyl or halo($C_3$-$C_6$)cycloalkoxy; wherein any thio moiety of said unsubstituted or substituted R$^2$ group is optionally and independently replaced by —S(O)— or —S(O)$_2$—; and wherein any carbonyl moiety of said unsubstituted or substituted R$^2$ group is optionally and independently replaced by a thiocarbonyl moiety;

T is N or CR$_3$;

R$^3$ is 1) H, halogen, ($C_1$-$C_6$)alkyl, ($C_1$-$C_6$)alkoxy, hydroxyl, hydroxy($C_1$-$C_6$)alkyl, hydroxy($C_1$-$C_6$)alkoxy, ($C_1$-$C_6$)alkanoylamino, ($C_1$-$C_6$)-alkoxycarbonylamino, ($C_1$-$C_6$)alkylaminocarbonylamino, di($C_1$-$C_6$)alkylaminocarbonylamino, $(C_1-C_6)$alkanesulfonylamino, $(C_1-C_6)$alkylaminosulfonylamino, or di$(C_1-C_6)$alkylaminosulfonyl-amino, 2) phenylamino or heteroarylamino in which each phenylamino and heteroarylamino group is optionally substituted with 1 to 5 groups independently selected from:

fluorine, chlorine, bromine, iodine, cyano, nitro, amino, hydroxy, carboxy, $(C_1-C_6)$alkyl, $(C_3-C_6)$cycloalkyl, $(C_4-C_7)$cycloalkylalkyl, $(C_2-C_6)$alkynyl, $(C_3-C_6)$-cycloalkyl$(C_2-C_4)$alkynyl, halo$(C_1-C_6)$alkyl, halo$(C_3-C_6)$cycloalkyl, halo$(C_4-C_7)$-cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkylalkylthio, halo$(C_1-C_6)$alkylthio, halo$(C_3-C_6)$cycloalkylthio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, amino-carbonyl, $(C_1-C_6)$alkylaminocarbonyl, and di$(C_1-C_6)$alkylaminocarbonyl, cyano$(C_1-C_6)$alkyl, hydroxy$(C_1-C_6)$alkyl, carboxy$(C_1-C_6)$alkyl, $(C_1-C_6)$alkoxy$(C_1-C_6)$alkyl, $(C_3-C_8)$cycloalkoxy$(C_1-C_6)$alkyl, $(C_4-C_8)$cycloalkylalkoxy$(C_1-C_6)$alkyl, halo$(C_1-C_6)$alkoxy$(C_1-C_6)$alkyl, halo$(C_3-C_6)$cycloalkoxy$(C_1-C_6)$alkyl, halo$(C_4-C_8)$-cycloalkylalkoxy$(C_1-C_6)$alkyl, $(C_1-C_8)$alkylthio$(C_1-C_6)$alkyl, $(C_3-C_8)$cycloalkylthio$(C_1-C_6)$alkyl, $(C_4-C_8)$cycloalkylalkylthio$(C_1-C_6)$alkyl, halo$(C_1-C_8)$alkylthio$(C_1-C_6)$alkyl, halo$(C_3-C_8)$cycloalkylthio$(C_1-C_6)$alkyl, halo$(C_4-C_8)$-cycloalkylalkylthio$(C_1-C_6)$alkyl, $(C_1-C_8)$alkanesulfinyl$(C_1-C_6)$alkyl, $(C_3-C_8)$-cycloalkanesulfinyl$(C_1-C_6)$alkyl, $(C_4-C_8)$ cycloalkyl-alkanesulfinyl$(C_1-C_6)$alkyl, halo$(C_1-C_8)$ alkanesulfinyl$(C_1-C_6)$alkyl, halo$(C_3-C_8)$cycloalkanesulfinyl$(C_1-C_6)$alkyl, halo$(C_4-C_8)$cycloalkylalkanesulfinyl$(C_1-C_6)$alkyl, $(C_1-C_8)$alkanesulfonyl$(C_1-C_6)$alkyl, $(C_3-C_8)$cycloalkanesulfonyl$(C_1-C_6)$alkyl, $(C_4-C_8)$cycloalkylalkanesulfonyl$(C_1-C_6)$alkyl, halo$(C_1-C_8)$alkanesulfonyl$(C_1-C_6)$alkyl, halo$(C_3-C_8)$cycloalkanesulfonyl$(C_1-C_6)$alkyl, halo$(C_4-C_8)$cycloalkylalkanesulfonyl$(C_1-C_6)$alkyl, $(C_1-C_8)$alkylamino$(C_1-C_6)$alkyl, di$(C_1-C_8)$alkylamino$(C_1-C_6)$alkyl, $(C_1-C_8)$alkoxycarbonyl$(C_1-C_6)$alkyl, $(C_1-C_8)$acyloxy$(C_1-C_6)$alkyl, aminocarbonyl$(C_1-C_6)$alkyl, $(C_1-C_8)$alkylaminocarbonyl$(C_1-C_6)$alkyl, di$(C_1-C_8)$alkylaminocarbonyl$(C_1-C_6)$alkyl $(C_1-C_8)$acylamino$(C_1-C_6)$alkyl, $(C_1-C_8)$alkoxycarbonylamino, $(C_1-C_8)$alkoxycarbonylamino$(C_1-C_6)$alkyl, aminocarboxy$(C_1-C_6)$alkyl, $(C_1-C_8)$alkylaminocarboxy$(C_1-C_6)$alkyl and di$(C_1-C_8)$alkylaminocarboxy$(C_1-C_6)$alkyl, or 3) a divalent radical selected from the group consisting of —$(CH_2)_2$—, —$(CH_2)_3$—, —$OCH_2$—, —$OCH_2CH_2$—, —$OC(=O)$—, —$NHC(=O)$—, —$OC(=O)NH$—, —$NHC(=O)NH$—, and $NHC(=O)CH_2$—, optionally substituted with up to 2 groups independently selected from $(C_1-C_3)$alkyl and halo$(C_1-C_3)$alkyl, which is bonded to $R^1$;

provided that:

1) when T is N or when T is $CR^3$ and $R^3$ is hydroxyl, halogen or optionally substituted phenylamino or heteroarylamino, then $R^2$ is not an optionally substituted alkoxy, alkylthio or amino group as follows: a substituted or unsubstituted $C_{12}$)alkoxy, $(C_1-C_6)$alkoxy$(C_1-C_6)$alkoxy, $(C_1-C_6)$alkylthio$(C_1-C_6)$alkoxy, aminocarbonylamino$(C_1-C_{12})$alkoxy, $(C_1-C_6)$alkanoylamino$(C_1-C_6)$alkoxy, $(C_3-C_4)$cycloalkylcarbonylamino$(C_1-C_6)$alkoxy, aminosulfonylamino$(C_1-C_{12})$ alkoxy, $(C_1-C_6)$alkanesulfonylamino$(C_1-C_6)$alkoxy, formylamino$(C_1-C_6)$alkoxy, $(C_1-C_6)$alkoxycarbonylamino$(C_1-C_6)$alkoxy, $(C_1-C_6)$alkylaminocarbonylamino$(C_1-C_6)$alkoxy, di$(C_1-C_6)$alkylaminocarbonylamino$(C_1-C_6)$alkoxy, aminocarbonyl$(C_1-C_6)$alkoxy, $(C_1-C_6)$alkylaminocarbonyl$(C_1-C_6)$alkoxy, aminocarboxy$(C_1-C_6)$alkoxy, $(C_1-C_6)$alkylaminocarboxy$(C_1-C_6)$alkoxy, $(C_1-C_{12})$alkoxycarbonylamino, $(C_1-C_{12})$alkylaminocarbonylamino, or $(C_1-C_{12})$alkanoylamino;

2) when T is N or when T is $CR^3$ and $R^3$ is hydroxyl, halogen or optionally substituted phenylamino or heteroarylamino, then $R^2$ is not an optionally substituted alkoxy, alkylthio or amino group as follows: a unsubstituted or substituted $(C_1-C_{12})$alkylthio, $(C_1-C_6)$alkoxy$(C_1-C_6)$alkylthio, $(C_1-C_6)$ alkylthio$(C_1-C_6)$alkylthio, aminocarbonylamino$(C_1-C_{12})$ alkylthio, $(C_1-C_6)$alkanoylamino$(C_1-C_6)$alkylthio, $(C_3-C_4)$ cycloalkylcarbonylamino$(C_1-C_6)$alkylthio, aminosulfonylamino$(C_1-C_{12})$alkylthio, $(C_1-C_6)$alkanesulfonylamino$(C_1-C_6)$alkylthio, formylamino$(C_1-C_6)$alkylthio, $(C_1-C_6)$alkoxycarbonylamino$(C_1-C_6)$alkylthio, $(C_1-C_6)$ alkylaminocarbonylamino$(C_1-C_6)$alkylthio, di$(C_1-C_6)$alkylaminocarbonylamino$(C_1-C_6)$alkylthio, aminocarbonyl$(C_1-C_6)$alkylthio, $(C_1-C_6)$alkylaminocarbonyl$(C_1-C_6)$alkylthio, aminocarboxy$(C_1-C_6)$alkylthio or $(C_1-C_6)$alkylaminocarboxy$(C_1-C_6)$alkylthio, wherein the thio moiety is replaced by —$S(O)$— or —$S(O)_2$—; and 3) when T is N or when T is $CR^3$ and $R^3$ is hydroxyl, halogen or optionally substituted phenylamino or heteroarylamino, $R^2$ is not an optionally substituted alkoxy, alkylthio or amino group as follows: a unsubstituted or substituted aminocarbonylamino$(C_1-C_{12})$alkoxy, aminocarbonylamino$(C_1-C_{12})$alkylthio, $(C_1-C_6)$alkanoylamino$(C_1-C_6)$alkoxy, $(C_1-C_6)$alkanoylamino$(C_1-C_6)$alkylthio, $(C_3-C_4)$ cycloalkylcarbonylamino$(C_1-C_6)$alkoxy, $(C_3-C_4)$ cycloalkylcarbonylamino$(C_1-C_6)$alkylthio, formylamino$(C_1-C_6)$alkoxy, formylamino$(C_1-C_6)$alkylthio, $(C_1-C_6)$ alkoxycarbonylamino$(C_1-C_6)$alkoxy, $(C_1-C_6)$ alkoxycarbonylamino$(C_1-C_6)$alkylthio, $(C_1-C_6)$ alkylaminocarbonylamino$(C_1-C_6)$alkoxy, di$(C_1-C_6)$ alkylaminocarbonylamino$(C_1-C_6)$alkoxy, $(C_1-C_6)$ alkylaminocarbonylamino$(C_1-C_6)$alkylthio, di$(C_1-C_6)$ alkylaminocarbonylamino$(C_1-C_6)$alkylthio, aminocarbonyl$(C_1-C_6)$alkoxy, aminocarbonyl$(C_1-C_6)$alkylthio, $(C_1-C_6)$ alkylaminocarbonyl-$(C_1-C_6)$alkoxy, $(C_1-C_6)$ alkylaminocarbonyl$(C_1-C_6)$alkylthio, aminocarboxy$(C_1-C_6)$ alkoxy, aminocarboxy$(C_1-C_6)$alkylthio, $(C_1-C_6)$ alkylaminocarboxy$(C_1-C_6)$alkoxy, $(C_1-C_6)$ alkylaminocarboxy$(C_1-C_6)$alkylthio, $(C_1-C_{12})$ alkoxycarbonylamino, $(C_1-C_{12})$alkylaminocarbonylamino, or $(C_1-C_{12})$alkanoylamino, wherein the carbonyl moiety is replaced by a thiocarbonyl moiety;

A is represented by the following Structural Formula:

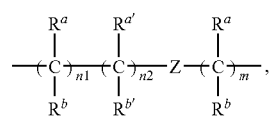

wherein:

$R^a$, $R^b$, $R^{a'}$, $R^{b'}$ for each occurrence, are independently hydrogen, $(C_1-C_6)$alkyl, halo$(C_1-C_6)$alkyl or $R^a$ and $R^b$ attached to a carbon atom taken together are an oxo or $R^{a'}$ and $R^{b'}$ attached to a carbon atom taken together are an oxo;

m, n1 and n2 are 0, 1 or 2 and m+n1+n2=2; provided that when T is N and Z is O, S or $NR^7$, then n1+n2=2;

Z is —O—, —S—, —(NR$^7$)—, or —(CR$^a$R$^b$)—, wherein R$^7$ is (C$_1$-C$_6$)alkyl, halo(C$_1$-C$_6$)alkyl or (C$_1$-C$_3$)alkoxy(C$_1$-C$_3$)alkyl;

Q is a divalent radical selected from

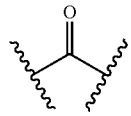
Q1

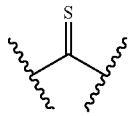
Q2

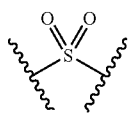
Q3

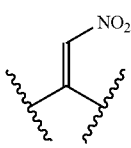
Q4

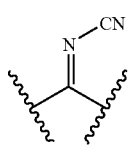
Q5

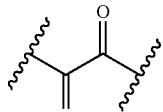
Q6

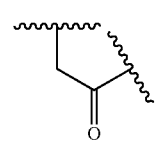
Q7

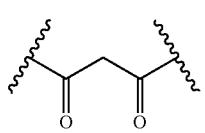
Q8

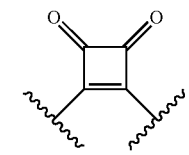
Q9

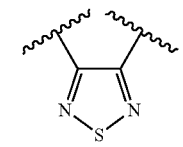
Q10

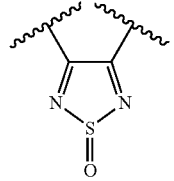
Q11

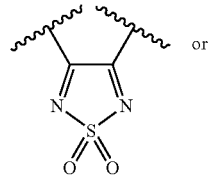
Q12 or

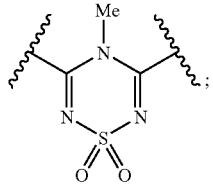
Q13 wherein A and N are attached to the truncated bonds

R$^4$ is H, (C$_1$-C$_6$)alkyl, halo(C$_1$-C$_6$)alkyl; (C$_1$-C$_3$)alkoxy (C$_1$-C$_3$)alkyl, or cyano(C$_1$-C$_6$)alkyl;

L is 1) a linear (C$_2$-C$_4$)alkyl chain when G is OH, OR$^9$, NH$_2$, NHR$^9$, NR$^9$R$^{10}$, NHC(=NH)NH$_2$, or NHC(=NH)NHR$^9$, or 2) a linear (C$_1$-C$_3$)alkyl chain when G is C(=NH)NH$_2$ or C(=NH)NHR$^9$;

L is optionally substituted by 1-4 groups independently selected from R$^5$, R$^6$, R$^8$ and R$^{11}$, one or more of the carbon atoms of L may be part of a 3-, 4-, 5-, 6-, or 7-membered saturated ring composed of carbon atoms, and 0-2 hetero atoms selected from 0 or 1 nitrogen atoms, 0 or 1 oxygen atoms, and 0 or 1 sulfur atoms; said saturated ring being optionally substituted with up to four groups selected from halogen, (C$_1$-C$_6$)alkyl, halo(C$_1$-C$_6$) alkyl, (C$_3$-C$_6$)cycloalkyl, halo(C$_3$-C$_6$)cycloalkyl, (C$_4$-C$_7$)cycloalkylalkyl, halo(C$_4$-C$_7$)cycloalkylalkyl, and oxo;

R$^5$, R$^6$, R$^8$ and R$^{11}$ is each independently selected from 1) hydrogen, hydroxy, (C$_1$-C$_{12}$)alkyl, (C$_3$-C$_8$)cycloalkyl, (C$_3$-C$_8$)cycloalkyl(C$_1$-C$_3$)alkyl, (C$_2$-C$_{12}$)alkenyl, (C$_5$-C$_8$)cycloalkyl(C$_1$-C$_3$)alkenyl, (C$_2$-C$_{12}$)alkynyl, (C$_3$-C$_8$)cycloalkyl(C$_1$-C$_3$)alkynyl, (C$_4$-C$_{12}$)bicycloalkyl(C$_1$-C$_3$)alkyl, (C$_8$-C$_{14}$)tricycloalkyl(C$_1$-C$_3$)alkyl, (C$_1$-C$_6$)alkoxy(C$_1$-C$_6$)alkyl, (C$_3$-C$_8$)cycloalkoxy(C$_1$-C$_3$)alkyl, (C$_1$-C$_6$)alkylthio(C$_1$-C$_6$)alkyl, (C$_3$-C$_8$)cycloalkylthio(C$_1$-C$_3$)alkyl, saturated heterocyclyl, and saturated heterocyclyl(C$_1$-C$_3$)alkyl wherein (a) hydrogen atoms in these groups are optionally substituted by 1 to 6 groups independently selected from halogen, cyano, hydroxyl, (C$_1$-C$_3$)alkyl, (C$_1$-C$_3$)alkoxy, (C$_3$-C$_6$)cycloalkyl, (C$_3$-C$_6$)cycloalkoxy, halo(C$_1$-C$_3$)alkyl, halo(C$_1$-C$_3$)alkoxy, halo(C$_3$-C$_6$)cycloalkyl, halo(C$_3$-C$_6$)cycloalkoxy and wherein (b) divalent sulfur atoms are optionally oxidized to sulfoxide or sulfone; or 2) phenyl, naphthyl, heteroaryl, phenyl(C$_1$-C$_3$)alkyl, naphthyl(C$_1$-C$_3$)alkyl, and heteroaryl(C$_1$-C$_3$)alkyl, each optionally substituted with 1 to 3 groups independently selected from:

fluorine, chlorine, bromine, iodine, cyano, nitro, amino, hydroxy, carboxy, (C$_1$-C$_6$)alkyl, (C$_3$-C$_6$)cycloalkyl, (C$_4$-C$_7$) cycloalkylalkyl, (C$_2$-C$_6$)alkynyl, (C$_3$-C$_6$)cycloalkyl-(C$_2$-C$_4$) alkynyl, halo(C$_1$-C$_6$)alkyl, halo(C$_3$-C$_6$)cycloalkyl, halo(C$_4$-C$_7$)cycloalkylalkyl, (C$_1$-C$_6$)alkoxy, (C$_3$-C$_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkylthio, ($C_4$-$C_7$)cycloalkylalkylthio, halo($C_1$-$C_6$)alkylthio, halo($C_3$-$C_6$)cycloalkylthio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)-cycloalkylalkanesulfonyl, ($C_1$-$C_6$)alkylamino, di($C_1$-$C_6$)alkylamino, ($C_1$-$C_6$)-alkoxy($C_1$-$C_6$)alkoxy, halo($C_1$-$C_6$)alkoxy($C_1$-$C_6$)alkoxy, ($C_1$-$C_6$)alkoxycarbonyl, aminocarbonyl, ($C_1$-$C_6$)alkylaminocarbonyl, di($C_1$-$C_6$)alkylaminocarbonyl, cyano($C_1$-$C_6$)alkyl, hydroxy($C_1$-$C_6$)alkyl, carboxy($C_1$-$C_6$)alkyl, ($C_1$-$C_6$)alkoxy($C_1$-$C_6$)alkyl, ($C_3$-$C_8$)cycloalkoxy($C_1$-$C_6$)alkyl, ($C_4$-$C_8$)cycloalkylalkoxy($C_1$-$C_6$)alkyl, halo($C_1$-$C_6$)alkoxy($C_1$-$C_6$)alkyl, halo($C_3$-$C_6$)cycloalkoxy($C_1$-$C_6$)alkyl, halo($C_4$-$C_8$)-cycloalkylalkoxy($C_1$-$C_6$)alkyl, ($C_1$-$C_8$)alkylthio($C_1$-$C_6$)alkyl, ($C_3$-$C_8$)cycloalkylthio($C_1$-$C_6$)alkyl, ($C_4$-$C_8$)cycloalkylalkylthio($C_1$-$C_6$)alkyl, halo($C_1$-$C_8$)alkylthio($C_1$-$C_6$)alkyl, halo($C_3$-$C_8$)cycloalkylthio($C_1$-$C_6$)alkyl, halo($C_4$-$C_8$)-cycloalkylalkylthio($C_1$-$C_6$)alkyl, ($C_1$-$C_8$)alkanesulfinyl($C_1$-$C_6$)alkyl, ($C_3$-$C_8$)-cycloalkanesulfinyl($C_1$-$C_6$)alkyl, ($C_3$-$C_8$)cycloalkylalkanesulfinyl($C_1$-$C_6$)alkyl, halo($C_1$-$C_8$)alkanesulfinyl($C_1$-$C_6$)alkyl, halo($C_3$-$C_8$)cycloalkanesulfinyl($C_1$-$C_6$)alkyl, halo($C_4$-$C_8$)cycloalkylalkanesulfinyl($C_1$-$C_6$)alkyl, ($C_1$-$C_8$)alkanesulfonyl($C_1$-$C_6$)alkyl, ($C_3$-$C_8$)cycloalkanesulfonyl($C_1$-$C_6$)alkyl, ($C_4$-$C_8$)cycloalkylalkanesulfonyl($C_1$-$C_6$)alkyl, halo($C_1$-$C_8$)alkanesulfonyl($C_1$-$C_6$)alkyl, halo($C_3$-$C_8$)cycloalkanesulfonyl($C_1$-$C_6$)alkyl, halo($C_4$-$C_8$)cycloalkylalkanesulfonyl($C_1$-$C_6$)alkyl, ($C_1$-$C_8$)alkylamino($C_1$-$C_6$)alkyl, di($C_1$-$C_8$)alkylamino($C_1$-$C_6$)alkyl, ($C_1$-$C_8$)alkoxycarbonyl($C_1$-$C_6$)alkyl, ($C_1$-$C_8$)acyloxy($C_1$-$C_6$)alkyl, aminocarbonyl($C_1$-$C_6$)alkyl, ($C_1$-$C_8$)alkylaminocarbonyl($C_1$-$C_6$)alkyl, di($C_1$-$C_8$)alkylaminocarbonyl($C_1$-$C_6$)alkyl and ($C_1$-$C_8$)acylamino($C_1$-$C_6$)alkyl, ($C_1$-$C_8$)alkoxycarbonylamino, ($C_1$-$C_8$)alkoxycarbonylamino($C_1$-$C_6$)alkyl, aminocarboxy($C_1$-$C_6$)alkyl, ($C_1$-$C_8$)alkylaminocarboxy($C_1$-$C_6$)alkyl and di($C_1$-$C_8$)alkylaminocarboxy($C_1$-$C_6$)alkyl, phenyl, naphthyl, heteroaryl, bicyclic heteroaryl, phenoxy, naphthyloxy, heteroaryloxy, bicyclic heteroaryloxy, phenylthio, naphthylthio, heteroarylthio, bicyclic heteroarylthio, phenylsulfinyl, naphthylsulfinyl, heteroarylsulfinyl, bicyclic heteroarylsulfinyl, phenylsulfonyl, naphthylsulfonyl, heteroarylsulfonyl, bicyclic heteroarylsulfonyl, phenyl($C_1$-$C_3$)alkyl, naphthyl($C_1$-$C_3$)alkyl, heteroaryl($C_1$-$C_3$)allyl, and bicyclic heteroaryl($C_1$-$C_3$)alkyl, wherein the aromatic and heteroaromatic groups are optionally substituted with 1 to 3 groups independently selected from fluorine, chlorine, cyano, ($C_1$-$C_3$)alkyl, halo($C_1$-$C_3$)alkyl, ($C_1$-$C_3$)alkoxy, halo($C_1$-$C_3$)-alkoxy, ($C_1$-$C_3$)alkanesulfonyl, and ($C_1$-$C_3$)alkoxycarbonyl;

G is OH, OR$^9$, NH$_2$, NHR$^9$, NR$^9$R$^{10}$, C($=$NH)NH$_2$, C($=$NH)NHR$^9$, NHC($=$NH)NH$_2$, or NHC($=$NH)NHR$^9$;

R$^9$ is a) ($C_1$-$C_{12}$)alkyl, ($C_4$-$C_{12}$)cycloalkylalkyl, halo($C_1$-$C_{12}$)alkyl, halo($C_4$-$C_{12}$)cycloalkylalkyl, ($C_2$-$C_{12}$)alkenyl, ($C_5$-$C_{12}$)cycloalkylalkenyl, halo($C_2$-$C_{12}$)alkenyl, halo($C_5$-$C_{12}$)cycloalkylalkenyl, ($C_2$-$C_{12}$)alkynyl, ($C_5$-$C_{12}$)cycloalkylalkynyl, halo($C_2$-$C_{12}$)alkynyl, halo($C_5$-$C_{12}$)cycloalkylalkynyl, ($C_1$-$C_6$)alkoxy($C_1$-$C_6$)alkyl, halo($C_1$-$C_6$)alkoxy($C_1$-$C_6$)alkyl, ($C_1$-$C_6$)alkylthio($C_1$-$C_6$)alkyl, halo($C_1$-$C_6$)alkylthio($C_1$-$C_6$)alkyl, ($C_1$-$C_6$)alkanesulfinyl($C_1$-$C_6$)alkyl, halo($C_1$-$C_6$)alkanesulfinyl($C_1$-$C_6$)alkyl, ($C_1$-$C_6$)alkanesulfonyl($C_1$-$C_6$)alkyl, halo($C_1$-$C_6$)alkanesulfonyl($C_1$-$C_6$)alkyl, aminocarbonyl($C_1$-$C_6$)alkyl, ($C_1$-$C_6$)alkylaminocarbonyl($C_1$-$C_6$)alkyl, di($C_1$-$C_6$)alkylaminocarbonyl($C_1$-$C_6$)alkyl, cyano($C_1$-$C_6$)alkyl, carboxy($C_1$-$C_6$)alkyl, ($C_1$-$C_6$)alkoxycarbonyl($C_1$-$C_6$)alkyl, saturated heterocyclyl, or saturated heterocyclyl($C_1$-$C_6$)alkyl or b) phenyl, naphthyl, heteroaryl, phenyl($C_1$-$C_3$)alkyl, naphthyl($C_1$-$C_3$)alkyl, or heteroaryl($C_1$-$C_3$)alkyl, each optionally substituted by 1 to 3 groups independently selected from:

1) fluorine, chlorine, bromine, iodine, cyano, nitro, amino, hydroxy, carboxy, ($C_1$-$C_6$)alkyl, ($C_3$-$C_6$)cycloalkyl, ($C_4$-$C_7$)cycloalkylalkyl, ($C_2$-$C_6$)alkynyl, ($C_3$-$C_6$)cycloalkyl-($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkylthio, ($C_4$-$C_7$)cycloalkylalkylthio, halo($C_1$-$C_6$)alkylthio, halo($C_3$-$C_6$)cycloalkylthio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkanesulfinyl, halo($C_3$-$C_6$)cycloalkane-sulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkane-sulfonyl, halo($C_4$-$C_7$)-cycloalkylalkanesulfonyl, ($C_1$-$C_6$)alkylamino, di($C_1$-$C_6$)alkylamino, ($C_1$-$C_6$)alkoxy-($C_1$-$C_6$)alkoxy, halo($C_1$-$C_6$)alkoxy($C_1$-$C_6$)alkoxy, ($C_1$-$C_6$)alkoxycarbonyl, aminocarbonyl, ($C_1$-$C_6$)alkylaminocarbonyl and di($C_1$-$C_6$)alkylaminocarbonyl, cyano($C_1$-$C_6$)alkyl, hydroxy($C_1$-$C_6$)alkyl, carboxy($C_1$-$C_6$)alkyl, ($C_1$-$C_6$)alkoxy($C_1$-$C_6$)alkyl, ($C_3$-$C_8$)cycloalkoxy($C_1$-$C_6$)alkyl, ($C_4$-$C_8$)cycloalkylalkoxy($C_1$-$C_6$)alkyl, halo($C_1$-$C_6$)alkoxy($C_1$-$C_6$)alkyl, halo($C_3$-$C_6$)cycloalkoxy($C_1$-$C_6$)alkyl, halo($C_4$-$C_8$)-cycloalkylalkoxy($C_1$-$C_6$)alkyl, ($C_1$-$C_8$)alkylthio($C_1$-$C_6$)alkyl, ($C_3$-$C_8$)cycloalkylthio($C_1$-$C_6$)alkyl, ($C_4$-$C_8$)cycloalkylalkylthio($C_1$-$C_6$)alkyl, halo($C_1$-$C_8$)alkylthio($C_1$-$C_6$)alkyl, halo($C_3$-$C_8$)cycloalkylthio($C_1$-$C_6$)alkyl, halo($C_4$-$C_8$)-cycloalkylalkylthio($C_1$-$C_6$)alkyl, ($C_1$-$C_8$)alkanesulfinyl($C_1$-$C_6$)alkyl, ($C_3$-$C_8$)-cycloalkanesulfinyl($C_1$-$C_6$)alkyl, ($C_4$-$C_8$)cycloalkylalkanesulfinyl($C_1$-$C_6$)alkyl, halo($C_1$-$C_8$)alkanesulfinyl($C_1$-$C_6$)alkyl, halo($C_3$-$C_8$)cycloalkanesulfinyl($C_1$-$C_6$)alkyl, halo($C_4$-$C_8$)cycloalkylalkanesulfinyl($C_1$-$C_6$)alkyl, ($C_1$-$C_8$)alkanesulfonyl($C_1$-$C_6$)alkyl, ($C_3$-$C_8$)cycloalkanesulfonyl($C_1$-$C_6$)alkyl, ($C_4$-$C_8$) cycloalkylalkanesulfonyl($C_1$-$C_6$)alkyl, halo($C_1$-$C_8$)alkanesulfonyl($C_1$-$C_6$)alkyl, halo($C_3$-$C_8$)cycloalkanesulfonyl($C_1$-$C_6$)alkyl, halo($C_4$-$C_8$)cycloalkylalkanesulfonyl($C_1$-$C_6$)alkyl, ($C_1$-$C_8$)alkylamino($C_1$-$C_6$)alkyl, di($C_1$-$C_8$)alkylamino($C_1$-$C_6$)alkyl, ($C_1$-$C_8$)alkoxycarbonyl($C_1$-$C_6$)alkyl, ($C_1$-$C_8$)acyloxy($C_1$-$C_6$)alkyl, aminocarbonyl($C_1$-$C_6$)alkyl, ($C_1$-$C_8$)alkylaminocarbonyl($C_1$-$C_6$)alkyl, di($C_1$-$C_8$)alkylaminocarbonyl($C_1$-$C_6$)alkyl ($C_1$-$C_8$)acylamino($C_1$-$C_6$)alkyl, ($C_1$-$C_8$)alkoxycarbonylamino, ($C_1$-$C_8$)alkoxycarbonylamino($C_1$-$C_6$)alkyl, aminocarboxy($C_1$-$C_6$)alkyl, ($C_1$-$C_8$)alkylamino-carboxy($C_1$-$C_6$)alkyl and di($C_1$-$C_8$)alkylaminocarboxy($C_1$-$C_6$)alkyl;

or 2) phenyl, naphthyl, heteroaryl, bicyclic heteroaryl, phenoxy, naphthyloxy, heteroaryloxy, bicyclic heteroaryloxy, phenylthio, naphthylthio, heteroarylthio, bicyclic heteroarylthio, phenylsulfinyl, naphthylsulfinyl, heteroarylsulfinyl, bicyclic heteroarylsulfinyl, phenylsulfonyl, naphthylsulfonyl, heteroarylsulfonyl, bicyclic heteroarylsulfonyl, phenyl($C_1$-$C_3$)alkyl, naphthyl($C_1$-$C_3$)alkyl, heteroaryl($C_1$-$C_3$)alkyl, and bicyclic heteroaryl($C_1$-$C_3$)alkyl, each optionally substituted with 1 to 3 groups independently selected from fluorine, chlorine, cyano, ($C_1$-$C_3$)alkyl, halo($C_1$-$C_3$)alkyl, ($C_1$-$C_3$)alkoxy, halo($C_1$-$C_3$)alkoxy, ($C_1$-$C_3$)alkanesulfonyl, and ($C_1$-$C_3$)-alkoxycarbonyl; or b) $R^9$ is a saturated divalent radical composed of carbon atoms, and 0, 1 or 2 hetero atoms selected from 0 or 1 nitrogen atoms, 0 or 1 oxygen atoms, and 0 or 1 sulfur atoms that is attached to any core carbon atom on L to form a saturated 3-, 4-, 5-, 6-, or 7-membered L-G ring; said L-G ring being optionally substituted with 1 to 4 groups selected from halogen, fluorine, $(C_1-C_8)$alkyl, halo$(C_1-C_8)$alkyl, $(C_3-C_8)$cycloalkyl, halo$(C_3-C_8)$cycloalkyl, hydroxy$(C_3-C_8)$cycloalkyl, $(C_3-C_8)$cycloalkyl$(C_1-C_3)$alkyl, halo$(C_3-C_8)$cycloalkyl$(C_1-C_3)$alkyl, hydroxylated $(C_3-C_8)$cycloalkyl$(C_1-C_3)$alkyl, $(C_1-C_8)$alkoxy, halo$(C_1-C_8)$alkoxy, $(C_3-C_8)$cycloalkoxy, halo$(C_3-C_8)$cycloalkoxy, hydroxy$(C_3-C_8)$cycloalkoxy, $(C_1-C_8)$alkoxy$(C_1-C_3)$alkyl, halo$(C_1-C_8)$alkoxy$(C_1-C_3)$alkyl, $(C_3-C_8)$cycloalkoxy$(C_1-C_3)$alkyl, halo$(C_3-C_8)$cycloalkoxy$(C_1-C_3)$alkyl, hydroxy$(C_3-C_8)$cycloalkoxy$(C_1-C_3)$alkyl, $(C_1-C_8)$cycloalkyl$(C_1-C_3)$alkoxy$(C_1-C_3)$alkyl, halo$(C_3-C_8)$cycloalkyl$(C_1-C_3)$alkoxy$(C_1-C_3)$alkyl, hydroxylated$(C_3-C_8)$cycloalkyl$(C_1-C_3)$alkoxy$(C_1-C_3)$alkyl, $(C_1-C_8)$alkylthio, halo$(C_1-C_8)$alkylthio, $(C_3-C_8)$cycloalkylthio, halo$(C_3-C_8)$cycloalkylthio, hydroxy$(C_3-C_8)$cycloalkylthio, $(C_3-C_8)$cycloalkyl$(C_1-C_3)$alkylthio, halo$(C_3-C_8)$cycloalkyl$(C_1-C_3)$alkylthio, hydroxylated$(C_3-C_8)$cycloalkyl$(C_1-C_3)$alkylthio, $(C_1-C_8)$alkylthio$(C_1-C_3)$alkyl, halo$(C_1-C_8)$alkylthio$(C_1-C_3)$alkyl, $(C_3-C_8)$cycloalkylthio$(C_1-C_3)$alkyl, halo$(C_3-C_8)$cycloalkylthio$(C_1-C_3)$alkyl, hydroxy$(C_3-C_8)$cycloalkylthio$(C_1-C_3)$alkyl, $(C_3-C_8)$cycloalkyl$(C_1-C_3)$alkylthio$(C_1-C_3)$alkyl, halo$(C_3-C_8)$cycloalkyl$(C_1-C_3)$alkylthio$(C_1-C_3)$alkyl, hydroxylated$(C_3-C_8)$cycloalkyl$(C_1-C_3)$alkylthio$(C_1-C_3)$alkyl and oxo; and $R^{10}$ is $(C_1-C_6)$alkyl or halo$(C_1-C_6)$alkyl.

Another embodiment of the invention is a pharmaceutical composition comprising a pharmaceutically acceptable carrier or diluent and an aspartic protease inhibitor disclosed herein (e.g., a compound represented by Structural Formula (I) or an enantiomer, a diastereomer, or a pharmaceutically acceptable salt thereof). The pharmaceutical composition is used in therapy, e.g., for inhibiting an aspartic protease mediated disorder in a subject.

Another embodiment of the invention is a method of antagonizing one or more aspartic proteases in a subject in need of such treatment. The method comprises administering to the subject an effective amount of an aspartic protease inhibitor disclosed herein (e.g., a compound represented by Structural Formula (I) or an enantiomer, a diastereomer or a pharmaceutically acceptable salt thereof).

Another embodiment of the invention is a method of treating or ameliorating an aspartic protease mediated disorder in a subject. The method comprises administering to the subject an effective amount of an aspartic protease inhibitor disclosed herein (e.g., a compound represented by Structural Formula (I) or an enantiomer, a diastereomer or a pharmaceutically acceptable salt thereof).

Another embodiment of the invention is a method of treating or ameliorating a renin mediated disorder mediated disorder in a subject. The method comprises administering to the subject an effective amount of an aspartic protease inhibitor disclosed herein (e.g., a compound represented by Structural Formula (I) or an enantiomer, a diastereomer or a pharmaceutically acceptable salt thereof).

Another embodiment of the invention is a method of treating hypertension in a subject. The method comprises administering to the subject an effective amount of an aspartic protease inhibitor disclosed herein (e.g., a compound represented by Structural Formula (I) or an enantiomer, a diastereomer or a pharmaceutically acceptable salt thereof).

Another embodiment of the invention is the use of an aspartic protease inhibitor disclosed herein (e.g., a compound represented by Structural Formula (I) or an enantiomer, a diastereomer or a pharmaceutically acceptable salt thereof)) for the manufacture of a medicament for antagonizing one or more aspartic proteases in a subject in need of such treatment.

Another embodiment of the invention is the use of an aspartic protease inhibitor disclosed herein (e.g., a compound represented by Structural Formula (I) or an enantiomer, a diastereomer or a pharmaceutically acceptable salt thereof)) for the manufacture of a medicament for treating or ameliorating an aspartic protease mediated disorder in a subject.

Another embodiment of the invention is the use of an aspartic protease inhibitor disclosed herein (e.g., a compound represented by Structural Formula (I) or an enantiomer, a diastereomer or a pharmaceutically acceptable salt thereof)) for the manufacture of a medicament for treating or ameliorating the renin mediated disorder in a subject.

Another embodiment of the invention is the use of an aspartic protease inhibitor disclosed herein (e.g., a compound represented by Structural Formula (I) or an enantiomer, a diastereomer or a pharmaceutically acceptable salt thereof)) for the manufacture of a medicament for treating hypertension in a subject.

DETAILED DESCRIPTION OF THE INVENTION

The present invention is directed to an aspartic protease inhibitor represented by Structural Formula (I) or an enantiomer, a diastereomer or a pharmaceutically acceptable salt thereof. Values and particular values for the variables in Structural Formula (I) are provided in the following paragraphs. For Structural Formula I:

$R^1$ is a) $(C_3-C_7)$ cycloalkyl; or b) phenyl, naphthyl, heteroaryl, or bicyclic heteroaryl each optionally substituted with 1 to 5 groups independently selected from: 1) fluorine, chlorine, bromine, cyano, nitro, $(C_1-C_6)$alkyl, $(C_3-C_6)$cycloalkyl, $(C_4-C_7)$cycloalkylalkyl, $(C_2-C_6)$alkenyl, $(C_5-C_6)$cycloalkenyl, $(C_5-C_8)$cycloalkylalkenyl, $(C_2-C_6)$alkynyl, $(C_3-C_6)$cycloalkylethynyl, halo$(C_1-C_6)$alkyl, halo$(C_3-C_6)$cycloalkyl, halo$(C_4-C_7)$-cycloalkylalkyl, halo$(C_2-C_6)$alkenyl, halo$(C_3-C_6)$alkynyl, halo$(C_3-C_6)$cyclalkylethynyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_3-C_6)$alkenyloxy, and $(C_1-C_6)$alkanesulfonyl; or 2) phenyl, heteroaryl, phenoxy, heteroaryloxy, phenylthio, heteroarylthio, benzyl, heteroarylmethyl, benzyloxy, and heteroaryloxy, each optionally substituted with 1 to 3 groups independently selected from: fluorine, chlorine, cyano, $(C_1-C_3)$alkyl, halo$(C_1-C_3)$alkyl, $(C_1-C_3)$-alkoxy, halo$(C_1-C_3)$alkoxy, and aminocarbonyl.

In a particular embodiment, $R^1$ is phenyl, 2-thienyl, 3-thienyl, 2-pyridyl, 2-imidazolyl, 2-thiazolyl, 2-benzothienyl, 4-benzofuryl, 4-benzothienyl, 7-benzofuryl, 2,3-dihydro-7-benzofuryl, 7-benzothienyl, 1,3-benzodioxol-4-yl, 7-indazolyl, or 8-quinolinyl each optionally substituted with 1 to 5 substituents independently selected from: fluorine, chlorine, bromine, cyano, methyl, ethyl, isopropyl, t-butyl, isobutyl, trifluoromethyl, allyl, cyclohexyl, cyclohexen-1-yl, cyclopropylethynyl, methoxy, trifluoromethoxy, neopentyloxy, methylthio, allyloxy, cyclopropylmethoxy, 2-(cyclopropyl) ethoxy, cyclopentyloxy, cyclopentylmethoxy, benzyloxy, hydroxyl, aminocarbonyl, methoxycarbonyl, phenyl, phenoxy, benzyloxy, and heteroaryloxy, wherein the phenyl phenoxy, benzyloxy and heteroaryloxy groups are optionally substituted with 1 to 3 substituents independently selected from fluorine, chlorine, cyano, methyl, trifluoromethyl, and aminocarbonyl.

In another particular embodiment, $R^1$ is phenyl, optionally substituted with 1 to 5 substituents independently selected from: fluorine, chlorine, bromine, cyano, methyl, ethyl, isopropyl, t-butyl, isobutyl, trifluoromethyl, allyl, cyclohexyl, cyclohexen-1-yl, cyclopropylethynyl, methoxy, trifluoromethoxy, neopentyloxy, methylthio, allyloxy, cyclopropylmethoxy, 2-(cyclopropyl)ethoxy, cyclopentyloxy, cyclopentylmethoxy, benzyloxy, hydroxyl, aminocarbonyl, methoxycarbonyl, phenyl, phenoxy, benzyloxy, and heteroaryloxy, wherein the phenyl phenoxy, benzyloxy and heteroaryloxy groups are optionally substituted with 1 to 3 substituents independently selected from fluorine, chlorine, cyano, methyl, trifluoromethyl, and aminocarbonyl.

In another particular embodiment, $R_1$ is phenyl optionally substituted with 1 to 5 substituents independently selected from the group consisting of fluorine, chlorine and methyl.

$R^2$ is $(C_1-C_8)$alkyl, $(C_3-C_7)$cycloalkylalkyl, fluoro$(C_1-C_8)$alkyl, fluoro$(C_3-C_7)$-cycloalkylalkyl, $(C_1-C_8)$alkoxy, $(C_3-C_7)$cycloalkylalkoxy, fluoro$(C_1-C_8)$alkoxy, hydroxy$(C_1-C_8)$alkyl, $(C_1-C_5)$alkoxy$(C_1-C_5)$alkyl, halo$(C_1-C_5)$alkylamino$(C_1-C_5)$allyl, $(C_1-C_5)$alkoxy$(C_1-C_5)$hydroxyalkyl, $(C_3-C_4)$cycloalkoxy$(C_1-C_5)$alkyl, fluoro$(C_1-C_5)$alkoxy$(C_1-C_5)$alkyl, fluoro$(C_3-C_4)$cycloalkoxy$(C_1-C_5)$alkyl, $(C_1-C_5)$alkylthio$(C_1-C_5)$alkyl, $(C_1-C_5)$alkoxy$(C_1-C_5)$alkoxy, hydroxy$(C_1-C_8)$alkoxy, $(C_3-C_4)$cycloalkoxy$(C_1-C_5)$alkoxy, fluoro$(C_1-C_5)$alkoxy$(C_1-C_5)$alkoxy, fluoro$(C_3-C_4)$cycloalkoxy$(C_1-C_5)$alkoxy, $(C_1-C_3)$alkoxy$(C_1-C_3)$alkoxy$(C_1-C_3)$alkyl, fluoro$(C_1-C_3)$-alkoxy$(C_1-C_3)$alkoxy$(C_1-C_3)$alkyl, aminocarbonylamino$(C_1-C_8)$alkyl, aminocarbonylamino$(C_1-C_8)$alkoxy, $(C_1-C_5)$alkanoylamino$(C_1-C_5)$alkyl, $(C_1-C_5)$alkanoylamino$(C_1-C_5)$alkoxy, fluoro$(C_1-C_5)$alkanoylamino$(C_1-C_5)$alkyl, fluoro$(C_1-C_5)$alkanoylamino$(C_1-C_5)$alkoxy, $(C_1-C_3)$alkoxy$(C_1-C_5)$alkanoylamino$(C_1-C_5)$alkyl, $(C_1-C_3)$alkoxy$(C_1-C_5)$alkanoylamino$(C_1-C_5)$alkoxy, $(C_3-C_4)$-cycloalkanecarbonylamino$(C_1-C_5)$alkyl, $(C_3-C_4)$cycloalkanecarbonylamino$(C_1-C_5)$alkoxy, aminosulfonylamino$(C_1-C_8)$alkyl, aminosulfonylamino$(C_1-C_8)$alkoxy, $(C_1-C_5)$alkanesulfonyl-amino$(C_1-C_5)$alkyl, $(C_1-C_5)$alkanesulfonylamino$(C_1-C_5)$alkoxy, formylamino$(C_1-C_5)$alkyl, formylamino$(C_1-C_5)$alkoxy, $(C_1-C_5)$alkoxycarbonylamino$(C_1-C_5)$alkyl, $(C_1-C_5)$alkoxycarbonylamino$(C_1-C_5)$alkoxy, $(C_1-C_5)$alkylaminocarbonylamino$(C_1-C_5)$alkyl, $(C_1-C_5)$alkylaminocarbonyl-amino$(C_1-C_5)$alkyl, di$(C_1-C_5)$alkylaminocarbonylamino$(C_1-C_5)$alkoxy, aminocarbonyl$(C_1-C_5)$alkyl, aminocarbonyl$(C_1-C_5)$alkoxy, $(C_1-C_5)$alkylaminocarbonyl$(C_1-C_5)$alkyl, $(C_1-C_5)$-alkylaminocarbonyl-$(C_1-C_5)$alkoxy, aminocarboxy$(C_1-C_5)$alkyl, aminocarboxy$(C_1-C_5)$alkoxy, $(C_1-C_5)$alkylamino-carboxy$(C_1-C_5)$alkyl, $(C_1-C_5)$alkylaminocarboxy$(C_1-C_5)$alkoxy, $(C_1-C_8)$-alkoxycarbonylamino, $(C_1-C_8)$alkylaminocarbonylamino, $(C_1-C_8)$alkanoylamino, fluoro$(C_1-C_8)$alkoxycarbonylamino, fluoro$(C_1-C_8)$alkylaminocarbonylamino, or fluoro$(C_1-C_8)$-alkanoylamino, or $(C_1-C_8)$oxoalkyl.

In a particular embodiment, $R^2$ is $(C_1-C_8)$alkyl, $(C_4-C_8)$cycloalkylalkyl, fluoro$(C_1-C_8)$alkyl, fluoro$(C_4-C_8)$-cycloalkylalkyl, hydroxy$(C_1-C_8)$alkyl, $(C_1-C_5)$alkoxy$(C_1-C_5)$alkyl, halo$(C_1-C_5)$alkylamino$(C_1-C_5)$alkyl, $(C_1-C_5)$alkoxy$(C_1-C_5)$hydroxyalkyl, $(C_3-C_4)$cycloalkoxy$(C_1-C_5)$alkyl, fluoro$(C_1-C_5)$alkoxy$(C_1-C_5)$alkyl, fluoro$(C_3-C_4)$cycloalkoxy$(C_1-C_5)$alkyl, $(C_1-C_5)$alkylthio$(C_1-C_5)$alkyl, $(C_1-C_5)$alkoxy$(C_1-C_5)$alkoxy, $(C_3-C_4)$cycloalkoxy$(C_1-C_5)$alkoxy, fluoro$(C_1-C_5)$alkoxy$(C_1-C_5)$alkoxy, fluoro$(C_3-C_4)$cycloalkoxy$(C_1-C_5)$alkoxy, $(C_1-C_3)$alkoxy$(C_1-C_3)$alkoxy$(C_1-C_3)$alkyl, fluoro$(C_1-C_3)$-alkoxy$(C_1-C_3)$alkoxy$(C_1-C_3)$alkyl, aminocarbonylamino$(C_1-C_8)$alkyl, $(C_1-C_5)$alkanoylamino$(C_1-C_5)$alkyl, fluoro$(C_1-C_5)$alkanoylamino$(C_1-C_5)$alkyl, $(C_1-C_3)$alkoxy$(C_1-C_5)$alkanoylamino$(C_1-C_5)$alkyl, $(C_3-C_4)$-cycloalkanecarbonylamino$(C_1-C_5)$alkyl, aminosulfonylamino$(C_1-C_8)$alkyl, $(C_1-C_5)$alkanesulfonylamino$(C_1-C_5)$alkyl, formylamino$(C_1-C_5)$alkyl, $(C_1-C_5)$ alkoxycarbonylamino$(C_1-C_5)$alkyl, $(C_1-C_5)$alkoxycarbonylamino$(C_1-C_5)$alkoxy, $(C_1-C_5)$alkylaminocarbonylamino$(C_1-C_5)$alkyl, $(C_1-C_5)$alkylaminocarbonylamino$(C_1-C_5)$alkyl, aminocarbonyl$(C_1-C_5)$alkyl, $(C_1-C_5)$alkylaminocarbonyl$(C_1-C_5)$alkyl, aminocarboxy$(C_1-C_5)$alkyl, aminocarboxy$(C_1-C_5)$alkoxy, $(C_1-C_5)$alkylamino-carboxy$(C_1-C_5)$alkyl, $(C_1-C_5)$alkylaminocarboxy$(C_1-C_5)$alkoxy, or $(C_1-C_8)$oxoalkyl, provided when T is N or when T is $CR^3$ and $R^3$ is OH or halogen, $R^2$ is not $(C_1-C_5)$alkoxy$(C_1-C_5)$alkoxy, $(C_3-C_4)$cycloalkoxy$(C_1-C_5)$alkoxy, fluoro$(C_1-C_5)$alkoxy$(C_1-C_5)$alkoxy, fluoro$(C_3-C_4)$cycloalkoxy$(C_1-C_5)$alkoxy$(C_1-C_5)$ alkoxycarbonyl-amino$(C_1-C_5)$alkoxy, aminocarboxy$(C_1-C_5)$alkoxy, or $(C_1-C_5)$alkylaminocarboxy$(C_1-C_5)$alkoxy.

In another particular embodiment, $R^2$ is $(C_1-C_5)$alkoxy $(C_1-C_5)$alkyl, $(C_1-C_5)$alkoxy$(C_1-C_5)$alkoxy, $(C_1-C_5)$alkoxycarbonylamino$(C_1-C_5)$alkyl, or $(C_1-C_5)$alkoxycarbonylamino$(C_1-C_5)$alkoxy.

In another particular embodiment, $R^2$ is methyl, ethyl, propyl, butyl, hexyl, 5-pentenyl, 3,3,3-trifluoropropyl, 4,4-difluoropentyl, 3-(cyclopropyl)propyl, 4-(cyclopropyl)butyl, 3-hydroxypropyl, 4-hydroxybutyl, 4-hydroxypentyl, 4-hydroxyhexyl, 5-hydroxyhexyl, 2-hydroxyethoxy, 5-oxohexyl, 3-ethoxypropyl, 4-methoxybutyl, 4-ethoxybutyl, 2-(ethoxy)ethoxy, 3-methoxypropoxy, 3-ethoxypropoxy, 3-propoxypropoxy, (2-(methoxy)ethoxy)methyl, 3-(2,2,2-trifluoroethylamino)propyl, 3-(formylamino)propyl, 3-(acetylamino)propyl, 3-(propionyl-amino)propyl, 3-(butanoylamino)propyl, 3-((2-methoxypropionyl)amino)propyl, 3-(cyclopropane-carbonylamino)propyl, 3-(trifluoroacetylamino)propyl, 3-(methoxycarbonylamino)propyl, 3-(ethoxycarbonylamino)propyl, 2-(methoxycarbonylamino)ethoxy, 2-(ethoxycarbonylamino)-ethoxy, 3-(methylaminocarbonylamino)propyl, 3-(dimethylaminocarbonylamino)propyl, 3-(aminocarbonyl)propyl, 3-(methylaminocarbonyl)propyl, 3-(ethylamino-carbonyl)propyl, methoxymethylcarbonylaminomethyl, or 3-(aminosulfonylamino)propyl, 2-(methoxy)-ethoxy, or 4-(methoxy)butoxy.

In another particular embodiment, $R^2$ is butoxy, hexyloxy, 2-cyclopropylethoxy, 2-(acetylamino)ethoxy, 2-(propionylamino)ethoxy, aminocarbonylmethoxy, methylamino-carbonylmethoxy, ethylaminocarbonylmethoxy, propylaminocarbonylmethoxy, 2-(methylaminocarbonyl)ethoxy, 2-(ethylaminocarbonyl)ethoxy, 2-(propylaminocarbonyl)ethoxy, or (2-(methoxy)ethoxy)carbonylamino.

In another particular embodiment, $R^2$ is 3-methoxypropoxy, 4-methoxybutyl, 2-(methoxycarbonylamino)ethoxy or 3-(methoxycarbonylamino)propyl.

$R^3$ is H, halogen, OH, $(C_1-C_4)$alkanoylamino, or $(C_1-C_3)$ alkoxy;

provided that when T is N or when T is $CR^3$ and $R^3$ is OH or halogen, $R^2$ is not an optionally substituted alkoxy, alkylthio or amino group as follows: $(C_1-C_8)$alkoxy, $(C_4-C_8)$cycloalkylalkoxy, fluoro$(C_1-C_8)$alkoxy, $(C_1-C_5)$alkoxy$(C_1-C_5)$alkoxy, hydroxy$(C_1-C_8)$alkoxy, $(C_3-C_4)$cycloalkoxy$(C_1-C_5)$alkoxy, fluoro$(C_1-C_5)$alkoxy$(C_1-C_5)$alkoxy, fluoro$(C_3-C_4)$cycloalkoxy$(C_1-C_5)$alkoxy, aminocarbonyl-amino$(C_1-C_8)$alkoxy, $(C_1-C_5)$alkanoylamino$(C_1-C_5)$alkoxy, fluoro$(C_1-C_5)$alkanoyl-amino$(C_1-C_5)$alkoxy, $(C_1-C_3)$alkoxy$(C_1-C_5)$alkanoylamino$(C_1-C_5)$alkoxy, $(C_3-C_4)$-cycloalkanecarbonylamino$(C_1-C_5)$alkoxy, aminosulfonylamino$(C_1-C_8)$alkoxy, $(C_1-C_5)$alkanesulfonylamino$(C_1-C_5)$alkoxy, formylamino$(C_1-C_5)$alkoxy, $(C_1-C_5)$alkoxycarbonylamino$(C_1-C_5)$alkoxy, di$(C_1-C_5)$alkylaminocarbonylamino($C_1$-$C_5$)alkoxy, aminocarbonyl($C_1$-$C_5$) alkoxy, ($C_1$-$C_5$)alkylaminocarbonyl($C_1$-$C_5$)alkoxy, aminocarboxy($C_1$-$C_5$)alkoxy, ($C_1$-$C_5$)alkylaminocarboxy ($C_1$-$C_5$)alkoxy, ($C_1$-$C_8$)alkoxycarbonylamino, ($C_1$-$C_8$)alkylaminocarbonylamino, ($C_1$-$C_8$)alkanoylamino, fluoro($C_1$-$C_8$)alkoxycarbonylamino, fluoro($C_1$-$C_8$)alkylaminocarbonylamino, or fluoro($C_1$-$C_8$)alkanoylamino.

In a particular embodiment, $R^3$ is H, F, OH, methoxy, acetylamino, propionylamino, (2-methylpropionyl)amino, or butanoylamino.

In another particular embodiment, $R^3$ is a divalent radical selected from —($CH_2$)$_2$—, —($CH_2$)$_3$—, —$OCH_2$—, —$OCH_2CH_2$—, —OC(=O)—, —NHC(=O)—, —OC(=O)NH—, —NHC(=O)NH—, —NHC(=O)$CH_2$—, optionally substituted with up to 2 groups independently selected from ($C_1$-$C_3$)alkyl or halo($C_1$-$C_3$)alkyl, which is bonded to $R^1$.

In another particular embodiment, $R^3$ is —OC(=O)— or —NHC(=O)—, in which the carbonyl carbon is bonded to $R^1$.

$R^4$ is H or ($C_1$-$C_6$)alkyl. In a particular embodiment, $R^4$ is H, methyl, ethyl, propyl or isopropyl. In another particular embodiment, $R^4$ is H or methyl. In another particular embodiment, $R^4$ is H.

$R^7$ is hydrogen, ($C_1$-$C_6$)alkyl, halo($C_1$-$C_6$)alkyl or ($C_1$-$C_3$)alkoxy($C_1$-$C_3$)alkyl. In a particular embodiment, $R^7$ is H or a ($C_1$-$C_6$)alkyl. In a particular embodiment, $R^7$ is methyl, ethyl, propyl or isopropyl.

$R^a$, $R^b$, $R^{a'}$ and $R^{b'}$, for each occurrence, are independently hydrogen, ($C_1$-$C_6$)alkyl, halo($C_1$-$C_6$)alkyl or $R^a$ and $R^b$ attached to a carbon atom taken together is an oxo or $R^{a'}$ and $R^{b'}$ taken together is an oxo. In a particular embodiment, $R^a$ and $R^b$, for each occurrence, are independently hydrogen, methyl or $R^a$ and $R^b$ attached to a carbon atom taken together is an oxo or $R^{a'}$ and $R^{b'}$ taken together is an oxo. In another particular embodiment, when Q is —C(O)— or C(S)—, G is $NR^9R^{10}$, n1 and n2 are both 1, m is 0, Z is —$NR^7$—, and $R^a$ and $R^b$ attached to a carbon atom taken together are an oxo, then $R^{a'}$ and $R^{b'}$ are both —H.

$R^5$ and $R^6$, for each occurrence, are independently a) hydrogen; or b) ($C_1$-$C_{10}$)alkyl, ($C_3$-$C_7$)cycloalkyl($C_1$-$C_2$) alkyl, ($C_4$-$C_{10}$)bicycloalkyl($C_1$-$C_2$)alkyl, ($C_8$-$C_{12}$)tricycloalkyl($C_1$-$C_2$)alkyl, ($C_1$-$C_6$)alkoxy($C_1$-$C_6$)alkyl, ($C_3$-$C_7$)cycloalkoxy($C_1$-$C_3$)alkyl, ($C_1$-$C_5$)alkylthio($C_1$-$C_5$)alkyl, or monocyclic or bicyclic saturated heterocyclyl($C_1$-$C_3$)alkyl wherein each of these groups are optionally substituted by 1 to 3 groups independently selected from halogen, cyano, hydroxyl, ($C_1$-$C_2$)alkyl, ($C_1$-$C_2$)alkoxy, ($C_3$-$C_6$)cycloalkyl, ($C_3$-$C_6$)cycloalkoxy, halo($C_1$-$C_2$)alkyl, halo($C_1$-$C_2$)alkoxy, halo($C_3$-$C_6$)cycloalkyl, and halo($C_3$-$C_6$)cycloalkoxy; or c) phenyl($C_1$-$C_2$)alkyl or heteroaryl($C_1$-$C_2$)alkyl each optionally substituted with 1 to 3 groups independently selected from fluorine, chlorine, cyano, ($C_1$-$C_3$)alkyl, halo($C_1$-$C_3$) alkyl, ($C_1$-$C_3$)alkoxy, and halo($C_1$-$C_3$)alkoxy.

In a particular embodiment, only one of $R^5$ or $R^6$ is hydrogen, and the other is b) ($C_1$-$C_{10}$)alkyl, ($C_3$-$C_7$)cycloalkyl($C_1$-$C_2$)alkyl, ($C_4$-$C_{10}$)bicycloalkyl($C_1$-$C_2$)alkyl, ($C_8$-$C_{12}$)tricycloalkyl($C_1$-$C_2$)alkyl, ($C_1$-$C_6$)alkoxy($C_1$-$C_6$)alkyl, ($C_3$-$C_7$)cycloalkoxy($C_1$-$C_3$)alkyl, ($C_1$-$C_5$)alkylthio($C_1$-$C_5$)alkyl, or monocyclic or bicyclic saturated heterocyclyl($C_1$-$C_3$)alkyl wherein each of these groups are optionally substituted by 1 to 3 groups independently selected from halogen, cyano, hydroxyl, ($C_1$-$C_2$)alkyl, ($C_1$-$C_2$)alkoxy, ($C_3$-$C_6$)cycloalkyl, ($C_3$-$C_6$)cycloalkoxy, halo($C_1$-$C_2$)alkyl, halo($C_1$-$C_2$)alkoxy, halo($C_3$-$C_6$)cycloalkyl, and halo($C_3$-$C_6$)cycloalkoxy; or c) phenyl($C_1$-$C_2$)alkyl or heteroaryl($C_1$-$C_2$)alkyl each optionally substituted with 1 to 3 groups independently selected from fluorine, chlorine, cyano, ($C_1$-$C_3$)alkyl, halo($C_1$-$C_3$) alkyl, ($C_1$-$C_3$)alkoxy, or halo($C_1$-$C_3$)alkoxy.

In another particular embodiment, $R^5$ is hydrogen, methyl, isobutyl, t-butylmethyl, 2,2,2-trifluoroethyl, 2-(trifluoromethyl)propyl, cyclopentylmethyl, cyclohexylmethyl, (3,3-difluorocyclobutyl)methyl, 3,4-difluorocyclopentyl)methyl, 4,4-difluoro-cyclohexylmethyl, (4-methylcyclohexyl)methyl, tert-butoxymethyl, (4-tetrahydropyranyl)methyl, benzyl, (1-fluorocyclohexyl)methyl, (4-fluorocyclohexyl)methyl, 1-hydroxy-2-methylpropyl, (cyclopentyl)(hydroxy)methyl, (cyclohexyl)(hydroxy)methyl, (cycloheptyl)(hydroxy)methyl, (1-hydroxycyclohexyl)methyl, (4-hydroxycyclohexyl)methyl, (4-hydroxy-4-methylcyclohexyl)methyl, 1-adamantylmethyl, (3-noradamantyl)(hydroxy)methyl, 2-methoxy-2-methylpropyl, 2,2-dimethyl-3-methoxypropyl, (3-tetrahydrofuryl)methyl, (3-tetrahydropyranyl)methyl, (4-tetrahydropyranyl)methyl and $R^6$ is hydrogen; or $R^5$ is hydrogen and $R^6$ is methyl, isobutyl, t-butylmethyl, 2,2,2-trifluoroethyl, 2-(trifluoromethyl)propyl, cyclopentylmethyl, cyclohexylmethyl, (3,3-difluorocyclobutyl)methyl, 3,4-difluorocyclopentyl)methyl, 4,4-difluoro-cyclohexylmethyl, (4-methylcyclohexyl)methyl, tert-butoxymethyl, (4-tetrahydropyranyl)methyl, benzyl, (1-fluorocyclohexyl) methyl, (4-fluorocyclohexyl)methyl, 1-hydroxy-2-methylpropyl, (cyclopentyl)(hydroxy)methyl, (cyclohexyl)(hydroxy)methyl, (cycloheptyl)(hydroxy)methyl, (1-hydroxycyclohexyl)methyl, (4-hydroxycyclohexyl)methyl, (4-hydroxy-4-methylcyclohexyl)methyl, 1-adamantylmethyl, (3-noradamantyl)(hydroxy)methyl, 2-methoxy-2-methylpropyl, 2,2-dimethyl-3-methoxypropyl, (3-tetrahydrofuryl)methyl, (3-tetrahydropyranyl)methyl, (4-tetrahydropyranyl)methyl.

In another particular embodiment, $R^5$ is cyclohexylmethyl, 1-adamantylmethyl, (3-tetrahydropyranyl)methyl, (4-tetrahydropyranyl)methyl, (3-oxepanyl)methyl or 6-(4-oxaspiro[2,5]octyl)methyl and $R^6$ is H; or $R^5$ is H and $R^6$ is (3-tetrahydropyranyl)methyl or (3-oxepanyl)methyl.

$R^9$ is a) hydrogen; b) ($C_1$-$C_6$)alkyl, halo($C_1$-$C_6$)alkyl, ($C_4$-$C_{10}$)cycloalkylalkyl, ($C_1$-$C_5$)alkoxy($C_1$-$C_5$)alkyl, aminocarbonyl($C_1$-$C_5$)alkyl, ($C_1$-$C_6$)alkylaminocarbonyl($C_1$-$C_6$) alkyl, or di($C_1$-$C_6$)alkyl-aminocarbonyl($C_1$-$C_6$)alkyl; or c) phenyl($C_1$-$C_2$)alkyl optionally substituted with 1 to 3 groups independently selected from fluorine, chlorine, cyano, ($C_1$-$C_3$)alkyl, halo($C_1$-$C_3$)alkyl, ($C_1$-$C_3$)alkoxy, and halo($C_1$-$C_3$) alkoxy. In a particular embodiment, $R^9$ is H or ($C_1$-$C_6$)alkyl. In another particular embodiment, $R^9$ is H, methyl or ethyl.

Q is Q1, Q2, Q4, Q5, Q6, Q7, Q9 or Q10. In a particular embodiment, Q is Q1 or Q2. In another particular embodiment, Q is Q1.

In a 1$^{st}$ specific embodiment, the aspartic protease inhibitor of the invention is represented by the Structural Formula (Ia), (Ib), (Ic), (Id), (Ie), (If), (Ig), (Ih), (Ii), (Ij) or (Ik) or an enantiomer, a diastereomer or a pharmaceutically acceptable salt thereof:

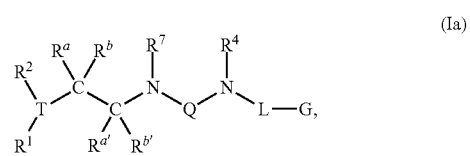

(Ia)

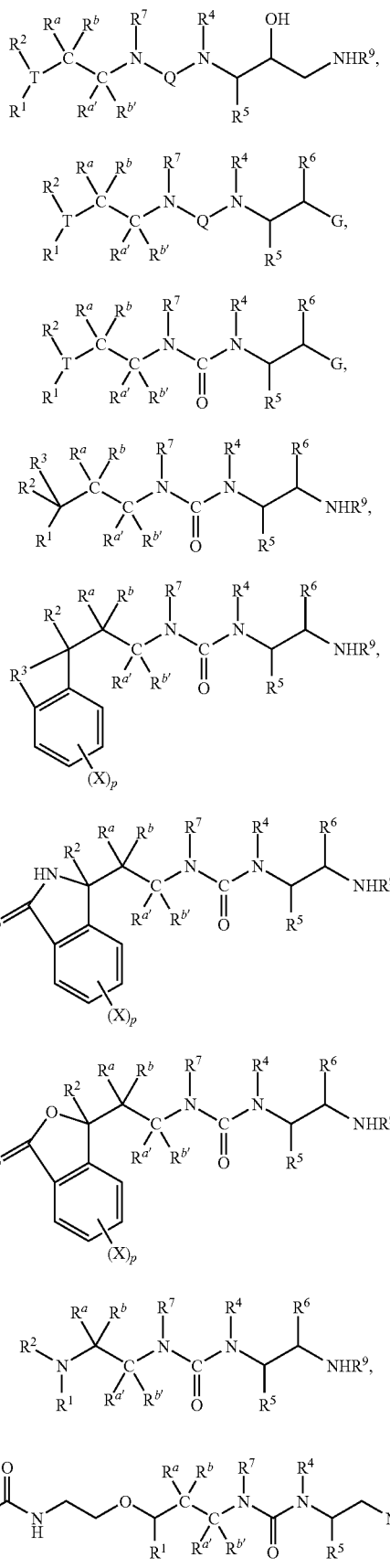

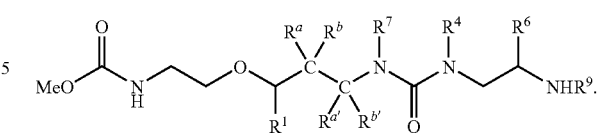

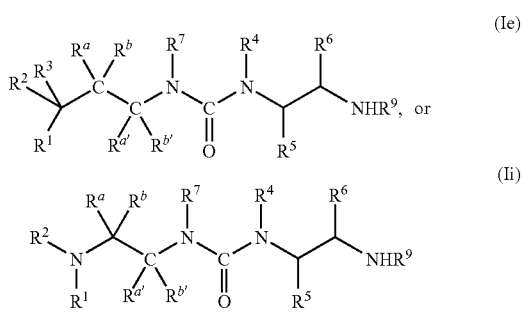

Value and particular values of the variables in Structural Formulas (Ia), (Ib), (Ic), (Id), (Ie), (If), (Ig), (Ih), (Ii), (Ij) and (Ik) are as described for Structural Formula (I).

In a 2$^{nd}$ specific embodiment, the aspartic protease inhibitor of the invention is represented by the Structural Formula or an enantiomer, a diastereomer or a pharmaceutically acceptable salt thereof, wherein:

$R^1$ is a) ($C_3$-$C_7$) cycloalkyl; or b) phenyl, naphthyl, heteroaryl, or bicyclic heteroaryl each optionally substituted with 1 to 5 groups independently selected from: 1) fluorine, chlorine, bromine, cyano, nitro, ($C_1$-$C_6$)alkyl, ($C_3$-$C_6$)cycloalkyl, ($C_4$-$C_7$)cycloalkylalkyl, ($C_2$-$C_6$)alkenyl, ($C_5$-$C_6$)cycloalkenyl, ($C_5$-$C_8$)cycloalkylalkenyl, ($C_2$-$C_6$)alkynyl, ($C_3$-$C_6$)cycloalkylethynyl, halo($C_1$-$C_6$)alkyl, halo($C_3$-$C_6$)cycloalkyl, halo($C_4$-$C_7$)-cycloalkylalkyl, halo($C_2$-$C_6$)alkenyl, halo($C_3$-$C_6$)alkynyl, halo($C_3$-$C_6$)cyclalkylethynyl, ($C_1$-$C_6$) alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_3$-$C_6$)alkenyloxy, and ($C_1$-$C_6$) alkanesulfonyl; or 2) phenyl, heteroaryl, phenoxy, heteroaryloxy, phenylthio, heteroarylthio, benzyl, heteroarylmethyl, benzyloxy, and heteroaryloxy, each optionally substituted with 1 to 3 groups independently selected from: fluorine, chlorine, cyano, ($C_1$-$C_3$)alkyl, halo($C_1$-$C_3$)alkyl, ($C_1$-$C_3$)-alkoxy, halo($C_1$-$C_3$) alkoxy, and aminocarbonyl;

$R^2$ for Structural Formula (Ie) is ($C_1$-$C_8$)alkyl, ($C_3$-$C_7$) cycloalkylalkyl, fluoro($C_1$-$C_8$)alkyl, fluoro($C_3$-$C_7$)-cycloalkylalkyl, ($C_1$-$C_8$)alkoxy, ($C_3$-$C_7$)cycloalkylalkoxy, fluoro($C_1$-$C_8$)alkoxy, hydroxy($C_1$-$C_8$)alkyl, ($C_1$-$C_5$)alkoxy ($C_1$-$C_5$)alkyl, halo($C_1$-$C_5$)alkylamino($C_1$-$C_5$)alkyl, ($C_1$-$C_5$) alkoxy($C_1$-$C_5$)hydroxyalkyl, ($C_3$-$C_4$)cycloalkoxy($C_1$-$C_5$) alkyl, fluoro($C_1$-$C_5$)alkoxy($C_1$-$C_5$)alkyl, fluoro($C_3$-$C_4$) cycloalkoxy($C_1$-$C_5$)alkyl, ($C_1$-$C_5$)alkylthio($C_1$-$C_5$)alkyl, ($C_1$-$C_5$)alkoxy($C_1$-$C_5$)alkoxy, hydroxy($C_1$-$C_8$)alkoxy, ($C_3$-$C_4$)cycloalkoxy($C_1$-$C_5$)alkoxy, fluoro($C_1$-$C_5$)alkoxy($C_1$-$C_5$) alkoxy, fluoro($C_3$-$C_4$)cycloalkoxy($C_1$-$C_5$)alkoxy, ($C_1$-$C_3$) alkoxy($C_1$-$C_3$)alkoxy($C_1$-$C_3$)alkyl, fluoro($C_1$-$C_3$)-alkoxy ($C_1$-$C_3$)alkoxy($C_1$-$C_3$)alkyl, aminocarbonylamino($C_1$-$C_8$) alkyl, aminocarbonylamino($C_1$-$C_8$)alkoxy, ($C_1$-$C_5$) alkanoylamino($C_1$-$C_5$)alkyl, ($C_1$-$C_5$)alkanoylamino($C_1$-$C_5$) alkoxy, fluoro($C_1$-$C_5$)alkanoylamino($C_1$-$C_5$)alkyl, fluoro ($C_1$-$C_5$)alkanoylamino($C_1$-$C_5$)alkoxy, ($C_1$-$C_3$)alkoxy($C_1$-

C$_5$)alkanoylamino(C$_1$-C$_5$)alkyl, (C$_1$-C$_3$)alkoxy(C$_1$-C$_5$)alkanoylamino(C$_1$-C$_5$)alkoxy, (C$_3$-C$_4$)-cycloalkanecarbonylamino(C$_1$-C$_5$)alkyl, (C$_3$-C$_4$)cycloalkanecarbonylamino(C$_1$-C$_5$)alkoxy, aminosulfonylamino(C$_1$-C$_8$)alkyl, aminosulfonylamino(C$_1$-C$_8$)alkoxy, (C$_1$-C$_5$)alkanesulfonylamino(C$_1$-C$_5$)alkyl, (C$_1$-C$_5$)alkanesulfonylamino(C$_1$-C$_5$)alkoxy, formylamino(C$_1$-C$_5$)alkyl, formylamino(C$_1$-C$_5$)alkoxy, (C$_1$-C$_5$)alkoxycarbonylamino(C$_1$-C$_5$)alkyl, (C$_1$-C$_5$)alkoxycarbonyl-amino(C$_1$-C$_5$)alkoxy, (C$_1$-C$_5$)alkylaminocarbonylamino(C$_1$-C$_5$)alkyl, (C$_1$-C$_5$)alkylaminocarbonyl-amino(C$_1$-C$_5$)alkyl, di(C$_1$-C$_5$)alkylaminocarbonylamino(C$_1$-C$_5$)alkoxy, aminocarbonyl(C$_1$-C$_5$)alkyl, aminocarbonyl(C$_1$-C$_5$)alkoxy, (C$_1$-C$_5$)alkylaminocarbonyl(C$_1$-C$_5$)alkyl, (C$_1$-C$_5$)-alkylaminocarbonyl-(C$_1$-C$_5$)alkoxy, aminocarboxy(C$_1$-C$_5$)alkyl, aminocarboxy(C$_1$-C$_5$)alkoxy, (C$_1$-C$_5$)alkylaminocarboxy(C$_1$-C$_5$)alkyl, (C$_1$-C$_5$)alkylaminocarboxy(C$_1$-C$_5$)alkoxy, (C$_1$-C$_8$)-alkoxycarbonylamino, (C$_1$-C$_8$)alkylaminocarbonylamino, (C$_1$-C$_8$)alkanoylamino, fluoro(C$_1$-C$_8$)alkoxycarbonylamino, fluoro(C$_1$-C$_8$)alkylaminocarbonylamino, or fluoro(C$_1$-C$_8$)-alkanoylamino, or (C$_1$-C$_8$)oxoalkyl;

R$^2$ for Structural Formula (Ii) is R$^2$ is (C$_1$-C$_8$)alkyl, (C$_3$-C$_7$)cycloalkylalkyl, fluoro(C$_1$-C$_8$)alkyl, fluoro(C$_3$-C$_7$)-cycloalkylalkyl, hydroxy(C$_1$-C$_8$)alkyl, (C$_1$-C$_5$)alkoxy(C$_1$-C$_5$)alkyl, halo(C$_1$-C$_5$)alkylamino(C$_1$-C$_5$)alkyl, (C$_1$-C$_5$)alkoxy(C$_1$-C$_5$)hydroxyalkyl, (C$_3$-C$_4$)cycloalkoxy(C$_1$-C$_5$)alkyl, fluoro(C$_1$-C$_5$)alkoxy(C$_1$-C$_5$)alkyl, fluoro(C$_3$-C$_4$)cycloalkoxy(C$_1$-C$_5$)alkyl, (C$_1$-C$_5$)alkylthio(C$_1$-C$_5$)alkyl, (C$_1$-C$_3$)alkoxy(C$_1$-C$_3$)alkoxy(C$_1$-C$_3$)alkyl, fluoro(C$_1$-C$_3$)-alkoxy(C$_1$-C$_3$)alkoxy(C$_1$-C$_3$)alkyl, aminocarbonylamino(C$_1$-C$_8$)alkyl, (C$_1$-C$_5$)alkanoylamino(C$_1$-C$_5$)alkyl, (C$_1$-C$_5$)alkanoylamino(C$_1$-C$_5$)alkoxy, fluoro(C$_1$-C$_5$)alkanoylamino(C$_1$-C$_5$)alkyl, (C$_1$-C$_3$)alkoxy(C$_1$-C$_5$)alkanoylamino(C$_1$-C$_5$)alkyl, (C$_3$-C$_4$)-cycloalkanecarbonylamino(C$_1$-C$_5$)alkyl, aminosulfonylamino(C$_1$-C$_8$)alkyl, (C$_1$-C$_5$)alkanesulfonylamino(C$_1$-C$_5$)alkyl, formylamino(C$_1$-C$_5$)alkyl, (C$_1$-C$_5$)alkoxycarbonylamino(C$_1$-C$_5$)alkyl, (C$_1$-C$_5$)alkylaminocarbonylamino(C$_1$-C$_5$)alkyl, (C$_1$-C$_5$)alkylaminocarbonylamino(C$_1$-C$_5$)alkyl, aminocarbonyl(C$_1$-C$_5$)alkyl, aminocarbonyl(C$_1$-C$_5$)alkoxy, (C$_1$-C$_5$)alkylaminocarbonyl(C$_1$-C$_5$)alkyl, aminocarboxy(C$_1$-C$_5$)alkyl, (C$_1$-C$_5$)alkylamino-carboxy(C$_1$-C$_5$)alkyl or (C$_1$-C$_8$)oxoalkyl;

R$^3$ for Structural Formula (Ie) is H, halogen, OH, (C$_1$-C$_4$)alkanoylamino, or (C$_1$-C$_3$)alkoxy; provided that when R$^3$ is OH or halogen, R$^2$ is not an optionally substituted alkoxy, alkylthio or amino group as follows: (C$_1$-C$_8$)alkoxy, (C$_4$-C$_8$)cycloalkylalkoxy, fluoro(C$_1$-C$_8$)alkoxy, (C$_1$-C$_5$)alkoxy(C$_1$-C$_5$)alkoxy, hydroxy(C$_1$-C$_8$)alkoxy, (C$_3$-C$_4$)cycloalkoxy(C$_1$-C$_5$)alkoxy, fluoro(C$_1$-C$_5$)alkoxy(C$_1$-C$_5$)alkoxy, fluoro(C$_3$-C$_4$)cycloalkoxy(C$_1$-C$_5$)alkoxy, aminocarbonyl-amino(C$_1$-C$_8$)alkoxy, (C$_1$-C$_5$)alkanoylamino(C$_1$-C$_5$)alkoxy, fluoro(C$_1$-C$_5$)alkanoyl-amino(C$_1$-C$_5$)alkoxy, (C$_1$-C$_3$)alkoxy(C$_1$-C$_5$)alkanoylamino(C$_1$-C$_5$)alkoxy, (C$_3$-C$_4$)-cycloalkanecarbonylamino(C$_1$-C$_5$)alkoxy, aminosulfonylamino(C$_1$-C$_8$)alkoxy, (C$_1$-C$_5$)alkanesulfonylamino(C$_1$-C$_5$)alkoxy, formylamino(C$_1$-C$_5$)alkoxy, (C$_1$-C$_5$)alkoxycarbonylamino(C$_1$-C$_5$)alkoxy, di(C$_1$-C$_5$)alkylaminocarbonylamino(C$_1$-C$_5$)alkoxy, aminocarbonyl(C$_1$-C$_5$)alkoxy, (C$_1$-C$_5$)alkylaminocarbonyl(C$_1$-C$_5$)alkoxy, aminocarboxy(C$_1$-C$_5$)alkoxy, (C$_1$-C$_5$)alkylaminocarboxy(C$_1$-C$_5$)alkoxy, (C$_1$-C$_8$)alkoxycarbonylamino, (C$_1$-C$_8$)alkylaminocarbonylamino, (C$_1$-C$_8$)alkanoylamino, fluoro(C$_1$-C$_8$)alkoxycarbonylamino, fluoro(C$_1$-C$_8$)alkylaminocarbonylamino, or fluoro(C$_1$-C$_8$)alkanoylamino; or R$^3$ is a divalent radical selected from —(CH$_2$)$_2$—, —(CH$_2$)$_3$—, —OCH$_2$—, —OCH$_2$CH$_2$—, —OC(=O)—, —NHC(=O)—, —OC(=O)NH—, —NHC(=O)NH—, —NHC(=O)CH$_2$—, optionally substituted with up to 2 groups independently selected from (C$_1$-C$_3$)alkyl or halo(C$_1$-C$_3$)alkyl, which is bonded to R$^1$;

R$^4$ is H or (C1-C6)alkyl;

R$^5$ and R$^6$, each is independently a) hydrogen; or b) (C$_1$-C$_{10}$)alkyl, (C$_3$-C$_7$)cycloalkyl(C$_1$-C$_2$)alkyl, (C$_4$-C$_{10}$)bicycloalkyl(C$_1$-C$_2$)alkyl, (C$_8$-C$_{12}$)tricycloalkyl(C$_1$-C$_2$)alkyl, (C$_1$-C$_6$)alkoxy(C$_1$-C$_6$)alkyl, (C$_3$-C$_7$)cycloalkoxy(C$_1$-C$_3$)alkyl, (C$_1$-C$_5$)alkylthio(C$_1$-C$_5$)alkyl, or monocyclic or bicyclic saturated heterocyclyl(C$_1$-C$_3$)alkyl wherein each of these groups are optionally substituted by 1 to 3 groups independently selected from halogen, cyano, hydroxyl, (C$_1$-C$_2$)alkyl, (C$_1$-C$_2$)alkoxy, (C$_3$-C$_6$)cycloalkyl, (C$_3$-C$_6$)cycloalkoxy, halo(C$_1$-C$_2$)alkyl, halo(C$_1$-C$_2$)alkoxy, halo(C$_3$-C$_6$)cycloalkyl, and halo(C$_3$-C$_6$)cycloalkoxy; or c) phenyl(C$_1$-C$_2$)alkyl or heteroaryl(C$_1$-C$_2$)alkyl each optionally substituted with 1 to 3 groups independently selected from fluorine, chlorine, cyano, (C$_1$-C$_3$)alkyl, halo(C$_1$-C$_3$)alkyl, (C$_1$-C$_3$)alkoxy, and halo(C$_1$-C$_3$)alkoxy;

R$^7$ is (C$_1$-C$_6$)alkyl, halo(C$_1$-C$_6$)alkyl or (C$_1$-C$_3$)alkoxy(C$_1$-C$_3$)alkyl;

R$^a$, R$^b$, R$^{a'}$, and R$^{b'}$, for each occurrence, is independently hydrogen, (C$_1$-C$_6$)alkyl, halo(C$_1$-C$_6$)alkyl or R$^a$ and R$^b$ taken together is an oxo or R$^{a'}$ and R$^{b'}$ taken together is an oxo; and R$^9$ is a) hydrogen; b) (C$_1$-C$_6$)alkyl, halo(C$_1$-C$_6$)alkyl, (C$_4$-C$_{10}$)cycloalkylalkyl, (C$_1$-C$_5$)alkoxy(C$_1$-C$_5$)alkyl, aminocarbonyl(C$_1$-C$_5$)alkyl, (C$_1$-C$_6$)alkylaminocarbonyl(C$_1$-C$_6$)alkyl, or di(C$_1$-C$_6$)alkyl-aminocarbonyl(C$_1$-C$_6$)alkyl; or c) phenyl(C$_1$-C$_2$)alkyl optionally substituted with 1 to 3 groups independently selected from fluorine, chlorine, cyano, (C$_1$-C$_3$)alkyl, halo(C$_1$-C$_3$)alkyl, (C$_1$-C$_3$)alkoxy, and halo(C$_1$-C$_3$)alkoxy.

In a 3$^{rd}$ specific embodiment, the aspartic protease inhibitor of the presented invention is represented by the Structural Formula (Ie) or (Ii), wherein one of R$^5$ or R$^6$ is H and the other is a) hydrogen; or b) (C$_1$-C$_{10}$)alkyl, (C$_3$-C$_7$)cycloalkyl(C$_1$-C$_2$)alkyl, (C$_4$-C$_{10}$)bicycloalkyl(C$_1$-C$_2$)alkyl, (C$_8$-C$_{12}$)tricycloalkyl(C$_1$-C$_2$)alkyl, (C$_1$-C$_6$)alkoxy(C$_1$-C$_6$)alkyl, (C$_3$-C$_7$)cycloalkoxy(C$_1$-C$_3$)alkyl, (C$_1$-C$_5$)alkylthio(C$_1$-C$_5$)alkyl, or monocyclic or bicyclic saturated heterocyclyl(C$_1$-C$_3$)alkyl, wherein each of these groups are optionally substituted by 1 to 3 groups independently selected from halogen, cyano, hydroxyl, (C$_1$-C$_2$)alkyl, (C$_1$-C$_2$)alkoxy, (C$_3$-C$_6$)cycloalkyl, (C$_3$-C$_6$)cycloalkoxy, halo(C$_1$-C$_2$)alkyl, halo(C$_1$-C$_2$)alkoxy, halo(C$_3$-C$_6$)cycloalkyl, and halo(C$_3$-C$_6$)cycloalkoxy; or c) phenyl(C$_1$-C$_2$)alkyl or heteroaryl(C$_1$-C$_2$)alkyl each optionally substituted with 1 to 3 groups independently selected from fluorine, chlorine, cyano, (C$_1$-C$_3$)alkyl, halo(C$_1$-C$_3$)alkyl, (C$_1$-C$_3$)alkoxy, and halo(C$_1$-C$_3$)alkoxy. The remaining variables are as described above in the 2nd specific embodiment.

In a 4$^{th}$ specific embodiment, the aspartic protease inhibitor of the presented invention is represented by the Structural Formula (Ie) or (Ii), wherein R$^1$ is phenyl, 2-thienyl, 3-thienyl, 2-pyridyl, 2-imidazolyl, 2-thiazolyl, 2-benzothienyl, 4-benzofuryl, 4-benzothienyl, 7-benzofuryl, 2,3-dihydro-7-benzofuryl, 7-benzothienyl, 1,3-benzodioxol-4-yl, 7-indazolyl, or 8-quinolinyl each optionally substituted with 1 to 5 substituents independently selected from: fluorine, chlorine, bromine, cyano, methyl, ethyl, isopropyl, t-butyl, isobutyl, trifluoromethyl, allyl, cyclohexyl, cyclohexen-1-yl, cyclopropylethynyl, methoxy, trifluoromethoxy, neopentyloxy, methylthio, allyloxy, cyclopropylmethoxy, 2-(cyclopropyl)ethoxy, cyclopentyloxy, cyclopentylmethoxy, benzyloxy, hydroxyl, aminocarbonyl, methoxycarbonyl, phenyl, phenoxy, benzyloxy, and heteroaryloxy, wherein the phenyl phenoxy, benzyloxy and heteroaryloxy groups are optionally substituted with 1 to 3 substituents independently selected from fluorine, chlorine, cyano, methyl, trifluoromethyl, and aminocarbonyl. More specifically, $R^1$ is phenyl, optionally substituted with 1 to 5 substituents independently selected from:
fluorine, chlorine, bromine, cyano, methyl, ethyl, isopropyl, t-butyl, isobutyl, trifluoromethyl, allyl, cyclohexyl, cyclohexen-1-yl, cyclopropylethynyl, methoxy, trifluoromethoxy, neopentyloxy, methylthio, allyloxy, cyclopropylmethoxy, 2-(cyclopropyl)ethoxy, cyclopentyloxy, cyclopentylmethoxy, benzyloxy, hydroxyl, aminocarbonyl, methoxycarbonyl, phenyl, phenoxy, benzyloxy, and heteroaryloxy, wherein the phenyl phenoxy, benzyloxy and heteroaryloxy groups are optionally substituted with 1 to 3 substituents independently selected from fluorine, chlorine, cyano, methyl, trifluoromethyl, and aminocarbonyl. Even more specifically, $R^1$ is phenyl optionally substituted with 1 to 5 substituents independently selected from the group consisting of fluorine, chlorine and methyl. Values and specific values for the remainder of the variables are as described above in the 2nd specific embodiment.

In a $5^{th}$ specific embodiment, the aspartic protease inhibitor of the present invention is represented by a Structural Formula (Ie) or (Ii), wherein $R^2$ is $(C_1-C_8)$alkyl, $(C_4-C_8)$cycloalkylalkyl, fluoro$(C_1-C_8)$alkyl, fluoro$(C_4-C_8)$-cycloalkylalkyl, hydroxy$(C_1-C_8)$alkyl, $(C_1-C_5)$alkoxy$(C_1-C_5)$alkyl, halo$(C_1-C_5)$alkylamino$(C_1-C_5)$alkyl, $(C_1-C_5)$alkoxy$(C_1-C_5)$hydroxyalkyl, $(C_3-C_4)$cycloalkoxy$(C_1-C_5)$alkyl, fluoro$(C_1-C_5)$alkoxy$(C_1-C_5)$alkyl, fluoro$(C_3-C_4)$cycloalkoxy$(C_1-C_5)$alkyl, $(C_1-C_5)$alkylthio$(C_1-C_5)$alkyl, $(C_1-C_5)$alkoxy$(C_1-C_5)$alkoxy, $(C_3-C_4)$cycloalkoxy$(C_1-C_5)$alkoxy, fluoro$(C_1-C_5)$alkoxy$(C_1-C_5)$alkoxy, fluoro$(C_3-C_4)$cycloalkoxy$(C_1-C_5)$alkoxy, $(C_1-C_3)$alkoxy$(C_1-C_3)$alkoxy$(C_1-C_3)$alkyl, fluoro$(C_1-C_3)$-alkoxy$(C_1-C_3)$alkoxy$(C_1-C_3)$alkyl, aminocarbonylamino$(C_1-C_8)$alkyl, $(C_1-C_5)$alkanoylamino$(C_1-C_5)$alkyl, fluoro$(C_1-C_5)$alkanoylamino$(C_1-C_5)$alkyl, $(C_1-C_3)$alkoxy$(C_1-C_5)$alkanoylamino$(C_1-C_5)$alkyl, $(C_3-C_4)$-cycloalkanecarbonylamino$(C_1-C_5)$alkyl, aminosulfonylamino$(C_1-C_8)$alkyl, $(C_1-C_5)$alkanesulfonyl-amino$(C_1-C_5)$alkyl, formylamino$(C_1-C_5)$alkyl, $(C_1-C_5)$alkoxycarbonylamino$(C_1-C_5)$alkyl, $(C_1-C_5)$alkoxycarbonylamino$(C_1-C_5)$alkoxy, $(C_1-C_5)$alkylaminocarbonylamino$(C_1-C_5)$alkyl, $(C_1-C_5)$alkylaminocarbonylamino$(C_1-C_5)$alkyl, aminocarbonyl$(C_1-C_5)$alkyl, $(C_1-C_5)$alkylaminocarbonyl$(C_1-C_5)$alkyl, aminocarboxy$(C_1-C_5)$alkyl, aminocarboxy$(C_1-C_5)$alkoxy, $(C_1-C_5)$alkylamino-carboxy$(C_1-C_5)$alkyl, $(C_1-C_5)$alkylaminocarboxy$(C_1-C_5)$alkoxy, or $(C_1-C_8)$oxoalkyl, provided when T is N or when T is $CR^3$ and $R^3$ is OH or halogen, $R^2$ is not $(C_1-C_5)$alkoxy$(C_1-C_5)$alkoxy, $(C_3-C_4)$cycloalkoxy$(C_1-C_5)$alkoxy, fluoro$(C_1-C_5)$alkoxy$(C_1-C_5)$alkoxy, fluoro$(C_3-C_4)$cycloalkoxy$(C_1-C_5)$alkoxy$(C_1-C_5)$alkoxycarbonyl-amino$(C_1-C_5)$alkoxy, aminocarboxy$(C_1-C_5)$alkoxy, or $(C_1-C_5)$alkylaminocarboxy$(C_1-C_5)$alkoxy. More specifically, $R^2$ is methyl, ethyl, propyl, butyl, hexyl, 5-pentenyl, 3,3,3-trifluoropropyl, 4,4-difluoropentyl, 3-(cyclopropyl)propyl, 4-(cyclopropyl)butyl, 3-hydroxypropyl, 4-hydroxybutyl, 4-hydroxypentyl, 4-hydroxyhexyl, 5-hydroxyhexyl, 2-hydroxyethoxy, 5-oxohexyl, 3-ethoxypropyl, 4-methoxybutyl, 4-ethoxybutyl, 2-(ethoxy)-ethoxy, 3-methoxypropoxy, 3-ethoxypropoxy, 3-propoxypropoxy, (2-(methoxy)ethoxy)methyl, 3-(2,2,2-trifluoroethylamino)propyl, 3-(formylamino)propyl, 3-(acetylamino)propyl, 3-(propionyl-amino)propyl, 3-(butanoylamino)propyl, 3-((2-methoxypropionyl)amino)propyl, 3-(cyclopropanecarbonylamino)propyl, 3-(trifluoroacetylamino)propyl, 3-(methoxycarbonylamino)propyl, 3-(ethoxycarbonylamino)propyl, 2-(methoxycarbonylamino)ethoxy, 2-(ethoxycarbonylamino)-ethoxy, 3-(methylaminocarbonylamino)propyl, 3-(dimethylaminocarbonyl-amino)propyl, 3-(aminocarbonyl)propyl, 3-(methylaminocarbonyl)propyl, 3-(ethylaminocarbonyl)propyl, methoxymethylcarbonylaminomethyl, or 3-(aminosulfonylamino)propyl, 2-(methoxy)-ethoxy, or 4-(methoxy)-butoxy.

Values and specific values for the remaining variables are as described above in the $4^{th}$ specific embodiment.

In a $6^{th}$ specific embodiment, the aspartic protease inhibitor of the present invention is represented by a Structural Formula (Ie) or (Ii), wherein:
$R^1$ is phenyl, 2-thienyl, 3-thienyl, 2-pyridyl, 2-imidazolyl, 2-thiazolyl, 2-benzothienyl, 4-benzofuryl, 4-benzothienyl, 7-benzofuryl, 2,3-dihydro-7-benzofuryl, 7-benzothienyl, 1,3-benzodioxol-4-yl, 7-indazolyl, or 8-quinolinyl each optionally substituted with 1 to 5 substituents independently selected from: fluorine, chlorine, bromine, cyano, methyl, ethyl, isopropyl, t-butyl, isobutyl, trifluoromethyl, allyl, cyclohexyl, cyclohexen-1-yl, cyclopropylethynyl, methoxy, trifluoromethoxy, neopentyloxy, methylthio, allyloxy, cyclopropylmethoxy, 2-(cyclopropyl)ethoxy, cyclopentyloxy, cyclopentylmethoxy, benzyloxy, hydroxyl, aminocarbonyl, methoxycarbonyl, phenyl, phenoxy, benzyloxy, and heteroaryloxy, wherein the phenyl phenoxy, benzyloxy and heteroaryloxy groups are optionally substituted with 1 to 3 substituents independently selected from fluorine, chlorine, cyano, methyl, trifluoromethyl, and aminocarbonyl. More specifically, $R^1$ is phenyl, optionally substituted with 1 to 5 substituents independently selected from: fluorine, chlorine, bromine, cyano, methyl, ethyl, isopropyl, t-butyl, isobutyl, trifluoromethyl, allyl, cyclohexyl, cyclohexen-1-yl, cyclopropylethynyl, methoxy, trifluoromethoxy, neopentyloxy, methylthio, allyloxy, cyclopropylmethoxy, 2-(cyclopropyl) ethoxy, cyclopentyloxy, cyclopentylmethoxy, benzyloxy, hydroxyl, aminocarbonyl, methoxycarbonyl, phenyl, phenoxy, benzyloxy, and heteroaryloxy, wherein the phenyl phenoxy, benzyloxy and heteroaryloxy groups are optionally substituted with 1 to 3 substituents independently selected from fluorine, chlorine, cyano, methyl, trifluoromethyl, and aminocarbonyl. Even more specifically, $R^1$ is phenyl optionally substituted with 1 to 5 substituents independently selected from the group consisting of fluorine, chlorine and methyl.

$R^2$ is $(C_1-C_8)$alkyl, $(C_4-C_8)$cycloalkylalkyl, fluoro$(C_1-C_8)$alkyl, fluoro$(C_4-C_8)$-cycloalkylalkyl, hydroxy$(C_1-C_8)$alkyl, $(C_1-C_5)$alkoxy$(C_1-C_5)$alkyl, halo$(C_1-C_5)$alkylamino$(C_1-C_5)$alkyl, $(C_1-C_5)$alkoxy$(C_1-C_5)$hydroxyalkyl, $(C_3-C_4)$cycloalkoxy$(C_1-C_5)$alkyl, fluoro$(C_1-C_5)$alkoxy$(C_1-C_5)$alkyl, fluoro$(C_3-C_4)$cycloalkoxy$(C_1-C_5)$alkyl, $(C_1-C_5)$alkylthio$(C_1-C_5)$alkyl, $(C_1-C_5)$alkoxy$(C_1-C_5)$alkoxy, $(C_3-C_4)$cycloalkoxy$(C_1-C_5)$alkoxy, fluoro$(C_1-C_5)$alkoxy$(C_1-C_5)$alkoxy, fluoro$(C_3-C_4)$cycloalkoxy$(C_1-C_5)$alkoxy, $(C_1-C_3)$alkoxy$(C_1-C_3)$alkoxy$(C_1-C_3)$alkyl, fluoro$(C_1-C_3)$-alkoxy$(C_1-C_3)$alkoxy$(C_1-C_3)$alkyl, aminocarbonylamino$(C_1-C_8)$alkyl, $(C_1-C_5)$alkanoylamino$(C_1-C_5)$alkyl, fluoro$(C_1-C_5)$alkanoylamino$(C_1-C_5)$alkyl, $(C_1-C_3)$alkoxy$(C_1-C_5)$alkanoylamino$(C_1-C_5)$alkyl, $(C_3-C_4)$-cycloalkanecarbonylamino$(C_1-C_5)$alkyl, aminosulfonylamino$(C_1-C_8)$alkyl, $(C_1-C_5)$alkanesulfonyl-amino$(C_1-C_5)$alkyl, formylamino$(C_1-C_5)$alkyl, $(C_1-C_5)$alkoxycarbonylamino$(C_1-C_5)$alkyl, $(C_1-C_5)$alkoxycarbonylamino$(C_1-C_5)$alkoxy, $(C_1-C_5)$alkylaminocarbonylamino$(C_1-C_5)$alkyl, $(C_1-C_5)$alkylaminocarbonylamino$(C_1-C_5)$alkyl, aminocarbonyl$(C_1-C_5)$alkyl, $(C_1-C_5)$alkylaminocarbonyl$(C_1-C_5)$alkyl, aminocarboxy$(C_1-C_5)$alkyl, aminocarboxy ($C_1$-$C_5$)alkoxy, ($C_1$-$C_5$)alkylamino-carboxy($C_1$-$C_5$)alkyl, ($C_1$-$C_5$)alkylaminocarboxy($C_1$-$C_5$)alkoxy, or ($C_1$-$C_8$) oxoalkyl, provided when T is N or when T is $CR^3$ and $R^3$ is OH or halogen, $R^2$ is not an optionally substituted alkoxy, alkylthio or amino group as follows: ($C_1$-$C_5$)alkoxy($C_1$-$C_5$) alkoxy, ($C_3$-$C_4$)cycloalkoxy($C_1$-$C_5$)alkoxy, fluoro($C_1$-$C_5$) alkoxy($C_1$-$C_5$)alkoxy, fluoro($C_3$-$C_4$)cycloalkoxy($C_1$-$C_5$) alkoxy($C_1$-$C_5$)alkoxycarbonyl-amino($C_1$-$C_5$)alkoxy, aminocarboxy($C_1$-$C_5$)alkoxy, or ($C_1$-$C_5$)alkylaminocarboxy ($C_1$-$C_5$)alkoxy. More specifically, $R^2$ is methyl, ethyl, propyl, butyl, hexyl, 5-pentenyl, 3,3,3-trifluoropropyl, 4,4-difluoropentyl, 3-(cyclopropyl)propyl, 4-(cyclopropyl)butyl, 3-hydroxypropyl, 4-hydroxybutyl, 4-hydroxypentyl, 4-hydroxyhexyl, 5-hydroxyhexyl, 2-hydroxyethoxy, 5-oxohexyl, 3-ethoxypropyl, 4-methoxybutyl, 4-ethoxybutyl, 2-(ethoxy)-ethoxy, 3-methoxypropoxy, 3-ethoxypropoxy, 3-propoxypropoxy, (2-(methoxy)ethoxy)methyl, 3-(2,2,2-trifluoroethylamino)propyl, 3-(formylamino)propyl, 3-(acetylamino)propyl, 3-(propionyl-amino)propyl, 3-(butanoylamino)propyl, 3-((2-methoxypropionyl)amino)propyl, 3-(cyclopropane-carbonylamino)propyl, 3-(trifluoroacetylamino)propyl, 3-(methoxycarbonylamino)propyl, 3-(ethoxycarbonylamino)propyl, 2-(methoxycarbonylamino)ethoxy, 2-(ethoxycarbonylamino)-ethoxy, 3-(methylaminocarbonylamino)propyl, 3-(dimethylaminocarbonylamino)propyl, 3-(aminocarbonyl)propyl, 3-(methylaminocarbonyl)propyl, 3-(ethylaminocarbonyl) propyl, methoxymethylcarbonylaminomethyl, or 3-(aminosulfonylamino)propyl, 2-(methoxy)-ethoxy, or 4-(methoxy)-butoxy.

$R^3$ for Structural Formula (Ie) is H, F, OH, methoxy, acetylamino, propionylamino, (2-methylpropionyl)amino, or butanoylamino;

$R^5$ is hydrogen, methyl, isobutyl, t-butylmethyl, 2,2,2-trifluoroethyl, 2-(trifluoromethyl)propyl, cyclopentylmethyl, cyclohexylmethyl, (3,3-difluorocyclobutyl)methyl, 3,4-difluorocyclopentyl)methyl, 4,4-difluoro-cyclohexylmethyl, (4-methylcyclohexyl)methyl, tert-butoxymethyl, (4-tetrahydropyranyl)methyl, benzyl, (1-fluorocyclohexyl)methyl, (4-fluorocyclohexyl)methyl, 1-hydroxy-2-methylpropyl, (cyclopentyl)(hydroxy)methyl, (cyclohexyl)(hydroxy)methyl, (cycloheptyl)(hydroxy)methyl, (1-hydroxycyclohexyl) methyl, (4-hydroxycyclohexyl)methyl, (4-hydroxy-4-methylcyclohexyl)methyl, 1-adamantylmethyl, (3-noradamantyl) (hydroxy)methyl, 2-methoxy-2-methylpropyl, 2,2-dimethyl-3-methoxypropyl, (3-tetrahydrofuryl)methyl, (3-tetrahydropyranyl)methyl, (4-tetrahydropyranyl)methyl and $R^6$ is hydrogen; or $R^5$ is hydrogen and $R^6$ is methyl, isobutyl, t-butylmethyl, 2,2,2-trifluoroethyl, 2-(trifluoromethyl)propyl, cyclopentylmethyl, cyclohexylmethyl, (3,3-difluorocyclobutyl)methyl, 3,4-difluorocyclopentyl)methyl, 4,4-difluoro-cyclohexylmethyl, (4-methylcyclohexyl)methyl, tert-butoxymethyl, (4-tetrahydropyranyl)methyl, benzyl, (1-fluorocyclohexyl) methyl, (4-fluorocyclohexyl)methyl, 1-hydroxy-2-methylpropyl, (cyclopentyl)(hydroxy)methyl, (cyclohexyl)(hydroxy)methyl, (cycloheptyl)(hydroxy)methyl, (1-hydroxycyclohexyl)methyl, (4-hydroxycyclohexyl)methyl, (4-hydroxy-4-methylcyclohexyl)methyl, 1-adamantylmethyl, (3-noradamantyl)(hydroxy)methyl, 2-methoxy-2-methylpropyl, 2,2-dimethyl-3-methoxypropyl, (3-tetrahydrofuryl)methyl, (3-tetrahydropyranyl)methyl, (4-tetrahydropyranyl)methyl;

Values and specific values of the remainder of the variables are as described above in the $2^{nd}$ specific embodiment.

More specifically, in the sixth specific embodiment, $R^4$ is H; $R^3$ is H; $R^5$ is cyclohexylmethyl, 1-adamantylmethyl, (3-tetrahydropyranyl)methyl, (4-tetrahydropyranyl)methyl, (3-oxepanyl)methyl or 6-(4-oxaspiro[2,5]octyl)methyl and $R^6$ is H; or $R^5$ is H and $R^6$ is (3-tetrahydropyranyl)methyl or (3-oxepanyl)methyl;

$R^7$ is methyl, ethyl, propyl or isopropyl;

$R^a$, $R^b$, $R^{a'}$ and $R^{b'}$, for each occurrence, are independently hydrogen, methyl or $R^a$ and $R^b$ attached to a carbon atom taken together are oxo or $R^{a'}$ and $R^{b'}$ attached to a carbon atom taken together are oxo; and $R^9$ is H, methyl or ethyl.

In a $7^{th}$ specific embodiment, the aspartic protease inhibitor of the present invention is represented by a Structural Formula (Ie) or (Ii), wherein $R^2$ is butoxy, hexyloxy, 2-cyclopropylethoxy, 2-(acetylamino)ethoxy, 2-(propionylamino) ethoxy, aminocarbonylmethoxy, methylaminocarbonylmethoxy, ethylaminocarbonylmethoxy, propylaminocarbonylmethoxy, 2-(methylaminocarbonyl) ethoxy, 2-(ethylaminocarbonyl)ethoxy, 2-(propylaminocarbonyl)ethoxy, or (2-(methoxy)ethoxy)carbonylamino.

Values and specific values for the remainder of the variables are as described above in the $4^{th}$ specific embodiment.

In an $8^{th}$ specific embodiment, the aspartic protease inhibitor of the present invention is represented by a Structural Formula (Ie) or (Ii), wherein:

$R^1$ is phenyl, 2-thienyl, 3-thienyl, 2-pyridyl, 2-imidazolyl, 2-thiazolyl, 2-benzothienyl, 4-benzofuryl, 4-benzothienyl, 7-benzofuryl, 2,3-dihydro-7-benzofuryl, 7-benzothienyl, 1,3-benzodioxol-4-yl, 7-indazolyl, or 8-quinolinyl each optionally substituted with 1 to 5 substituents independently selected from: fluorine, chlorine, bromine, cyano, methyl, ethyl, isopropyl, t-butyl, isobutyl, trifluoromethyl, allyl, cyclohexyl, cyclohexen-1-yl, cyclopropylethynyl, methoxy, trifluoromethoxy, neopentyloxy, methylthio, allyloxy, cyclopropylmethoxy, 2-(cyclopropyl)ethoxy, cyclopentyloxy, cyclopentylmethoxy, benzyloxy, hydroxyl, aminocarbonyl, methoxycarbonyl, phenyl, phenoxy, benzyloxy, and heteroaryloxy, wherein the phenyl phenoxy, benzyloxy and heteroaryloxy groups are optionally substituted with 1 to 3 substituents independently selected from fluorine, chlorine, cyano, methyl, trifluoromethyl, and aminocarbonyl. More specifically, $R^1$ is phenyl, optionally substituted with 1 to 5 substituents independently selected from: fluorine, chlorine, bromine, cyano, methyl, ethyl, isopropyl, t-butyl, isobutyl, trifluoromethyl, allyl, cyclohexyl, cyclohexen-1-yl, cyclopropylethynyl, methoxy, trifluoromethoxy, neopentyloxy, methylthio, allyloxy, cyclopropylmethoxy, 2-(cyclopropyl) ethoxy, cyclopentyloxy, cyclopentylmethoxy, benzyloxy, hydroxyl, aminocarbonyl, methoxycarbonyl, phenyl, phenoxy, benzyloxy, and heteroaryloxy, wherein the phenyl phenoxy, benzyloxy and heteroaryloxy groups are optionally substituted with 1 to 3 substituents independently selected from fluorine, chlorine, cyano, methyl, trifluoromethyl, and aminocarbonyl. Even more specifically, $R^1$ is phenyl optionally substituted with 1 to 5 substituents independently selected from the group consisting of fluorine, chlorine and methyl.

$R^2$ is butoxy, hexyloxy, 2-cyclopropylethoxy, 2-(acetylamino)ethoxy, 2-(propionylamino)ethoxy, aminocarbonylmethoxy, methylamino-carbonylmethoxy, ethylaminocarbonylmethoxy, propylaminocarbonylmethoxy, 2-(methylaminocarbonyl)ethoxy, 2-(ethylaminocarbonyl) ethoxy, 2-(propylaminocarbonyl)ethoxy, or (2-(methoxy) ethoxy)carbonylamino.

$R^3$ for Structural Formula (Ie) is H, F, OH, methoxy, acetylamino, propionylamino, (2-methylpropionyl)amino, or butanoylamino;

$R^5$ is hydrogen, methyl, isobutyl, t-butylmethyl, 2,2,2-trifluoroethyl, 2-(trifluoromethyl)propyl, cyclopentylmethyl, cyclohexylmethyl, (3,3-difluorocyclobutyl)methyl, 3,4-difluorocyclopentyl)methyl, 4,4-difluoro-cyclohexylmethyl, (4-methylcyclohexyl)methyl, tert-butoxymethyl, (4-tetrahydropyranyl)methyl, benzyl, (1-fluorocyclohexyl)methyl, (4-fluorocyclohexyl)methyl, 1-hydroxy-2-methylpropyl, (cyclopentyl)(hydroxy)methyl, (cyclohexyl)(hydroxy)methyl, (cycloheptyl)(hydroxy)methyl, (1-hydroxycyclohexyl) methyl, (4-hydroxycyclohexyl)methyl, (4-hydroxy-4-methylcyclohexyl)methyl, 1-adamantylmethyl, (3-noradamantyl) (hydroxy)methyl, 2-methoxy-2-methylpropyl, 2,2-dimethyl-3-methoxypropyl, (3-tetrahydrofuryl)methyl, (3-tetrahydropyranyl)methyl, (4-tetrahydropyranyl)methyl and $R^6$ is hydrogen; or $R^5$ is hydrogen and $R^6$ is methyl, isobutyl, t-butylmethyl, 2,2,2-trifluoroethyl, 2-(trifluoromethyl)propyl, cyclopentylmethyl, cyclohexylmethyl, (3,3-difluorocyclobutyl)methyl, 3,4-difluorocyclopentyl)methyl, 4,4-difluoro-cyclohexylmethyl, (4-methylcyclohexyl)methyl, tert-butoxymethyl, (4-tetrahydropyranyl)methyl, benzyl, (1-fluorocyclohexyl) methyl, (4-fluorocyclohexyl)methyl, 1-hydroxy-2-methylpropyl, (cyclopentyl)(hydroxy)methyl, (cyclohexyl)(hydroxy)methyl, (cycloheptyl)(hydroxy)methyl, (1-hydroxycyclohexyl)methyl, (4-hydroxycyclohexyl)methyl, (4-hydroxy-4-methylcyclohexyl)methyl, 1-adamantylmethyl, (3-noradamantyl)(hydroxy)methyl, 2-methoxy-2-methylpropyl, 2,2-dimethyl-3-methoxypropyl, (3-tetrahydrofuryl)methyl, (3-tetrahydropyranyl)methyl, (4-tetrahydropyranyl)methyl.

Values and specific values of the remainder of the variables are as described in the $2^{nd}$ specific embodiment.

More specifically, in $8^{th}$ specific embodiment, $R^4$ is H; $R^3$ is H; $R^5$ is cyclohexylmethyl, 1-adamantylmethyl, (3-tetrahydropyranyl)methyl, (4-tetrahydropyranyl)methyl, (3-oxepanyl)methyl or 6-(4-oxaspiro[2,5]octyl)methyl and $R^6$ is H; or $R^5$ is H and $R^6$ is (3-tetrahydropyranyl)methyl or (3-oxepanyl)methyl;

$R^7$ is methyl, ethyl, propyl or isopropyl;

$R^a$, $R^b$, $R^{a'}$ and $R^{b'}$, for each occurrence, are independently hydrogen, methyl or $R^a$ and $R^b$ attached to a carbon atom taken together are oxo or $R^{a'}$ and $R^{b'}$ attached to a carbon atom taken together are oxo; and $R^9$ is H, methyl or ethyl.

In a $9^{th}$ specific embodiment, the aspartic protease inhibitor of the present invention is represented by a Structural Formula (Ie) or (Ii), wherein $R^2$ for Structural Formula (Ie) is $(C_1-C_5)$alkoxy$(C_1-C_5)$alkyl, $(C_1-C_5)$alkoxy$(C_1-C_5)$alkoxy, $(C_1-C_5)$alkoxycarbonylamino$(C_1-C_5)$alkyl, or $(C_1-C_5)$ alkoxycarbonylamino$(C_1-C_5)$alkoxy, provided when $R^3$ is halogen or OH, $R^2$ is not $(C_1-C_5)$alkoxy$(C_1-C_5)$alkoxy or $(C_1-C_5)$alkoxycarbonylamino$(C_1-C_5)$alkoxy. More specifically, $R^2$ is 3-methoxypropoxy, 4-methoxybutyl, 2-(methoxycarbonylamino)ethoxy or 3-(methoxycarbonylamino) propyl.

$R^2$ for Structural Formula (Ii) is $(C_1-C_5)$alkoxy$(C_1-C_5)$ alkyl or $(C_1-C_5)$alkoxycarbonylamino$(C_1-C_5)$alkyl. More specifically, $R^2$ is 4-methoxybutyl or 3-(methoxycarbonylamino)propyl. The remaining variables are as described above in the $8^{th}$ specific embodiment.

More specifically, in $9^{th}$ specific embodiment, $R^4$ is H; $R^3$ is H; $R^5$ is cyclohexylmethyl, 1-adamantylmethyl, (3-tetrahydropyranyl)methyl, (4-tetrahydropyranyl)methyl, (3-oxepanyl)methyl or 6-(4-oxaspiro[2,5]octyl)methyl and $R^6$ is H; or $R^5$ is H and $R^6$ is (3-tetrahydropyranyl)methyl or (3-oxepanyl)methyl;

$R^7$ is methyl, ethyl, propyl or isopropyl;

$R^a$, $R^b$, $R^{a'}$ and $R^{b'}$, for each occurrence, are independently hydrogen, methyl or $R^a$ and $R^b$ attached to a carbon atom taken together are oxo or $R^{a'}$ and $R^{b'}$ attached to a carbon atom taken together are oxo; and $R^9$ is H, methyl or ethyl.

In a $10^{th}$ specific embodiment, the aspartic protease inhibitor of the present invention is represented by a Structural Formula (If), (Ig) or (Ih)

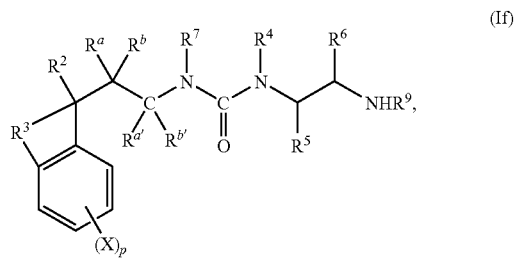

(If)

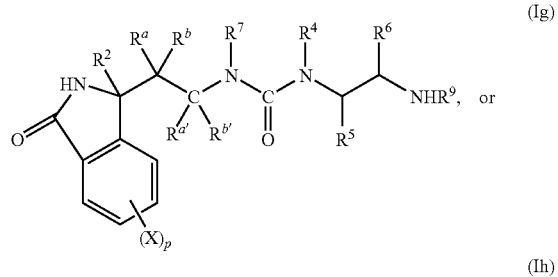

(Ig)

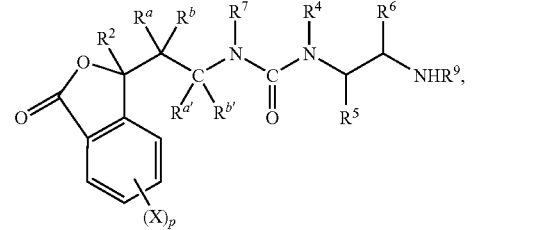

(Ih)

or an enantiomer, a diastereomer or a pharmaceutically acceptable salt thereof, wherein:

$R^3$ in Structural Formula (If) is a divalent radical selected from —$(CH_2)_2$—, —$(CH_2)_3$—, —$OCH_2$—, —$OCH_2CH_2$—, —$OC(=O)$—, —$NHC(=O)$—, —$OC(=O)NH$—, —$NHC(=O)NH$—, —$NHC(=O)CH_2$—, optionally substituted with 1 to 2 groups independently selected from $(C_1-C_3)$alkyl or halo$(C_1-C_3)$alkyl;

X is fluorine, chlorine, cyano, $(C_1-C_3)$alkyl, halo$(C_1-C_3)$ alkyl, $(C_1-C_3)$-alkoxy, halo$(C_1-C_3)$alkoxy, and aminocarbonyl; and p is 0 or an integer from 1 to 4.

Values and specific values of the remainder of the variables are as described above in the $2^{nd}$ specific embodiment.

In an $11^{th}$ specific embodiment, the aspartic protease inhibitor of the present invention is represented by a Structural Formula (If), (Ig) or (Ih), wherein $R^3$, X and p are as described above in the $10^{th}$ specific embodiment.

$R^1$ is phenyl, 2-thienyl, 3-thienyl, 2-pyridyl, 2-imidazolyl, 2-thiazolyl, 2-benzothienyl, 4-benzofuryl, 4-benzothienyl, 7-benzofuryl, 2,3-dihydro-7-benzofuryl, 7-benzothienyl, 1,3-benzodioxol-4-yl, 7-indazolyl, or 8-quinolinyl each optionally substituted with 1 to 5 substituents independently selected from: fluorine, chlorine, bromine, cyano, methyl, ethyl, isopropyl, t-butyl, isobutyl, trifluoromethyl, allyl, cyclohexyl, cyclohexen-1-yl, cyclopropylethynyl, methoxy, trifluoromethoxy, neopentyloxy, methylthio, allyloxy, cyclopropylmethoxy, 2-(cyclopropyl)ethoxy, cyclopentyloxy, cyclopentylmethoxy, benzyloxy, hydroxyl, aminocarbonyl, methoxycarbonyl, phenyl, phenoxy, benzyloxy, and heteroaryloxy, wherein the phenyl phenoxy, benzyloxy and heteroaryloxy groups are optionally substituted with 1 to 3 substituents independently selected from fluorine, chlorine, cyano, methyl, trifluoromethyl, and aminocarbonyl. More specifically, $R^1$ is phenyl, optionally substituted with 1 to 5 substituents independently selected from: fluorine, chlorine, bromine, cyano, methyl, ethyl, isopropyl, t-butyl, isobutyl, trifluoromethyl, allyl, cyclohexyl, cyclohexen-1-yl, cyclopropylethynyl, methoxy, trifluoromethoxy, neopentyloxy, methylthio, allyloxy, cyclopropylmethoxy, 2-(cyclopropyl)ethoxy, cyclopentyloxy, cyclopentylmethoxy, benzyloxy, hydroxyl, aminocarbonyl, methoxycarbonyl, phenyl, phenoxy, benzyloxy, and heteroaryloxy, wherein the phenyl phenoxy, benzyloxy and heteroaryloxy groups are optionally substituted with 1 to 3 substituents independently selected from fluorine, chlorine, cyano, methyl, trifluoromethyl, and aminocarbonyl. Even more specifically, $R^1$ is phenyl optionally substituted with 1 to 5 substituents independently selected from the group consisting of fluorine, chlorine and methyl. Values and specific values for the remainder of the variables are as described above in the $2^{nd}$ specific embodiment In a $12^{th}$ specific embodiment, the aspartic protease inhibitor of the present invention is represented by a Structural Formula (If), (Ig) or (Ih), wherein $R^3$, X and p are as described above in the $10^{th}$ specific embodiment.

$R^2$ is $(C_1-C_8)$alkyl, $(C_4-C_8)$cycloalkylalkyl, fluoro$(C_1-C_8)$alkyl, fluoro$(C_4-C_8)$-cycloalkylalkyl, hydroxy$(C_1-C_8)$alkyl, $(C_1-C_5)$alkoxy$(C_1-C_5)$alkyl, halo$(C_1-C_5)$alkylamino$(C_1-C_5)$alkyl, $(C_1-C_5)$alkoxy$(C_1-C_5)$hydroxyalkyl, $(C_3-C_4)$cycloalkoxy$(C_1-C_5)$alkyl, fluoro$(C_1-C_5)$alkoxy$(C_1-C_5)$alkyl, fluoro$(C_3-C_4)$cycloalkoxy$(C_1-C_5)$alkyl, $(C_1-C_5)$alkylthio$(C_1-C_5)$alkyl, $(C_1-C_5)$alkoxy$(C_1-C_5)$alkoxy, $(C_3-C_4)$cycloalkoxy$(C_1-C_5)$alkoxy, fluoro$(C_1-C_5)$alkoxy$(C_1-C_5)$alkoxy, fluoro$(C_3-C_4)$cycloalkoxy$(C_1-C_5)$alkoxy, $(C_1-C_3)$alkoxy$(C_1-C_3)$alkoxy$(C_1-C_3)$alkyl, fluoro$(C_1-C_3)$-alkoxy$(C_1-C_3)$alkoxy$(C_1-C_3)$alkyl, aminocarbonylamino$(C_1-C_8)$alkyl, $(C_1-C_5)$alkanoylamino$(C_1-C_5)$alkyl, fluoro$(C_1-C_5)$alkanoylamino$(C_1-C_5)$alkyl, $(C_1-C_3)$alkoxy$(C_1-C_5)$alkanoylamino$(C_1-C_5)$alkyl, $(C_3-C_4)$-cycloalkanecarbonylamino$(C_1-C_5)$alkyl, aminosulfonylamino$(C_1-C_8)$alkyl, $(C_1-C_5)$alkanesulfonylamino$(C_1-C_5)$alkyl, formylamino$(C_1-C_5)$alkyl, $(C_1-C_5)$alkoxycarbonylamino$(C_1-C_5)$alkyl, $(C_1-C_5)$alkoxycarbonylamino$(C_1-C_5)$alkoxy, $(C_1-C_5)$alkylaminocarbonylamino$(C_1-C_5)$alkyl, $(C_1-C_5)$alkylaminocarbonylamino$(C_1-C_5)$alkyl, aminocarbonyl$(C_1-C_5)$alkyl, $(C_1-C_5)$alkylaminocarbonyl$(C_1-C_5)$alkyl, aminocarboxy$(C_1-C_5)$alkyl, aminocarboxy$(C_1-C_5)$alkoxy, $(C_1-C_5)$alkylamino-carboxy$(C_1-C_5)$alkyl, $(C_1-C_5)$alkylaminocarboxy$(C_1-C_5)$alkoxy, or $(C_1-C_8)$oxoalkyl. More specifically, $R^2$ is methyl, ethyl, propyl, butyl, hexyl, 5-pentenyl, 3,3,3-trifluoropropyl, 4,4-difluoropentyl, 3-(cyclopropyl)propyl, 4-(cyclopropyl)butyl, 3-hydroxypropyl, 4-hydroxybutyl, 4-hydroxypentyl, 4-hydroxyhexyl, 5-hydroxyhexyl, 2-hydroxyethoxy, 5-oxohexyl, 3-ethoxypropyl, 4-methoxybutyl, 4-ethoxybutyl, 2-(ethoxy)-ethoxy, 3-methoxypropoxy, 3-ethoxypropoxy, 3-propoxypropoxy, (2-(methoxy)ethoxy)methyl, 3-(2,2,2-trifluoroethylamino)propyl, 3-(formylamino)propyl, 3-(acetylamino)propyl, 3-(propionyl-amino)propyl, 3-(butanoylamino)propyl, 3-((2-methoxypropionyl)amino)propyl, 3-(cyclopropanecarbonylamino)propyl, 3-(trifluoroacetylamino)propyl, 3-(methoxycarbonylamino)propyl, 3-(ethoxycarbonylamino)propyl, 2-(methoxycarbonylamino)ethoxy, 2-(ethoxycarbonylamino)-ethoxy, 3-(methylaminocarbonylamino)propyl, 3-(dimethylaminocarbonyl-amino)propyl, 3-(aminocarbonyl)propyl, 3-(methylaminocarbonyl)propyl, 3-(ethylamino-carbonyl)propyl, methoxymethylcarbonylaminomethyl, or 3-(aminosulfonylamino)propyl, 2-(methoxy)-ethoxy, or 4-(methoxy)-butoxy.

The remaining variables are as described above in the $11^{th}$ specific embodiment.

In a $13^{th}$ specific embodiment, the aspartic protease inhibitor of the present invention is represented by a Structural Formula (If), (Ig) or (Ig), wherein $R^3$, X and p are as described above in the $10^{th}$ specific embodiment.

$R^5$ is hydrogen, methyl, isobutyl, t-butylmethyl, 2,2,2-trifluoroethyl, 2-(trifluoromethyl)propyl, cyclopentylmethyl, cyclohexylmethyl, (3,3-difluorocyclobutyl)methyl, 3,4-difluorocyclopentyl)methyl, 4,4-difluoro-cyclohexylmethyl, (4-methylcyclohexyl)methyl, tert-butoxymethyl, (4-tetrahydropyranyl)methyl, benzyl, (1-fluorocyclohexyl)methyl, (4-fluorocyclohexyl)methyl, 1-hydroxy-2-methylpropyl, (cyclopentyl)(hydroxy)methyl, (cyclohexyl)(hydroxy)methyl, (cycloheptyl)(hydroxy)methyl, (1-hydroxycyclohexyl)methyl, (4-hydroxycyclohexyl)methyl, (4-hydroxy-4-methylcyclohexyl)methyl, 1-adamantylmethyl, (3-noradamantyl)(hydroxy)methyl, 2-methoxy-2-methylpropyl, 2,2-dimethyl-3-methoxypropyl, (3-tetrahydrofuryl)methyl, (3-tetrahydropyranyl)methyl, (4-tetrahydropyranyl)methyl and $R^6$ is hydrogen; or $R^5$ is hydrogen and $R^6$ is methyl, isobutyl, t-butylmethyl, 2,2,2-trifluoroethyl, 2-(trifluoromethyl)propyl, cyclopentylmethyl, cyclohexylmethyl, (3,3-difluorocyclobutyl)methyl, 3,4-difluorocyclopentyl)methyl, 4,4-difluoro-cyclohexylmethyl, (4-methylcyclohexyl)methyl, tert-butoxymethyl, (4-tetrahydropyranyl)methyl, benzyl, (1-fluorocyclohexyl)methyl, (4-fluorocyclohexyl)methyl, 1-hydroxy-2-methylpropyl, (cyclopentyl)(hydroxy)methyl, (cyclohexyl)(hydroxy)methyl, (cycloheptyl)(hydroxy)methyl, (1-hydroxycyclohexyl)methyl, (4-hydroxycyclohexyl)methyl, (4-hydroxy-4-methylcyclohexyl)methyl, 1-adamantylmethyl, (3-noradamantyl)(hydroxy)methyl, 2-methoxy-2-methylpropyl, 2,2-dimethyl-3-methoxypropyl, (3-tetrahydrofuryl)methyl, (3-tetrahydropyranyl)methyl, (4-tetrahydropyranyl)methyl.

Values and specific values for the remainder of the variables are as described in the $12^{th}$ specific embodiment.

More specifically, in $13^{th}$ specific embodiment, $R^4$ is H; $R^3$ is H; $R^5$ is cyclohexylmethyl, 1-adamantylmethyl, (3-tetrahydropyranyl)methyl, (4-tetrahydropyranyl)methyl, (3-oxepanyl)methyl or 6-(4-oxaspiro[2,5]octyl)methyl and $R^6$ is H; or $R^5$ is H and $R^6$ is (3-tetrahydropyranyl)methyl or (3-oxepanyl)methyl;

$R^7$ is methyl, ethyl, propyl or isopropyl;

$R^a$, $R^b$, $R^{a'}$ and $R^{b'}$, for each occurrence, are independently hydrogen, methyl or $R^a$ and $R^b$ attached to a carbon atom taken together are oxo or $R^{a'}$ and $R^{b'}$ attached to a carbon atom taken together are oxo; and $R^9$ is H, methyl or ethyl.

In a $14^{th}$ specific embodiment, the aspartic protease inhibitor of the present invention is represented by a Structural Formula (If), (Ig) or (Ih), wherein $R^3$, X and p are as described above in the $10^{th}$ specific embodiment.

$R^2$ is butoxy, hexyloxy, 2-cyclopropylethoxy, 2-(acetylamino)ethoxy, 2-(propionylamino)ethoxy, aminocarbonylmethoxy, methylamino-carbonylmethoxy, ethylaminocarbonylmethoxy, propylaminocarbonylmethoxy, 2-(methylaminocarbonyl)ethoxy, 2-(ethylaminocarbonyl) ethoxy, 2-(propylaminocarbonyl)ethoxy, or (2-(methoxy) ethoxy)carbonylamino.

$R^1$ is phenyl, 2-thienyl, 3-thienyl, 2-pyridyl, 2-imidazolyl, 2-thiazolyl, 2-benzothienyl, 4-benzofuryl, 4-benzothienyl, 7-benzofuryl, 2,3-dihydro-7-benzofuryl, 7-benzothienyl, 1,3-benzodioxol-4-yl, 7-indazolyl, or 8-quinolinyl each optionally substituted with 1 to 5 substituents independently selected from: fluorine, chlorine, bromine, cyano, methyl, ethyl, isopropyl, t-butyl, isobutyl, trifluoromethyl, allyl, cyclohexyl, cyclohexen-1-yl, cyclopropylethynyl, methoxy, trifluoromethoxy, neopentyloxy, methylthio, allyloxy, cyclopropylmethoxy, 2-(cyclopropyl)ethoxy, cyclopentyloxy, cyclopentylmethoxy, benzyloxy, hydroxyl, aminocarbonyl, methoxycarbonyl, phenyl, phenoxy, benzyloxy, and heteroaryloxy, wherein the phenyl phenoxy, benzyloxy and heteroaryloxy groups are optionally substituted with 1 to 3 substituents independently selected from fluorine, chlorine, cyano, methyl, trifluoromethyl, and aminocarbonyl. More specifically, $R^1$ is phenyl, optionally substituted with 1 to 5 substituents independently selected from: fluorine, chlorine, bromine, cyano, methyl, ethyl, isopropyl, t-butyl, isobutyl, trifluoromethyl, allyl, cyclohexyl, cyclohexen-1-yl, cyclopropylethynyl, methoxy, trifluoromethoxy, neopentyloxy, methylthio, allyloxy, cyclopropylmethoxy, 2-(cyclopropyl) ethoxy, cyclopentyloxy, cyclopentylmethoxy, benzyloxy, hydroxyl, aminocarbonyl, methoxycarbonyl, phenyl, phenoxy, benzyloxy, and heteroaryloxy, wherein the phenyl phenoxy, benzyloxy and heteroaryloxy groups are optionally substituted with 1 to 3 substituents independently selected from fluorine, chlorine, cyano, methyl, trifluoromethyl, and aminocarbonyl. Even more specifically, $R^1$ is phenyl optionally substituted with 1 to 5 substituents independently selected from the group consisting of fluorine, chlorine and methyl.

Values and specific values for the remaining variables are as described above in the 2nd specific embodiment.

In a 15$^{th}$ specific embodiment, the aspartic protease inhibitor of the present invention is represented by a Structural Formula (If), (Ig) or (Ih), wherein $R^3$, X and p are as described above in the 10$^{th}$ specific embodiment.

$R^5$ is hydrogen, methyl, isobutyl, t-butylmethyl, 2,2,2-trifluoroethyl, 2-(trifluoromethyl)propyl, cyclopentylmethyl, cyclohexylmethyl, (3,3-difluorocyclobutyl)methyl, 3,4-difluorocyclopentyl)methyl, 4,4-difluoro-cyclohexylmethyl, (4-methylcyclohexyl)methyl, tert-butoxymethyl, (4-tetrahydropyranyl)methyl, benzyl, (1-fluorocyclohexyl)methyl, (4-fluorocyclohexyl)methyl, 1-hydroxy-2-methylpropyl, (cyclopentyl)(hydroxy)methyl, (cyclohexyl)(hydroxy)methyl, (cycloheptyl)(hydroxy)methyl, (1-hydroxycyclohexyl) methyl, (4-hydroxycyclohexyl)methyl, (4-hydroxy-4-methylcyclohexyl)methyl, 1-adamantylmethyl, (3-noradamantyl) (hydroxy)methyl, 2-methoxy-2-methylpropyl, 2,2-dimethyl-3-methoxypropyl, (3-tetrahydrofuryl)methyl, (3-tetrahydropyranyl)methyl, (4-tetrahydropyranyl)methyl and $R^6$ is hydrogen; or $R^5$ is hydrogen and $R^6$ is methyl, isobutyl, t-butylmethyl, 2,2,2-trifluoroethyl, 2-(trifluoromethyl)propyl, cyclopentylmethyl, cyclohexylmethyl, (3,3-difluorocyclobutyl)methyl, 3,4-difluorocyclopentyl)methyl, 4,4-difluoro-cyclohexylmethyl, (4-methylcyclohexyl)methyl, tert-butoxymethyl, (4-tetrahydropyranyl)methyl, benzyl, (1-fluorocyclohexyl) methyl, (4-fluorocyclohexyl)methyl, 1-hydroxy-2-methylpropyl, (cyclopentyl)(hydroxy)methyl, (cyclohexyl)(hydroxy)methyl, (cycloheptyl)(hydroxy)methyl, (1-hydroxycyclohexyl)methyl, (4-hydroxycyclohexyl)methyl, (4-hydroxy-4-methylcyclohexyl)methyl, 1-adamantylmethyl, (3-noradamantyl)(hydroxy)methyl, 2-methoxy-2-methylpropyl, 2,2-dimethyl-3-methoxypropyl, (3-tetrahydrofuryl)methyl, (3-tetrahydropyranyl)methyl, (4-tetrahydropyranyl)methyl.

Values and specific values of the remainder of the variables are as described in the 14$^{th}$ specific embodiment.

More specifically, in 15$^{th}$ specific embodiment, $R^4$ is H; $R^3$ is H; $R^5$ is cyclohexylmethyl, 1-adamantylmethyl, (3-tetrahydropyranyl)methyl, (4-tetrahydropyranyl)methyl, (3-oxepanyl)methyl or 6-(4-oxaspiro[2,5]octyl)methyl and $R^6$ is H; or $R^5$ is H and $R^6$ is (3-tetrahydropyranyl)methyl or (3-oxepanyl)methyl;

$R^7$ is methyl, ethyl, propyl or isopropyl;

$R^a$, $R^b$, $R^{a'}$ and $R^{b'}$, for each occurrence, are independently hydrogen, methyl or $R^a$ and $R^b$ attached to a carbon atom taken together are oxo or $R^{a'}$ and $R^{b'}$ attached to a carbon atom taken together are oxo; and $R^9$ is H, methyl or ethyl.

In a 16$^{th}$ specific embodiment, the aspartic protease inhibitor of the present invention is represented by a Structural Formula (If), wherein $R^3$, X and p are as described above in the 10$^{th}$ specific embodiment.

$R^2$ is $(C_1-C_5)$alkoxy$(C_1-C_5)$alkyl, $(C_1-C_5)$alkoxy$(C_1-C_5)$ alkoxy, $(C_1-C_5)$alkoxycarbonylamino$(C_1-C_5)$alkyl, or $(C_1-C_5)$alkoxycarbonylamino$(C_1-C_5)$alkoxy. More specifically, $R^2$ is 3-methoxypropoxy, 4-methoxybutyl, 2-(methoxycarbonylamino)ethoxy or 3-(methoxycarbonylamino)propyl.

$R^5$ is hydrogen, methyl, isobutyl, t-butylmethyl, 2,2,2-trifluoroethyl, 2-(trifluoromethyl)propyl, cyclopentylmethyl, cyclohexylmethyl, (3,3-difluorocyclobutyl)methyl, 3,4-difluorocyclopentyl)methyl, 4,4-difluoro-cyclohexylmethyl, (4-methylcyclohexyl)methyl, tert-butoxymethyl, (4-tetrahydropyranyl)methyl, benzyl, (1-fluorocyclohexyl)methyl, (4-fluorocyclohexyl)methyl, 1-hydroxy-2-methylpropyl, (cyclopentyl)(hydroxy)methyl, (cyclohexyl)(hydroxy)methyl, (cycloheptyl)(hydroxy)methyl, (1-hydroxycyclohexyl) methyl, (4-hydroxycyclohexyl)methyl, (4-hydroxy-4-methylcyclohexyl)methyl, 1-adamantylmethyl, (3-noradamantyl) (hydroxy)methyl, 2-methoxy-2-methylpropyl, 2,2-dimethyl-3-methoxypropyl, (3-tetrahydrofuryl)methyl, (3-tetrahydropyranyl)methyl, (4-tetrahydropyranyl)methyl and $R^6$ is hydrogen; or $R^5$ is hydrogen and $R^6$ is methyl, isobutyl, t-butylmethyl, 2,2,2-trifluoroethyl, 2-(trifluoromethyl)propyl, cyclopentylmethyl, cyclohexylmethyl, (3,3-difluorocyclobutyl)methyl, 3,4-difluorocyclopentyl)methyl, 4,4-difluoro-cyclohexylmethyl, (4-methylcyclohexyl)methyl, tert-butoxymethyl, (4-tetrahydropyranyl)methyl, benzyl, (1-fluorocyclohexyl) methyl, (4-fluorocyclohexyl)methyl, 1-hydroxy-2-methylpropyl, (cyclopentyl)(hydroxy)methyl, (cyclohexyl)(hydroxy)methyl, (cycloheptyl)(hydroxy)methyl, (1-hydroxycyclohexyl)methyl, (4-hydroxycyclohexyl)methyl, (4-hydroxy-4-methylcyclohexyl)methyl, 1-adamantylmethyl, (3-noradamantyl)(hydroxy)methyl, 2-methoxy-2-methylpropyl, 2,2-dimethyl-3-methoxypropyl, (3-tetrahydrofuryl)methyl, (3-tetrahydropyranyl)methyl, (4-tetrahydropyranyl)methyl.

$R^1$ is phenyl, 2-thienyl, 3-thienyl, 2-pyridyl, 2-imidazolyl, 2-thiazolyl, 2-benzothienyl, 4-benzofuryl, 4-benzothienyl, 7-benzofuryl, 2,3-dihydro-7-benzofuryl, 7-benzothienyl, 1,3-benzodioxol-4-yl, 7-indazolyl, or 8-quinolinyl each optionally substituted with 1 to 5 substituents independently selected from: fluorine, chlorine, bromine, cyano, methyl, ethyl, isopropyl, t-butyl, isobutyl, trifluoromethyl, allyl, cyclohexyl, cyclohexen-1-yl, cyclopropylethynyl, methoxy, trifluoromethoxy, neopentyloxy, methylthio, allyloxy, cyclopropylmethoxy, 2-(cyclopropyl)ethoxy, cyclopentyloxy, cyclopentylmethoxy, benzyloxy, hydroxyl, aminocarbonyl, methoxycarbonyl, phenyl, phenoxy, benzyloxy, and heteroaryloxy, wherein the phenyl phenoxy, benzyloxy and heteroaryloxy groups are optionally substituted with 1 to 3 substituents independently selected from fluorine, chlorine, cyano, methyl, trifluoromethyl, and aminocarbonyl. More specifically, $R^1$ is phenyl, optionally substituted with 1 to 5 substituents independently selected from: fluorine, chlorine, bromine, cyano, methyl, ethyl, isopropyl, t-butyl, isobutyl, trifluoromethyl, allyl, cyclohexyl, cyclohexen-1-yl, cyclopropylethynyl, methoxy, trifluoromethoxy, neopentyloxy, methylthio, allyloxy, cyclopropylmethoxy, 2-(cyclopropyl)ethoxy, cyclopentyloxy, cyclopentylmethoxy, benzyloxy, hydroxyl, aminocarbonyl, methoxycarbonyl, phenyl, phenoxy, benzyloxy, and heteroaryloxy, wherein the phenyl phenoxy, benzyloxy and heteroaryloxy groups are optionally substituted with 1 to 3 substituents independently selected from fluorine, chlorine, cyano, methyl, trifluoromethyl, and aminocarbonyl. Even more specifically, $R^1$ is phenyl optionally substituted with 1 to 5 substituents independently selected from the group consisting of fluorine, chlorine and methyl.

The remaining variables are as described above in the $2^{nd}$ specific embodiment.

More specifically, in $16^{th}$ specific embodiment, $R^4$ is H; $R^3$ is H; $R^5$ is cyclohexylmethyl, 1-adamantylmethyl, (3-tetrahydropyranyl)methyl, (4-tetrahydropyranyl)methyl, (3-oxepanyl)methyl or 6-(4-oxaspiro[2,5]octyl)methyl and $R^6$ is H; or $R^5$ is H and $R^6$ is (3-tetrahydropyranyl)methyl or (3-oxepanyl)methyl;

$R^7$ is methyl, ethyl, propyl or isopropyl;

$R^a$, $R^b$, $R^{a'}$ and $R^{b'}$, for each occurrence, are independently hydrogen, methyl or $R^a$ and $R^b$ attached to a carbon atom taken together are oxo or $R^{a'}$ and $R^{b'}$ attached to a carbon atom taken together are oxo; and $R^9$ is H, methyl or ethyl.

In a $17^{th}$ specific embodiment, the aspartic protease inhibitor of the present invention is represented by Structural Formulas (Ij) or (Ik), or an enantiomer, a diastereomer or pharmaceutically acceptable salt thereof:

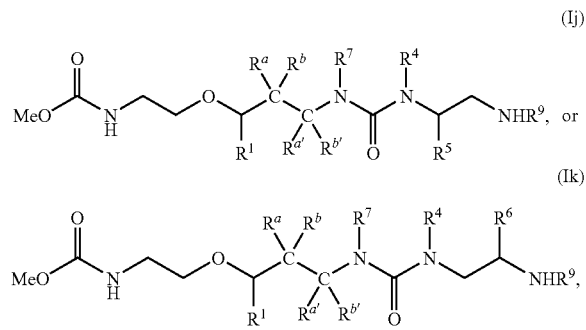

wherein values or specific values for the variables are as described above in the $2^{nd}$ specific embodiment.

In a $18^{th}$ specific embodiment, the aspartic protease inhibitor of the present invention is represented by a Structural Formulas (Ij) or (Ik), wherein $R^1$ is phenyl, 2-thienyl, 3-thienyl, 2-pyridyl, 2-imidazolyl, 2-thiazolyl, 2-benzothienyl, 4-benzofuryl, 4-benzothienyl, 7-benzofuryl, 2,3-dihydro-7-benzofuryl, 7-benzothienyl, 1,3-benzodioxol-4-yl, 7-indazolyl, or 8-quinolinyl each optionally substituted with 1 to 5 substituents independently selected from: fluorine, chlorine, bromine, cyano, methyl, ethyl, isopropyl, t-butyl, isobutyl, trifluoromethyl, allyl, cyclohexyl, cyclohexen-1-yl, cyclopropylethynyl, methoxy, trifluoromethoxy, neopentyloxy, methylthio, allyloxy, cyclopropylmethoxy, 2-(cyclopropyl)ethoxy, cyclopentyloxy, cyclopentylmethoxy, benzyloxy, hydroxyl, aminocarbonyl, methoxycarbonyl, phenyl, phenoxy, benzyloxy, and heteroaryloxy, wherein the phenyl phenoxy, benzyloxy and heteroaryloxy groups are optionally substituted with 1 to 3 substituents independently selected from fluorine, chlorine, cyano, methyl, trifluoromethyl, and aminocarbonyl. More specifically, $R^1$ is phenyl, optionally substituted with 1 to 5 substituents independently selected from:

fluorine, chlorine, bromine, cyano, methyl, ethyl, isopropyl, t-butyl, isobutyl, trifluoromethyl, allyl, cyclohexyl, cyclohexen-1-yl, cyclopropylethynyl, methoxy, trifluoromethoxy, neopentyloxy, methylthio, allyloxy, cyclopropylmethoxy, 2-(cyclopropyl)ethoxy, cyclopentyloxy, cyclopentylmethoxy, benzyloxy, hydroxyl, aminocarbonyl, methoxycarbonyl, phenyl, phenoxy, benzyloxy, and heteroaryloxy, wherein the phenyl phenoxy, benzyloxy and heteroaryloxy groups are optionally substituted with 1 to 3 substituents independently selected from fluorine, chlorine, cyano, methyl, trifluoromethyl, and aminocarbonyl. Even more specifically, $R^1$ is phenyl optionally substituted with 1 to 5 substituents independently selected from the group consisting of fluorine, chlorine and methyl. Values and specific values for the remainder of the variables are as described above in the $2^{nd}$ specific embodiment.

In a $19^{th}$ specific embodiment, the aspartic protease inhibitor of the present invention is represented by a Structural Formulas (Ij) or (Ik), wherein $R^5$ for Structural Formula (Ij) is hydrogen, methyl, isobutyl, t-butylmethyl, 2,2,2-trifluoroethyl, 2-(trifluoromethyl)propyl, cyclopentylmethyl, cyclohexylmethyl, (3,3-difluorocyclobutyl)methyl, 3,4-difluorocyclopentyl)methyl, 4,4-difluoro-cyclohexylmethyl, (4-methylcyclohexyl)methyl, tert-butoxymethyl, (4-tetrahydropyranyl)methyl, benzyl, (1-fluorocyclohexyl)methyl, (4-fluorocyclohexyl)methyl, 1-hydroxy-2-methylpropyl, (cyclopentyl)(hydroxy)methyl, (cyclohexyl)(hydroxy)methyl, (cycloheptyl)(hydroxy)methyl, (1-hydroxycyclohexyl)methyl, (4-hydroxycyclohexyl)methyl, (4-hydroxy-4-methylcyclohexyl)methyl, 1-adamantylmethyl, (3-noradamantyl)(hydroxy)methyl, 2-methoxy-2-methylpropyl, 2,2-dimethyl-3-methoxypropyl, (3-tetrahydrofuryl)methyl, (3-tetrahydropyranyl)methyl, (4-tetrahydropyranyl)methyl. $R^6$ for Structural Formula (Ik) is methyl, isobutyl, t-butylmethyl, 2,2,2-trifluoroethyl, 2-(trifluoromethyl)propyl, cyclopentylmethyl, cyclohexylmethyl, (3,3-difluorocyclobutyl)methyl, 3,4-difluorocyclopentyl)methyl, 4,4-difluoro-cyclohexylmethyl, (4-methylcyclohexyl)methyl, tert-butoxymethyl, (4-tetrahydropyranyl)methyl, benzyl, (1-fluorocyclohexyl)methyl, (4-fluorocyclohexyl)methyl, 1-hydroxy-2-methylpropyl, (cyclopentyl)(hydroxy)methyl, (cyclohexyl)(hydroxy)methyl, (cycloheptyl)(hydroxy)methyl, (1-hydroxycyclohexyl)methyl, (4-hydroxycyclohexyl)methyl, (4-hydroxy-4-methylcyclohexyl)methyl, 1-adamantylmethyl, (3-noradamantyl)(hydroxy)methyl, 2-methoxy-2-methylpropyl, 2,2-dimethyl-3-methoxypropyl, (3-tetrahydrofuryl)methyl, (3-tetrahydropyranyl)methyl, (4-tetrahydropyranyl)methyl;

Values and specific values for the remainder of the variables are as described above in the $18^{th}$ specific embodiment.

More specifically, in $19^{th}$ specific embodiment, $R^4$ is H; $R^3$ is H; $R^5$ for Structural Formula (Ij) is cyclohexylmethyl, 1-adamantylmethyl, (3-tetrahydropyranyl)methyl, (4-tetrahydropyranyl)methyl, (3-oxepanyl)methyl or 6-(4-oxaspiro[2,5]octyl)methyl; $R^6$ for Structural (Ik) is (3-tetrahydropyranyl)methyl or (3-oxepanyl)methyl;

$R^7$ is methyl, ethyl, propyl or isopropyl;

$R^a$, $R^b$, $R^{a'}$ and $R^{b'}$, for each occurrence, are independently hydrogen, methyl or $R^a$ and $R^b$ attached to a carbon atom taken together are oxo or $R^{a'}$ and $R^{b'}$ attached to a carbon atom taken together are oxo; and $R^9$ is H, methyl or ethyl.

In a 20$^{th}$ specific embodiment, the aspartic protease inhibitor of the present invention is represented by a Structural Formulas (II):

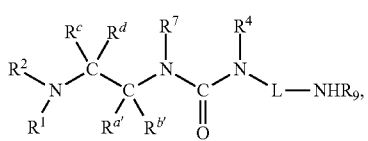

or an enantiomer, a diastereomer or a pharmaceutically acceptable salt thereof, wherein $R^c$ and $R^d$ are independently H, (C1-C6)alkyl, or halo(C1-C6)alkyl. $R^2$ is $(C_1-C_8)$alkyl, $(C_3-C_7)$cycloalkylalkyl, fluoro$(C_1-C_8)$alkyl, fluoro$(C_3-C_7)$-cycloalkylalkyl, hydroxy$(C_1-C_8)$alkyl, $(C_1-C_5)$alkoxy$(C_1-C_5)$alkyl, halo$(C_1-C_5)$alkylamino$(C_1-C_5)$allyl, $(C_1-C_5)$alkoxy$(C_1-C_5)$hydroxyalkyl, $(C_3-C_4)$cycloalkoxy$(C_1-C_5)$alkyl, fluoro$(C_1-C_5)$alkoxy$(C_1-C_5)$alkyl, fluoro$(C_3-C_4)$cycloalkoxy$(C_1-C_5)$alkyl, $(C_1-C_5)$alkylthio$(C_1-C_5)$alkyl, $(C_1-C_3)$alkoxy$(C_1-C_3)$alkoxy$(C_1-C_3)$alkyl, fluoro$(C_1-C_3)$-alkoxy$(C_1-C_3)$alkoxy$(C_1-C_3)$alkyl, aminocarbonylamino$(C_1-C_8)$alkyl, $(C_1-C_5)$alkanoylamino$(C_1-C_5)$alkyl, $(C_1-C_5)$alkanoylamino$(C_1-C_5)$alkoxy, fluoro$(C_1-C_5)$alkanoylamino$(C_1-C_5)$alkyl, $(C_1-C_3)$alkoxy$(C_1-C_5)$alkanoylamino$(C_1-C_5)$alkyl, $(C_3-C_4)$-cycloalkanecarbonylamino$(C_1-C_5)$alkyl, aminosulfonylamino$(C_1-C_8)$alkyl, $(C_1-C_5)$alkanesulfonylamino$(C_1-C_5)$alkyl, formylamino$(C_1-C_5)$alkyl, $(C_1-C_5)$alkoxycarbonylamino$(C_1-C_5)$alkyl, $(C_1-C_5)$alkylaminocarbonylamino$(C_1-C_5)$alkyl, $(C_1-C_5)$alkylaminocarbonylamino$(C_1-C_5)$alkyl, aminocarbonyl$(C_1-C_5)$alkyl, aminocarbonyl$(C_1-C_5)$alkoxy, $(C_1-C_5)$alkylaminocarbonyl$(C_1-C_5)$alkyl, aminocarboxy$(C_1-C_5)$alkyl, $(C_1-C_5)$alkylamino-carboxy$(C_1-C_5)$alkyl or $(C_1-C_8)$oxoalkyl.

Values and specific values of the remainder of the variables are as described above in the 2$^{nd}$ specific embodiment.

In a 21$^{st}$ specific embodiment, the aspartic protease inhibitor of the present invention is represented by a Structural Formulas (II) or an enantiomer, a diastereomer or a pharmaceutically acceptable salt thereof, wherein:

$R^1$ is phenyl, 2-thienyl, 3-thienyl, 2-pyridyl, 2-imidazolyl, 2-thiazolyl, 2-benzothienyl, 4-benzofuryl, 4-benzothienyl, 7-benzofuryl, 2,3-dihydro-7-benzofuryl, 7-benzothienyl, 1,3-benzodioxol-4-yl, 7-indazolyl, or 8-quinolinyl each optionally substituted with 1 to 5 substituents independently selected from: fluorine, chlorine, bromine, cyano, methyl, ethyl, isopropyl, t-butyl, isobutyl, trifluoromethyl, allyl, cyclohexyl, cyclohexen-1-yl, cyclopropylethynyl, methoxy, trifluoromethoxy, neopentyloxy, methylthio, allyloxy, cyclopropylmethoxy, 2-(cyclopropyl)ethoxy, cyclopentyloxy, cyclopentylmethoxy, benzyloxy, hydroxyl, aminocarbonyl, methoxycarbonyl, phenyl, phenoxy, benzyloxy, and heteroaryloxy, wherein the phenyl phenoxy, benzyloxy and heteroaryloxy groups are optionally substituted with 1 to 3 substituents independently selected from fluorine, chlorine, cyano, methyl, trifluoromethyl, and aminocarbonyl. More specifically, $R^1$ is phenyl, optionally substituted with 1 to 5 substituents independently selected from: fluorine, chlorine, bromine, cyano, methyl, ethyl, isopropyl, t-butyl, isobutyl, trifluoromethyl, allyl, cyclohexyl, cyclohexen-1-yl, cyclopropylethynyl, methoxy, trifluoromethoxy, neopentyloxy, methylthio, allyloxy, cyclopropylmethoxy, 2-(cyclopropyl)ethoxy, cyclopentyloxy, cyclopentylmethoxy, benzyloxy, hydroxyl, aminocarbonyl, methoxycarbonyl, phenyl, phenoxy, benzyloxy, and heteroaryloxy, wherein the phenyl phenoxy, benzyloxy and heteroaryloxy groups are optionally substituted with 1 to 3 substituents independently selected from fluorine, chlorine, cyano, methyl, trifluoromethyl, and aminocarbonyl. Even more specifically, $R^1$ is phenyl optionally substituted with 1 to 5 substituents independently selected from the group consisting of fluorine, chlorine and methyl.

Values and specific values for the remainder of the variables are as described above in the 20$^{th}$ specific embodiment.

In a 22$^{nd}$ specific embodiment, the aspartic protease inhibitor of the present invention is represented by a Structural Formulas (II) or an enantiomer, a diastereomer or a pharmaceutically acceptable salt thereof, wherein:

$R^5$ is hydrogen, methyl, isobutyl, t-butylmethyl, 2,2,2-trifluoroethyl, 2-(trifluoromethyl)propyl, cyclopentylmethyl, cyclohexylmethyl, (3,3-difluorocyclobutyl)methyl, 3,4-difluorocyclopentyl)methyl, 4,4-difluoro-cyclohexylmethyl, (4-methylcyclohexyl)methyl, tert-butoxymethyl, (4-tetrahydropyranyl)methyl, benzyl, (1-fluorocyclohexyl)methyl, (4-fluorocyclohexyl)methyl, 1-hydroxy-2-methylpropyl, (cyclopentyl)(hydroxy)methyl, (cyclohexyl)(hydroxy)methyl, (cycloheptyl)(hydroxy)methyl, (1-hydroxycyclohexyl)methyl, (4-hydroxycyclohexyl)methyl, (4-hydroxy-4-methylcyclohexyl)methyl, 1-adamantylmethyl, (3-noradamantyl)(hydroxy)methyl, 2-methoxy-2-methylpropyl, 2,2-dimethyl-3-methoxypropyl, (3-tetrahydrofuryl)methyl, (3-tetrahydropyranyl)methyl, (4-tetrahydropyranyl)methyl and $R^6$ is hydrogen; or $R^5$ is hydrogen and $R^6$ is methyl, isobutyl, t-butylmethyl, 2,2,2-trifluoroethyl, 2-(trifluoromethyl)propyl, cyclopentylmethyl, cyclohexylmethyl, (3,3-difluorocyclobutyl)methyl, 3,4-difluorocyclopentyl)methyl, 4,4-difluoro-cyclohexylmethyl, (4-methylcyclohexyl)methyl, tert-butoxymethyl, (4-.tetrahydropyranyl)methyl, benzyl, (1-fluorocyclohexyl)methyl, (4-fluorocyclohexyl)methyl, 1-hydroxy-2-methylpropyl, (cyclopentyl)(hydroxy)methyl, (cyclohexyl)(hydroxy)methyl, (cycloheptyl)(hydroxy)methyl, (1-hydroxycyclohexyl)methyl, (4-hydroxycyclohexyl)methyl, (4-hydroxy-4-methylcyclohexyl)methyl, 1-adamantylmethyl, (3-noradamantyl)(hydroxy)methyl, 2-methoxy-2-methylpropyl, 2,2-dimethyl-3-methoxypropyl, (3-tetrahydrofuryl)methyl, (3-tetrahydropyranyl)methyl, (4-tetrahydropyranyl)methyl.

Values and specific values of the remainder of the variables are as described above in the 21$^{st}$ specific embodiment.

More specifically, in 22$^{nd}$ specific embodiment, $R^4$ is H; $R^3$ is H; $R^5$ is cyclohexylmethyl, 1-adamantylmethyl, (3-tetrahydropyranyl)methyl, (4-tetrahydropyranyl)methyl, (3-oxepanyl)methyl or 6-(4-oxaspiro[2,5]octyl)methyl and $R^6$ is H; or $R^5$ is H and $R^6$ is (3-tetrahydropyranyl)methyl or (3-oxepanyl)methyl;

$R^7$ is methyl, ethyl, propyl or isopropyl;

$R^a$, $R^b$, $R^{a'}$ and $R^{b'}$, for each occurrence, are independently hydrogen, methyl or $R^a$ and $R^b$ attached to a carbon atom taken together are oxo or $R^{a'}$ and $R^{b'}$ attached to a carbon atom taken together are oxo; and $R^9$ is H, methyl or ethyl.

In a 23$^{rd}$ specific embodiment, the aspartic protease inhibitor of the present invention is represented by a Structural Formulas (Ii) or an enantiomer, a diastereomer or a pharmaceutically acceptable salt thereof, wherein $R^2$ is $(C_1-C_5)$alkoxy$(C_1-C_5)$alkyl or $(C_1-C_5)$alkoxycarbonylamino$(C_1-C_5)$alkyl. More specifically, $R^2$ is 4-methoxybutyl or 3-(methoxycarbonylamino)propyl.

Values or specific values for the remainder of the variables are as described above in the $22^{nd}$ specific embodiment.

More specifically, in $23^{rd}$ specific embodiment, $R^4$ is H; $R^3$ is H; $R^5$ is cyclohexylmethyl, 1-adamantylmethyl, (3-tetrahydropyranyl)methyl, (4-tetrahydropyranyl)methyl, (3-oxepanyl)methyl or 6-(4-oxaspiro[2,5]octyl)methyl and $R^6$ is H; or $R^5$ is H and $R^6$ is (3-tetrahydropyranyl)methyl or (3-oxepanyl)methyl;

$R^7$ is methyl, ethyl, propyl or isopropyl;

$R^a$, $R^b$, $R^{a'}$ and $R^{b'}$, for each occurrence, are independently hydrogen, methyl or $R^a$ and $R^b$ attached to a carbon atom taken together are oxo or $R^{a'}$ and $R^{b'}$ attached to a carbon atom taken together are oxo; and $R^9$ is H, methyl or ethyl.

In one embodiment, the aspartic protease inhibitor of the present invention is each of the following compounds or their enantiomers, diastereomers, or pharmaceutically acceptable salts:

| Example No. | Structure | Name |
|---|---|---|
| 1-isomer 1 | 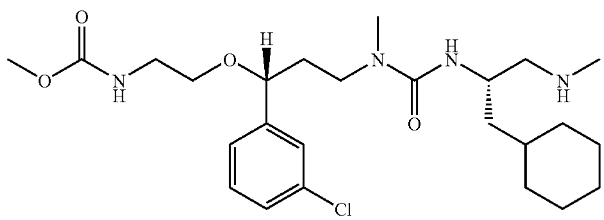 | methyl (4S,10R)-10-(3-chlorophenyl)-4-(cyclohexylmethyl)-7-methyl-6-oxo-11-oxa-2,5,7-triazatridecan-13-ylcarbamate |
| 1-isomer 2 | 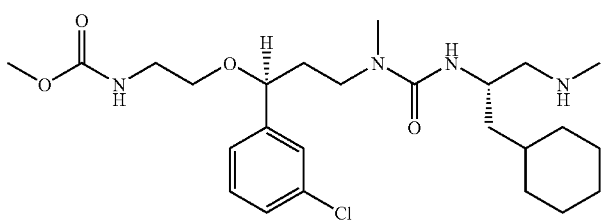 | methyl (4S,10S)-10-(3-chlorophenyl)-4-(cyclohexylmethyl)-7-methyl-6-oxo-11-oxa-2,5,7-triazatridecan-13-ylcarbamate |
| 2 | 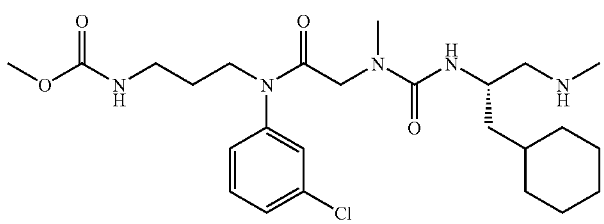 | (S)-methyl 10-(3-chlorophenyl)-4-(cyclohexylmethyl)-7-methyl-6,9-dioxo-2,5,7,10-tetraazatridecan-13-ylcarbamate |
| 3 | 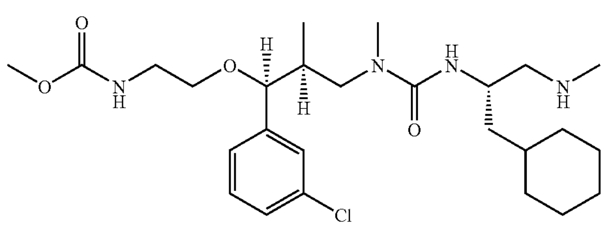 | methyl (4S,9S,10S)-10-(3-chlorophenyl)-4-(cyclohexylmethyl)-7,9-dimethyl-6-oxo-11-oxa-2,5,7-triazatridecan-13-ylcarbamate |
| 4 | 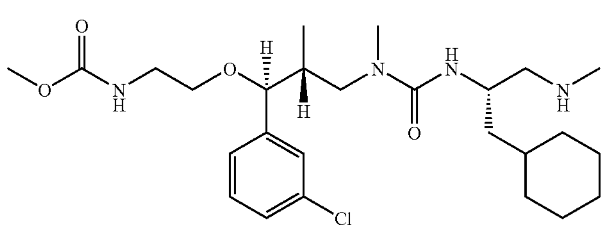 | methyl (4S,9R,10S)-10-(3-chlorophenyl)-4-(cyclohexylmethyl)-7,9-dimethyl-6-oxo-11-oxa-2,5,7-triazatridecan-13-ylcarbamate |

-continued

| Example No. | Structure | Name |
|---|---|---|
| 5 | 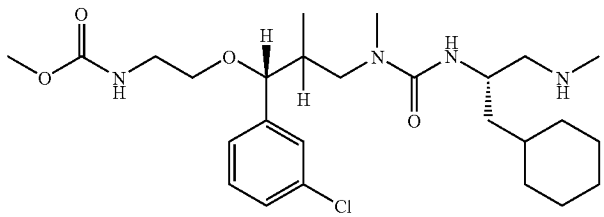 | methyl (4S,10R)-10-(3-chlorophenyl)-4-(cyclohexylmethyl)-7,9-dimethyl-6-oxo-11-oxa-2,5,7-triazatridecan-13-ylcarbamate |
| 6 | 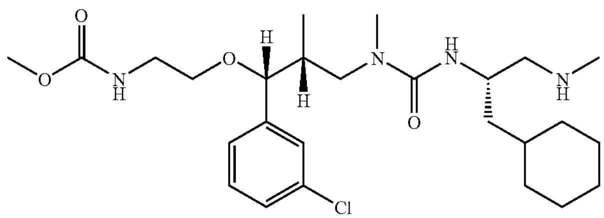 | methyl (4S,9R,10R)-10-(3-chlorophenyl)-4-(cyclohexylmethyl)-7,9-dimethyl-6-oxo-11-oxa-2,5,7-triazatridecan-13-ylcarbamate |
| 7 | 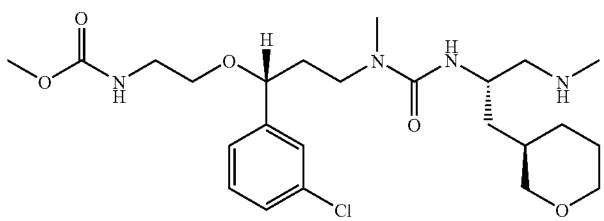 | methyl (4S,10R)-10-(3-chlorophenyl)-7-methyl-6-oxo-4-(((R)-tetrahydro-2H-pyran-3-yl)methyl)-11-oxa-2,5,7-triazatridecan-13-ylcarbamate |
| 8 | 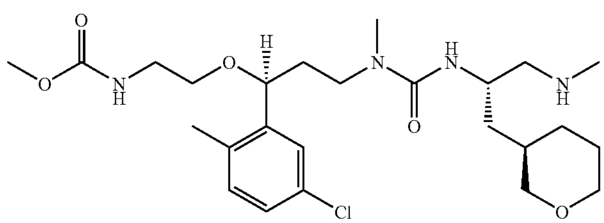 | methyl (4S,10S)-10-(5-chloro-2-methylphenyl)-7-methyl-6-oxo-4-(((R)-tetrahydro-2H-pyran-3-yl)methyl)-11-oxa-2,5,7-triazatridecan-13-ylcarbamate |
| 9 | 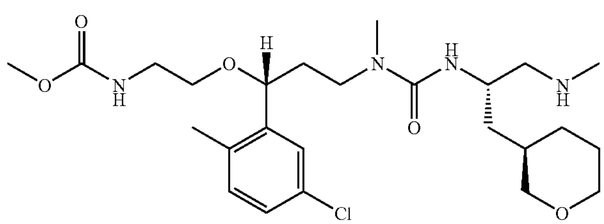 | methyl (4S,10R)-10-(5-chloro-2-methylphenyl)-7-methyl-6-oxo-4-(((R)-tetrahydro-2H-pyran-3-yl)methyl)-11-oxa-2,5,7-triazatridecan-13-ylcarbamate |
| 10 | 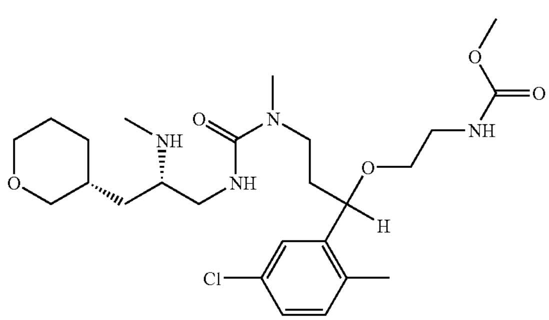 | methyl (3S)-10-(5-chloro-2-methylphenyl)-7-methyl-6-oxo-3-(((R)-tetrahydro-2H-pyran-3-yl)methyl)-11-oxa-2,5,7-triazatridecan-13-ylcarbamate |

-continued

| Example No. | Structure | Name |
|---|---|---|
| 11 | 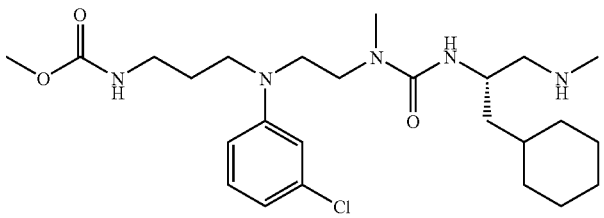 | (S)-methyl 10-(3-chlorophenyl)-4-(cyclohexylmethyl)-7-methyl-6-oxo-2,5,7,10-tetraazatridecan-13-ylcarbamate |
| 12 | 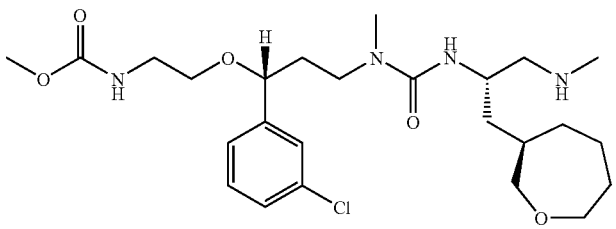 | methyl (4S,10R)-10-(3-chlorophenyl)-7-methyl-4-((R)-oxepan-3-ylmethyl)-6-oxo-11-oxa-2,5,7-triazatridecan-13-ylcarbamate |
| 13 | 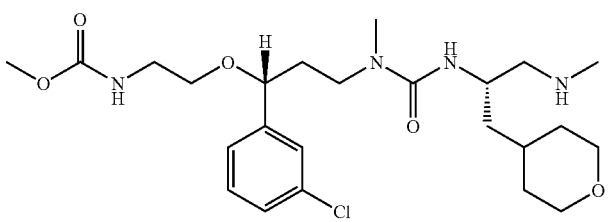 | methyl (4S,10R)-10-(3-chlorophenyl)-7-methyl-6-oxo-4-((tetrahydro-2H-pyran-4-yl)methyl)-11-oxa-2,5,7-triazatridecan-13-ylcarbamate |
| 14 | 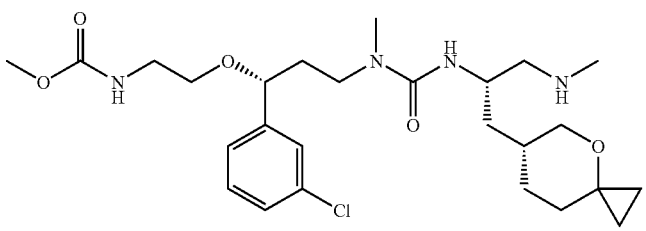 | methyl (4S,10R)-10-(3-chlorophenyl)-7-methyl-6-oxo-4-(((R)-4-oxaspiro[2.5]octan-6-yl)methyl)-11-oxa-2,5,7-triazatridecan-13-ylcarbamate |
| 15 | 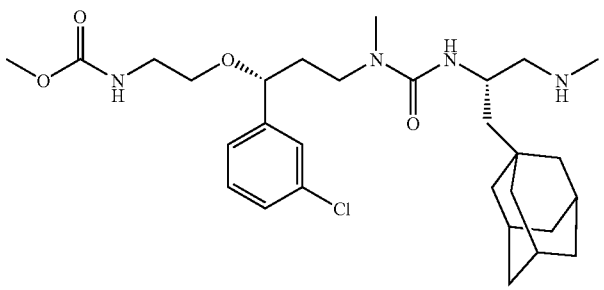 | methyl (4S,10R)-10-(3-chlorophenyl)-4-(1-adamantylmethyl)-7-methyl-6-oxo-11-oxa-2,5,7-triazatridecan-13-ylcarbamate |
| 16 | 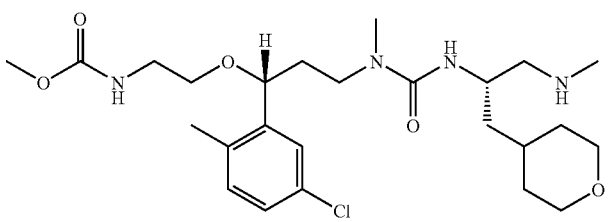 | methyl (4S,10R)-10-(5-chloro-2-methylphenyl)-7-methyl-6-oxo-4-((tetrahydro-2H-pyran-4-yl)methyl)-11-oxa-2,5,7-triazatridecan-13-ylcarbamate |

-continued

| Example No. | Structure | Name |
|---|---|---|
| 17 | 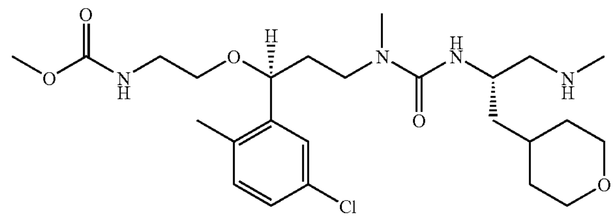 | methyl (4S,10S)-10-(5-chloro-2-methylphenyl)-7-methyl-6-oxo-4-((tetrahydro-2H-pyran-4-yl)methyl)-11-oxa-2,5,7-triazatridecan-13-ylcarbamate |
| 18 | 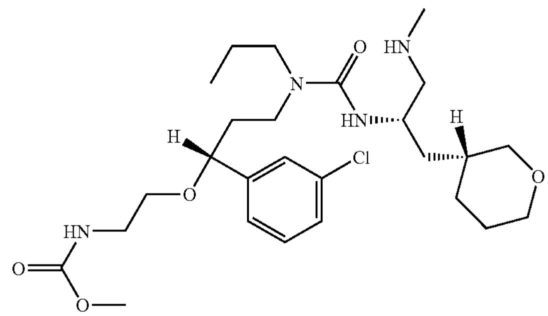 | methyl (4S,10R)-10-(3-chlorophenyl)-7-ethyl-6-oxo-4-(((R)-tetrahydro-2H-pyran-3-yl)methyl)-11-oxa-2,5,7-triazatridecan-13-ylcarbamate |
| 19 | 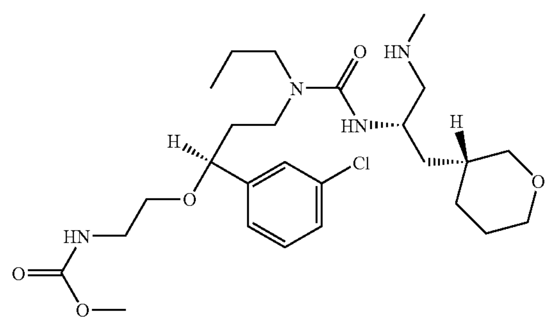 | methyl (4S,10S)-10-(3-chlorophenyl)-7-ethyl-6-oxo-4-(((R)-tetrahydro-2H-pyran-3-yl)methyl)-11-oxa-2,5,7-triazatridecan-13-ylcarbamate |
| 20 | 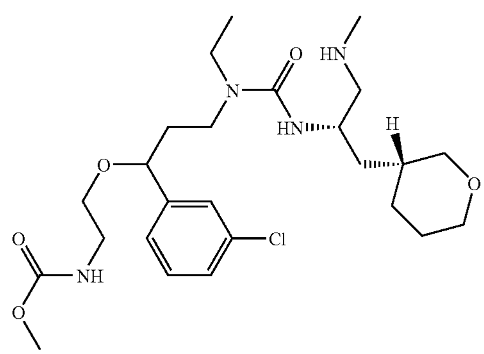 | methyl (4S)-10-(3-chlorophenyl)-7-ethyl-6-oxo-4-(((R)-tetrahydro-2H-pyran-3-yl)methyl)-11-oxa-2,5,7-triazatridecan-13-ylcarbamate |
| 21 | 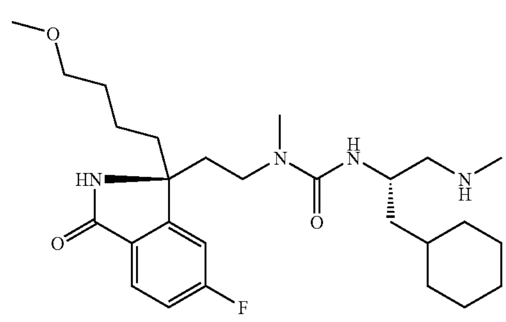 | 3-((S)-1-cyclohexyl-3-(methylamino)propan-2-yl)-1-(2-((S)-6-fluoro-1-(4-methoxybutyl)-3-oxoisoindolin-1-yl)ethyl)-1-methylurea |

| Example No. | Structure | Name |
|---|---|---|
| 22 | 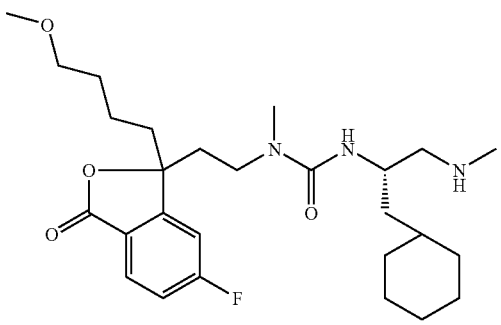 | 3-((S)-1-cyclohexyl-3-(methylamino)propan-2-yl)-1-(2-(6-fluoro-1-(4-methoxybutyl)-3-oxo-1,3-dihydroisobenzofuran-1-yl)ethyl)-1-methylurea |
| 23 | 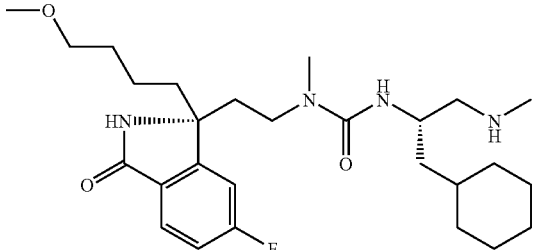 | 3-((S)-1-cyclohexyl-3-(methylamino)propan-2-yl)-1-(2-((S)-6-fluoro-1-(4-methoxybutyl)-3-oxoisoindolin-1-yl)ethyl)-1-methylurea |
| 24 | 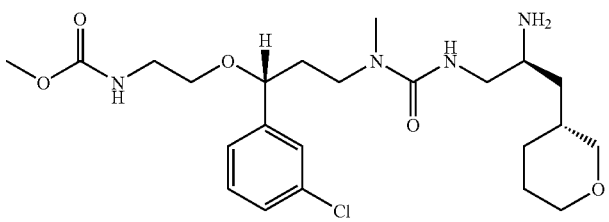 | methyl 2-((R)-3-(3-((S)-2-amino-3-((R)-tetrahydro-2H-pyran-3-yl)propyl)-1-methylureido)-1-(3-chlorophenyl)propoxy)ethyl carbamate |
| 25 | 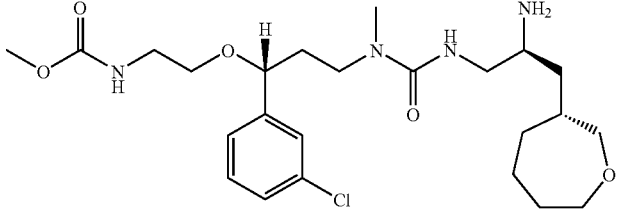 | methyl 2-((R)-3-(3-((S)-2-amino-3-((R)-oxepan-3-yl)propyl)-1-methylureido)-1-(3-chlorophenyl)propoxy)ethyl-carbamate |
| 26 | 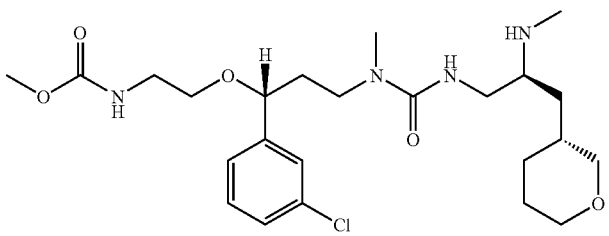 | methyl (3S,10R)-10-(3-chlorophenyl)-7-methyl-6-oxo-3-(((R)-tetrahydro-2H-pyran-3-yl)methyl)-11-oxa-2,5,7-triazatridecan-13-ylcarbamate |
| 27 | 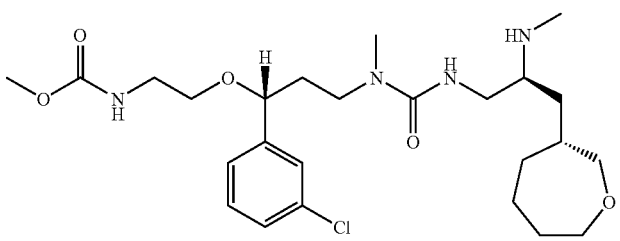 | methyl (3S,10R)-10-(3-chlorophenyl)-7-methyl-3-((R)-oxepan-3-ylmethyl)-6-oxo-11-oxa-2,5,7-triazatridecan-13-ylcarbamate |

| Example No. | Structure | Name |
|---|---|---|
| 28 | 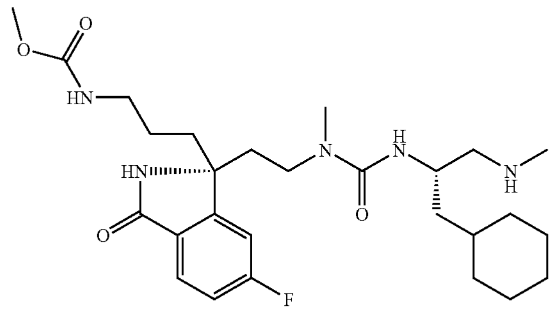 | methyl 3-((R)-1-(2-(3-((S)-1-cyclohexyl-3-(methylamino)propan-2-yl)-1-methylureido)ethyl)-6-fluoro-3-oxoisoindolin-1-yl)propylcarbamate |
| 29 | 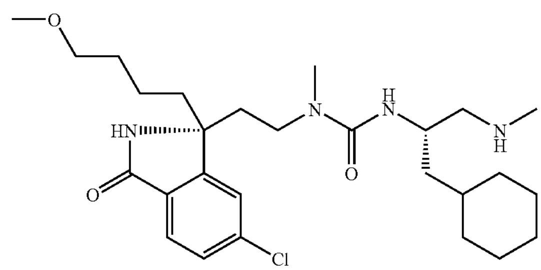 | 1-(2-((R)-6-chloro-1-(4-methoxybutyl)-3-oxoisoindolin-1-yl)ethyl)-3-((S)-1-cyclohexyl-3-(methylamino)propan-2-yl)-1-methylurea |
| 30 | 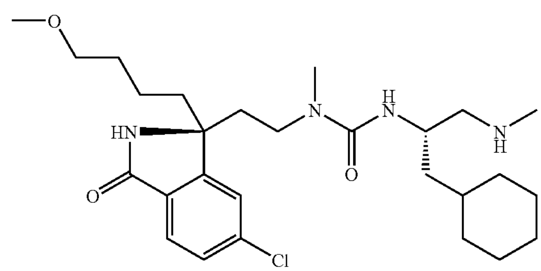 | 1-(2-((S)-6-chloro-1-(4-methoxybutyl)-3-oxoisoindolin-1-yl)ethyl)-3-((S)-1-cyclohexyl-3-(methylamino)propan-2-yl)-1-methylurea |
| 31 | 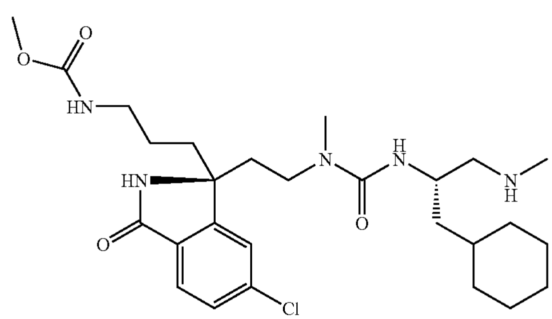 | methyl 3-((S)-6-chloro-1-(2-(3-((S)-1-cyclohexyl-3-(methylamino)propan-2-yl)-1-methylureido)ethyl)-3-oxoisoindolin-1-yl)propylcarbamate |
| 32 | 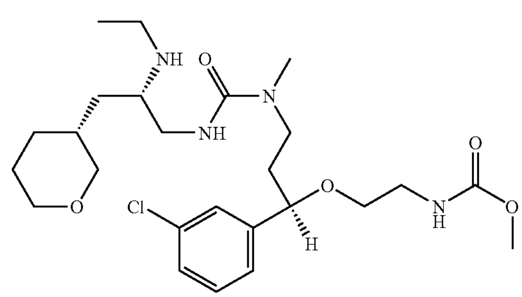 | methyl (4S,11R)-11-(3-chlorophenyl)-8-methyl-7-oxo-4-(((R)-tetrahydro-2H-pyran-3-yl)methyl)-12-oxa-3,6,8-triazatetradecan-14-ylcarbamate |

-continued

| Example No. | Structure | Name |
|---|---|---|
| 33 | 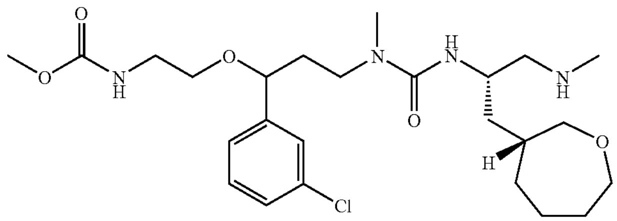 | methyl (4S)-10-(3-chlorophenyl)-7-methyl-4-((R)-oxepan-3-ylmethyl)-6-oxo-11-oxa-2,5,7-triazatridecan-13-ylcarbamate |
| 34 | 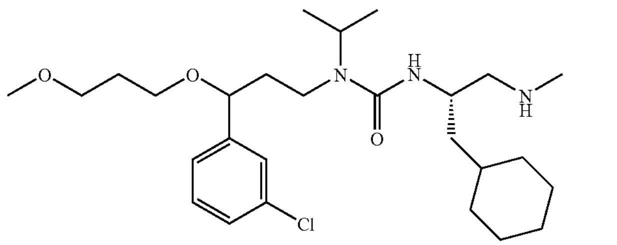 | 1-(3-(3-chlorophenyl)-3-(3-methoxypropoxy)propyl)-3-((S)-1-cyclohexyl-3-(methylamino)propan-2-yl)-1-isopropylurea |
| 35 | 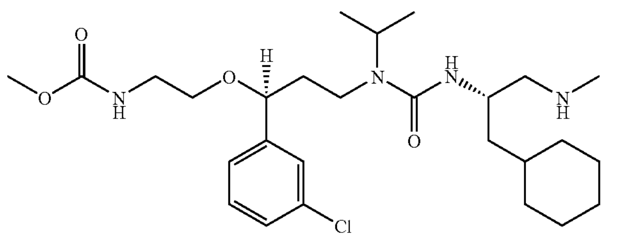 | methyl (4S,10S)-10-(3-chlorophenyl)-4-(cyclohexylmethyl)-7-isopropyl-6-oxo-11-oxa-2,5,7-triazatridecan-13-ylcarbamate |
| 36 | 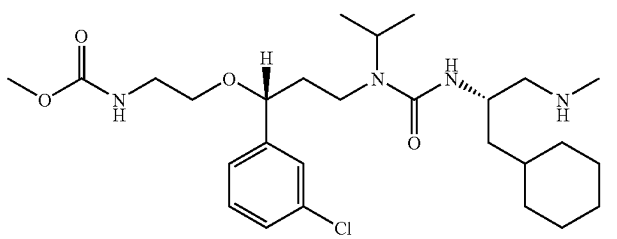 | methyl (4S,10R)-10-(3-chlorophenyl)-4-(cyclohexylmethyl)-7-isopropyl-6-oxo-11-oxa-2,5,7-triazatridecan-13-ylcarbamate |
| 37 | 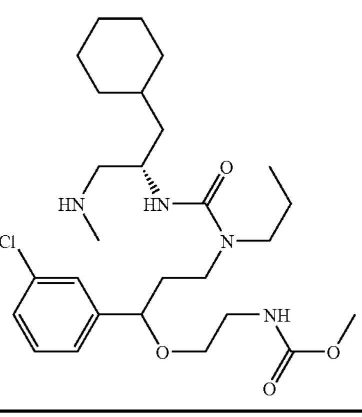 | methyl (4S)-10-(3-chlorophenyl)-4-(cyclohexylmethyl)-6-oxo-7-propyl-11-oxa-2,5,7-triazatridecan-13-ylcarbamate |

In another embodiment, preferred aspartic protease inhibitor of the present invention is each of the following compounds or their enantiomers, diastereomers, or pharmaceutically acceptable salts:

| Example No. | Name |
|---|---|
| 1 isomer 1 | methyl (4S,10R)-10-(3-chlorophenyl)-4-(cyclohexylmethyl)-7-methyl-6-oxo-11-oxa-2,5,7-triazatridecan-13-ylcarbamate |
| 4 | methyl (4S,9R,10S)-10-(3-chlorophenyl)-4-(cyclohexylmethyl)-7,9-dimethyl-6-oxo-11-oxa-2,5,7-triazatridecan-13-ylcarbamate |
| 5 | methyl (4S,10R)-10-(3-chlorophenyl)-4-(cyclohexylmethyl)-7,9-dimethyl-6-oxo-11-oxa-2,5,7-triazatridecan-13-ylcarbamate |
| 6 | methyl (4S,9R,10R)-10-(3-chlorophenyl)-4-(cyclohexylmethyl)-7,9-dimethyl-6-oxo-11-oxa-2,5,7-triazatridecan-13-ylcarbamate |
| 7 | methyl (4S,10R)-10-(3-chlorophenyl)-7-methyl-6-oxo-4-(((R)-tetrahydro-2H-pyran-3-yl)methyl)-11-oxa-2,5,7-triazatridecan-13-ylcarbamate |
| 9 | methyl (4S,10R)-10-(5-chloro-2-methylphenyl)-7-methyl-6-oxo-4-(((R)-tetrahydro-2H-pyran-3-yl)methyl)-11-oxa-2,5,7-triazatridecan-13-ylcarbamate |
| 10 | methyl (3S)-10-(5-chloro-2-methylphenyl)-7-methyl-6-oxo-3-(((R)-tetrahydro-2H-pyran-3-yl)methyl)-11-oxa-2,5,7-triazatridecan-13-ylcarbamate |
| 12 | methyl (4S,10R)-10-(3-chlorophenyl)-7-methyl-4-((R)-oxepan-3-ylmethyl)-6-oxo-11-oxa-2,5,7-triazatridecan-13-ylcarbamate |
| 13 | methyl (4S,10R)-10-(3-chlorophenyl)-7-methyl-6-oxo-4-((tetrahydro-2H-pyran-4-yl)methyl)-11-oxa-2,5,7-triazatridecan-13-ylcarbamate |
| 14 | methyl (4S,10R)-10-(3-chlorophenyl)-7-methyl-6-oxo-4-(((R)-4-oxaspiro[2.5]octan-6-yl)methyl)-11-oxa-2,5,7-triazatridecan-13-ylcarbamate |
| 15 | methyl (4S,10R)-10-(3-chlorophenyl)-4-((1-adamantyl)methyl)-7-methyl-6-oxo-11-oxa-2,5,7-triazatridecan-13-ylcarbamate |
| 17 | methyl (4S,10S)-10-(5-chloro-2-methylphenyl)-7-methyl-6-oxo-4-((tetrahydro-2H-pyran-4-yl)methyl)-11-oxa-2,5,7-triazatridecan-13-ylcarbamate |
| 18 | methyl (4S,10R)-10-(3-chlorophenyl)-7-ethyl-6-oxo-4-(((R)-tetrahydro-2H-pyran-3-yl)methyl)-11-oxa-2,5,7-triazatridecan-13-ylcarbamate |
| 20 | methyl (4S)-10-(3-chlorophenyl)-7-ethyl-6-oxo-4-(((R)-tetrahydro-2H-pyran-3-yl)methyl)-11-oxa-2,5,7-triazatridecan-13-ylcarbamate |
| 21 | 3-((S)-1-cyclohexyl-3-(methylamino)propan-2-yl)-1-(2-((S)-6-fluoro-1-(4-methoxybutyl)-3-oxoisoindolin-1-yl)ethyl)-1-methylurea |
| 24 | methyl 2-((R)-3-(3-((S)-2-amino-3-((R)-tetrahydro-2H-pyran-3-yl)propyl)-1-methylureido)-1-(3-chlorophenyl)propoxy)ethylcarbamate |
| 25 | methyl 2-((R)-3-(3-((S)-2-amino-3-((R)-oxepan-3-yl)propyl)-1-methylureido)-1-(3-chlorophenyl)propoxy)ethylcarbamate |
| 26 | methyl (3S,10R)-10-(3-chlorophenyl)-7-methyl-6-oxo-3-(((R)-tetrahydro-2H-pyran-3-yl)methyl)-11-oxa-2,5,7-triazatridecan-13-ylcarbamate |
| 27 | methyl (3S,10R)-10-(3-chlorophenyl)-7-methyl-3-((R)-oxepan-3-ylmethyl)-6-oxo-11-oxa-2,5,7-triazatridecan-13-ylcarbamate |
| 30 | 1-(2-((S)-6-chloro-1-(4-methoxybutyl)-3-oxoisoindolin-1-yl)ethyl)-3-((S)-1-cyclohexyl-3-(methylamino)propan-2-yl)-1-methylurea |
| 31 | methyl 3-((S)-6-chloro-1-(2-(3-((S)-1-cyclohexyl-3-(methylamino)propan-2-yl)-1-methylureido)ethyl)-3-oxoisoindolin-1-yl)propylcarbamate |
| 33 | methyl (4S)-10-(3-chlorophenyl)-7-methyl-4-((R)-oxepan-3-ylmethyl)-6-oxo-11-oxa-2,5,7-triazatridecan-13-ylcarbamate |
| 36 | methyl (4S,10R)-10-(3-chlorophenyl)-4-(cyclohexylmethyl)-7-isopropyl-6-oxo-11-oxa-2,5,7-triazatridecan-13-ylcarbamate |
| 37 | methyl (4S)-10-(3-chlorophenyl)-4-(cyclohexylmethyl)-6-oxo-7-propyl-11-oxa-2,5,7-triazatridecan-13-ylcarbamate |

In another embodiment, more preferred aspartic protease inhibitor of the present invention is each of the following compounds or their enantiomers, diastereomers, or pharmaceutically acceptable salts:

| Example No. | Name |
|---|---|
| 1 isomer 1 | methyl (4S,10R)-10-(3-chlorophenyl)-4-(cyclohexylmethyl)-7-methyl-6-oxo-11-oxa-2,5,7-triazatridecan-13-ylcarbamate |
| 6 | methyl (4S,9R,10R)-10-(3-chlorophenyl)-4-(cyclohexylmethyl)-7,9-dimethyl-6-oxo-11-oxa-2,5,7-triazatridecan-13-ylcarbamate |
| 7 | methyl (4S,10R)-10-(3-chlorophenyl)-7-methyl-6-oxo-4-(((R)-tetrahydro-2H-pyran-3-yl)methyl)-11-oxa-2,5,7-triazatridecan-13-ylcarbamate |
| 9 | methyl (4S,10R)-10-(5-chloro-2-methylphenyl)-7-methyl-6-oxo-4-(((R)-tetrahydro-2H-pyran-3-yl)methyl)-11-oxa-2,5,7-triazatridecan-13-ylcarbamate |
| 12 | methyl (4S,10R)-10-(3-chlorophenyl)-7-methyl-4-((R)-oxepan-3-ylmethyl)-6-oxo-11-oxa-2,5,7-triazatridecan-13-ylcarbamate |

| Example No. | Name |
|---|---|
| 14 | methyl (4S,10R)-10-(3-chlorophenyl)-7-methyl-6-oxo-4-(((R)-4-oxaspiro[2.5]octan-6-yl)methyl)-11-oxa-2,5,7-triazatridecan-13-ylcarbamate |
| 15 | methyl (4S,10R)-10-(3-chlorophenyl)-4-((1-adamantyl)methyl)-7-methyl-6-oxo-11-oxa-2,5,7-triazatridecan-13-ylcarbamate |
| 18 | methyl (4S,10R)-10-(3-chlorophenyl)-7-ethyl-6-oxo-4-(((R)-tetrahydro-2H-pyran-3-yl)methyl)-11-oxa-2,5,7-triazatridecan-13-ylcarbamate |
| 20 | methyl (4S)-10-(3-chlorophenyl)-7-ethyl-6-oxo-4-(((R)-tetrahydro-2H-pyran-3-yl)methyl)-11-oxa-2,5,7-triazatridecan-13-ylcarbamate |
| 25 | methyl 2-((R)-3-(3-((S)-2-amino-3-((R)-oxepan-3-yl)propyl)-1-methylureido)-1-(3-chlorophenyl)propoxy)ethylcarbamate |
| 27 | methyl (3S,10R)-10-(3-chlorophenyl)-7-methyl-3-((R)-oxepan-3-ylmethyl)-6-oxo-11-oxa-2,5,7-triazatridecan-13-ylcarbamate |
| 30 | 1-(2-((S)-6-chloro-1-(4-methoxybutyl)-3-oxoisoindolin-1-yl)ethyl)-3-((S)-1-cyclohexyl-3-(methylamino)propan-2-yl)-1-methylurea |
| 31 | methyl 3-((S)-6-chloro-1-(2-(3-((S)-1-cyclohexyl-3-(methylamino)propan-2-yl)-1-methylureido)ethyl)-3-oxoisoindolin-1-yl)propylcarbamate |
| 36 | methyl (4S,10R)-10-(3-chlorophenyl)-4-(cyclohexylmethyl)-7-isopropyl-6-oxo-11-oxa-2,5,7-triazatridecan-13-ylcarbamate |
| 37 | methyl (4S)-10-(3-chlorophenyl)-4-(cyclohexylmethyl)-6-oxo-7-propyl-11-oxa-2,5,7-triazatridecan-13-ylcarbamate |

In another embodiment, highly preferred aspartic protease inhibitor of the present invention is each of the following compounds or their enantiomers, diastereomers, or pharmaceutically acceptable salts:

| Example No. | Name |
|---|---|
| 1 isomer 1 | methyl (4S,10R)-10-(3-chlorophenyl)-4-(cyclohexylmethyl)-7-methyl-6-oxo-11-oxa-2,5,7-triazatridecan-13-ylcarbamate |
| 7 | methyl (4S,10R)-10-(3-chlorophenyl)-7-methyl-6-oxo-4-(((R)-tetrahydro-2H-pyran-3-yl)methyl)-11-oxa-2,5,7-triazatridecan-13-ylcarbamate |
| 9 | methyl (4S,10R)-10-(5-chloro-2-methylphenyl)-7-methyl-6-oxo-4-(((R)-tetrahydro-2H-pyran-3-yl)methyl)-11-oxa-2,5,7-triazatridecan-13-ylcarbamate |
| 12 | methyl (4S,10R)-10-(3-chlorophenyl)-7-methyl-4-((R)-oxepan-3-ylmethyl)-6-oxo-11-oxa-2,5,7-triazatridecan-13-ylcarbamate |
| 14 | methyl (4S,10R)-10-(3-chlorophenyl)-7-methyl-6-oxo-4-(((R)-4-oxaspiro[2.5]octan-6-yl)methyl)-11-oxa-2,5,7-triazatridecan-13-ylcarbamate |
| 18 | methyl (4S,10R)-10-(3-chlorophenyl)-7-ethyl-6-oxo-4-(((R)-tetrahydro-2H-pyran-3-yl)methyl)-11-oxa-2,5,7-triazatridecan-13-ylcarbamate |
| 20 | methyl (4S)-10-(3-chlorophenyl)-7-ethyl-6-oxo-4-(((R)-tetrahydro-2H-pyran-3-yl)methyl)-11-oxa-2,5,7-triazatridecan-13-ylcarbamate |

When any variable (e.g., aryl, heterocyclyl, $R^1$, $R^2$, etc.) occurs more than once in a compound, its definition on each occurrence is independent of any other occurrence.

"Alkyl" means a saturated aliphatic branched or straight-chain mono- or di-valent hydrocarbon radical having the specified number of carbon atoms. Thus, "($C_1$-$C_8$)alkyl" means a radical having from 1-8 carbon atoms in a linear or branched arrangement. "($C_1$-$C_6$)alkyl" includes methyl, ethyl, propyl, butyl, pentyl, and hexyl.

"Alkylene" means —$[CH_2]_x$—, wherein x is a positive integer. x is typically a positive integer from 1-10, more typically from 1-5, even more typically 2-4 and more typically yet from 2-3. Alkylene groups are optionally substituted at any one or more substitutable carbon atom, i.e., a carbon atom that is bonded to hydrogen, wherein the hydrogen is replaced with a substituent.

"Alkenylene" is an alkylene group in which at least one single bond connecting adjacent methylene groups has been replaced with a double bond. Alkenylene groups are optionally substituted at any one or more substitutable carbon atom, i.e., a carbon atom that is bonded to hydrogen, wherein the hydrogen is replaced with a substituent.

"Alkynylene" is an alkylene group in which at least one single bond connecting adjacent methylene groups has been replaced with a double bond. Alkynylene groups are optionally substituted at any one or more substitutable carbon atom, i.e., a carbon atom that is bonded to hydrogen, wherein the hydrogen is replaced with a substituent.

"Cycloalkyl" means a saturated aliphatic cyclic hydrocarbon radical having the specified number of carbon atoms. Thus, ($C_3$-$C_7$)cycloalkyl means a radical having from 3-7 carbon atoms arranged in a ring. ($C_3$-$C_7$)cycloalkyl includes cyclopropyl, cyclobutyl, cyclopentyl, cyclohexyl, and cycloheptyl.

Haloalkyl and halocycloalkyl include mono, poly, and perhaloalkyl groups where the halogens are independently selected from fluorine, chlorine, and bromine.

Saturated heterocyclic rings are 4-, 5-, 6-, and 7-membered heterocyclic rings containing 1 to 4 heteroatoms independently selected from N, O, and S, and include pyrrolidine, piperidine, tetrahydrofuran, tetrahydropyran, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, morpholine, thiomorpholine, thiomorpholine 1,1-dioxide, tetrahydro-2H-1,2-thiazine 1,1-dioxide, and isothiazolidine 1,1-dioxide. Oxo substituted saturated heterocyclic rings include tetrahydrothiophene 1-oxide, tetrahydrothiophene 1,1-dioxide, thiomorpholine 1-oxide, thiomorpholine 1,1-dioxide, tetrahydro-2H-1,2-thiazine 1,1-dioxide, and isothiazolidine 1,1-dioxide, pyrrolidin-2-one, piperidin-2-one, piperazin-2-one, and morpholin-2-one.

"Heteroaryl" means a monovalent heteroaromatic monocyclic or polycyclic ring radical containing 1 to 4 heteroatoms independently selected from N, O, and S. Heteroaryl rings include furyl, thienyl, thiophenyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridinyl-N-oxide, pyridazinyl, pyrimidinyl, pyrazinyl, indolizinyl, indolyl, isoindolyl, benzo[b]furyl, benzo[b]thienyl, indazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, 1,2,3-triazolyl, 1,2,4-triazolyl, 1,3,4-oxadiazolyl, 1,2,5-thiadiazolyl, 1,2,5-thiadiazolyl-1-oxide, 1,2,5-thiadiazolyl-1,1-dioxide, 1,2,4-triazinyl, 1,3,5-triazinyl, tetrazolyl, and pteridinyl.

Bicyclic heteroaryl rings are bicyclo[4.4.0] and bicyclo[4,3.0] fused ring systems of which at least one ring is aromatic containing 1 to 4 heteroatoms independently selected from N, O, and S, and include indolizine, indole, isoindole, benzo[b]thiophene, quinoline, isoquinoline, quinazoline, purine, benzothiophene, benzofuran, 2,3-dihydrobenzofuran, cinnoline, phthalazine, benzodioxole, benzimidazole, indazole, benzisoxazole, benzoxazole, and benzothiazole, quinoxaline, 1,8-naphthyridine, and pteridine.

Bicycloalkyl rings are fused, bridged and spiro ring systems and include bicyclo[1.1.0]butane, bicyclo[1.2.0]pentane, bicyclo[2.2.0]hexane, bicyclo[3.2.0]heptane, bicyclo[3.3.0]octane, bicyclo[4.2.0]octane, bicyclo[2.2.1]heptane, bicyclo[2.2.2]octane, bicyclo[3.2.1]octane, bicyclo[3.2.2]nonane, bicyclo[3.3.1]nonane, bicyclo[3.3.2]decane and bicyclo[3.3.3]undecane, spiro[2.2]pentane, spiro[2.3]hexane, spiro[3.3]heptane, spiro[2.4]heptane, spiro[3.4]octane and spiro[2.5]octane.

"Alkoxy" means an alkyl radical attached through an oxygen linking atom. "($C_1$-$C_4$)-alkoxy" includes the methoxy, ethoxy, propoxy, and butoxy.

"Aromatic" means an unsaturated cycloalkyl ring system.

"Aryl" means an aromatic monocyclic or polycyclic ring system. Aryl systems include phenyl, naphthalenyl, fluorenyl, indenyl, azulenyl, and anthracenyl.

"Hetero" refers to the replacement of at least one carbon atom member in a ring system with at least one heteroatom selected from N, S, and O. A hetero ring may have 1, 2, 3, or 4 carbon atom members replaced by a heteroatom.

"Oxo" refers to =O. When an oxo group is a substituent on a carbon atom, they form a carbonyl group (—C(O)—). When one oxo group is a substituent on a sulfur atom, they form a sulfinyl (sulfoxide —S(O)—) group. When two oxo groups are a substituent on a sulfur atom, they form a sulfonyl (sulfone —S(O)$_2$—) group.

"Unsaturated ring" means a ring containing one or more double bonds and include cyclopentene, cyclohexene, cycloheptene, cyclohexadiene, benzene, pyrroline, pyrazole, 4,5-dihydro-1H-imidazole, imidazole, 1,2,3,4-tetrahydropyridine, 1,2,3,6-tetrahydropyridine, pyridine and pyrimidine.

Enantiomers, Diastereomers, and Salts

Certain compounds of Formula I may exist in various stereoisomeric or tautomeric forms. The invention encompasses all such forms, including active compounds in the form of essentially pure enantiomers, racemic mixtures, and tautomers, including forms those not depicted structurally.

The compounds of the invention may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts.

Pharmaceutically acceptable acidic/anionic salts include, the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphospate, polygalacturonate, salicylate, stearate, subacetate, succinate, sulfate, tannate, tartrate, teoclate, tosylate, and triethiodide salts.

The compounds of the invention include pharmaceutically acceptable anionic salt forms, wherein the anionic salts include the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphospate, polygalacturonate, salicylate, stearate, subacetate, succinate, sulfate, tannate, tartrate, teoclate, tosylate, and triethiodide salts.

The anionic salt form of a compound of the invention includes the acetate, bromide, camsylate, chloride, edisylate, fumarate, hydrobromide, hydrochloride, iodide, isethionate, lactate, mesylate, maleate, napsylate, salicylate, sulfate, and tosylate salts.

When a disclosed compound or its pharmaceutically acceptable salt is named or depicted by structure, it is to be understood that solvates or hydrates of the compound or its pharmaceutically acceptable salts are also included. "Solvates" refer to crystalline forms wherein solvent molecules are incorporated into the crystal lattice during crystallization. Solvate may include water or nonaqueous solvents such as ethanol, isopropanol, DMSO, acetic acid, ethanolamine, and EtOAc. Solvates, wherein water is the solvent molecule incorporated into the crystal lattice, are typically referred to as "hydrates." Hydrates include stoichiometric hydrates as well as compositions containing variable amounts of water.

When a disclosed compound or its pharmaceutically acceptable salt is named or depicted by structure, it is to be understood that the compound, including solvates thereof, may exist in crystalline forms, non-crystalline forms or a mixture thereof. The compound or its pharmaceutically acceptable salts or solvates may also exhibit polymorphism (i.e. the capacity to occur in different crystalline forms). These different crystalline forms are typically known as "polymorphs." It is to be understood that when named or depicted by structure, the disclosed compound and its pharmaceutically acceptable salts, solvates or hydrates also include all polymorphs thereof. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. One of ordinary skill in the art will appreciate that different polymorphs may be produced, for example, by changing or adjusting the conditions used in solidifying the compound. For example, changes in temperature, pressure, or solvent may result in different polymorphs. In addition, one polymorph may spontaneously convert to another polymorph under certain conditions.

It may be necessary and/or desirable during synthesis to protect sensitive or reactive groups on any of the molecules concerned. Representative conventional protecting groups are described in T. W. Greene and P. G. M. Wuts "Protective Groups in Organic Synthesis" John Wiley & Sons, Inc., New York 1999. Protecting groups may be added and removed using methods well known in the art.

The invention also includes various isomers and mixtures thereof. "Isomer" refers to compounds that have the same composition and molecular weight but differ in physical and/or chemical properties. The structural difference may be in constitution (geometric isomers) or in the ability to rotate the plane of polarized light (stereoisomers).

Certain of the disclosed aspartic protease inhibitors may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. The symbol "*" in a structural formula represents the presence of a chiral carbon center. "R" and "S" represent the configuration of substituents around one or more chiral carbon atoms. Thus, "R*" and "S*" denote the relative configurations of substituents around one or more chiral carbon atoms. When a chiral center is not defined as R or S, a mixture of both configurations is present.

"Racemate" or "racemic mixture" means a compound of equimolar quantities of two enantiomers, wherein such mixtures exhibit no optical activity; i.e., they do not rotate the plane of polarized light.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration.

Atoms (other than H) attached to a carbocyclic ring may be in a cis or trans configuration. In the "cis" configuration, the substituents are on the same side in relationship to the plane of the ring; in the "trans" configuration, the substituents are on opposite sides in relationship to the plane of the ring. A mixture of "cis" and "trans" species is designated "cis/trans".

The point at which a group or moiety is attached to the remainder of the compound or another group or moiety can be indicated by "∿" which represents "⋯⋯‖‖", "━■" or "___".

"R," "S," "S*," "R*," "E," "Z," "cis," and "trans," indicate configurations relative to the core molecule.

The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid); forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

When a disclosed compound is named or depicted by structure without indicating the stereochemistry, and the inhibitor has at least one chiral center, it is to be understood that the name or structure encompasses one enantiomer of inhibitor free from the corresponding optical isomer, a racemic mixture of the inhibitor and mixtures enriched in one enantiomer relative to its corresponding optical isomer.

When a disclosed aspartic protease inhibitor is named or depicted by structure without indicating the stereochemistry and has at least two chiral centers, it is to be understood that the name or structure encompasses a diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s).

The compounds of the invention are useful for ameliorating or treating disorders or diseases in which decreasing the levels of aspartic protease products is effective in treating the disease state or in treating infections in which the infectious agent depends upon the activity of an aspartic protease. In hypertension, elevated levels of angiotensin I, the product of renin catalyzed cleavage of angiotensinogen are present. Thus, the compounds of the invention can be used in the treatment of hypertension, heart failure such as (acute and chronic) congestive heart failure; left ventricular dysfunction; cardiac hypertrophy; cardiac fibrosis; cardiomyopathy (e.g., diabetic cardiac myopathy and post-infarction cardiac myopathy); supraventricular and ventricular arrhythmias; atrial fibrillation; atrial flutter; detrimental vascular remodeling; myocardial infarction and its sequelae; atherosclerosis; angina (whether unstable or stable); renal failure conditions, such as diabetic nephropathy; glomerulonephritis; renal fibrosis; scleroderma; glomerular sclerosis; microvascular complications, for example, diabetic retinopathy; renal vascular hypertension; vasculopathy; neuropathy; complications resulting from diabetes, including nephropathy, vasculopathy, retinopathy and neuropathy, diseases of the coronary vessels, proteinuria, albumenuria, post-surgical hypertension, metabolic syndrome, obesity, restenosis following angioplasty, eye diseases and associated abnormalities including raised intra-ocular pressure, glaucoma, retinopathy, abnormal vascular growth and remodeling, angiogenesis-related disorders, such as neovascular age related macular degeneration; hyperaldosteronism, anxiety states, and cognitive disorders (Fisher N. D.; Hollenberg N. K. *Expert Opin. Investig. Drugs.* 2001, 10, 417-26).

Elevated levels of βamyloid, the product of the activity of the well-characterized aspartic protease β-secretase (BACE) activity on amyloid precursor protein, are widely believed to be responsible for the development and progression of amyloid plaques in the brains of Alzheimer's disease patients. The secreted aspartic proteases of *Candida albicans* are associated with its pathogenic virulence (Naglik, J. R.; Challacombe, S. J.; Hube, B. *Microbiology and Molecular Biology Reviews* 2003, 67, 400-428). The viruses HIV and HTLV depend on their respective aspartic proteases for viral maturation. *Plasmodium falciparum* uses plasmepsins I and II to degrade hemoglobin.

A pharmaceutical composition of the invention may, alternatively or in addition to a compound of Formula I, comprise a pharmaceutically acceptable salt of a compound of Formula I or a prodrug or pharmaceutically active metabolite of such a compound or salt and one or more pharmaceutically acceptable carriers therefor.

The compositions of the invention are aspartic protease inhibitors. Said compositions contain compounds having a mean inhibition constant ($IC_{50}$) against aspartic proteases of between about 5,000 nM to about 0.01 nM; preferably between about 50 nM to about 0.01 nM; and more preferably between about 5 nM to about 0.01 nM.

The compositions of the invention reduce blood pressure. Said compositions include compounds having an $IC_{50}$ for renin of between about 5,000 nM to about 0.01 nM; preferably between about 50 nM to about 0.01 nM; and more preferably between about 5 nM to about 0.01 nM.

The invention includes a therapeutic method for treating or ameliorating an aspartic protease mediated disorder in a subject in need thereof comprising administering to a subject in need thereof an effective amount of a compound of Formula I, or the enantiomers, diastereomers, or salts thereof or composition thereof.

Administration methods include administering an effective amount (i.e., a therapeutically effective amount) of a compound or composition of the invention at different times during the course of therapy or concurrently in a combination form. The methods of the invention include all known therapeutic treatment regimens.

"Prodrug" means a pharmaceutically acceptable form of an effective derivative of a compound (or a salt thereof) of the invention, wherein the prodrug may be: 1) a relatively active precursor which converts in vivo to a compound of the invention; 2) a relatively inactive precursor which converts in vivo to a compound of the invention; or 3) a relatively less active component of the compound that contributes to therapeutic activity after becoming available in vivo (i.e., as a metabolite). See "Design of Prodrugs", ed. H. Bundgaard, Elsevier, 1985.

"Metabolite" means a pharmaceutically acceptable form of a metabolic derivative of a compound (or a salt thereof) of the invention, wherein the derivative is an active compound that contributes to therapeutic activity after becoming available in vivo.

"Effective amount" means that amount of active compound agent that elicits the desired biological response in a subject. Such response includes alleviation of the symptoms of the disease or disorder being treated. The effective amount of a compound of the invention in such a therapeutic method is from about 10 mg/kg/day to about 0.01 mg/kg/day, preferably from about 0.5 mg/kg/day to 5 mg/kg/day.

The invention includes the use of a compound of the invention for the preparation of a composition for treating or ameliorating an aspartic protease mediated chronic disorder or disease or infection in a subject in need thereof, wherein the composition comprises a mixture one or more compounds of the invention and an optional pharmaceutically acceptable carrier.

"Pharmaceutically acceptable carrier" means compounds and compositions that are of sufficient purity and quality for use in the formulation of a composition of the invention and that, when appropriately administered to an animal or human, do not produce an adverse reaction.

"Aspartic protease mediated disorder or disease" includes disorders or diseases associated with the elevated expression or overexpression of aspartic proteases and conditions that accompany such diseases.

An embodiment of the invention includes administering a renin inhibiting compound of Formula I or composition thereof in a combination therapy (U.S. Pat. No. 5,821,232, U.S. Pat. No. 6,716,875, U.S. Pat. No. 5,663,188, Fossa, A. A.; DePasquale, M. J.; Ringer, L. J.; Winslow, R. L. "Synergistic effect on reduction in blood pressure with coadministration of a renin inhibitor or an angiotensin-converting enzyme inhibitor with an angiotensin II receptor antagonist" *Drug Development Research* 1994, 33(4), 422-8) with one or more additional agents for the treatment of hypertension including α-blockers, β-blockers, calcium channel blockers, diuretics, natriuretics, saluretics, centrally acting antiphypertensives, angiotensin converting enzyme (ACE) inhibitors, dual ACE and neutral endopeptidase (NEP) inhibitors, angiotensin-receptor blockers (ARBs), aldosterone synthase inhibitor, aldosterone-receptor antagonists, or endothelin receptor antagonist.

α-Blockers include doxazosin, prazosin, tamsulosin, and terazosin.

β-Blockers for combination therapy are selected from atenolol, bisoprol, metoprolol, acetutolol, esmolol, celiprolol, taliprolol, acebutolol, oxprenolol, pindolol, propanolol, bupranolol, penbutolol, mepindolol, carteolol, nadolol, carvedilol, and their pharmaceutically acceptable salts.

Calcium channel blockers include dihydropyridines (DHPs) and non-DHPs. The preferred DHPs are selected from the group consisting of amlodipine, felodipine, ryosidine, isradipine, lacidipine, nicardipine, nifedipine, nigulpidine, niludipine, nimodiphine, nisoldipine, nitrendipine, and nivaldipine and their pharmaceutically acceptable salts. Non-DHPs are selected from flunarizine, prenylamine, diltiazem, fendiline, gallopamil, mibefradil, anipamil, tiapamil, and verampimil and their pharmaceutically acceptable salts.

A diuretic is, for example, a thiazide derivative selected from amiloride, chlorothiazide, hydrochlorothiazide, methylchlorothiazide, and chlorothalidon.

ACE inhibitors include alacepril, benazepril, benazaprilat, captopril, ceronapril, cilazapril, delapril, enalapril, enalaprilat, fosinopril, lisinopril, moexipiril, moveltopril, perindopril, quinapril, quinaprilat, ramipril, ramiprilat, spirapril, temocapril, trandolapril, and zofenopril. Preferred ACE inhibitors are benazepril, enalpril, lisinopril, and ramipril.

Dual ACE/NEP inhibitors are, for example, omapatrilat, fasidotril, and fasidotrilat.

Preferred ARBs include candesartan, eprosartan, irbesartan, losartan, olmesartan, tasosartan, telmisartan, and valsartan.

Preferred aldosterone synthase inhibitors are anastrozole, fadrozole, and exemestane.

Preferred aldosterone-receptor antagonists are spironolactone and eplerenone.

A preferred endothelin antagonist is, for example, bosentan, enrasentan, atrasentan, darusentan, sitaxentan, and tezosentan and their pharmaceutically acceptable salts.

An embodiment of the invention includes administering an HIV protease inhibiting compound of Formula I or composition thereof in a combination therapy with one or more additional agents for the treatment of AIDS reverse transcriptase inhibitors, non-nucleoside reverse transcriptase inhibitors, other HIV protease inhibitors, HIV integrase inhibitors, entry inhibitors (including attachment, co-receptor and fusion inhibitors), antisense drugs, and immune stimulators.

Preferred reverse transcriptase inhibitors are zidovudine, didanosine, zalcitabine, stavudine, lamivudine, abacavir, tenofovir, and emtricitabine.

Preferred non-nucleoside reverse transcriptase inhibitors are nevirapine, delaviridine, and efavirenz.

Preferred HIV protease inhibitors are saquinavir, ritonavir, indinavir, nelfinavir, amprenavir, lopinavir, atazanavir, and fosamprenavir.

Preferred HIV integrase inhibitors are L-870,810 and S-1360.

Entry inhibitors include compounds that bind to the CD4 receptor, the CCR5 receptor or the CXCR4 receptor. Specific examples of entry inhibitors include enfuvirtide (a peptidomimetic of the HR2 domain in gp41) and sifurvitide.

A preferred attachment and fusion inhibitor is enfuvirtide.

An embodiment of the invention includes administering β-secretase inhibiting compound of Formula I or composition thereof in a combination therapy with one or more additional agents for the treatment of Alzheimer's disease including tacrine, donepezil, rivastigmine, galantamine, and memantine.

An embodiment of the invention includes administering a plasmepsin inhibiting compound of Formula I or composition thereof in a combination therapy with one or more additional agents for the treatment of malaria including artemisinin, chloroquine, halofantrine, hydroxychloroquine, mefloquine, primaquine, pyrimethamine, quinine, sulfadoxine Combination therapy includes co-administration of the compound of the invention and said other agent, sequential administration of the compound and the other agent, administration of a composition containing the compound and the other agent, or simultaneous administration of separate compositions containing of the compound and the other agent.

The invention further includes the process for making the composition comprising mixing one or more of the present compounds and an optional pharmaceutically acceptable carrier; and includes those compositions resulting from such a process, which process includes conventional pharmaceutical techniques.

The compositions of the invention include ocular, oral, nasal, transdermal, topical with or without occlusion, intravenous (both bolus and infusion), and injection (intraperitoneally, subcutaneously, intramuscularly, intratumorally, or parenterally). The composition may be in a dosage unit such as a tablet, pill, capsule, powder, granule, liposome, ion exchange resin, sterile ocular solution, or ocular delivery device (such as a contact lens and the like facilitating immediate release, timed release, or sustained release), parenteral solution or suspension, metered aerosol or liquid spray, drop, ampoule, auto-injector device, or suppository; for administration ocularly, orally, intranasally, sublingually, parenterally, or rectally, or by inhalation or insufflation.

Compositions of the invention suitable for oral administration include solid forms such as pills, tablets, caplets, capsules (each including immediate release, timed release, and sustained release formulations), granules and powders; and, liquid forms such as solutions, syrups, elixirs, emulsions, and suspensions. Forms useful for ocular administration include sterile solutions or ocular delivery devices. Forms useful for parenteral administration include sterile solutions, emulsions, and suspensions.

The compositions of the invention may be administered in a form suitable for once-weekly or once-monthly administration. For example, an insoluble salt of the active compound may be adapted to provide a depot preparation for intramuscular injection (e.g., a decanoate salt) or to provide a solution for ophthalmic administration.

The dosage form containing the composition of the invention contains a therapeutically effective amount of the active ingredient necessary to provide a therapeutic effect. The composition may contain from about 5,000 mg to about 0.5 mg (preferably, from about 1,000 mg to about 0.5 mg) of a compound of the invention or salt form thereof and may be constituted into any form suitable for the selected mode of administration. The composition may be administered about 1 to about 5 times per day. Daily administration or post-periodic dosing may be employed.

For oral administration, the composition is preferably in the form of a tablet or capsule containing, e.g., 500 to 0.5 milligrams of the active compound. Dosages will vary depending on factors associated with the particular patient being treated (e.g., age, weight, diet, and time of administration), the severity of the condition being treated, the compound being employed, the mode of administration, and the strength of the preparation.

The oral composition is preferably formulated as a homogeneous composition, wherein the active ingredient is dispersed evenly throughout the mixture, which may be readily subdivided into dosage units containing equal amounts of a compound of the invention. Preferably, the compositions are prepared by mixing a compound of the invention (or an enantiomer, a diastereomer or pharmaceutically acceptable salt thereof) with one or more optionally present pharmaceutical carriers (such as a starch, sugar, diluent, granulating agent, lubricant, glidant, binding agent, and disintegrating agent), one or more optionally present inert pharmaceutical excipients (such as water, glycols, oils, alcohols, flavoring agents, preservatives, coloring agents, and syrup), one or more optionally present conventional tableting ingredients (such as corn starch, lactose, sucrose, sorbitol, talc, stearic acid, magnesium stearate, dicalcium phosphate, and any of a variety of gums), and an optional diluent (such as water).

Binder agents include starch, gelatin, natural sugars (e.g., glucose and beta-lactose), corn sweeteners and natural and synthetic gums (e.g., acacia and tragacanth). Disintegrating agents include starch, methyl cellulose, agar, and bentonite.

Tablets and capsules represent an advantageous oral dosage unit form. Tablets may be sugarcoated or film-coated using standard techniques. Tablets may also be coated or otherwise compounded to provide a prolonged, control-release therapeutic effect. The dosage form may comprise an inner dosage and an outer dosage component, wherein the outer component is in the form of an envelope over the inner component. The two components may further be separated by a layer that resists disintegration in the stomach (such as an enteric layer) and permits the inner component to pass intact into the duodenum or a layer which delays or sustains release. A variety of enteric and non-enteric layer or coating materials (such as polymeric acids, shellacs, acetyl alcohol, and cellulose acetate or combinations thereof) may be used.

Compounds of the invention may also be administered via a slow release composition; wherein the composition includes a compound of the invention and a biodegradable slow release carrier (e.g., a polymeric carrier) or a pharmaceutically acceptable non-biodegradable slow release carrier (e.g., an ion exchange carrier).

Biodegradable and non-biodegradable slow release carriers are well known in the art. Biodegradable carriers are used to form particles or matrices which retain an active agent(s) and which slowly degrade/dissolve in a suitable environment (e.g., aqueous, acidic, basic and the like) to release the agent. Such particles degrade/dissolve in body fluids to release the active compound(s) therein. The particles are preferably nanoparticles (e.g., in the range of about 1 to 500 nm in diameter, preferably about 50-200 nm in diameter, and most preferably about 100 nm in diameter). In a process for preparing a slow release composition, a slow release carrier and a compound of the invention are first dissolved or dispersed in an organic solvent. The resulting mixture is added into an aqueous solution containing an optional surface-active agent(s) to produce an emulsion. The organic solvent is then evaporated from the emulsion to provide a colloidal suspension of particles containing the slow release carrier and the compound of the invention.

The compound of Formula I may be incorporated for administration orally or by injection in a liquid form such as aqueous solutions, suitably flavored syrups, aqueous or oil suspensions, flavored emulsions with edible oils such as cottonseed oil, sesame oil, coconut oil or peanut oil and the like, or in elixirs or similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone, and gelatin. The liquid forms in suitably flavored suspending or dispersing agents may also include synthetic and natural gums. For parenteral administration, sterile suspensions and solutions are desired. Isotonic preparations, which generally contain suitable preservatives, are employed when intravenous administration is desired.

The compounds may be administered parenterally via injection. A parenteral formulation may consist of the active ingredient dissolved in or mixed with an appropriate inert liquid carrier. Acceptable liquid carriers usually comprise aqueous solvents and other optional ingredients for aiding solubility or preservation. Such aqueous solvents include sterile water, Ringer's solution, or an isotonic aqueous saline solution. Other optional ingredients include vegetable oils (such as peanut oil, cottonseed oil, and sesame oil), and organic solvents (such as solketal, glycerol, and formyl). A sterile, non-volatile oil may be employed as a solvent or suspending agent. The parenteral formulation is prepared by dissolving or suspending the active ingredient in the liquid carrier whereby the final dosage unit contains from 0.005 to 10% by weight of the active ingredient. Other additives include preservatives, isotonizers, solubilizers, stabilizers, and pain-soothing agents. Injectable suspensions may also be prepared, in which case appropriate liquid carriers, suspending agents and the like may be employed.

Compounds of the invention may be administered intranasally using a suitable intranasal vehicle.

Compounds of the invention may also be administered topically using a suitable topical transdermal vehicle or a transdermal patch.

For ocular administration, the composition is preferably in the form of an ophthalmic composition. The ophthalmic compositions are preferably formulated as eye-drop formulations and filled in appropriate containers to facilitate administration to the eye, for example a dropper fitted with a suitable pipette. Preferably, the compositions are sterile and aqueous based, using purified water. In addition to the compound of the invention, an ophthalmic composition may contain one or more of: a) a surfactant such as a polyoxyethylene fatty acid ester; b) a thickening agents such as cellulose, cellulose derivatives, carboxyvinyl polymers, polyvinyl polymers, and polyvinylpyrrolidones, typically at a concentration in the range of about 0.05 to about 5.0% (wt/vol); c) (as an alternative to or in addition to storing the composition in a container containing nitrogen and optionally including a free oxygen absorber such as Fe), an anti-oxidant such as butylated hydroxyanisol, ascorbic acid, sodium thiosulfate, or butylated hydroxytoluene at a concentration of about 0.00005 to about 0.1% (wt/vol); d) ethanol at a concentration of about 0.01 to 0.5% (wt/vol); and e) other excipients such as an isotonic agent, buffer, preservative, and/or pH-controlling agent. The pH of the ophthalmic composition is desirably within the range of 4 to 8.

Methods of Preparation

In the discussion below, $R^1$, $R^2$, T, $R^3$, A, Q, L, G, $R^4$, $R^5$, $R^6$, $R^7$, $R^8$, $R^9$, $R^{10}$, $R^{11}$, $R^a$, $R^b$, $R^{a'}$ and $R^{b'}$ are defined as described above for compounds of Structural Formula I. In cases where the synthetic intermediates and final products of Structural Formula I described below contain potentially reactive functional groups, for example amino, hydroxyl, thiol and carboxylic acid groups, that may interfere with the desired reaction, it may be advantageous to employ protected forms of the intermediate. Methods for the selection, introduction and subsequent removal of protecting groups are well known to those skilled in the art. (T. W. Greene and P. G. M. Wuts "Protective Groups in Organic Synthesis" John Wiley & Sons, Inc., New York 1999)

In a first process of the invention, a compound of Structural Formula I is prepared by reaction of an intermediate of Structural Formula II with an amine intermediate of Structural Formula III:

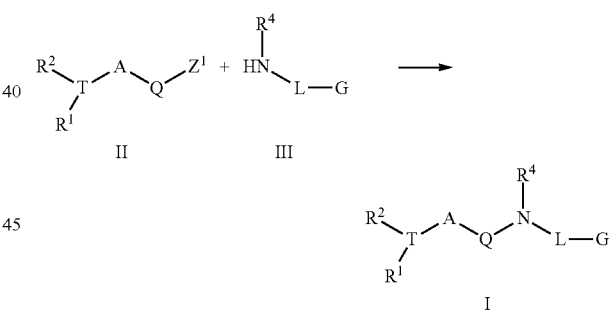

wherein $Z^1$ in II is a leaving group such as halide, alkanesulfonate, haloalkanesulfonate, arylsulfonate, aryloxide, heteroaryloxide, azole, azolium salt, or alkoxide.

In a second process of the invention, a compound of Structural Formula I is prepared by reaction of a compound of Structural Formula IV with a compound of Structural Formula V wherein $Z^1$ is a leaving group such as halide, alkanesulfonate, haloalkanesulfonate, arylsulfonate, aryloxide, heteroaryloxide, azole, azolium salt, or alkoxide:

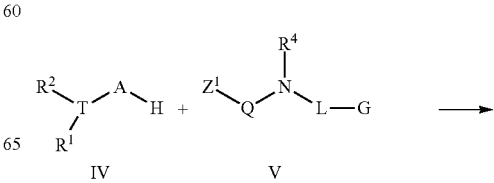

-continued

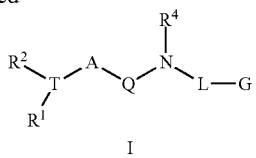
I wherein the H atom in IV is attached to a nitrogen atom that is part of A.

In a third process of the invention, compounds of Structural Formula I can be prepared from other compounds of Structural Formula I and protected compounds of Structural Formula I:

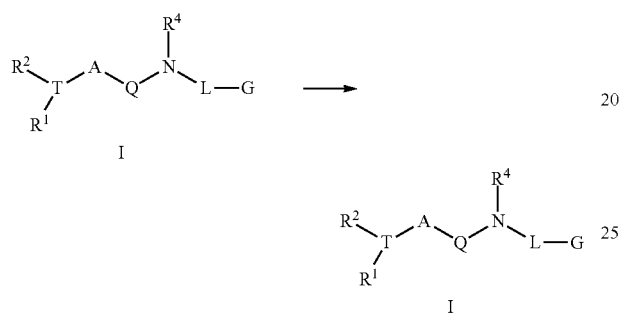

For example, when a bromophenyl, iodophenyl or trifluoromethanesulfonyloxyphenyl group is present in a compound of Structural Formula I, it may be transformed into a biphenyl using a Suzuki coupling, to an alkynylbenzene using a Sonogashira coupling, to an allylbenzene using a Stille coupling, to a cyanobenzene using CuCN or to a methoxycarbonylbenzene using a palladium catalyzed carbonylation in the presence of methanol. Another example is the transformation of a compound of Structural Formula I wherein $R^3$=OH to the analogous compound wherein $R^3$=H by dehydration followed by hydrogenation or in a single step by deoxygenation using Raney nickel. Another example is the deoxygenation of a compound of Structural Formula I wherein Q=Q11 to a compound of Structural Formula I where Q=Q10. Another example is the reaction of a compound of Structural Formula I wherein $R^2$=OH and $R^3$=H with an alcohol in the presence of acid to afford a compound of Formula I wherein $R^2$ is a group attached through an ether linkage. Another example is the alkylation of a compound of Structural Formula I wherein $R^1$ is a hydroxyphenyl group to provide a compound of Structural Formula I wherein $R^1$ is an alkoxyphenyl, cycloalkoxyphenyl, cycloalkylalkoxyphenyl, or arylalkoxyphenyl group.

Intermediates of Structural Formula II wherein $Z^1$=chlorine and Q is Q1, Q6 or Q8 that is attached to a carbon atom that is part of A are prepared from intermediates VI:

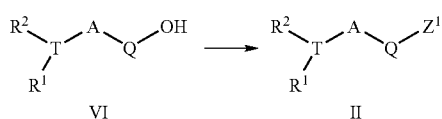

by reaction with, for example, thionyl chloride or oxalyl chloride, or phosphorous oxychloride.

Intermediates of Structural Formula II wherein Q is Q9 or Q11 or Q12, Q is attached to a nitrogen atom that is part of A and $Z^1$ is methoxy are prepared from intermediates of Structural Formula IV by reaction with 3,4-dimethoxy-3-cyclobutene-1,2-dione, 3,4-dimethoxy-1,2,5-thiadiazole-1-oxide and 3,4-dimethoxy-1,2,5-thiadiazole-1,1-dioxide respectively:

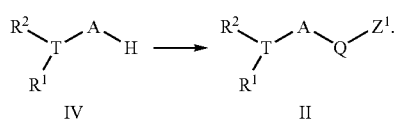

Intermediates of Structural Formula II wherein Q is Q1, Q1 is attached to a nitrogen atom that is part of A and $Z^1$ is chlorine, 1-imidazolyl, or p-nitrophenoxy are prepared from intermediates of Structural Formula IV wherein H is attached to a nitrogen atom that is part of A by reaction with phosgene, 1,1'-carbonyldiimidazole, or p-nitrophenyl chloroformate respectively.

Intermediates of Structural Formula IV wherein H is attached to a nitrogen atom that is part of A are prepared from intermediates of Structural Formula VII:

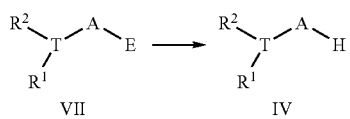

wherein E is an amine protecting group, including carbamate, amide, and sulfonamide protecting groups known in the art (T. W. Greene and P. G. M. Wuts "Protective Groups in Organic Synthesis" John Wiley & Sons, Inc., New York 1999).

When T in intermediates of Structural Formula VII is $CR^3$, the intermediate is represented by the Structural Formula VII':

Intermediates of Structural Formula VIIa wherein $R^3$ is OH, are prepared from intermediates of Structural Formula VIII by addition of an organometallic reagent of formula $R^2M$ where M is for example Li, MgCl, MgBr, or MgI to the carbonyl group of VIII:

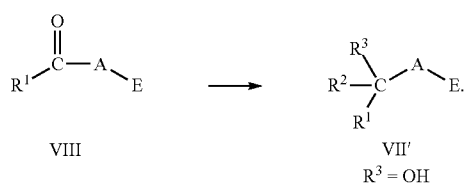

Intermediates of Structural Formula VII' wherein $R^3$=OH and $R^2$ is a group $R^cO$— attached by an ether linkage, are prepared from alcohol intermediates of Structural Formula IX by reaction under basic conditions with alkylating agents of Structural Formula X wherein $Z^2$ is a leaving group such as halide, alkanesulfonate, haloalkanesulfonate or arylsulfonate:

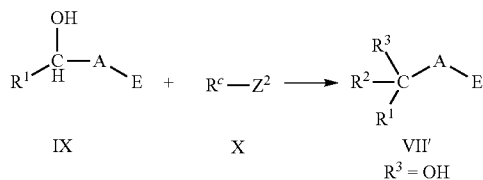

or by reaction with an alcohol of Structural Formula $R^cOH$ under acidic conditions.

Alcohol intermediates of Structural Formula IX are prepared by reduction of ketone intermediates of Structural Formula VIII with, for example, a hydride reducing agent such as $NaBH_4$, $LiAlH_4$ or diisobutylaluminum hydride:

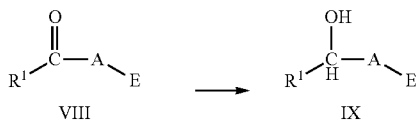

or by addition of an organometallic reagent of Structural Formula XI wherein M is, for example, Li, MgCl, MgBr, or MgI to an aldehyde of Structural Formula XII:

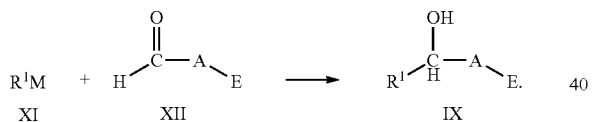

Ketone intermediates of Structural Formula VIII are prepared by the addition of an organometallic reagent of Structural Formula XI to a carboxylic acid derivative of Structural Formula XIII wherein $Z^3$ is an alkoxide, dialkylamino group, or an N-alkoxy-N-alkylamino group:

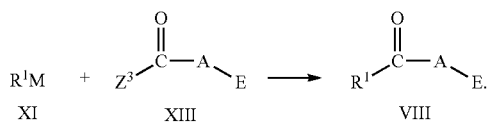

Organometallic reagents of formula XI are prepared by known process including halogen-lithium exchange, ortholithiation and treatment of halides $R^1X$-Hal with magnesium or lithium metal.

Aldehyde intermediates of Structural Formula XII are prepared by reduction of carboxylic acid derivatives of XIII wherein $Z^3$ is an alkoxy or an N-alkoxy-N-alkylamino group using, for example, a hydride reducing agent such as $LiAlH_4$ or diisobutylaluminum hydride:

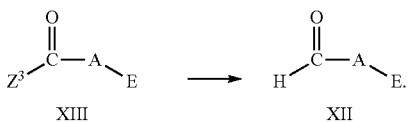

Ketone intermediates of Structural Formula VIII are also prepared by oxidation of alcohol intermediates of Structural Formula IX:

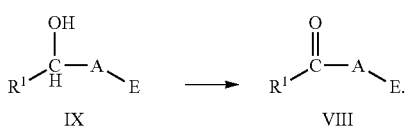

In a fourth process of the invention, optionally protected compounds of Structural Formula I, wherein T is $CR^3$ and $R^3$ is OH, are prepared from ketone compounds of Structural Formula XIV by addition of an organometallic compound $R_2M$:

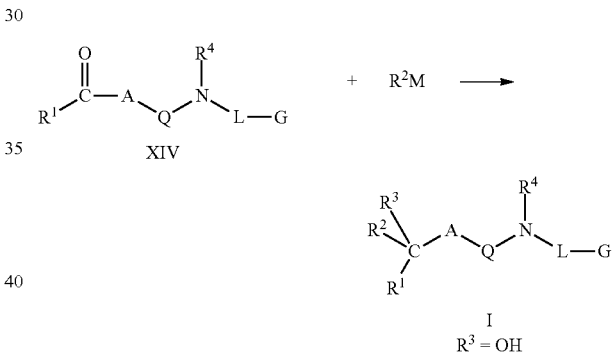

Intermediates of Structural Formula XIV wherein Q is Q1 and Q1 is attached to a carbon atom that is part of A are prepared by coupling of intermediates of formula XV and amine intermediates of Structural Formula III using peptide forming reagents or by activating XV as an acid chloride:

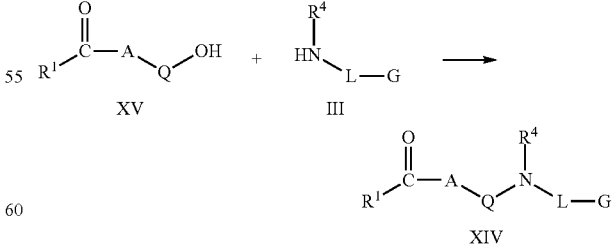

Intermediates of Structural Formula XV in which Q=Q1, Q3, Q6, Q7 and Q8 are prepared from cyclic anhydrides of formula XVI by reaction with organometallic reagents of formula $R^1M$:

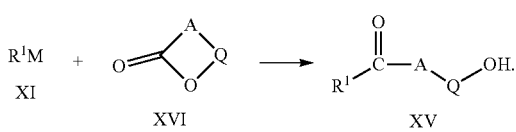

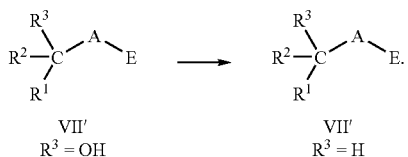

In a fifth process of the invention, optionally protected compounds of Structural Formula I wherein T is $CR^3$, $R^3$ is H and $R^2$ is $R^cO$— attached through an ether linkage, are prepared from compounds of Structural Formula XVII by reaction with an alcohol $R^2H$, wherein $R^2$ is selected from the subset of $R^2$ that terminates in an oxygen atom, under acidic conditions:

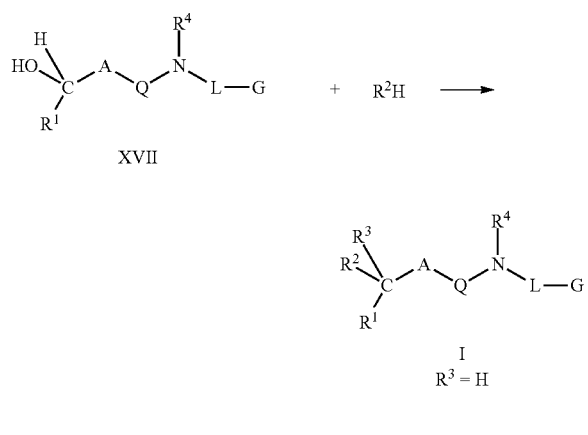

Alcohol intermediates of Structural Formula XVII are prepared by reduction of ketone intermediates XIV:

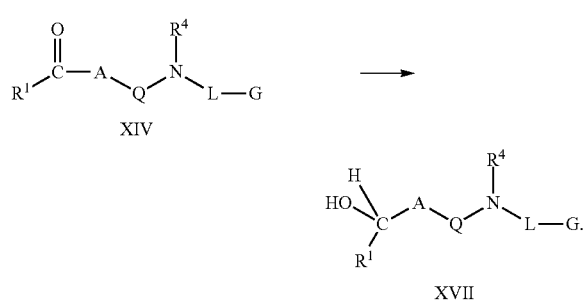

Intermediates of Structural Formulas III and V wherein L is a $C_2$ alkyl chain are prepared from natural and unnatural α-amino acids and by other methods (Lucet, D.; Le Gall, T.; Mioskowski, C. *Angew. Chem. Int. Ed.* 1998, 37, 2580-2617). Likewise, intermediates of Structural Formulas III and V wherein L is a $C_3$ or $C_4$ alkyl chain are prepared from β- and γ-amino acids, respectively.

Intermediates of Structural Formula VII' wherein $R^3$ is H and $R^2$ is a group attached through a carbon atom are prepared from intermediates of Structural Formula VII wherein T is $CR^3$, $R^3$ is OH and $R^2$ is a group attached through a carbon atom either by elimination of water and hydrogenation or by direct dehydroxylation for example using Raney nickel:

In the discussion below, $R^1$, $R^2$, T, $R^3$, A, Q, L, G, $R^4$, $R^5$, $R^6$, $R^7$, $R^8$, $R^9$, $R^{10}$, $R^{11}$, $R^a$, $R^b$, $R^{a'}$ and $R^{b'}$ are defined as described above for compounds of Structural Formula Ia. In cases where the synthetic intermediates and final products of Structural Formula I described below contain potentially reactive functional groups, for example amino, hydroxyl, thiol and carboxylic acid groups, that may interfere with the desired reaction, it may be advantageous to employ protected forms of the intermediate. Methods for the selection, introduction and subsequent removal of protecting groups are well known to those skilled in the art. (T. W. Greene and P. G. M. Wuts "Protective Groups in Organic Synthesis" John Wiley & Sons, Inc., New York 1999)

In a first process of the invention, a compound of Structural Formula Ia is prepared by reaction of an intermediate of Structural Formula IIa with an amine intermediate of Structural Formula III:

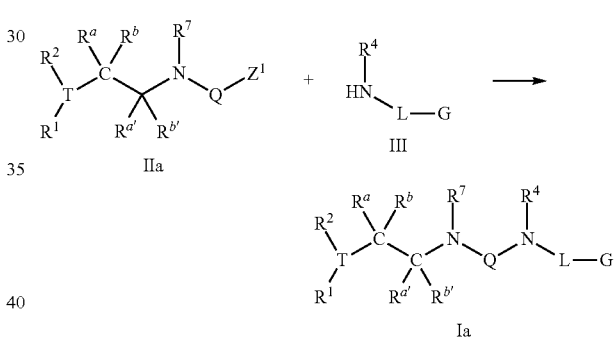

wherein $Z^1$ in II is a leaving group such as halide, alkanesulfonate, haloalkanesulfonate, arylsulfonate, aryloxide, heteroaryloxide, azole, azolium salt, or alkoxide.

In a second process of the invention, a compound of Structural Formula Ia is prepared by reaction of a compound of Structural Formula IVa with a compound of Structural Formula V wherein $Z^1$ is a leaving group such as halide, alkanesulfonate, haloalkanesulfonate, arylsulfonate, aryloxide, heteroaryloxide, azole, azolium salt, or alkoxide:

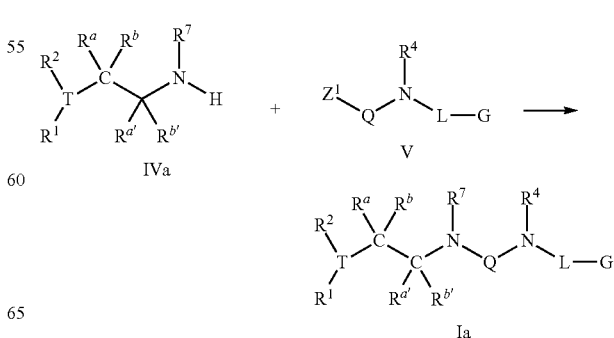

wherein the H atom in IV is attached to a nitrogen atom that is part of A.

In a third process of the invention, compounds of Structural Formula Ia can be prepared from other compounds of Structural Formula Ia and protected compounds of Structural Formula Ia:

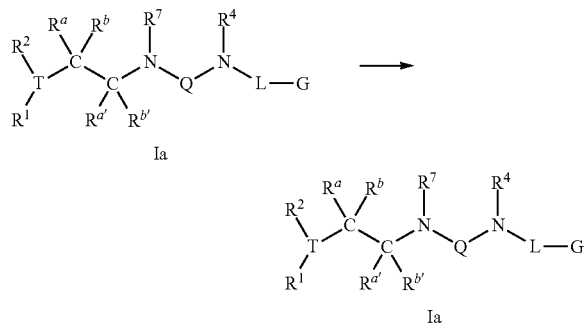

For example, when a bromophenyl, iodophenyl or trifluoromethanesulfonyloxyphenyl group is present in a compound of Structural Formula Ia, it may be transformed into a biphenyl using a Suzuki coupling, to an alkynylbenzene using a Sonogashira coupling, to an allylbenzene using a Stille coupling, to a cyanobenzene using CuCN or to a methoxycarbonylbenzene using a palladium catalyzed carbonylation in the presence of methanol. Another example is the transformation of a compound of Structural Formula Ia wherein $R^3$=OH to the analogous compound wherein $R^3$=H by dehydration followed by hydrogenation or in a single step by deoxygenation using Raney nickel. Another example is the deoxygenation of a compound of Structural Formula Ia wherein Q=Q11 to a compound of Structural Formula Ia where Q=Q10. Another example is the reaction of a compound of Structural Formula Ia wherein $R^2$=OH and $R^3$=H with an alcohol in the presence of acid to afford a compound of Formula Ia wherein $R^2$ is a group attached through an ether linkage. Another example is the alkylation of a compound of Structural Formula Ia wherein $R^1$ is a hydroxyphenyl group to provide a compound of Structural Formula Ia wherein $R^1$ is an alkoxyphenyl, cycloalkoxyphenyl, cycloalkylalkoxyphenyl, or arylalkoxyphenyl group.

Intermediates of Structural Formula IIa wherein $Z^1$=chlorine and Q is Q1, Q6 or Q8 that is attached to a carbon atom that is part of A are prepared from intermediates VIa:

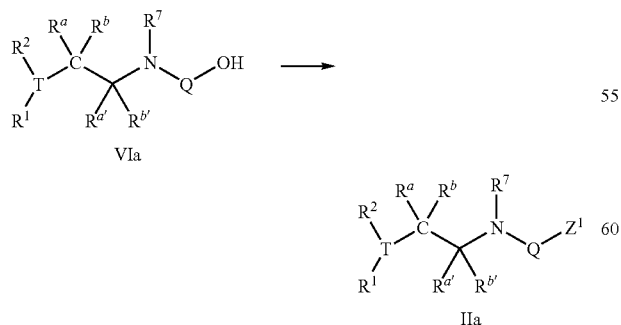

by reaction with, for example, thionyl chloride or oxalyl chloride, or phosphorous oxychloride.

Intermediates of Structural Formula IIa wherein Q is Q9 or Q11 or Q12, Q is attached to a nitrogen atom that is part of A and $Z^1$ is methoxy are prepared from intermediates of Structural Formula IVa by reaction with 3,4-dimethoxy-3-cyclobutene-1,2-dione, 3,4-dimethoxy-1,2,5-thiadiazole-1-oxide and 3,4-dimethoxy-1,2,5-thiadiazole-1,1-dioxide respectively:

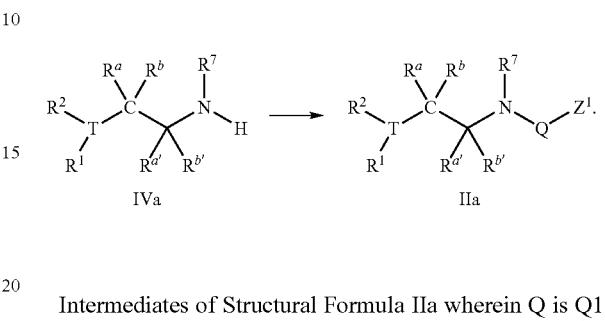

Intermediates of Structural Formula IIa wherein Q is Q1, Q1 is attached to a nitrogen atom that is part of A and $Z^1$ is chlorine, 1-imidazolyl, or p-nitrophenoxy are prepared from intermediates of Structural Formula IVa wherein H is attached to a nitrogen atom that is part of A by reaction with phosgene, 1,1'-carbonyldiimidazole, or p-nitrophenyl chloroformate respectively.

Intermediates of Structural Formula IVa wherein H is attached to a nitrogen atom that is part of A are prepared from intermediates of Structural Formula VIIa:

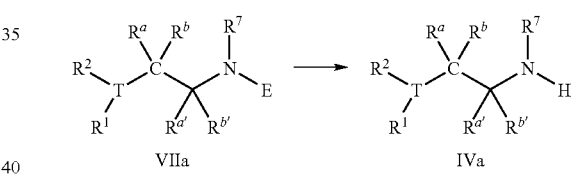

wherein E is an amine protecting group, including carbamate, amide, and sulfonamide protecting groups known in the art (T. W. Greene and P. G. M. Wuts "Protective Groups in Organic Synthesis" John Wiley & Sons, Inc., New York 1999).

When T in intermediates of Structural Formula VIIa is $CR^3$, the intermediate is represented by the Structural Formula VII'a:

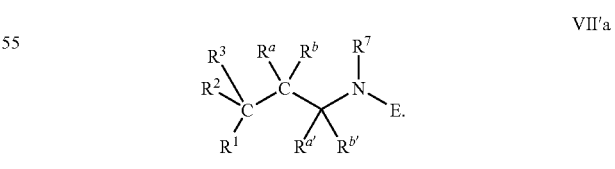

Intermediates of Structural Formula VII'a wherein $R^3$ is OH, are prepared from intermediates of Structural Formula VIIIa by addition of an organometallic reagent of formula $R^2M$ where M is for example Li, MgCl, MgBr, or MgI to the carbonyl group of VIIIa:

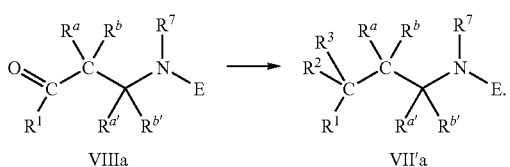

Intermediates of Structural Formula VII'a wherein $R^3$=OH and $R^2$ is a group $R^cO$— attached by an ether linkage, are prepared from alcohol intermediates of Structural Formula IXa by reaction under basic conditions with alkylating agents of Structural Formula X wherein $Z^2$ is a leaving group such as halide, alkanesulfonate, haloalkanesulfonate or arylsulfonate:

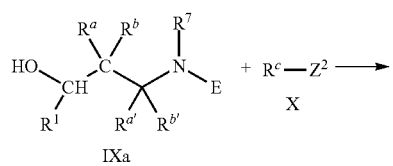

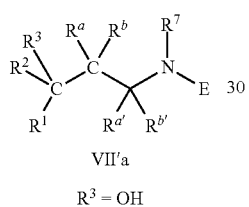

or by reaction with an alcohol of Structural Formula $R^cOH$ under acidic conditions.

Alcohol intermediates of Structural Formula IXa are prepared by reduction of ketone intermediates of Structural Formula VIIIa with, for example, a hydride reducing agent such as $NaBH_4$, $LiAlH_4$ or diisobutylaluminum hydride:

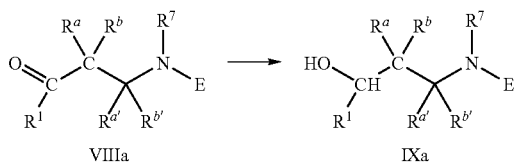

or by addition of an organometallic reagent of Structural Formula XI wherein M is, for example, Li, MgCl, MgBr, or MgI to an aldehyde of Structural Formula XIIa:

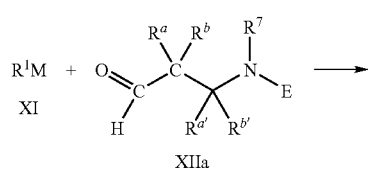

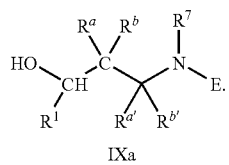

Ketone intermediates of Structural Formula VIIIa are prepared by the addition of an organometallic reagent of Structural Formula XI to a carboxylic acid derivative of Structural Formula XIIIa wherein $Z^3$ is an alkoxide, dialkylamino group, or an N-alkoxy-N-alkylamino group:

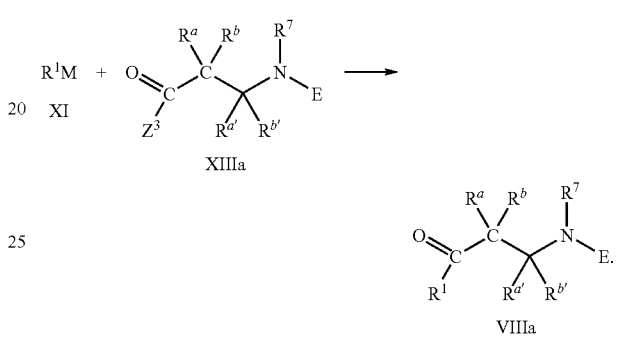

Organometallic reagents of formula XI are prepared by known process including halogen-lithium exchange, ortho-lithiation and treatment of halides $R^1$X-Hal with magnesium or lithium metal.

Aldehyde intermediates of Structural Formula XIIa are prepared by reduction of carboxylic acid derivatives of XIIIa wherein $Z^3$ is an alkoxy or an N-alkoxy-N-alkylamino group using, for example, a hydride reducing agent such as $LiAlH_4$ or diisobutylaluminum hydride:

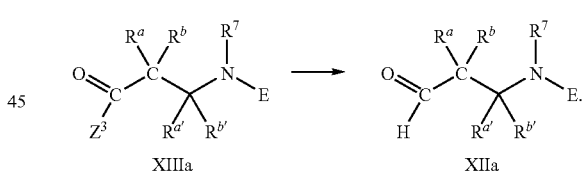

Ketone intermediates of Structural Formula VIIIa are also prepared by oxidation of alcohol intermediates of Structural Formula IXa:

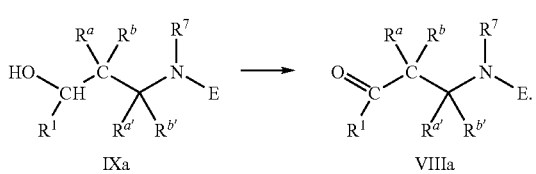

In a fourth process of the invention, optionally protected compounds of Structural Formula Ia, wherein T is $CR^3$ and $R^3$ is OH, are prepared from ketone compounds of Structural Formula XIVa by addition of an organometallic compound $R_2M$:

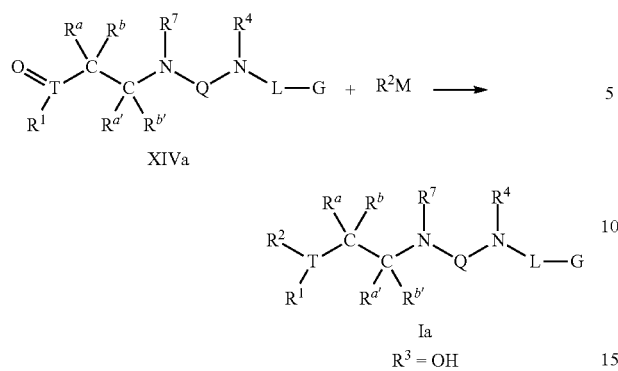

Intermediates of Structural Formula XIVa wherein Q is Q1 and Q1 is attached to a carbon atom that is part of A are prepared by coupling of intermediates of formula XVa and amine intermediates of Structural Formula III using peptide forming reagents or by activating XVa as an acid chloride:

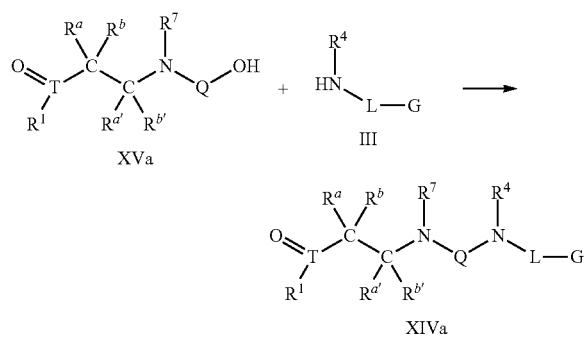

Intermediates of Structural Formula XVa in which Q=Q1, Q3, Q6, Q7 and Q8 are prepared from cyclic anhydrides of formula XVIa by reaction with organometallic reagents of formula $R^1XM$:

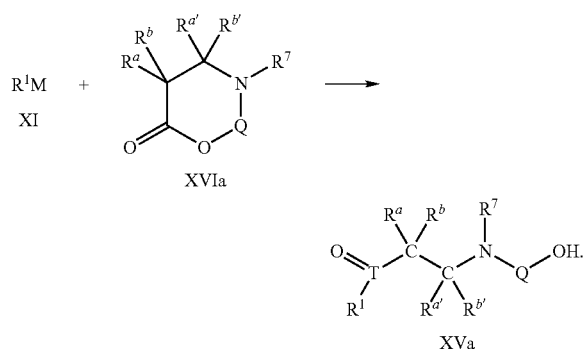

In a fifth process of the invention, optionally protected compounds of Structural Formula Ia wherein T is $CR^3$, $R^3$ is H and $R^2$ is $R^cO-$ attached through an ether linkage, are prepared from compounds of Structural Formula XVIIa by reaction with an alcohol $R^2H$, wherein $R^2$ is selected from the subset of $R^2$ that terminates in an oxygen atom, under acidic conditions:

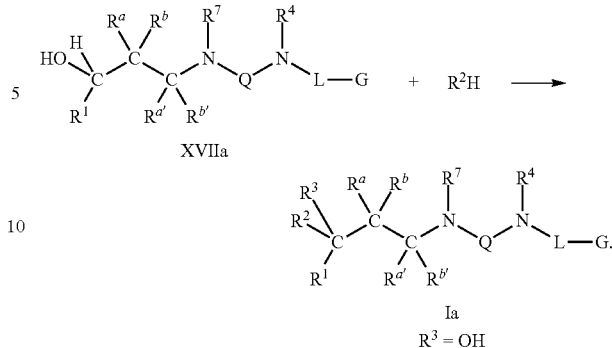

Alcohol intermediates of Structural Formula XVIIa are prepared by reduction of ketone intermediates XIVa:

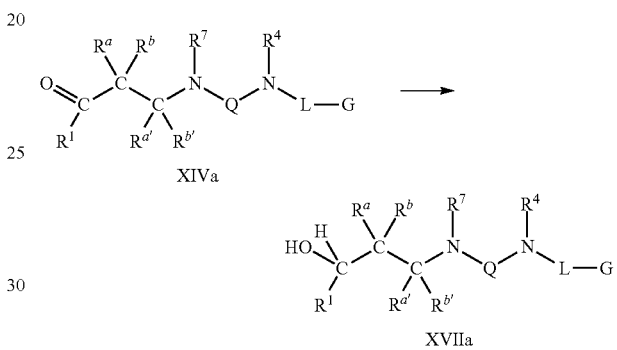

Intermediates of Structural Formulas IIIa and Va wherein L is a $C_2$ alkyl chain are prepared from natural and unnatural α-amino acids and by other methods (Lucet, D.; Le Gall, T.; Mioskowski, C. *Angew. Chem. Int. Ed.* 1998, 37, 2580-2617). Likewise, intermediates of Structural Formulas IIIa and Va wherein L is a $C_3$ or $C_4$ alkyl chain are prepared from β- and γ-amino acids, respectively.

Intermediates of Structural Formula VII'a wherein T is $CR^3$, $R^3$ is H and $R^2$ is a group attached through a carbon atom are prepared from intermediates of Structural Formula VII'a wherein T is $CR^3$, $R^3$ is OH and $R^2$ is a group attached through a carbon atom either by elimination of water and hydrogenation or by direct dehydroxylation for example using Raney nickel:

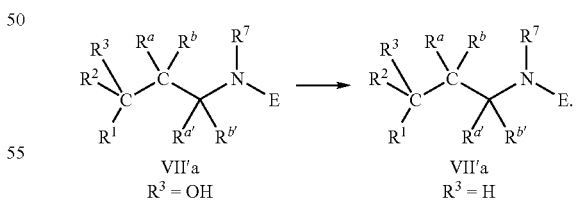

The invention is further defined by reference to the examples, which are intended to be illustrative and not limiting.

Representative compounds of the invention can be synthesized in accordance with the general synthetic schemes described above and are illustrated in the examples that follow. The methods for preparing the various starting materials used in the schemes and examples are well within the knowledge of persons skilled in the art.

The following abbreviations have the indicated meanings:

| Abbreviation | Meaning |
|---|---|
| Boc | tert-butoxy carbonyl or t-butoxy carbonyl |
| (Boc)$_2$O | di-tert-butyl dicarbonate |
| brine | saturated aqueous NaCl |
| CH$_2$Cl$_2$ | methylene chloride |
| CH$_3$CN or MeCN | acetonitrile |
| Compd | compound |
| DIEA | N,N-diisopropylethylamine |
| DMAP | 4-(dimethylamino)pyridine |
| DMF | N,N-dimethylformamide |
| EDC | 1-[3-(dimethylamino)propyl]-3-ethylcarbodiimide |
| Et | ethyl |
| Et$_2$O | ethyl ether |
| EtOAc | ethyl acetate |
| Fmoc | 1-[[(9H-fluoren-9-ylmethoxy)carbonyl]oxy]- |
| Fmoc-OSu | 1-[[(9H-fluoren-9-ylmethoxy)carbonyl]oxy]-2,5-pyrrolidinedione |
| h, hr | hour |
| HOBt | 1-hydroxybenzotriazole |
| HATU | 2-(7-Aza-1H-benzotriazole-1-yl)-1,1,3,3-tetramethyluronium hexafluorophosphate |
| HBTU | 2-(1H-Benzotriazole-1-yl)-1,1,3,3-tetramethyluronium hexafluorophosphate |
| KHMDS | potassium hexamethyldisilazane |
| LAH or LiAlH$_4$ | lithium aluminum hydride |
| LC-MS | liquid chromatography-mass spectroscopy |
| LHMDS | lithium hexamethyldisilazane |
| Me | methyl |
| MeCN | acetonitrile |
| MeOH | methanol |
| MsCl | methanesulfonyl chloride |
| min | minute |
| MS | mass spectrum |
| NaH | sodium hydride |
| NaHCO$_3$ | sodium bicarbonate |
| NaN$_3$ | sodium azide |
| NaOH | sodium hydroxide |
| Na$_2$SO$_4$ | sodium sulfate |
| NMP | N-methylpyrrolidinone |
| Pd$_2$(dba)$_3$ | tris(dibenzylideneacetone)dipalladium(0) |
| Ph | phenyl |
| rt | room temperature |
| satd | saturated |
| SOCl$_2$ | thionyl chloride |
| TBAF | tetrabutylammonium fluoride |
| TEA | triethylamine or Et$_3$N |
| TEAF | tetraethylammonium fluoride |
| TEMPO | 2,2,6,6-tetramethyl-1-piperidinyloxy, free radical |
| Teoc | 1-[2-(trimethylsilyl)ethoxycarbonyloxy]- |
| Teoc-OSu | 1-[2-(trimethylsilyl)ethoxycarbonyloxy]pyrrolidin-2,5-dione |
| TFA | trifluoroacetic acid |
| THF | tetrahydrofuran |
| TMSCl | chlorotrimethylsilane or trimethylsilyl chloride |
| $t_R$ | retention time |

EXEMPLIFICATION

Purification Methods

Prep HPLC refers to preparative reverse phase HPLC on a C-18 column eluted with a water/acetonitrile gradient containing 0.01% TFA run on a Gilson 215 system.

Column chromatography and flash chromatography refer to normal phase chromatography on a silica gel column or cartridge eluted with an hexanes/EtOAc gradient.

Analytical Methods

LC-MS (3 min)
Column: Chromolith SpeedRod, RP-18e, 50×4.6 mm; Mobil phase: A: 0.01% TFA/water, B: 0.01% TFA/CH$_3$CN; Flow rate: 1 mL/min; Gradient:

| Time (min) | A % | B % |
|---|---|---|
| 0.0 | 90 | 10 |
| 2.0 | 10 | 90 |
| 2.4 | 10 | 90 |
| 2.5 | 90 | 10 |
| 3.0 | 90 | 10 |

MS Conditions: Electrospray ionization.

Preparation A

Methyl 2-(1-(3-chlorophenyl)-3-(methylamino)propoxy)ethylcarbamate

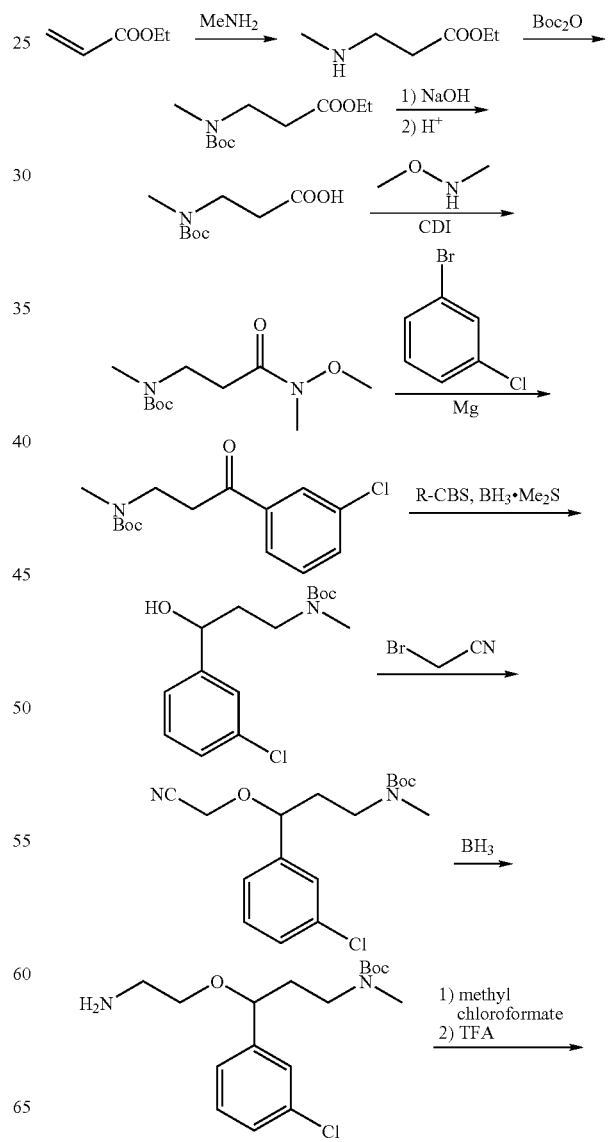

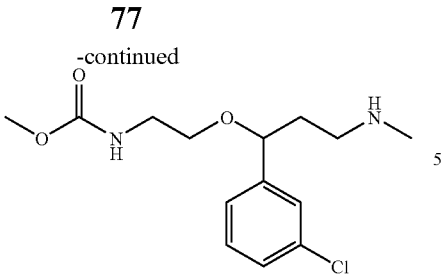

Step 1. Ethyl 3-(methylamino)propanoate

At 0° C., a solution of ethyl acrylate in alcohol (2M, 1000 mL, 2 mol) was added drop wise to a solution of MeNH$_2$ in alcohol (33%, 540 mL, 4 mol). The resulting mixture was stirred for 3 h. Upon completion of the reaction, monitored by TLC, the solvent and volatiles were removed under reduced pressure to give ethyl 3-(methylamino)propanoate (250 g, crude) as an oil, which was used in the next step without further purification.

Step 2. Ethyl 3-(tert-butoxycarbonyl(methyl)amino)propanoate

To a solution of ethyl 3-(methylamino)propanoate (125 g, 0.96 mol) and TEA (193 g, 1.92 mol) in CH$_2$Cl$_2$ at 0° C. was added drop wise Boc$_2$O (208 g, 0.96 mol). After the addition, the resulting mixture was stirred overnight. The mixture was poured into water (1000 mL), separated, and the organic layer was washed with brine, dried over anhydrous Na$_2$SO$_4$, and concentrated to give ethyl 3-(tert-butoxycarbonyl(methyl) amino)propanoate (205 g, crude) as an oil which was used in the next step without further purification.

Step 3. 3-(tert-butoxycarbonyl(methyl)amino)propanoic acid

To a mixture of sodium hydroxide (112 g, 2.8 mol) in THF (1200 mL) and EtOH (1800 mL) was added ethyl 3-(tert-butoxycarbonyl(methyl)amino)propanoate (300 g, 1.4 mol). The resulting mixture was stirred for 3 h. The mixture was diluted with water (1000 mL) and evaporated to remove volatiles. The water phase was washed with CH$_2$Cl$_2$ (800 mL×3). The inorganic layer was cooled in an ice bath and acidified with 1 N HCl until the pH was adjusted to 1-2. CH$_2$Cl$_2$ (1000 mL×4) was quickly added to extract the product acid. The organic phase was dried over anhydrous Na$_2$SO$_4$ and concentrated to give 3-(tert-butoxycarbonyl(methyl)amino)propanoic acid (208 g, 73.2%) as oil, which was used in the next step without further purification.

Step 4. tert-butyl 3-(methoxy(methyl)amino)-3-oxopropyl(methyl)carbamate

To a solution of 3-(tert-butoxycarbonyl(methyl)amino) propanoic acid (130 g, 0.64 mol) in anhydrous THF was added CDI at 0° C. The resulting mixture was stirred for 1 h at 0° C. To this mixture was added a solution of O,N-dimethylhydroxylamine hydrochloric salt (145.2 g, 0.9 mol) and TEA (90.1 g, 0.9 mol) in THF at rt. The resulting mixture was stirred overnight. Solvent and volatiles were removed under reduced pressure. The residue was purified via column chromatography to give tert-butyl 3-(methoxy(methyl)amino)-3-oxopropyl(methyl)carbamate (120 g, 75.5%) as a colorless oil. $^1$HNMR (CDCl$_3$, 400 MHz) 1.45 (s, 9H), 2.62-2.71 (m, 2H), 2.87 (s, 3H), 3.17 (s, 3H), 3.48-3.56 (m, 2H), 3.68 (s, 3H)

Step 5. tert-butyl 3-(3-chlorophenyl)-3-oxopropyl(methyl)carbamate

A solution of 1-bromo-3-chloro-benzene (57 g, 0.3 mmol) in dry THF (300 mL) was added drop wise to Mg (10.8 g, 0.45 mmol) at room temperature under N$_2$. The mixture was stirred at refluxed for 1 h. The Grignard reagent was added drop wise to a solution of tert-butyl 3-(methoxy(methyl) amino)-3-oxopropyl(methyl)carbamate (37 g, 0.15 mmol) in dry THF (300 mL) at −78° C. After addition, the mixture was allowed to stir at room temperature overnight. The mixture was quenched with saturated NH$_4$Cl and extracted with ethyl acetate. The combined organic layers were washed with brine, dried over Na$_2$SO$_4$ and concentrated in vacuo to give the crude product, which was purified through column chromatography. $^1$H NMR (CDCl$_3$, 400 MH$_z$) δ 1.42 (s, 9H), 2.89 (s, 3H), 3.18 (m, 2H), 3.62 (t, 2H), 7.42 (m, 1H), 7.52 (m, 1H), 7.82 (m, 1H), 7.91 (m, 1H).

Step 6. tert-butyl 3-(3-chlorophenyl)-3-hydroxypropyl(methyl)carbamate

To a solution R—CBS (20.2 mL, 20.2 mmol) and BH$_3$.Me$_2$S (30.3 mL, 303 mmol) in THF (250 mL) was added a solution of tert-butyl 3-(3-chlorophenyl)-3-oxopropyl(methyl)carbamate (60 g, 0.202 mol) in THF (300 mL) at −15° C. After addition, the mixture was stirred at room temperature for 1 hour. Methanol was added drop wise carefully at −15° C. The solvent was removed under reduced pressure, the residue was purified by column chromatography on silica gel eluting with AcOEt/petroleum ether (1:15→1:8) to provide the light yellow oil. $^1$H NMR (CDCl$_3$, 400 MH$_z$) δ 1.49 (s, 9H), 1.70 (m, 1H), 1.94 (m, 1H), 2.87 (s, 3H), 3.01 (m, 1H), 3.96 (m, 1H), 4.52 (m, 1H), 7.26 (m, 4H).

Step 7. tert-butyl 3-(3-chlorophenyl)-3-(cyanomethoxy)propyl(methyl)carbamate To a suspension of NaH (0.65 g, 27 mmol) and tert-butyl 3-(3-chlorophenyl)-3-hydroxypropyl(methyl)carbamate (2.7 g, 9 mmol) in CH$_3$CN (60 mL) at 0-5° C. was added drop wise a solution of bromoacetonitrile (3.3 g, 27 mmol) in CH$_3$CN (20 mL), the reaction mixture was stirred for overnight at room temperature. The reaction mixture was poured into saturated aqueous NH$_4$Cl, ethyl acetate (50 mL) was added. The organic layer was washed with water (3×20 mL) and brine, dried over Na$_2$SO$_4$, filtered and concentrated in vacuo to afford the crude product, which was used for the next step without purification.

Step 8. tert-butyl 3-(2-aminoethoxy)-3-(3-chlorophenyl)propyl(methyl)carbamate A solution of tert-butyl 3-(3-chlorophenyl)-3-(cyanomethoxy)propyl(methyl)carbamate (3 g, 8.9 mmol) in THF (50 mL) was heated to reflux and BH$_3$.Me$_2$S was added drop wise. The reaction mixture was heated to reflux overnight. MeOH was added to the mixture at −15° C. The solution was removed in vacuo to give the crude product, which was used for the next step without purification.

Step 9. tert-butyl 3-(2-(methoxycarbonyl)aminoethoxy)-3-(3-chlorophenyl)propyl(methyl)carbamate To a 0° C. solution of tert-butyl 3-(2-aminoethoxy)-3-(3-chlorophenyl)propyl(methyl)carbamate (6 g, 4.11 mmol), Et₃N (1.25 g, 12.3 mL), DMAP (0.25 g, 2.06 mmol) in dry CH₂Cl₂ (100 mL), methyl chloroformate (1.9 g, 20.6 mmol) in dry CH₂Cl₂ (30 mL) was added drop wise. After addition, the reaction mixture was stirred for 1-2 h at 0-5° C. The reaction was quenched with water. The aqueous layer was extracted with CH₂Cl₂, the combined organic layers were washed with 10% citric acid and brine, then dried over Na₂SO₄, filtered and concentrated to the crude product. The crude product was purified by silica gel to afford tert-butyl 3-(2-(methoxycarbonyl)aminoethoxy)-3-(3-chlorophenyl)propyl(methyl)carbamate (600 mg, 40%). $^1$H NMR (CDCl₃, 400 MH$_z$) δ 1.49 (s, 9H), 1.83 (m, 2H), 2.80 (s, 3H), 3.31 (m, 7H), 3.65 (s, 3H), 4.13 (m, 1H), 7.26 (m, 4H).

The mixture of isomers can be further purified by column chromatography (varying the ratio of petroleum ether:ethyl acetate was 30:1→15:1→8:1). The obtained product was purified by preparative chiral HPLC to give the pure isomer (R)-tert-butyl 3-(2-(methoxycarbonylamino)ethoxy)-3-(3-chlorophenyl)propyl(methyl)carbamate.

Step 10. methyl 2-(1-(3-chlorophenyl)-3-(methylamino)propoxy)ethylcarbamate tert-butyl 3-(2-(methoxycarbonyl)aminoethoxy)-3-(3-chlorophenyl)propyl(methyl)carbamate (100 mg) was dissolved in a solution of 20% (V/V) TFA/CH₂Cl₂ (8 mL). The reaction mixture was stirred at room temperature for 1 h, then concentrated in vacuo to afford methyl 2-(1-(3-chlorophenyl)-3-(methylamino)propoxy)ethylcarbamate (150 mg, 100%), was used for the next step without purification.
The following compounds were prepared following procedures analogous to those described above:
1) (R)-methyl 2-(1-(3-chlorophenyl)-3-(methylamino)propoxy)ethylcarbamate was obtained using (R)-tert-butyl 3-(2-(methoxycarbonyl)aminoethoxy)-3-(3-chlorophenyl)propyl(methyl)carbamate.
2) methyl 2-(1-(3-chlorophenyl)-3-(isopropylamino)propoxy)ethylcarbamate using isopropylamine in Step 1 and NaBH₄ in Step 6.
3) methyl 2-(1-(3-chlorophenyl)-3-(ethylamino)propoxy)ethylcarbamate using ethylamine in Step 1 and NaBH₄ in Step 6.
4) methyl 2-(1-(3-chlorophenyl)-3-(propylamino)propoxy)ethylcarbamate using propylamine in Step 1 and NaBH₄ in Step 6.

Preparation B methyl 2-(1-(5-chloro-2-methylphenyl)-3-(methylamino)propoxy)ethylcarbamate

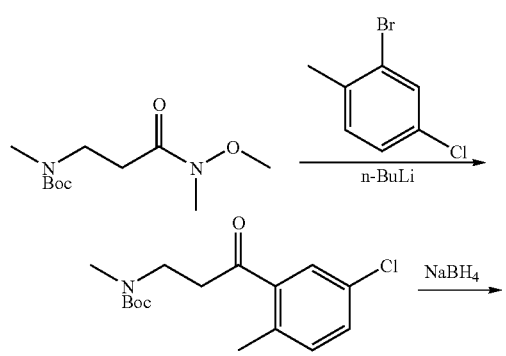

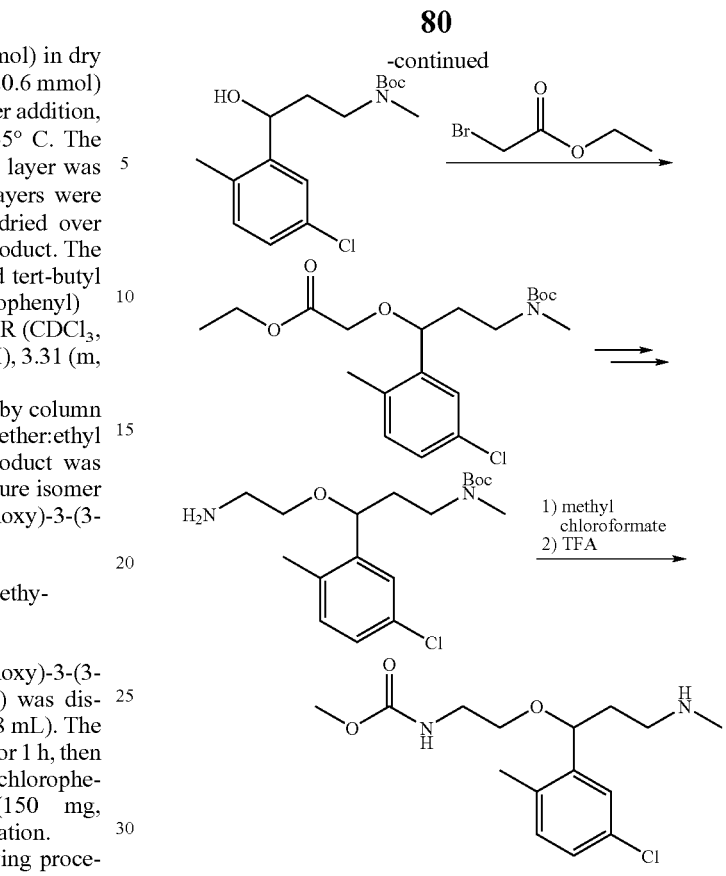

Step 1. tert-butyl 3-(5-chloro-2-methylphenyl)-3-oxopropyl(methyl)carbamate

To a solution of 2-bromo-4-chloro-1-methylbenzene (25 g, 0.123 mol) in anhydrous THF (150 mL) at −78° C. under N₂ was added drop wise a solution of n-BuLi (2.5 M, 49 mL, 1.18 mol). After stirring at −78° C. for 1 h, a solution of tert-butyl 3-(5-chloro-2-methylphenyl)-3-oxopropyl(methyl)carbamate (26 g, 0.104 mol) in anhydrous THF (150 mL) was added drop wise. After addition, the reaction mixture was allowed to warm to room temperature and stirred overnight. The mixture was quenched with saturated NH₄Cl, extracted three times with ethyl acetate, and dried over Na₂SO₄. Solvent removal and flash column chromatography afford tert-butyl 3-(5-chloro-2-methylphenyl)-3-oxopropyl(methyl)carbamate (3.3 g, yield 9%). $^1$H NMR (CDCl₃, 400 MH$_z$) δ 1.44 (s, 9H), 2.45 (s, 3H), 2.90 (s, 3H), 3.10 (m, 2H), 3.60 (m, 2H), 7.10 (m, 3H).

Step 2. tert-butyl 3-(5-chloro-2-methylphenyl)-3-hydroxypropyl(methyl)carbamate

To a solution of tert-butyl 3-(5-chloro-2-methylphenyl)-3-oxopropyl(methyl)carbamate (1.3 g, 4.2 mmol) in MeOH (26 mL) was added NaBH₄ (0.64 g, 16.7 mmol) in portions. After addition, the mixture was stirred at room temperature overnight. The solvent was removed in vacuo to the residue, which was portioned between water and EtOAc. The organic layers were washed with brine, dried over Na₂SO₄, filtered and concentrated. $^1$H NMR (CDCl₃, 400 MH$_z$) δ 1.49 (s, 9H), 1.65 (s, 3H), 1.94 (m, 2H), 2.87 (s, 3H), 7.26 (m, 4H).

Step 3. ethyl 2-(3-(tert-butoxycarbonyl(methyl) amino)-1-(5-chloro-2-methylphenyl)propoxy)acetate To a suspension of NaH (0.5 g, 12.5 mmol) in THF (400 mL) at 0-5° C. was added drop wise a solution of tert-butyl 3-(5-chloro-2-methylphenyl)-3-hydroxypropyl(methyl)carbamate (1.3 g, 4.15 mmol) in anhydrous THF/DMF (24/16 mL), the reaction mixture was stirred for 1 h at room temperature. A solution of ethyl bromoacetate (2.1 g, 12.5 mmol) in anhydrous THF (13 mL) was added drop wise to the above mixture, the reaction mixture was stirred at room temperature overnight. The reaction mixture was poured into saturated aqueous $NH_4Cl$, and then extracted with ethyl acetate. The organic layer was washed with water and brine, dried over $Na_2SO_4$, filtered and concentrated in vacuo to afford crude ethyl 2-(3-(tert-butoxycarbonyl(methyl)amino)-1-(5-chloro-2-methylphenyl)propoxy)acetate (800 mg, 60%), which was used for next step without purification. $^1$H NMR ($CDCl_3$, 400 $MH_z$) δ 1.45 (s, 9H), 1.68 (s, 3H), 1.87 (m, 2H), 2.25 (m, 2H), 2.90 (s, 3H), 4.63 (m, 1H), 7.13 (m, 2H), 7.38 (m, 1H).

Step 4. tert-butyl 3-(5-chloro-2-methylphenyl)-3-(2-hydroxyethoxy)propyl(methyl)carbamate To a solution of ethyl 2-(3-(tert-butoxycarbonyl(methyl) amino)-1-(5-chloro-2-methylphenyl) propoxy)acetate (800 mg, 2 mmol) in MeOH (16 mL) was added $NaBH_4$ (305 mg, 8 mmol) in portions while the temperature was lower than 40° C. After addition, the mixture was stirred at room temperature for 2-3 h. The solvent was removed in vacuo to the residue, which was partitioned between water and ethyl acetate. The organic layer was washed with $H_2O$ and brine, dried over $Na_2SO_4$, filtered and concentrated in vacuo. The residue was purified on silica gel chromatography to afford tert-butyl 3-(5-chloro-2-methylphenyl)-3-(2-hydroxyethoxy)propyl (methyl)carbamate (400 mg, 56%). $^1$H NMR ($CDCl_3$, 400 $MH_z$) δ 1.22 (m, 3H), 1.43 (m, 9H), 1.87 (m, 2H), 2.21 (s, 3H), 2.87 (s, 3H), 3.39 (m, 2H), 3.80 (m, 1H), 4.00 (m, 1H), 4.61 (m, 1H), 7.08 (m, 2H), 7.37 (m, 1H).

Step 5. 2-(3-(tert-butoxycarbonyl(methyl)amino)-1-(5-chloro-2-methylphenyl)propoxy)ethyl methanesulfonate To a solution of tert-butyl 3-(5-chloro-2-methylphenyl)-3-(2-hydroxyethoxy)propyl(methyl) carbamate (400 mg, 1.12 mmol) in dry $CH_2Cl_2$ (20 mL) was added $Et_3N$ (283 mg, 2.8 mmol) at 0° C. Then MsCl (192 mg, 1.68 mmol) was added drop wise at the same temperature. After addition, the reaction was allowed to warm to room temperature gradually. The reaction was quenched with water (100 mL). The aqueous layer was extracted with $CH_2Cl_2$, the combined organic layers was washed with 10% citric acid, sat. $NaHCO_3$ and brine, then dried over $Na_2SO_4$, filtered and concentrated to give 2-(3-(tert-butoxycarbonyl(methyl)amino)-1-(5-chloro-2-methylphenyl)propoxy)ethyl methanesulfonate (370 mg, 76%), which was used in the next step without purification.

Step 6. tert-butyl 3-(2-azidoethoxy)-3-(5-chloro-2-methylphenyl)propyl(methyl)carbamate 2-(3-(tert-Butoxycarbonyl(methyl)amino)-1-(5-chloro-2-methylphenyl)propoxy)ethyl methanesulfonate (414 mg, 0.95 mmol) was dissolved into anhydrous DMF (15 mL), solid $NaN_3$ (186 mg, 2.86 mmol) was added and the reaction mixture was heated to 80° C. overnight. The reaction mixture was cooled to room temperature and diluted with ethyl acetate, the organic phase was washed with water and brine, dried over $Na_2SO_4$ and concentrated in vacuo to the crude product (270 mg, 74%), which was used for next step without purification.

Step 7. tert-butyl 3-(2-aminoethoxy)-3-(5-chloro-2-methylphenyl)propyl(methyl)carbamate tert-Butyl 3-(2-azidoethoxy)-3-(5-chloro-2-methylphenyl)propyl(methyl)carbamate (270 mg, 0.707 mmol) was dissolved in $THF/H_2O$ (5 mL, 20:1), $PPh_3$ (741 mg, 2.83 mmol) was added in portions. The reaction mixture was stirred at room temperature overnight. The reaction mixture was concentrated in vacuo and used without further purification.

Step 8. tert-butyl 3-(2-(methoxycarbonyl)aminoethoxy)-3-(2-methyl-5-chlorophenyl)propyl(methyl) carbamate To a solution of tert-butyl 3-(2-aminoethoxy)-3-(5-chloro-2-methylphenyl)propyl(methyl) carbamate (250 mg, 0.707 mmol) and DMAP (43 mg, 0.35 mmol) in dry $CH_2Cl_2$ (10 mL), $Et_3N$ (213 mg, 2.11 mmol) was added. The resulting mixture was cooled to 0-5° C. using an ice-water bath, a solution of methyl chloroformate (332 mg, 3.55 mmol) was added drop wise. After addition, the reaction mixture was stirred for 1-2 h at 0-5° C. Upon completion of the reaction water was added. The aqueous layer was extracted with $CH_2Cl_2$, the combined organic layers were washed with 10% citric acid and brine, then dried over $Na_2SO_4$, filtered and concentrated to the crude product, which was purified by silica gel to afford tert-butyl 3-(2-(methoxycarbonyl)aminoethoxy)-3-(2-methyl-5-chlorophenyl)propyl(methyl)carbamate (180 mg, 62%). $^1$H NMR ($CDCl_3$, 400 $MH_z$) δ 1.43 (m, 9H), 2.24 (s, 3H), 2.95 (s, 3H), 3.05 (m, 2H), 3.47 (m, 2H), 3.61 (s, 3H), 4.54 (m, 1H), 7.10 (m, 2H), 7.32 (m, 1H).

Step 9. methyl 2-(1-(5-chloro-2-methylphenyl)-3-(methylamino)propoxy)ethylcarbamate tert-butyl 3-(2-(methoxycarbonyl)aminoethoxy)-3-(2-methyl-5-chlorophenyl)propyl(methyl)carbamate (110 mg) was dissolved in a solution of 20% (V/V) $TFA/CH_2Cl_2$ (10 mL). The reaction mixture was stirred at room temperature for 1 h. The reaction mixture was concentrated in vacuo to afford methyl 2-(1-(5-chloro-2-methylphenyl)-3-(methylamino) propoxy)ethylcarbamate (120 mg, 100%).

Preparation C methyl 2-((1R*,2R*)-1-(3-chlorophenyl)-2-methyl-3-(methylamino)propoxy)ethylcarbamate

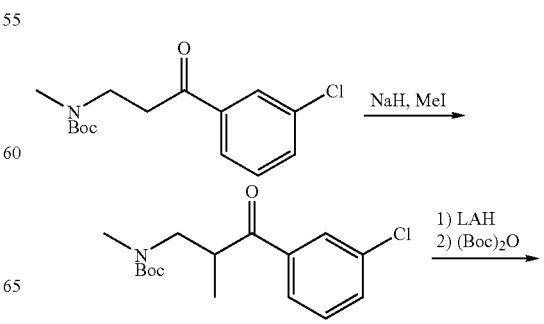

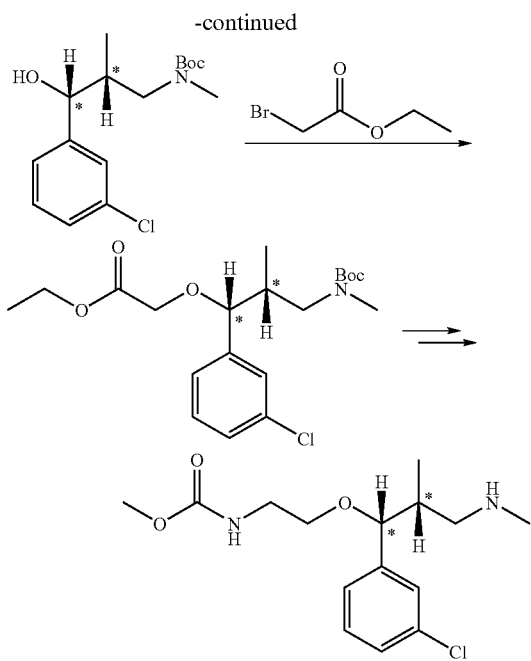

Step 1. tert-butyl 3-(3-chlorophenyl)-2-methyl-3-oxopropyl(methyl)carbamate

To NaH (680 mg, 1.7 mmol) in THF (10 mL) was added tert-butyl 3-(3-chlorophenyl)-3-oxopropyl(methyl)carbamate (2.4 g, 8.5 mmol) in THF (5 mL) at 0° C. over 3 min. After a few minutes THF (100 mL) was added. And an additional 10 min, $CH_3I$ (1.32 g, 9.3 mmol) was added drop wise. The mixture was stirred for 16 h at room temperature. Then the mixture was quenched with $NH_4Cl$ and 1N HCl was added until pH=4 was reached. The mixture was extracted with ethyl acetate. The organic layers was dried over $Na_2SO_4$, filtered, and concentrated in vacuo. The residue was purified by chromatography to give the product (2.0 g, 79%).

Step 2. 1-(3-chlorophenyl)-2-methyl-3-(methylamino)propan-1-ol

A solution of tert-butyl 3-(3-chlorophenyl)-2-methyl-3-oxopropyl(methyl)carbamate (2.8 g, 9.4 mmol) in THF (20 mL) was added slowly to a suspension of LAH (537 mg, 14.1 mmol) in THF (10 mL). The mixture was then stirred at 50° C. for 4 h. The mixture was cooled to 0° C. and 4 g of ice was added into the reaction. The mixture was stirred for 30 min at room temperature, diluted with ethyl acetate, dried over $Na_2SO_4$, filtered and concentrated to give the crude product. The residue was purified by chromatography to obtain pure 1-(3-chlorophenyl)-2-methyl-3-(methylamino)propan-1-ol (930 mg, 32%).

Step 3. tert-butyl (2R*,3R*)-3-(3-chlorophenyl)-3-hydroxy-2-methylpropyl(methyl)carbamate A mixture of 1-(3-chlorophenyl)-2-methyl-3-(methylamino)propan-1-ol (900 mg, 4.2 mmol) and $Boc_2O$ (920 mg, 4.2 mmol) in anhydrous $CH_2Cl_2$ was heated to reflux for 2 h. The mixture was cooled and diluted with $CH_2Cl_2$. The organic layer was first washed with dilute sodium hydrogen sulphate solution followed by water. The organic layer was then dried over $Na_2SO_4$, filtered, and concentrated. The residue was purified by chromatography to give the pure product (1.05 g, 80%). The product was purified by preparative HPLC to give tert-butyl (2R*,3R*)-3-(3-chlorophenyl)-3-hydroxy-2-methylpropyl(methyl)carbamate (360 mg) and tert-butyl (2S*,3R*)-3-(3-chlorophenyl)-3-hydroxy-2-methylpropyl(methyl)carbamate (340 mg).

Step 4-10. methyl 2-((1R*,2R*)-1-(3-chlorophenyl)-2-methyl-3-(methylamino)propoxy)ethylcarbamate methyl 2-((1R*,2R*)-1-(3-chlorophenyl)-2-methyl-3-(methylamino)propoxy)ethylcarbamate was obtained using procedures analogous to PREPARATION B, Steps 3-9, using tert-butyl (2R*,3R*)-3-(3-chlorophenyl)-3-hydroxy-2-methylpropyl(methyl)carbamate in Step 3.
The following compounds were prepared following procedures analogous to those described above:
1) methyl 2-((1R*,2S*)-1-(3-chlorophenyl)-2-methyl-3-(methylamino)propoxy)ethylcarbamate using tert-butyl (2S*,3R*)-3-(3-chlorophenyl)-3-hydroxy-2-methylpropyl(methyl)carbamate in Step 4.

Preparation D 3-(3-chlorophenyl)-N-isopropyl-3-(3-methoxypropoxy)propan-1-amine

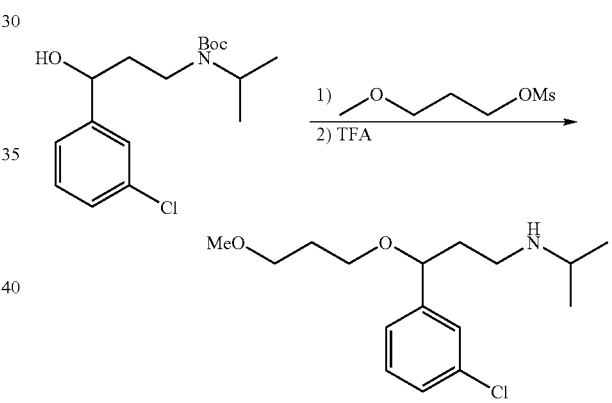

Step 1. 3-(3-chlorophenyl)-N-isopropyl-3-(3-methoxypropoxy)propan-1-amine 3-methoxypropyl methanesulfonate was prepared using procedures described in U.S. Prov. App No. 05/036,230 (PCT App No. 60/616,770).
tert-butyl 3-(3-chlorophenyl)-3-hydroxypropyl(isopropyl)carbamate was obtained using procedures analogous to Preparation A, Steps 1-6, using isopropylamine in Step 1 and $NaBH_4$ in Step 6. To a 0° C. solution of tert-butyl 3-(3-chlorophenyl)-3-hydroxypropyl(isopropyl)carbamate (158 mg, 0.48 mmol) in THF (5 mL) was added NaH (60 mg, 1.45 mmol) and the reaction was allowed to stir for 5 minutes. 3-methoxypropyl methanesulfonate (810 mg, 4.8 mmol) was then added and the reaction was heated to reflux for 2.5 hrs. After cooling to room temperature, the reaction was quenched with saturated ammonium chloride solution at 0° C. The aqueous layer was extracted with EtOAc (2×). The combined organic layers were dried over $MgSO_4$, filtered, evaporated and purified via ISCO to afford tert-butyl 3-(3- chlorophenyl)-3-(3-methoxypropoxy)propyl(isopropyl)carbamate. MS ESI+ve m/z 422 (M+Na).

tert-butyl 3-(3-chlorophenyl)-3-(3-methoxypropoxy)propyl(isopropyl)carbamate was dissolved in a solution of 20% (V/V) TFA/CH$_2$Cl$_2$ (10 mL) and allowed to stir for 1 hour. The solvent and reagent were evaporated before re-dissolving in CH$_2$Cl$_2$ and washing with NaHCO$_3$ saturated solution. The crude 3-(3-chlorophenyl)-N-isopropyl-3-(3-methoxypropoxy)propan-1-amine was isolated (138 mg) and used as is. MS ESI+ve m/z 299 (M+).

Preparation E methyl 3-(N-(3-chlorophenyl)-2-(methylamino)acetamido)propylcarbamate

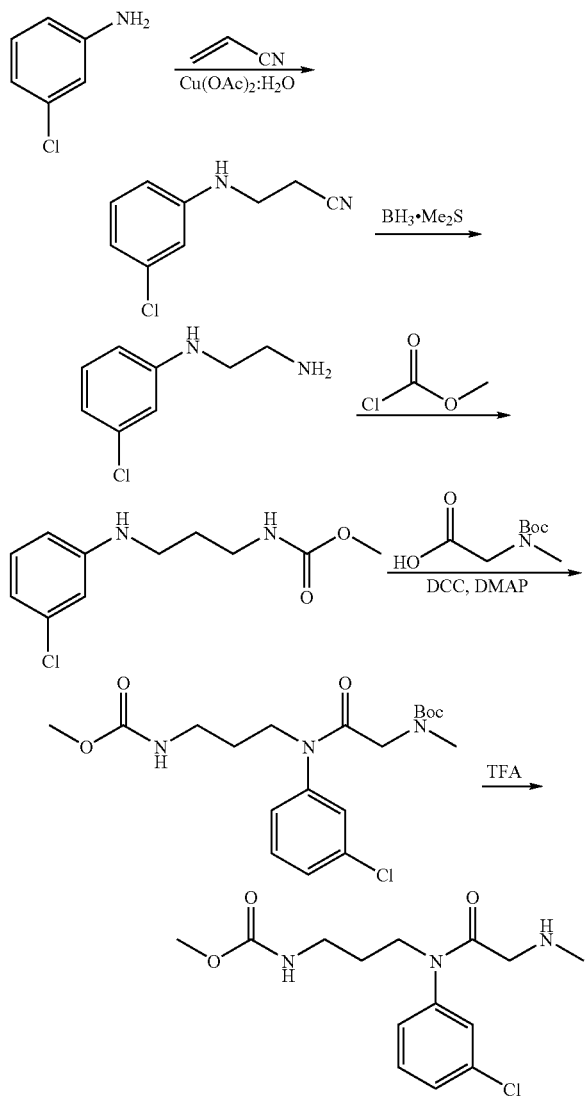

Step 1. 3-(3-chlorophenylamino)propanenitrile

A solution of 3-chlorobenzenamine (10 g, 0.079 mol), Cu(OAc)$_2$ (0.5 g, 5% by weight of m-chloroaniline), and acrylonitrile, was heated to reflux. Refluxing was continued for 3 h with the temperature rising to about 130° C. After the reaction was complete, acrylonitrile was stripped under reduced pressure and the residue purified by column chromatography to afford the pure product 3-(3-chlorophenylamino)propanenitrile (8 g, yield 67%). $^1$HNMR δ 2.6 (m, 2H), 3.5 (m, 2H), 4.1 (m, 1H), 6.45 (m, 1H), 6.55 (m, 1H), 7.1 (m, 1H).

Step 2. N$^1$-(3-chlorophenyl)propane-1,3-diamine 3-(3-chlorophenylamino)propanenitrile (2 g, 0.011 mol) was dissolved in anhydrous THF (20 mL) and heated to reflux under nitrogen. A solution of BH$_3$.MeS in THF was added drop wise and stirred at reflux overnight. The resulting solution was cooled to room temperature. Methanol was added drop wise to quench the reaction. After evaporation of the solution, the crude product was purified by column chromatography to afford the pure product N$^1$-(3-chlorophenyl)propane-1,3-diamine (1.89 g, yield 95%)

Step 4. methyl 3-(3-chlorophenylamino)propylcarbamate

To a solution of N$^1$-(3-chlorophenyl)propane-1,3-diamine (1 g, 5.4 mmol) in dry CH$_2$Cl$_2$ (10 mL), Et$_3$N (1.65 g, 2.27 mL) was added. The resulting mixture was cooled to 0-5° C., a solution of methyl chloroformate (4.0 g, 43 mmol, 5 eq) in dry CH$_2$Cl$_2$ (5 mL) was added drop wise. After addition, the reaction mixture was stirred for 1-2 h at 0-5° C. Upon completion of the reaction, water (15 mL) was added. The aqueous layer was extracted with CH$_2$Cl$_2$ (3×30 mL). The combined organic layers were washed with 10% citric acid (2×10 mL) and brine, then dried over Na$_2$SO$_4$, filtered and concentrated to the crude product which was purified by preparative HPLC to afford methyl 3-(3-chlorophenylamino)propylcarbamate (1.18 g, yield 98%).

Step 5. tert-butyl 2-((3-chlorophenyl)(3-(methoxycarbonylamino)propyl)amino)-2-oxoethyl(methyl) carbamate To a solution of 2-(tert-butoxycarbonyl(methyl)amino) acetic acid in CH$_2$Cl$_2$ at 0° C. under argon atmosphere was added DMAP, methyl 3-(3-chlorophenylamino)propylcarbamate and DCC. The reaction mixture was allowed to stir at room temperature for 24 h. The resulting suspension was filtered, the filtrate concentrated under reduced pressure and the crude residue was subjected to silica gel chromatography to give tert-butyl 2-((3-chlorophenyl)(3-(methoxycarbonylamino)propyl)amino)-2-oxoethyl(methyl)carbamate. $^1$H NMR δ 0.7-0.9 (m, 4H), 1.0-1.15 (m, 1H), 1.3 (s, 3H), 1.4 (s, 9H), 1.65 (m, 2H), 2.85 (m, 3H), 3.7 (m, 4H), 3.75 (m, 2H), 5.65 (m, 1H), 7.0-7.2 (m, 1H), 7.25 (m, 2H), 7.4 (m, 2H).

Step 6. methyl 3-(N-(3-chlorophenyl)-2-(methylamino)acetamido)propylcarbamate tert-butyl 2-((3-chlorophenyl)(3-(methoxycarbonylamino)propyl)amino)-2-oxoethyl(methyl)carbamate (130 mg, 0.31 mmol) was dissolved in a solution of 20% (V/V) TFA/CH$_2$Cl$_2$ (4 mL). The reaction mixture was stirred at room temperature for 1 h, a solution of saturated sodium bicarbonate was added drop wise to adjust the pH=7-8. The resulting mixture was extracted with CH$_2$Cl$_2$ (3×10 mL), washed with brine, dried over Na$_2$SO$_4$, concentrated in vacuo to afford methyl 3-(N-(3-chlorophenyl)-2-(methylamino)acetamido)propylcarbamate (95 mg, 95%).

Preparation F methyl 3-((3-chlorophenyl)(2-(methylamino)ethyl)amino)propylcarbamate

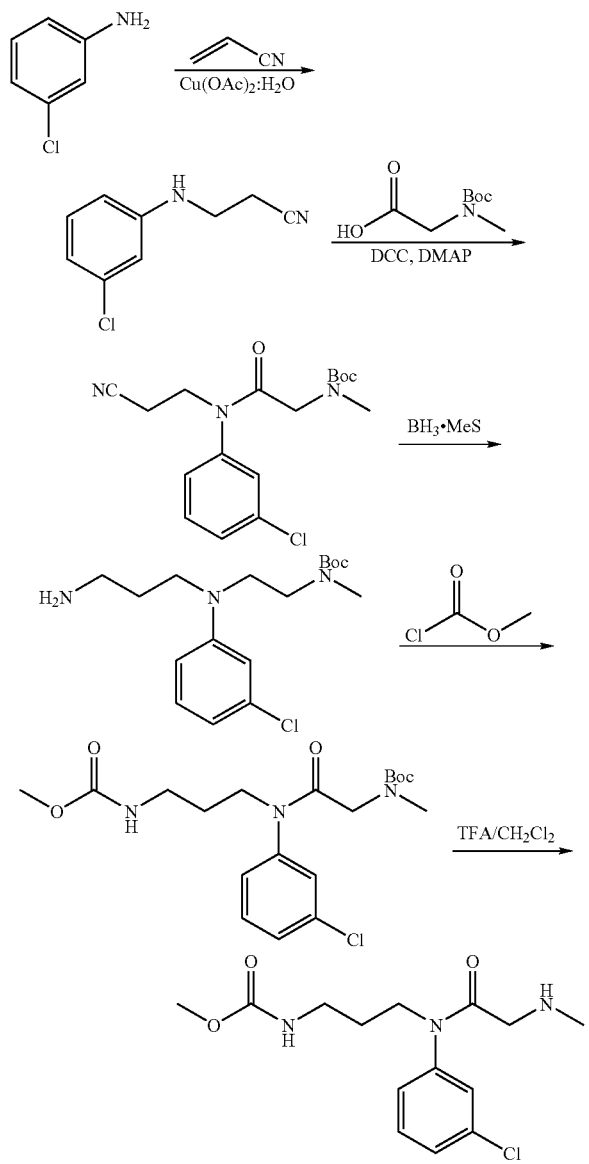

Step 1. 3-(3-chlorophenylamino)propanenitrile

To a solution of 3-chlorobenzenamine (10 g, 0.079 mol) and acrylonitrile (5.0 g, 0.095 mol), Cu(OAc)$_2$ (0.5 g, 5% by weight of 3-chlorobenzenamine), were heated under reflux, beginning at about 95° C. The reaction is heated at reflux for 3 h with the temperature rising to ~130° C. Upon completion of the reaction, the acrylonitrile was stripped under reduced pressure. The residue was purified by column chromatography to afford the pure product 3-(3-chlorophenylamino)propanenitrile (8 g, yield 67%).

Step 2. tert-butyl 2-((3-chlorophenyl)(2-cyanoethyl)amino)-2-oxoethyl(methyl)carbamate To a solution of 2-(tert-butoxycarbonyl(methyl)amino) acetic acid (1.05 g, 0.0056 mol) in CH$_2$Cl$_2$ at 0° C. under argon atmosphere was added DMAP (0.021 g), 3-(3-chlorophenylamino)propanenitrile (1 g, 0.0056 mol) and DCC (1.27 g, 0.0061 mol). The reaction mixture was allowed to stir at room temperature for 24 h. The resulting suspension was filtered, the filtrate concentrated under reduced pressure and the crude residue was subjected to silica gel chromatography to give the tert-butyl 2-((3-chlorophenyl)(2-cyanoethyl)amino)-2-oxoethyl(methyl)carbamate (1.2 g, 80%). $^1$H NMR (CDCl$_3$) δ 1.45 (s, 9H), 2.7 (m, 2H), 2.85 (m, 2H), 3.6-3.75 (m, 2H), 3.9 (m, 2H), 7.1-7.3 (m, 2H), 7.4 (m, 2H).

Step 5. tert-butyl 2-((3-aminopropyl)(3-chlorophenyl)amino)ethyl(methyl)carbamate tert-butyl 2-((3-chlorophenyl)(2-cyanoethyl)amino)-2-oxoethyl(methyl)carbamate (500 mg, 1.4 mmol) was dissolved in anhydrous THF (10 mL) and heated to reflux under nitrogen atmosphere. A solution of BH$_3$.MeS in THF was added drop wise and stirring was continued under reflux overnight. The resulting solution was cooled to room temperature. Methanol was added drop wise to quench the reaction. After evaporation of the solution, the crude product was purified by column chromatography to afford the pure product tert-butyl 2-((3-aminopropyl)(3-chlorophenyl)amino) ethyl(methyl)carbamate (500 g, yield 99%).

Step 6. tert-butyl 243-(methoxycarbonylamino)propyl)(3-chlorophenyl)amino)ethyl(methyl)carbamate To a solution of tert-butyl 2-((3-aminopropyl)(3-chlorophenyl)amino)ethyl(methyl)carbamate (300 mg, 0.88 mmol) in dry CH$_2$Cl$_2$ (5 mL), Et$_3$N (583 mg, 5.3 mmol) was added. The resulting mixture was cooled to 0-5° C. and a solution of methyl chloroformate (965 mg, 10.3 mmol, 5 eq) in dry CH$_2$Cl$_2$ (5 mL) was added dropwise. After addition, the reaction mixture was stirred for 1-2 h at 0-5° C. Upon completion of the reaction, water (10 mL) was added, the aqueous layer was extracted with CH$_2$Cl$_2$ (3×8 mL), the combined organic layers were washed with 10% citric acid (2×5 mL) and brine, then dried over Na$_2$SO$_4$. The filtrate was concentrated to the crude product which was purified by preparative HPLC to tert-butyl 2-((3-(methoxycarbonylamino)propyl)(3-chlorophenyl)amino)ethyl(methyl)carbamate (200 mg, yield 83%).

Step 7. methyl 3-((3-chlorophenyl)(2-(methylamino)ethyl)amino)propylcarbamate tert-butyl 2-((3-(methoxycarbonylamino)propyl)(3-chlorophenyl)amino)ethyl(methyl)carbamate (50 mg, 0.31 mmol) was dissolved in a solution of 20% (V/V) TFA/CH$_2$Cl$_2$ (4 mL). The reaction mixture was stirred at room temperature for 1 h, a solution of saturated sodium bicarbonate was added dropwise to adjust pH=7-8. The resulting mixture was extracted with CH$_2$Cl$_2$ (3×10 mL), washed with brine, dried over Na$_2$SO$_4$, concentrated in vacuo to afford methyl 3-((3-chlorophenyl)(2-(methylamino)ethyl)amino) propylcarbamate (40 mg, 95%).

Preparation G

(S)-5-fluoro-3-(4-methoxybutyl)-3-(2-(methylamino)ethyl)isoindolin-1-one

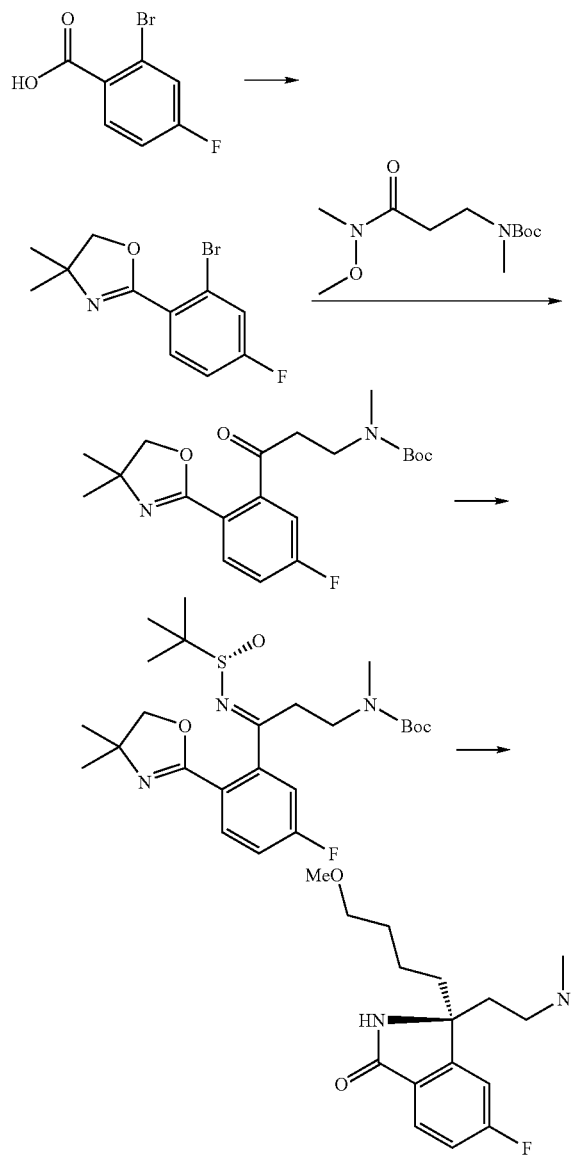

Step 1. 2-(2-Bromo-4-fluorophenyl)-4,4-dimethyl-4,5-dihydrooxazole

To a solution of 2-bromo-4-iodofluorobenzoic acid (5.0 g, 22.8 mmol) in dry dichloromethane (50 mL) was added DMF (2 drops) followed by addition of oxalyl chloride (3.0 mL, 34.2 mmol) drop wise at room temperature. The reaction mixture was stirred over night at room temperature then the solvent and excess reagents were evaporated by rotovap. The residue was dissolved in dry dichloromethane (40 mL) and a solution of 2-amino-2-methyl-1-propanol (5.1 g, 57.0 mmol) in dichloromethane (10 mL) was added drop wise. The reaction was stirred at room temperature for 4 h. The solvent was removed in vacuo and the resulting residue was dissolved in ethyl acetate (100 mL), washed with water (50 mL), 1N HCl (3×50 mL), and brine (50 mL), dried over sodium sulfate, filtered and concentrated. The residue was dissolved in dry toluene (80 mL) and cooled to 0° C. Thionyl chloride (5.0 mL, 68.4 mmol) was added drop wise, stirred at 0° C. for 30 min, then room temperature for 1 h. The reaction mixture was diluted with ethyl acetate and poured into a stirred solution of saturated aqueous NaHCO₃ portion wise (vigorous gas evolution). The aqueous layer was extracted with ethyl acetate. The combined organic phases were dried over sodium sulfate, filtered, and concentrated. The residue was purified by column chromatography on silica gel (120 g column, 0% ethyl acetate in hexanes to 60% ethyl acetate in hexanes) to give product (4.2 g, 68%). $^1$H NMR (CDCl$_3$) $\delta$7.87 (brs, 1H), 7.40 (dd, J=8.2, 2.7 Hz, 1H), 7.07-7.14 (m, 1H), 4.25 (s, 2H), 1.48 (s, 6H); MS EI m/z 271 (M+H)$^+$.

Step 2. tert-Butyl 3-(methoxy(methyl)amino)-3-oxopropyl(methyl)carbamate

To a stirred solution of 3-[(tert-butoxycarbonyl)(methyl)amino]-propanoic acid (5.0 g, 24.6 mmol), N,O-dimethylhydroxylamine hydrochloride (3.1 g, 32.0 mmol) and HBTU (11.2 g, 29.5 mmol) in DMF (50 mL) at 0° C. was added triethylamine (10.2 mL, 73.8 mmol). The mixture was stirred at room temperature over night and the solvent was removed under reduced pressure. The residue was taken up in ethyl acetate (300 mL), washed with water (100 mL) and 0.6 N NaOH solution (100 mL). The aqueous phases were back extracted with ethyl acetate (100 mL). The combined organic phases were dried over sodium sulfate, filtered and concentrated. The residue was purified by column chromatography on silica gel (120 g column, 0% ethyl acetate in hexanes to 100% ethyl acetate in hexanes) to give product (6.0 g, 99%). $^1$H NMR (CDCl$_3$) $\delta$3.69 (s, 3H), 3.52 (t, J=6.2 Hz, 2H), 3.18 (s, 3H), 2.88 (s, 3H), 2.66 (brs, 2H), 1.45 (s, 9H); MS EI m/z 269 (M+Na)$^+$.

Step 3. tert-Butyl 3-(2-(4,4-dimethyl-4,5-dihydrooxazol-2-yl)-5-fluorophenyl)-3-oxopropyl(methyl)carbamate A stirred solution of 2-(2-bromo-4-fluorophenyl)-4,4-dimethyl-4,5-dihydrooxazole (1.2 g, 4.7 mmol) in dry THF (6 mL) was cooled to −78° C. and a solution of tert-buLi (1.7 M in pentane, 5.5 mL, 9.3 mmol) was added drop wise. After 30 min, a solution of tert-butyl 3-(methoxy(methyl)amino)-3-oxopropyl(methyl)carbamate (0.77 g, 3.1 mmol) in dry THF (5 mL) was added. The cooling bath was allowed to warm to −20° C. and the reaction mixture was stirred between −20° C. and 0° C. for 4 h. After warming to room temperature, the mixture was added 0.2N HCl (50 mL). The mixture was extracted with ethyl acetate (2×100 mL). The combined organic extracts were washed with brine, dried over Na$_2$SO$_4$, filtered and concentrated. The residue was purified by column chromatography on silica gel (120 g column, 0% ethyl acetate in hexanes to 60% ethyl acetate in hexanes) to give product (0.72 g, 61%). $^1$H NMR (CDCl$_3$) $\delta$7.62 (brs, 1H), 6.88 (t, J=7.5 Hz, 1H), 6.79 (brs, 1H), 3.80-4.00 (m, 2H), 3.30 (t, J=7.0 Hz, 2H), 2.76 (brs, 2H), 2.59 (s, 3H), 1.13 (s, 15H); MS EI m/z 379 (M+H)$^+$.

Step 4. (S)-tert-Butyl 3-(2-(4,4-dimethyl-4,5-dihydrooxazol-2-yl)-5-fluorophenyl)-3-(tert-butylsulfinimino)propyl(methyl)carbamate To a mixture of tert-butyl 342-(4,4-dimethyl-4,5-dihydrooxazol-2-yl)-5-fluorophenyl)-3-oxopropyl(methyl)carbamate (837 mg, 2.2 mmol) and titanium ethoxide (1.4 mL, 6.6 mmol) in dry 1,4-dioxane (4 mL) in a sealed tube under nitrogen was added (S)-(−)-2-methyl-2-propanesulfinamide (402 mg, 3.3 mmol). The tube was sealed and heated at 90° C. for 72 h. After cooling to room temperature, the reaction mixture was poured into a stirred mixture of ethyl acetate and brine, stirred for 2 h, filtered through Celite, separated. The aqueous phase was extracted with ethyl acetate twice. The combined organic phases were dried over sodium sulfate, filtered and concentrated. The residue was purified by column chromatography on silica gel (120 g column, 0% ethyl acetate in hexanes to 60% ethyl acetate in hexanes) to give product (570 mg, 54%).

$^1$H NMR (CD$_3$OD) δ7.88-8.00 (m, 1H), 7.20-7.30 (m, 1H), 7.04-7.14 (m, 1H), 4.08-4.20 (m, 2H), 3.40-3.80 (m, 2H), 2.76-3.20 (m, 2H), 2.89 (brs, 3H), 1.30-1.50 (m, 24H); MS EI m/z 482 (M+H)$^+$.

Step 5. (S)-5-Fluoro-3-(4-methoxybutyl)-3-(2-(methylamino)ethyl)isoindolin-1-one To a solution of (S)-tert-butyl 3-(2-(4,4-dimethyl-4,5-dihydrooxazol-2-yl)-5-fluorophenyl)-3-(tert-butylsulfinimino)propyl(methyl)carbamate (240 mg, 0.5 mmol) in dry toluene (3 mL) at 100° C. was added 4-methoxybutylmagnesium chloride (2.0 M, 1.25 mL, 2.5 mmol, prepared by refluxing 4-methoxybutylchloride and magnesium in THF for 4 h). The reaction was heated at 100° C. for 30 min. After cooling to room temperature, the reaction mixture was poured into a mixture of ethyl acetate and brine, separated. The aqueous phase was extracted with ethyl acetate twice. The combined organic phases were dried over sodium sulfate, filtered and concentrated. The residue was purified via column chromatography. The residue was dissolved in methanol (8 mL), put in a sealed tube and added methanesulfonic acid (0.5 mL). The tube was then sealed and heated at 100° C. for 6 h. After cooling to room temperature, the reaction mixture was purified by preparative HPLC (C-18 column, 2 to 40% CH$_3$CN in H$_2$O containing 0.01% CF$_3$CO$_2$H over 20 min, 20 mL min$^{-1}$) to afford product as TFA salt (8.2 mg, 4%). $^1$H NMR (CD$_3$OD) δ 7.79 (dd, J=8.2, 5.0 Hz, 1H), 7.36 (dd, J=8.5, 2.0 Hz, 1H), 7.29 (td, J=8.4, 2.1 Hz, 1H), 3.28 (t, J=6.2 Hz, 2H), 3.24 (s, 3H), 2.80-2.90 (m, 1H), 2.60 (s, 3H), 2.40-2.48 (m, 1H), 2.26-2.32 (m, 2H), 1.96-2.02 (m, 2H), 1.42-1.52 (m, 2H), 1.14-1.24 (m, 1H), 0.74-0.86 (m, 1H); MS EI m/z 295 (M+H)$^+$.

The following compounds were prepared following procedures analogous to those described above:
1) (R)-5-fluoro-3-(4-methoxybutyl)-3-(2-(methylamino)ethyl)isoindolin-1-one using (R)-(−)-2-methyl-2-propanesulfinamide in Step 4.

Preparation H 5-chloro-3-(4-methoxybutyl)-3-(2-(methylamino)ethyl)isoindolin-1-one

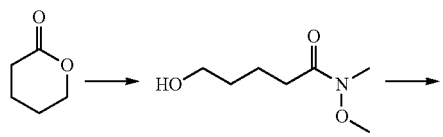

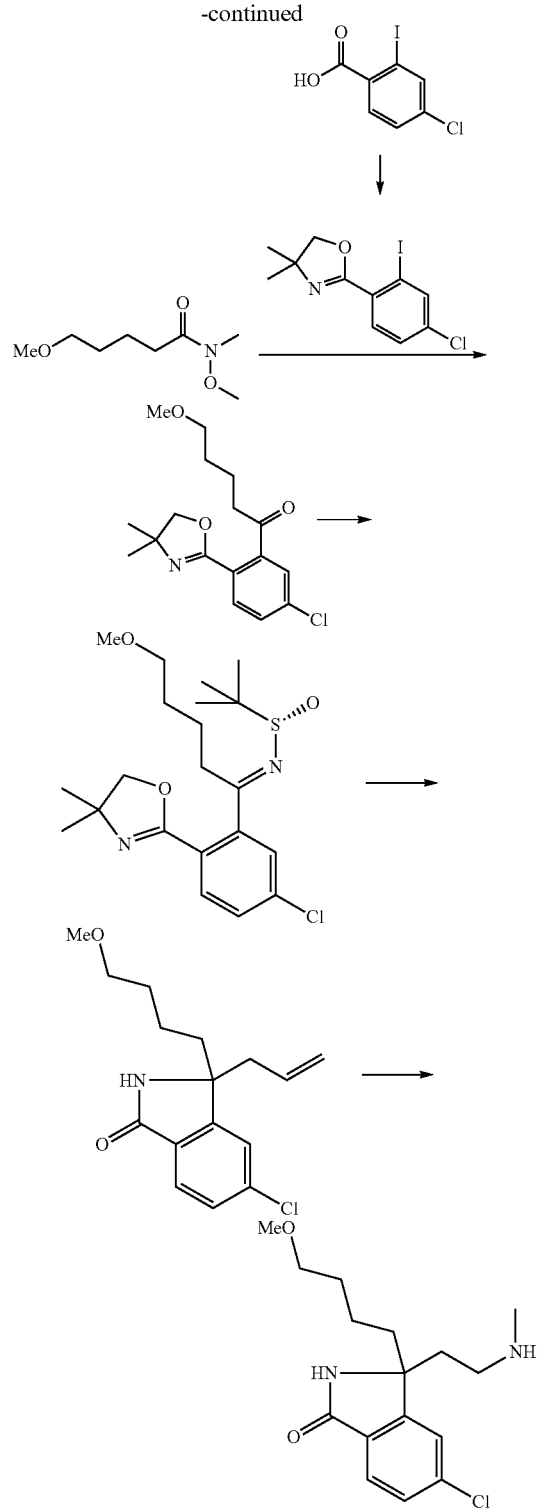

Step 1.
5-Hydroxy-N-methoxy-N-methylpentanamide

To a stirred suspension of N,O-dimethylhydroxyamine hydrochloride (14.6 g, 150 mmol) in dry dichloromethane (150 mL) was added a solution of trimethylaluminum (2.0 M solution in toluene, 75 mL, 150 mmol) drop wise at room temperature. After stirring for 30 min, tetrahydropyran-2-one (10 g, 100 mmol) in dry dichloromethane (50 mL) was added drop wise. The reaction mixture was stirred over night. After cooling to 0° C., 1N HCl (80 mL, 80 mmol) was added slowly (exothermic reaction), diluted with dichloromethane (200 mL). The two layers were separated and the aqueous layer was extracted with dichloromethane twice. The combined organic phases were dried over sodium sulfate, filtered and concentrated. The residue was purified by column chromatography on silica gel (120 g column, 0% methanol in dichloromethane to 20% methanol in dichloromethane) to give product (9.7 g, 60%). $^1$H NMR (CDCl$_3$) δ 3.68 (s, 3H), 3.63 (t, J=6.1 Hz, 2H), 3.17 (s, 3H), 2.46 (t, J=7.0 Hz, 2H), 1.69-1.74 (m, 2H), 1.58-1.64 (m, 2H). MS EI m/z 162 (M+H)$^+$.

Step 2. N,5-dimethoxy-N-methylpentanamide

To sodium hydride (60% in mineral oil, 2.6 g, 66.3 mmol) in dry DMF (40 mL) was added a solution of 5-hydroxy-N-methoxy-N-methylpentanamide (8.9 g, 55.2 mmol) in DMF (50 mL) slowly at 0° C. After 30 min, methyl iodide (4.1 mL, 66.3 mmol) was added and the reaction was stirred over night. Starting material remained and more sodium hydride ((60% in mineral oil, 1 g, 25 mmol) and methyl iodide (1.7 mL, 27.2 mmol) was added followed by additional stirring for 6 h. The solvent was evaporated under vacuum. The residue was diluted with dichloromethane and treated with brine. The aqueous layer was extracted with dichloromethane. The combined organic phases were dried over sodium sulfate, filtered and concentrated. The residue was purified by column chromatography on silica gel (120 g column, 80% ethyl acetate in hexanes to 100% ethyl acetate) to give product (5.3 g, 55%). $^1$H NMR (CDCl$_3$) δ 3.68 (s, 3H), 3.39 (t, J=6.4 Hz, 2H), 3.32 (s, 3H), 3.17 (s, 3H), 2.45 (t, J=6.8 Hz, 2H), 1.58-1.74 (m, 4H). MS EI m/z 176 (M+H)$^+$.

Step 3a-b. 5-Chloro-2-(4,4-dimethyl-4,5-dihydrooxazol-2-yl)phenyl)-5-methoxypentan-1-one Step 3a. 2-(4-Chloro-2-iodophenyl)-4,4-dimethyl-4,5-dihydrooxazole To a solution of 4-chloro-2-iodobenzoic acid (10 g, 35.4 mmol) in dry dichloromethane (100 mL) was added DMF (4 drops) followed by addition of oxalyl chloride (4.65 mL, 53.1 mmol) drop wise at room temperature. The reaction mixture was stirred for 4 h then the solvent and excess reagents were evaporated by rotovap. The residue was dissolved in dry dichloromethane (80 mL), added a solution of 2-amino-2-methyl-1-propanol (7.9 g, 8.5 mL, 88.5 mmol) in dichloromethane (20 mL), and stirred at room temperature over night. The solvent was removed, the resulting residue was dissolved in ethyl acetate (200 mL), washed with water (100 mL), 1N HCl (3×100 mL), and brine (100 mL), dried over sodium sulfate, filtered and concentrated. The residue was dissolved in dry toluene (200 mL) and cooled to 0° C. Thionyl chloride (7.75 mL, 106.2 mmol) was added drop wise, stirred at 0° C. for 30 min, then room temperature for 3 h. The reaction mixture was diluted with ethyl acetate (400 mL) and poured into a stirred solution of saturated aqueous NaHCO$_3$ (400 mL) portion wise (vigorous gas evolution). The two layers were separated and the aqueous layer was extracted with ethyl acetate. The combined organic phases were dried over sodium sulfate, filtered and concentrated. The residue was purified by column chromatography on silica gel (120 g column, 0% ethyl acetate in hexanes to 60% ethyl acetate in hexanes) to give product (10.5 g, 88%). NMR (CDCl$_3$) δ 8.04 (d, J=2.0 Hz, 1H), 7.67 (brs, 1H), 7.39 (dd, J=9.7, 1.5 Hz, 1H), 4.25 (s, 2H), 1.48 (s, 6H); MS EI m/z 336 (M+H)$^+$.

Step 3b. 5-Chloro-2-(4,4-dimethyl-4,5-dihydrooxazol-2-yl)phenyl)-5-methoxypentan-1-one To a solution of 2-(4-chloro-2-iodophenyl)-4,4-dimethyl-4,5-dihydrooxazole (2.3 g, 6.8 mmol) in dry THF (20 mL) at −78° C. was added n-butyl lithium (2.5 M in hexane, 2.8 mL, 7.0 mmol) drop wise. After stirring for 20 min, N,5-dimethoxy-N-methylpentanamide (1.0 g, 5.7 mmol) was added. The reaction mixture was warmed slowly to 0° C. then stored in refrigerator (4° C.) over night. The reaction was then warmed to room temperature and stirred 2 h. The reaction was quenched with 1N HCl, diluted with brine and ethyl acetate. After separation, the organic phases were dried over sodium sulfate, filtered and concentrated. The residue was purified by column chromatography on silica gel (120 g column, 0% ethyl acetate in hexanes to 50% ethyl acetate in hexanes) to give product (1.0 g, 45%).
$^1$H NMR (CDCl$_3$) δ 7.99 (d, J=9.2 Hz, 1H), 7.67 (brs, 1H), 7.66 (d, J=9.1 Hz, 1H), 4.59 (s, 2H), 3.42 (t, J=6.1 Hz, 2H), 3.33 (s, 3H), 3.01 (t, J=7.3 Hz, 2H), 1.76-1.84 (m, 2H), 1.74 (s, 6H), 1.64-1.70 (m, 2H); MS EI m/z 324 (M+H)$^+$.

Step 4. (S)—N-1-(2-(4,4-dimethyl-4,5-dihydrooxazol-2-yl)-5-fluorophenyl)-5-methoxy-pentylidene tert-butanesulfinamide To a mixture of 1-(5-chloro-2-(4,4-dimethyl-4,5-dihydrooxazol-2-yl)phenyl)-5-methoxypentan-1-one (1 g, 3.1 mmol) and titanium ethoxide (1.9 mL, 9.3 mmol) in dry 1,4-dioxane (4 mL) in seal tube was added (S)-(−)-2-methyl-2-propanesulfinamide (0.75 g, 6.2 mmol) and heated at 90° C. for 72 h. After cooling to room temperature, the reaction mixture was poured into a stirred mixture of ethyl acetate and brine, stirred for 2 h, filtered through Celite, the organic phase was dried over sodium sulfate, filtered and concentrated. The residue was purified by column chromatography on silica gel (120 g column, 0% ethyl acetate in hexanes to 60% ethyl acetate in hexanes) to give product (0.8 g, 60%).
$^1$H NMR (CD$_3$OD) δ 7.89 (d, J=8.2 Hz, 1H), 7.51 (d, J=8.2 Hz, 1H), 7.27 (brs, 1H), 4.10 (brs, 2H), 3.42 (t, J=5.9 Hz, 2H), 3.30 (s, 3H), 2.70-2.82 (m, 2H), 1.60-1.84 (m, 4H), 1.28-1.36 (m, 6H) 1.20 (s, 91-1); MS EI m/z 427 (M+H)$^+$.

Step 5. 3-Allyl-5-chloro-3-(4-methoxybutyl)isoindolin-1-one

To a solution of (S)—N-1-(2-(4,4-dimethyl-4,5-dihydrooxazol-2-yl)-5-fluorophenyl)-5-methoxy-pentylidene tert-butanesulfinamide (300 mg, 0.7 mmol) in dry toluene (7 mL) was added allylmagnesium bromide (1.0 M in diethyl ether, 2.1 mL, 2.1 mmol) at room temperature, stirred over night. The reaction mixture was poured into brine, diluted with ethyl acetate. After separation, the organic phase was dried over sodium sulfate, filtered and concentrated. The residue was dissolved in methanol (10 mL) in sealed tube, added methanesulfonic acid (0.5 mL), sealed and heated at 100° C. for 4 h. After cooling to room temperature, the reaction mixture was concentrated, partitioned between ethyl acetate and brine. The aqueous phase was extracted with ethyl acetate three times. The combined organic phases were dried over sodium sulfate, filtered and concentrated. The residue was purified by column chromatography on silica gel (40 g column, 0% ethyl acetate in hexanes to 100% ethyl acetate in hexanes) to give product (87 mg, 42%).

$^1$H NMR (CDCl$_3$) δ 7.72 (d, J=8.2 Hz, 1H), 7.41 (dd, J=7.9, 1.7 Hz, 1H), 7.32 (d, J=1.7 Hz, 1H), 6.71 (brs, 1H), 5.48-5.59 (m, 1H), 5.02-5.08 (m, 2H), 3.23-3.27 (m, 2H), 3.25 (s, 3H), 2.60 (dd, J=13.8, 7.3 Hz, 1H), 2.48 (dd, J=13.8, 7.0 Hz, 1H), 1.80-1.96 (m, 2H), 1.44-1.52 (m, 2H), 1.24-1.34 (m, 1H), 0.84-0.96 (m, 1H). MS EI m/z 294 (M+H)$^+$.

Step 6. 5-Chloro-3-(4-methoxybutyl)-3-(2-(methylamino)ethyl)isoindolin-1-one

To a solution of 3-allyl-5-chloro-3-(4-methoxybutyl)isoindolin-1-one (87 mg, 0.3 mmol) in THF (9 mL)/water (3 mL) was added sodium periodate (316 mg, 1.5 mmol) followed by 2 drops of osmium tetroxide solution (2.5% solution in 2-propanol), stirred over night. The reaction mixture was concentrated, diluted with ethyl acetate and brine. After separation, the organic phases were dried over sodium sulfate, filtered and concentrated. The residue was dissolved in methanol (20 mL), added methylamine (33% solution in ethanol, 0.3 mL, 3 mmol), methylamine hydrochloride (56 mg, 0.9 mmol), and sodium cyanoborohydride (93 mg, 1.5 mmol), stirred over night. The reaction mixture was concentrated, purified by reverse phase HPLC to give product as TFA salt (56 mg, 32%). $^1$H NMR (CD$_3$OD) δ 7.73 (d, J=8.2 Hz, 1H), 7.65 (d, J=1.8 Hz, 1H), 7.56 (dd, J=8.2, 1.5 Hz, 1H), 3.28 (t, J=6.1 Hz, 2H), 3.24 (s, 3H), 2.78-2.86 (m, 1H), 2.60 (s, 3H), 2.40-2.48 (m, 1H), 2.26-2.32 (m, 2H), 1.96-2.22 (m, 2H), 1.42-1.52 (m, 2H), 1.14-1.24 (m, 1H), 0.72-0.84 (m, 1H); MS EI m/z 311 (M+H)$^+$.

Preparation I

5-Fluoro-3-(4-methoxybutyl)-3-(2-(methylamino)ethyl)isobenzofuran-1(3H)-one

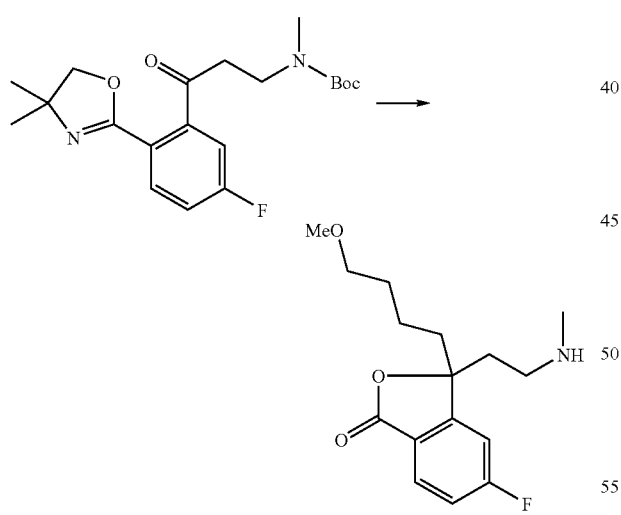

Step 1. 5-Fluoro-3-(4-methoxybutyl)-3-(2-(methylamino)ethyl)isobenzofuran-1(3H)-one To a solution of tert-butyl 3-(2-(4,4-dimethyl-4,5-dihydrooxazol-2-yl)-5-fluorophenyl)-3-oxopropyl(methyl)carbamate (153 mg, 0.4 mmol) in dry toluene (2 mL) at −30° C. was added 4-methoxybutylmagnesium chloride (2.0 M, 0.6 mL, 1.2 mmol, prepared by refluxing 4-methoxybutylchloride and magnesium in THF for 4 h). The reaction was stirred at −30° C. for 2 h. After warming to room temperature, the reaction mixture was poured into a mixture of ethyl acetate and brine, separated. The aqueous phase was extracted with ethyl acetate once. The combined organic phases were dried over sodium sulfate, filtered and concentrated. The residue was purified by column chromatography on silica gel (40 g column, EtOAc/Hexanes) to give the Grignard-addition adduct (130 mg, 70%). A portion of the adduct (30 mg, 0.064 mmol) was dissolved in acetonitrile (4 mL), put in a seal tube and added concentrated sulfuric acid (3 drops). The tube was then sealed and heated at 100° C. for 2 h. After cooling to room temperature, the reaction mixture was purified by preparative HPLC (C-18 column, 2 to 60% CH$_3$CN in H$_2$O containing 0.01% CF$_3$CO$_2$H over 20 min, 20 mL min$^{-1}$) to afford product as TFA salt (17 mg, 65%).

$^1$H NMR (CD$_3$OD) δ 7.96 (dd, J=8.5, 4.7 Hz, 1H), 7.49 (d, J=8.2 Hz, 1H), 7.44 (t, J=8.5 Hz, 1H), 3.28-3.38 (m, 2H), 3.29 (s, 3H), 2.98-3.06 (m, 1H), 2.74-2.84 (m, 1H), 2.70 (s, 3H), 2.51-2.61 (m, 1H), 2.32-2.42 (m, 1H), 2.04-2.24 (m, 2H), 1.50-1.62 (m, 2H), 1.22-1.34 (m, 1H), 0.90-1.02 (m, 1H); MS EI m/z 296 (M+H)$^+$.

Preparation J (S)-methyl 3-(6-chloro-1-(2-(methylamino)ethyl)-3-oxoisoindolin-1-yl)propylcarbamate

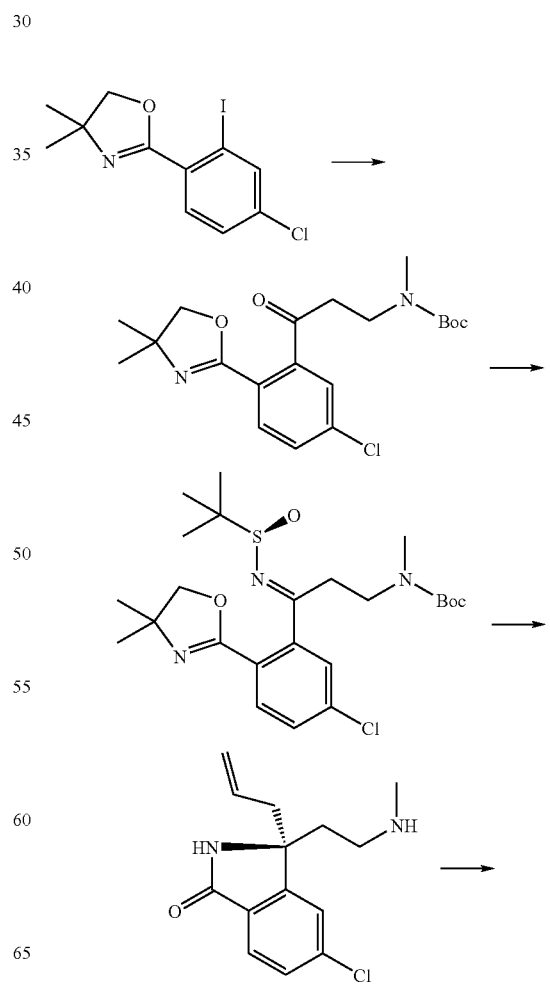

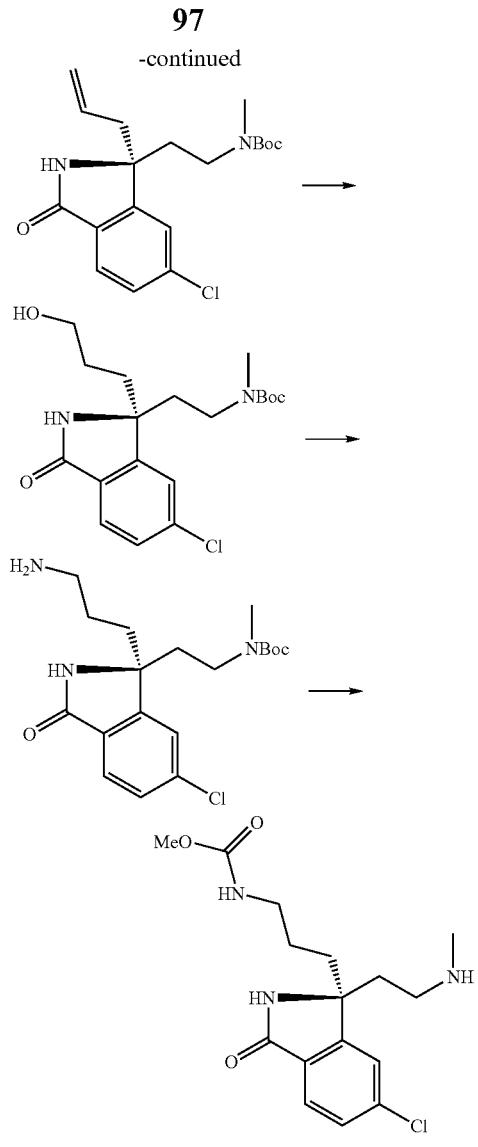

Step 1. tert-Butyl 3-(5-chloro-2-(4,4-dimethyl-4,5-dihydrooxazol-2-yl)phenyl)-3-oxopropyl(methyl)carbamate To a solution of 2-(4-chloro-2-iodophenyl)-4,4-dimethyl-4,5-dihydrooxazole (3.3 g, 9.7 mmol) in dry THF (30 mL) at −78° C. was added n-butyl lithium (2.5 M in hexane, 4.0 mL, 10.0 mmol) drop wise. After stirring for 30 min, a solution of tert-butyl 3-(methoxy(methyl)amino)-3-oxopropyl(methyl)carbamate (2.0 g, 8.1 mmol) in dry THF (5 mL) was added. The reaction mixture was warmed slowly to 0° C. then stored in refrigerator (4° C.) over night. The reaction was then warmed to room temperature and stirred 7 h. The reaction was quenched with 1N HCl, diluted with brine and ethyl acetate. After separation, the organic phases were dried over sodium sulfate, filtered and concentrated. The residue was purified by column chromatography on silica gel (120 g column, 0% ethyl acetate in hexanes to 50% ethyl acetate in hexanes) to give product (1.2 g, 38%). $^1$H NMR (CD$_3$OD) δ 7.75 (d, J=7.6 Hz, 1H), 7.55-7.60 (m, 2H), 4.10-4.20 (m, 2H), 3.58 (t, J=6.8 Hz, 2H), 3.05-3.15 (m, 2H), 2.88 (s, 3H), 1.43 (s, 9H), 1.35 (s, 6H); MS EI m/z 395 (M+H)$^+$.

Step 2. (R)-tert-Butyl 3-(2-(4,4-dimethyl-4,5-dihydrooxazol-2-yl)-5-chlorophenyl)-3-(tert-butylsulfinimino)propyl(methyl)carbamate To a mixture of tert-butyl 3-(5-chloro-2-(4,4-dimethyl-4,5-dihydrooxazol-2-yl)phenyl)-3-oxopropyl(methyl)carbamate (1.1 g, 2.79 mmol) and titanium ethoxide (1.7 mL, 8.4 mmol) in dry 1,4-dioxane (4 mL) in seal tube under nitrogen was added (R)-(+)-2-methyl-2-propanesulfinamide (0.67 g, 5.6 mmol). The tube was sealed and heated at 90° C. for 72 h. After cooling to room temperature, the reaction mixture was poured into a stirred mixture of ethyl acetate and brine, stirred for 2 h, filtered through Celite, separated. The aqueous phase was extracted with ethyl acetate twice. The combined organic phases were dried over sodium sulfate, filtered and concentrated. The residue was purified by column chromatography on silica gel (120 g column, 0% ethyl acetate in hexanes to 60% ethyl acetate in hexanes) to give product (630 mg, 45%). $^1$H NMR (CD$_3$OD) δ7.82-7.92 (m, 1H), 7.44-7.58 (m, 1H), 7.28-7.38 (m, 1H), 4.07-4.20 (m, 2H), 3.34-3.80 (m, 2H), 2.74-3.20 (m, 2H), 2.88 (brs, 3H), 1.16-1.48 (m, 24H); MS EI m/z 498 (M+H)$^+$.

Step 3. (S)-3-Allyl-5-chloro-3-(2-(methylamino)ethyl)isoindolin-1-one

To a solution of (R)-tert-butyl 3-(tert-butylsulfinylimino)-3-(5-chloro-2-(4,4-dimethyl-4,5-dihydrooxazol-2-yl)phenyl)propyl(methyl)carbamate (630 mg, 1.27 mmol) in dry toluene (13 mL) was added allymagnesium bromide (1.0 M in diethyl ether, 3.8 mL, 3.8 mmol) at room temperature, stirred over night. The reaction mixture was poured into brine, diluted with ethyl acetate. After separation, the organic phase was dried over sodium sulfate, filtered and concentrated. The residue was dissolved in methanol (15 mL) in seal tube, added methanesulfonic acid (1.0 mL), sealed and heated at 100° C. for 4 h. After cooling to room temperature, the reaction mixture was purified by preparative HPLC (C-18 column, 2 to 50% CH$_3$CN in H$_2$O containing 0.01% CF$_3$CO$_2$H over 20 min, 20 mL min$^{-1}$) to afford product as TFA salt (220 mg, 45%). $^1$H NMR (CD$_3$OD) δ 7.72 (d, J=8.2 Hz, 1H), 7.68 (d, J=1.8 Hz, 1H), 7.56 (dd, J=8.2, 1.7 Hz, 1H), 5.36-5.48 (m, 1H), 4.99-5.09 (m, 2H), 2.80-2.90 (m, 1H), 2.69 (d, J=7.3 Hz, 2H), 2.60 (s, 3H), 2.41-2.49 (m, 1H), 2.32 (dd, J=9.6, 7.0 Hz, 2H); MS EI m/z 265 (M+H)$^+$.

Step 4. (5)-tert-Butyl 2-(1-allyl-6-chloro-3-oxoisoindolin-1-yl)ethyl(methyl)carbamate A mixture of (S)-3-allyl-5-chloro-3-(2-(methylamino)ethyl)isoindolin-1-one trifluoroacetic acid salt (220 mg, 0.58 mmol), di-tert-butyl dicarbonate (272 mg, 1.25 mmol) and triethylamine (0.35 mL, 2.49 mmol) in dry THF (10 mL) was stirred at room temperature over night. The reaction mixture was partitioned between brine and ethyl acetate. After separation, the organic phase was dried over sodium sulfate, filtered and concentrated. The residue was purified by column chromatography on silica gel (40 g column, 0% ethyl acetate in hexanes to 100% ethyl acetate in hexanes) to give product (120 mg, 57%). $^1$H NMR (CDCl$_3$) δ 7.72 (d, J=7.9 Hz, 1H), 7.38-7.52 (m, 2H), 5.42-5.58 (m, 1H), 4.98-5.10 (m, 2H), 2.40-3.28 (m, 7H), 2.00-2.18 (m, 2H), 1.40 (s, 9H); MS EI m/z 365 (M+H)$^+$.

Step 5. (S)-tert-Butyl 2-(6-chloro-1-(3-hydroxypropyl)-3-oxoisoindolin-1-yl)ethyl(methyl)carbamate To a solution of (S)-tert-Butyl 2-(1-allyl-6-chloro-3-oxoisoindolin-1-yl)ethyl(methyl)carbamate (120 mg, 0.33 mmol) in dry THF (6 mL) at 0° C. was added borane in THF (1.0 M, 1.64 mL, 1.64 mmol) drop wise. After stirring for 2 h, 1N NaOH (3 mL) and hydrogen peroxide (50% aqueous solution, 0.5 mL) were added. The reaction mixture was stirred at room temperature for 3 h and then partitioned between brine and ethyl acetate. After separation, the organic phase was dried over sodium sulfate, filtered and concentrated. The residue was purified by column chromatography on silica gel (40 g column, 0% methanol in dichloromethane to 20% methanol in dichloromethane) to give product (98 mg, 78%). $^1$H NMR (CD$_3$OD) δ 7.71 (d, J=8.2 Hz, 1H), 7.62 (brs, 1H), 7.49 (d, J=7.9 Hz, 1H), 3.40-3.47 (m, 2H), 2.78-3.10 (m, 2H), 2.70 (brs, 3H), 2.08-2.26 (m, 2H), 1.95-2.04 (m, 2H), 1.39 (s, 9H), 0.92-1.02 (m, 2H); MS EI m/z 283 (M+H-Boc)$^+$.

Step 6. (S)-tert-Butyl 2-(1-(3-aminopropyl)-6-chloro-3-oxoisoindolin-1-yl)ethyl(methyl)carbamate To a solution of (S)-tert-butyl 2-(6-chloro-1-(3-hydroxypropyl)-3-oxoisoindolin-1-yl)ethyl(methyl)carbamate (98 mg, 0.25 mmol) in dry dichloromethane (2 mL) at room temperature was added triethylamine (52 mg, 0.51 mmol) and methanesulfonyl chloride (44 mg, 0.38 mmol). The reaction mixture was stirred over night and then concentrated. The residue was dissolved in DMF (3 mL), added sodium azide (162 mg, 2.5 mmol) and heated at 60° C. for 2 h. The solvent was evaporated under reduced pressure and the residue was partitioned between brine and ethyl acetate. After separation, the organic phase was dried over sodium sulfate, filtered and concentrated. The residue was purified by preparative HPLC (C-18 column, 10 to 95% CH$_3$CN in H$_2$O containing 0.01% CF$_3$CO$_2$H over 20 min, 20 mL min$^{-1}$) to give an azide. The azide was dissolved in a mixture of THF (15 mL) and water (1.5 mL) and was added triphenylphosphine (131 mg, 0.5 mmol). The reaction mixture was stirred at room temperature for 48 h and then concentrated. The residue was purified by preparative HPLC (C-18 column, 5 to 70% CH$_3$CN in H$_2$O containing 0.01% CF$_3$CO$_2$H over 20 min, 20 mL min$^{-1}$) to afford product as TFA salt (71 mg, 56%). NMR (CD$_3$OD) δ 7.65-7.76 (m, 2H), 7.51-7.59 (m, 1H), 2.59-3.10 (m, 7H), 1.94-2.50 (m, 4H), 1.40-1.50 (m, 1H), 1.39 (s, 9H), 0.98-1.10 (m, 1H); MS EI m/z 382 (M+H)$^+$.

Step 7. (S)-Methyl 3-(6-chloro-1-(2-(methylamino) ethyl)-3-oxoisoindolin-1-yl)propylcarbamate To a solution of (S)-tert-butyl 2-(1-(3-aminopropyl)-6-chloro-3-oxoisoindolin-1-yl)ethyl(methyl)carbamate trifluoroacetic acid salt (71 mg, 0.14 mmol) in dry dichloromethane (10 mL) at room temperature was added triethylamine (56 mg, 0.56 mmol) and methylchloroformate (26 mg, 0.3 mmol). After stirring for 1.5 h, methanol (2 mL) was added. The reaction mixture was stirred for 2 h and then concentrated. The residue was dissolved in dichloromethane (3 mL) and added trifluoroacetic acid (5 mL). After stirring for 2 h, the solvent and excess reagent were evaporated under reduced pressure. The residue was purified by preparative HPLC (C-18 column, 5 to 70% CH$_3$CN in H$_2$O containing 0.01% CF$_3$CO$_2$H over 20 min, 20 mL min$^{-1}$) to afford product and a minor amount of (R) isomer as TFA salt (45 mg, 69%). $^1$H NMR (CD$_3$OD) δ 7.73 (d, J=7.9 Hz, 1H), 7.65 (d, J=1.8 Hz, 1H), 7.56 (dd, J=8.2, 1.2 Hz, 1H), 3.58 (s, 3H), 3.00 (t, J=7.0 Hz, 2H), 2.80-2.88 (m, 1H), 2.60 (s, 3H), 2.40-2.49 (m, 1H), 2.26-2.37 (m, 2H) 1.90-2.02 (m, 2H) 1.24-1.38 (m, 1H) 0.83-0.96 (m, 1H); MS EI m/z 340 (M+H)$^+$.

The following compounds were prepared following procedures analogous to those described above:
1) (R)-methyl 3-(6-fluoro-1-(2-(methylamino)ethyl)-3-oxoisoindolin-1-yl)propylcarbamate using (S)-tert-butyl 3-(tert-butylsulfinylimino)-3-(2-(4,4-dimethyl-4,5-dihydrooxazol-2-yl)-5-fluorophenyl)propyl(methyl)carbamate in Step 3.

Preparation K tert-butyl (S)-2-amino-3-((R)-tetrahydro-2H-pyran-3-yl)propyl(methyl)carbamate

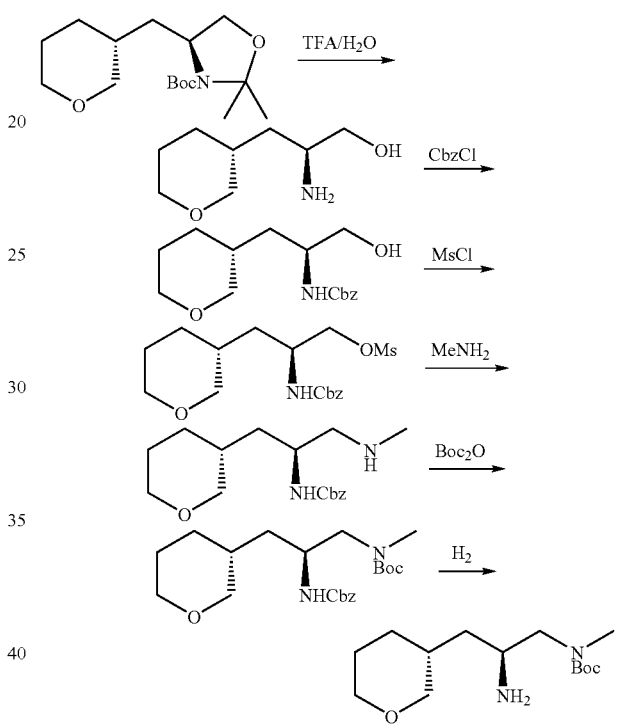

Step 1. (S)-2-amino-3-((R)-tetrahydro-2H-pyran-3-yl)propan-1-ol (S)-tert-butyl 2,2-dimethyl-4-(((R)-tetrahydro-2H-pyran-3-yl)methyl)oxazolidine-3-carboxylate was prepared using procedures described in U.S. Prov. App. No. 06/043,920 (PCT App No. 60/736,564).

(S)-tert-butyl 2,2-dimethyl-4-(((R)-tetrahydro-2H-pyran-3-yl)methyl)oxazolidine-3-carboxylate (32 g) was dissolved in a mixture of TFA (160 mL) and water (160 mL). The mixture was stirred at room temperature for 10 min. The mixture was then concentrated in vacuo to give the crude product (50 g), which was used for the next step without further purification.

Step 2. benzyl (S)-1-hydroxy-3-((R)-tetrahydro-2H-pyran-3-yl)propan-2-ylcarbamate To a solution of (S)-2-amino-3-((R)-tetrahydro-2H-pyran-3-yl)propan-1-ol (50 g, 312.5 mmol) and K$_2$CO$_3$ (129.375 g, 937.5 mmol) in dioxane (250 mL) and water (250 mL) at 0° C. was added CbzCl (106.6 g, 625 mmol) dropwise. The reaction mixture was stirred at room temperature until the staring material disappeared. The organic solvent was distilled and the residue was dissolved in AcOEt (200 mL). The organic phase was separated and the water was extracted with AcOEt (3×100 ml). The combined organic phase was washed with water (3×50 ml), dried over Na$_2$SO$_4$, and concentrated in vacuo to give the residue, which was purified by column to give the product (26 g). $^1$H NMR (CD$_3$OD) 1.1-1.3 (m, 2H), 1.4-1.5 (m, 1H), 1.5-1.7 (m, 3H), 1.8-1.9 (m, 1H), 2.6-2.8 (m, 1H), 3.0-3.1 (t, 1H), 3.3-3.4 (m, 1H), 3.5-3.6 (m, 1H), 3.6-3.8 (m, 2H), 3.8-3.9 (m, 2H), 5.0-5.1 (s, 2H), 7.3-7.4 (m, 5H).

Step 3. (S)-2-(benzyloxycarbonylamino)-3-((R)-tetrahydro-2H-pyran-3-yl)propyl methanesulfonate To a solution of benzyl (S)-1-hydroxy-3-((R)-tetrahydro-2H-pyran-3-yl)propan-2-ylcarbamate (26 g, 69.99 mmol) and triethylamine (21.21 g, 210 mmol) in CH$_2$Cl$_2$ at 0° C. was added mesyl chloride (16.1 g, 140 mmol) dropwise. The reaction mixture was stirred at room temperature until the staring material disappeared. The reaction was quenched with ice-cold water, extracted with CH$_2$Cl$_2$ (3×100 ml), washed with water (3×50 ml), dried over Na$_2$SO$_4$, and concentrated in vacuo to give the product (36 g), which was used for the next step without purification.

Step 4. benzyl (S)-1-(methylamino)-3-((R)-tetrahydro-2H-pyran-3-yl)propan-2-ylcarbamate To the ethanol solution of MeNH$_2$ (360 mL) was added (S)-2-(benzyloxycarbonylamino)-3-((R)-tetrahydro-2H-pyran-3-yl)propyl methanesulfonate (36 g, 106.7 mmol). The mixture was stirred at 30-40° C. overnight. Upon completion of the reaction, the solution was concentrated to give the product (40 g), which was used without further purification.

Step 5. benzyl (S)-1-(N-methyl-tert-butoxycarbonylamino)-3-((R)-tetrahydro-2H-pyran-3-yl)propan-2-ylcarbamate To the solution of benzyl (S)-1-(methylamino)-3-((R)-tetrahydro-2H-pyran-3-yl)propan-2-ylcarbamate (40 g, 130.5 mmol) and TEA (39.6 g, 391.5 mmol) in CH$_2$Cl$_2$ (400 mL) was added Boc$_2$O (56.9 g, 261 mmol). The mixture was stirred at room temperature until the starting material disappeared. The mixture was concentrated in vacuo to give the crude product, which was purified through column chromatography to give the product (20 g). $^1$H NMR (CD$_3$OD) δ 1.2-1.4 (m, 3H), 1.4-1.5 (s, 9H), 1.5-1.6 (m, 2H), 1.6-1.7 (m, 1H), 1.8-1.9 (m, 1H), 2.8-2.9 (s, 3H), 2.9-3.1 (m, 2H), 3.3-3.4 (m, 1H), 3.5-3.6 (m, 12H), 3.7-3.9 (dd, 3H), 5.0-5.1 (s, 2H), 7.3-7.4 (m, 5H).

Step 6. tert-butyl (S)-2-amino-3-((R)-tetrahydro-2H-pyran-3-yl)propyl(methyl)carbamate To a solution of benzyl (S)-1-(N-methyl-tert-butoxycarbonylamino)-3-((R)-tetrahydro-2H-pyran-3-yl)propan-2-ylcarbamate (20 g, 49.2 mmol) in MeOH (400 mL) was added Pd(OH)$_2$ (2 g). The reaction bottle was degassed and filled into H$_2$. Upon completion of the reaction, the mixture was filtered through Celite, dried over Na$_2$SO$_4$, and concentrated to give the product (12 g). $^1$H NMR (CD$_3$OD) δ 1.0-1.2 (m, 3H), 1.4-1.5 (m, 9H), 1.6-1.7 (m, 2H), 1.7-1.9 (m, 2H), 2.8-2.9 (s, 3H), 2.9-3.1 (m, 4H), 3.3-3.4 (m, 1H), 3.8-3.9 (m, 2H).

Compounds of Formula I were prepared as described below:

Example 1 methyl (4S,10R)-10-(3-chlorophenyl)-4-(cyclohexylmethyl)-7-methyl-6-oxo-11-oxa-2,5,7-triazatridecan-13-ylcarbamate

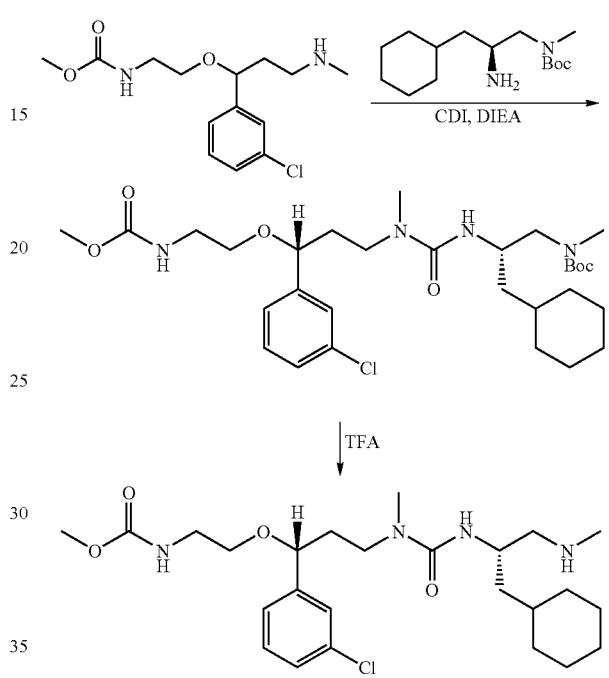

Step 1. tert-butyl (S)-2-(3-(3-(2-(methoxycarbonylamino)ethoxy)-3-(3-chlorophenyl)propyl)-3-methylureido)-3-cyclohexylpropyl(methyl)carbamate At 0° C., CDI (48.6 mg, 0.3 mmol) was added to a solution of (S)-tert-butyl 2-amino-3-cyclohexylpropyl(methyl)carbamate (81 mg, 0.3 mmol), prepared using procedures described in U.S. Prov. App No. 05/036,230 (PCT App No. 60/616,770), and DIEA (161 mg, 1.25 mmol) in anhydrous CH$_2$Cl$_2$ (8 mL) followed by stirring for 1 h. The solution was added to methyl 2-(1-(3-chlorophenyl)-3-(methylamino)propoxy)ethylcarbamate (75 mg, 0.25 mmol) in anhydrous CH$_2$Cl$_2$ (4 mL). The reaction mixture was allowed to warm to room temperature and stirred overnight. After the reaction was completed, the solvent was removed in vacuo. The product was purified with preparative TLC to afford tert-butyl (S)-2-(3-(3-(2-(methoxycarbonylamino)ethoxy)-3-(3-chlorophenyl)propyl)-3-methylureido)-3-cyclohexylpropyl(methyl)carbamate (70 mg, 50%).

Step 2. methyl (4S,10R)-10-(3-chlorophenyl)-4-(cyclohexylmethyl)-7-methyl-6-oxo-11-oxa-2,5,7-triazatridecan-13-ylcarbamate tert-butyl (S)-2-(3-((R)-3-(2-(methoxycarbonylamino)ethoxy)-3-(3-chlorophenyl)propyl)-3-methylureido)-3-cyclohexylpropyl(methyl)carbamate (40 mg) was dissolved in a solution of 20% (V/V) TFA/CH$_2$Cl$_2$ (5 mL). The reaction mixture was concentrated in vacuo. The residue was purified by Preparative HPLC to afford isomer 1 methyl (4S,10R)-10-(3-chlorophenyl)-4-(cyclohexylmethyl)-7-methyl-6-oxo-11-oxa-2,5,7-triazatridecan-13-ylcarbamate (8.88 mg, 27%) LC-MS (3 min) tR=2.195 m/z=497. 1H NMR (CD3OD) d 0.99 (m, 2H), 1.54 (m, 1H), 1.70 (m, 4H), 1.87 (m, 3H), 2.73 (s, 3H), 2.94 (s, 3H), 3.09 (m, 1H), 3.63 (s, 3H), 4.26 (m, 2H), 7.29 (m, 4H). isomer 1 methyl (4S,10R)-10-(3-chlorophenyl)-4-(cyclohexylmethyl)-7-methyl-6-oxo-11-oxa-2,5,7-triazatridecan-13-ylcarbamate and isomer 2 methyl (4S,10S)-10-(3-chlorophenyl)-4-(cyclohexylmethyl)-7-methyl-6-oxo-11-oxa-2,5,7-triazatridecan-13-ylcarbamate. LC-MS (3 min) tR=2.149 m/z=497. 1H NMR (CD3OD) d 0.96 (m, 2H), 1.25 (m, 5H), 1.54 (m, 1H), 1.69 (m, 4H), 1.89 (m, 3H), 2.71 (s, 3H), 2.93 (s, 3H), 3.06 (m, 1H0, 3.64 (s, 3H), 4.14 (m, 1H), 4.30 (m, 1H), 7.31 (m, 4H).

Example 2

(S)-methyl 10-(3-chlorophenyl)-4-(cyclohexylmethyl)-7-methyl-6,9-dioxo-2,5,7,10-tetraazatridecan-13-ylcarbamate The title compound was prepared following procedures analogous to those described in Example 1 using methyl 3-(N-(3-chlorophenyl)-2-(methylamino)acetamido)propylcarbamate in Step 1. LC-MS (3 min) tR=2.089 m/z=510. 1H NMR (CD$_3$OD) d 0.83 (m, 2H), 1.37 (m, 1H), 1.69 (m, 1H), 2.62 (s, 3H), 2.70 (s, 3H), 3.50 (s, 3H), 3.89 (m, 1H), 4.06 (m, 1H), 7.23 (m, 1H), 7.39 (m, 3H).

Example 3 methyl (4S,9S,10S)-10-(3-chlorophenyl)-4-(cyclohexylmethyl)-7,9-dimethyl-6-oxo-11-oxa-2,5,7-triazatridecan-13-ylcarbamate The title compound was prepared following procedures analogous to those described in Example 1 using methyl 2-((1R*,2R*)-1-(3-chlorophenyl)-2-methyl-3-(methylamino)propoxy)ethylcarbamate in Step 1. LC-MS (3 min) tR=2.23 m/z=511. 1H NMR (CD3OD) d 0.78 (d, 3H), 0.81-1.07 (m, 2H), 1.10-1.40 (m, 5H), 1.42-1.57 (m, 1H), 1.60-1.75 (m, 4H), 1.84 (d, 1H), 2.04 (m, 1H), 2.67 (s, 3H), 2.89 (s, 3H), 2.96 (m, 1H), 3.04 (m, 1H), 3.61 (s, 3H), 4.13 (m, 1H), 4.23 (d, 1H), 7.16 (m, 1H), 7.26 (m, 3H).

Example 4 methyl (4S,9R,10S)-10-(3-chlorophenyl)-4-(cyclohexylmethyl)-7,9-dimethyl-6-oxo-11-oxa-2,5,7-triazatridecan-13-ylcarbamate The title compound was prepared following procedures analogous to those described in Example 1 using methyl 2-((1R*,2S*)-1-(3-chlorophenyl)-2-methyl-3-(methylamino)propoxy)ethylcarbamate in Step 1. 1H NMR (CD3OD) d 0.80 (d, 3H), 0.85-1.05 (m, 2H), 1.10-1.47 (m, 5H), 1.5-1.75 (m, 5H), 1.80 (d, 1H), 2.0 (b, 1H), 2.70 (s, 3H), 2.95 (s, 3H), 3.10 (m, 2H), 3.65 (s, 3H), 4.10-4.30 (m, 2H), 7.15-7.40 (m, 4H)

Example 5 methyl (4S,10R)-10-(3-chlorophenyl)-4-(cyclohexylmethyl)-7,9-dimethyl-6-oxo-11-oxa-2,5,7-triazatridecan-13-ylcarbamate The title compound was prepared following procedures analogous to those described in Example 1 using methyl 2-((1R*,2S*)-1-(3-chlorophenyl)-2-methyl-3-(methylamino)propoxy)ethylcarbamate in Step 1. LC-MS (3 min) tR=2.184 m/z=511. 1H NMR (CD3OD) d 0.71 (m, 3H), 0.80-1.10 (m, 2H), 1.12-1.40 (m, 6H), 1.52 □m, 1H□, 1.60-1.80 (m, 4H), 1.85 (d, 1H), 2.10-2.20 (m, 1H), 2.71 (d, 3H), 2.91 (s, 3H), 2.97 (m, 1H), 3.07 (m, 1H), 3.65 (s, 3H), 4.05-4.20 (m, 2H), 7.22 (m, 1H), 7.33 (m, 3H).

Example 6 methyl (4S,9R,10R)-10-(3-chlorophenyl)-4-(cyclohexylmethyl)-7,9-dimethyl-6-oxo-11-oxa-2,5,7-triazatridecan-13-ylcarbamate The title compound was prepared following procedures analogous to those described in Example 1 using methyl 2-((1R*,2R*)-1-(3-chlorophenyl)-2-methyl-3-(methylamino)propoxy)ethylcarbamate in Step 1. LC-MS (3 min) tR=2.234 m/z=511. 1H NMR (CD3OD) d 0.69 (d, 3H), 0.85-0.90 (m, 1H), 1.00 (m, 1H), 1.10-1.40 (, 7H), 1.60-1.80 (m, 4H), 1.85 (d, 1H), 2.10 (m, 1H), 2.71 (s, 3H), 2.91 (s, 3H), 3.07 (m, 1H), 3.61 (s, 3H), 4.02-4.20 (m, 2H), 7.21 (m, 1H), 7.32 (m, 3H).

Example 7 methyl (4S,10R)-10-(3-chlorophenyl)-7-methyl-6-oxo-4-(((R)-tetrahydro-2H-pyran-3-yl)methyl)-11-oxa-2,5,7-triazatridecan-13-ylcarbamate The title compound was prepared following procedures analogous to those described in Example 1 using (R)-methyl 2-(1-(3-chlorophenyl)-3-(methylamino)propoxy)ethylcarbamate and tert-butyl (S)-2-amino-3-((R)-tetrahydro-2H-pyran-3-yl)propyl(methyl)carbamate in Step 1. LC-MS (3 min) tR=1.811 m/z=499. $^1$H NMR (CD3OD) d 1.30 (m, 1H), 1.44 (m, 2H), 1.62 (m, 3H), 1.86 (m, 3H), 2.70 (s, 3H), 2.93 (s, 3H), 3.08 (m, 2H), 3.61 (s, 3H), 3.86 (m, 2H), 4.18 (m, 2H), 7.30 (m, 4H).

Example 8 methyl (4S,10S)-10-(5-chloro-2-methylphenyl)-7-methyl-6-oxo-4-(((R)-tetrahydro-2H-pyran-3-yl)methyl)-11-oxa-2,5,7-triazatridecan-13-ylcarbamate The title compound was prepared following procedures analogous to those described in Example 1 using methyl 2-(1-(5-chloro-2-methylphenyl)-3-(methylamino)propoxy)ethylcarbamate and tert-butyl (S)-2-amino-3-((R)-tetrahydro-2H-pyran-3-yl)propyl(methyl)carbamate in Step 1. LC-MS (3 min) tR=2.08 m/z=513. 1H NMR (CD3OD) d 1.29 (m, 1H), 1.45 (m, 2H), 1.62 (m, 3H), 1.84 (m, 3H), 2.29 (s, 3H), 2.71 (s, 3H), 2.95 (s, 3H), 3.10 (m, 2H), 3.63 (s, 3H), 3.85 (m, 2H), 4.05 (m, 1H), 4.55 (m, 1H), 7.13 (m, 2H), 7.36 (m, 1H).

Example 9 methyl (4S,10R)-10-(5-chloro-2-methylphenyl)-7-methyl-6-oxo-4-(((R)-tetrahydro-2H-pyran-3-yl)methyl)-11-oxa-2,5,7-triazatridecan-13-ylcarbamate The title compound was prepared following procedures analogous to those described in Example 1 using methyl 2-(1-(5-chloro-2-methylphenyl)-3-(methylamino)propoxy)ethylcarbamate and tert-butyl (S)-2-amino-3-((R)-tetrahydro-2H-pyran-3-yl)propyl(methyl)carbamate in Step 1. LC- MS (3 min) tR=2.138 m/z=513. 1H NMR (CD3OD) d 1.29 (m, 1H), 1.45 (m, 2H), 1.61 (m, 2H), 2.30 (s, 3H), 2.71 (s, 3H), 2.96 (s, 3H), 3.09 (m, 2H), 3.39 (m, 2H), 3.63 (s, 3H), 3.80 (m, 1H), 3.91 (m, 1H), 4.14 (m, 1H), 4.51 (m, 1H), 7.14 (m, 2H), 7.36 (m, 1H)

Example 10 methyl (3S)-10-(5-chloro-2-methylphenyl)-7-methyl-6-oxo-3-(((R)-tetrahydro-2H-pyran-3-yl)methyl)-11-oxa-2,5,7-triazatridecan-13-ylcarbamate The title compound was prepared following procedures analogous to those described in Example 1 using methyl 2-(1-(5-chloro-2-methylphenyl)-3-(methylamino)propoxy)ethylcarbamate and tert-butyl (S)-1-amino-3-((R)-tetrahydro-2H-pyran-3-yl)propan-2-yl(methyl)carbamate, prepared using procedures described in U.S. Prov. App. No. 06/043,920 (PCT App No. 60/736,564), in Step 1. LC-MS (3 min) tR=1.694 m/z=513. 1H NMR (CD3OD) d 1.10-1.30 (m, 1H), 1.35-1.50 (m, 2H), 1.60 (m, 2H), 1.65-1.85 (m, 3H), 1.92 (m, 1H), 2.24 (s, 3H), 2.70 (s, 3H), 2.90 (s, 3H), 3.60 (s, 3H), 3.80 (m, 2H), 4.48 (m, 1H), 7.10 (m, 2H), 7.30 (s, 1H).

Example 11

(S)-methyl 10-(3-chlorophenyl)-4-(cyclohexylmethyl)-7-methyl-6-oxo-2,5,7,10-tetraazatridecan-13-ylcarbamate The title compound was prepared following procedures analogous to those described in Example 1 using methyl 3-((3-chlorophenyl)(2-(methylamino)ethyl)amino)propylcarbamate in Step 1. LC-MS (3 min) tR=2.313 m/z=496. 1H NMR (CD3OD) d 0.95 (m, 2H), 1.72 (m, 7H), 2.70 (s, 3H), 2.91 (s, 3H), 3.05 (m, 1H), 3.13 (t, 2H), 3.36 (m, 3H), 3.63 (s, 3H), 6.68 (d, 1H), 6.77 (d, 1H), 6.84 (s, 1H), 7.15 (m, 1H).

Example 12 methyl (4S,10R)-10-(3-chlorophenyl)-7-methyl-4-((R)-oxepan-3-ylmethyl)-6-oxo-11-oxa-2,5,7-triazatridecan-13-ylcarbamate The title compound was prepared following procedures analogous to those described in Example 1 using (R)-methyl 2-(1-(3-chlorophenyl)-3-(methylamino)propoxy)ethylcarbamate and 2-(trimethylsilyl)ethyl (S)-2-amino-3-((R)-oxepan-3-yl)propyl(methyl)carbamate in Step 1 and using Et4N+F− to remove the Teoc protecting group in Step 2. LC-MS (3 min) tR=1.889 m/z=513. 1H NMR (CD3OD) d 1.49 (m, 4H), 2.70 (s, 3H), 2.91 (s, 3H), 3.08 (m, 1H), 3.62 (s, 3H), 4.10 (m, 1H), 4.26 (m, 1H), 7.30 (m, 4H).

Example 13 methyl (4S,10R)-10-(3-chlorophenyl)-7-methyl-6-oxo-4-((tetrahydro-2H-pyran-4-yl)methyl)-11-oxa-2,5,7-triazatridecan-13-ylcarbamate The title compound was prepared following procedures analogous to those described in Example 1 using (R)-methyl 2-(1-(3-chlorophenyl)-3-(methylamino)propoxy)ethylcarbamate and (S)-2-(trimethylsilyl)ethyl 2-amino-3-(tetrahydro-2H-pyran-4-yl)propyl(methyl)carbamate, prepared using procedures described in U.S. Prov. App. No. 06/043,920 (PCT App No. 60/736,564), in Step 1 and using Et4N+F− to remove the Teoc protecting group in Step 2. LC-MS (3 min) tR=1.708 m/z=499. 1H NMR (CD3OD) d 1.30 (m, 3H), 1.56 (m, 3H), 1.70 (m, 1H), 1.86 (m, 2H), 2.71 (s, 3H), 2.92 (s, 3H), 2.98 (m, 1H), 3.08 (m, 1H), 3.54 (m, 1H), 3.62 (s, 3H), 3.89 (m, 2H), 4.22 (m, 2H), 7.27 (m, 4H).

Example 14 methyl (4S,10R)-10-(3-chlorophenyl)-7-methyl-6-oxo-4-(((R)-4-oxaspiro[2.5]octan-6-yl)methyl)-11-oxa-2,5,7-triazatridecan-13-ylcarbamate The title compound was prepared following procedures analogous to those described in Example 1 using (R)-methyl 2-(1-(3-chlorophenyl)-3-(methylamino)propoxy)ethylcarbamate and 2-(trimethylsilyl)ethyl (S)-2-amino-3-((R)-4-oxaspiro[2.5]oct-6-yl)propyl(methyl)carbamate, prepared using procedures described in U.S. Prov. App. No. 06/043,920 (PCT App No. 60/736,564), in Step 1 and using Et4N+F− to remove the Teoc protecting group in Step 2. LC-MS (3 min) tR=1.35 m/z=526. 1H NMR (CD3OD) d 7.30 (m, 4H), 4.26 (m, 1H), 4.13 (m, 1H), 3.61 (s, 3H), 2.92 (s, 3H), 2.71 (s, 3H), 0.71 (m, 1H), 0.58 (m, 1H), 0.46 (m, 1H), 0.36 (m, 1H).

Example 15 methyl (4S,10R)-10-(3-chlorophenyl)-4-((1-adamantyl)methyl)-7-methyl-6-oxo-11-oxa-2,5,7-triazatridecan-13-ylcarbamate The title compound was prepared following procedures analogous to those described in Example 1 using (R)-methyl 2-(1-(3-chlorophenyl)-3-(methylamino)propoxy)ethylcarbamate and (S)-2-(trimethylsilyl)ethyl 2-amino-3-(1-adamantyl)propyl(methyl)carbamate, prepared using procedures described in U.S. Prov. App. No. 06/043,920 (PCT App No. 60/736,564), in Step 1 and using Et4N+F− to remove the Teoc protecting group in Step 2. LC-MS (3 min) tR=1.63 m/z=550. 1H NMR (CD3OD) d 7.29 (m, 4H), 4.25 (m, 1H), 3.62 (s, 3H), 2.91 (s, 3H), 2.71 (s, 3H).

Example 16 methyl (4S,10R)-10-(5-chloro-2-methylphenyl)-7-methyl-6-oxo-4-((tetrahydro-2H-pyran-4-yl)methyl)-11-oxa-2,5,7-triazatridecan-13-ylcarbamate The title compound was prepared following procedures analogous to those described in Example 1 using methyl 2-(1-(5-chloro-2-methylphenyl)-3-(methylamino)propoxy)ethylcarbamate and (S)-2-(trimethylsilyl)ethyl 2-amino-3-(tetrahydro-2H-pyran-4-yl)propyl(methyl)carbamate in Step 1 and using Et4N+F− to remove the Teoc protecting group in Step 2. LC-MS (3 min) tR=1.615 m/z=513. 1H NMR (CD3OD) d 1.21 (m, 1H), 1.35 (m, 2H), 1.60 (m, 3H), 1.71 (m, 1H), 1.84 (m, 2H), 2.29 (s, 3H), 2.70 (d, 3H), 2.95 (s, 3H), 3.05 (m, 2H), 3.47 (m, 2H), 3.62 (s, 3H), 3.89 (m, 2H), 4.14 (m, 1H), 4.55 (m, 1H), 7.13 (m, 2H), 7.34 (m, 1H).

Example 17 methyl (4S,10S)-10-(5-chloro-2-methylphenyl)-7-methyl-6-oxo-4-((tetrahydro-2H-pyran-4-yl)methyl)-11-oxa-2,5,7-triazatridecan-13-ylcarbamate The title compound was prepared following procedures analogous to those described in Example 1 using methyl 2-(1-(5-chloro-2-methylphenyl)-3-(methylamino)propoxy)ethylcarbamate and (S)-2-(trimethylsilyl)ethyl 2-amino-3-(tetrahydro-2H-pyran-4-yl)propyl(methyl)carbamate in Step 1 and using Et4N+F− to remove the Teoc protecting group in Step 2. LC-MS (3 min) tR=2.048 m/z=513. 1H NMR (CD3OD) d 1.30 (m, 3H), 1.60 (m, 3H), 1.74 (m, 3H), 3.29 (s, 3H), 2.72 (s, 3H), 2.95 (s, 3H), 3.00 (m, 1H), 3.07 (m, 1H), 3.39 (m, 2H), 3.62 (s, 3H), 3.90 (m, 2H), 4.21 (m, 1H), 4.51 (m, 1H), 7.14 (m, 2H), 7.34 (m, 1H).

Example 18 methyl (4S,10R)-10-(3-chlorophenyl)-6-oxo-7-propyl-4-(((R)-tetrahydro-2H-pyran-3-yl)methyl)-11-oxa-2,5,7-triazatridecan-13-ylcarbamate

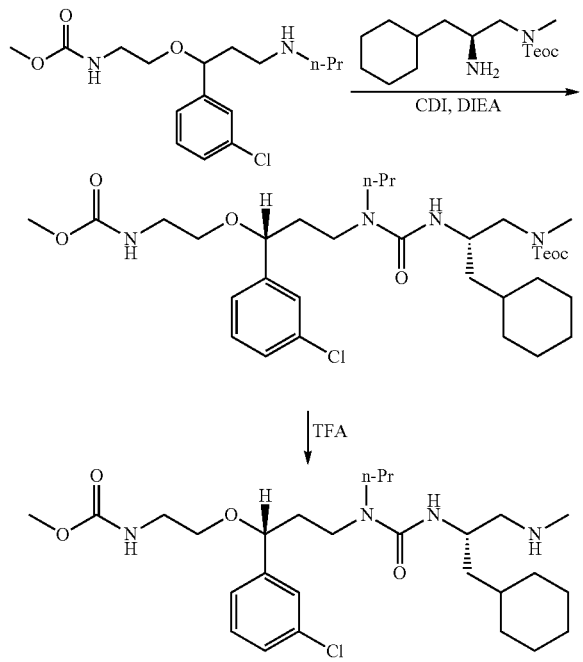

Step 1. 2-(trimethylsilyl)ethyl (S)-2-(3-(3-(2-(methoxycarbonylamino)ethoxy)-3-(3-chlorophenyl)propyl)-3-propylureido)-3-((R)-tetrahydro-2H-pyran-3-yl)propyl(methyl)carbamate 2-(trimethylsilyl)ethyl (S)-2-(3-(3-(2-(methoxycarbonylamino)ethoxy)-3-(3-chlorophenyl)propyl)-3-propylureido)-3-((R)-tetrahydro-2H-pyran-3-yl)propyl(methyl)carbamate was obtained following procedures analogous to Step 1, Example 1, using methyl 2-(1-(3-chlorophenyl)-3-(propylamino)propoxy)ethylcarbamate and 2-(trimethylsilyl)ethyl (S)-2-amino-3-((R)-tetrahydro-2H-pyran-3-yl)propyl(methyl)carbamate in Step 1. The mixture of isomers was further separated by HPLC (AD-H, 4.6×250 mm, hexane/isopropanol, 0.025% diisopropylethylamine, 40 min, 1 ml/min) to afford 2-(trimethylsilyl)ethyl (S)-2-(3-((R)-3-(2-(methoxycarbonylamino)ethoxy)-3-(3-chlorophenyl)propyl)-3-propylureido)-3-((R)-tetrahydro-2H-pyran-3-yl)propyl(methyl)carbamate (31 mg) and 2-(trimethylsilyl)ethyl (S)-2-(3-(3-(2-(methoxycarbonylamino)ethoxy)-3-((S)-3-chlorophenyl)propyl)-3-propylureido)-3-((R)-tetrahydro-2H-pyran-3-yl)propyl(methyl)carbamate (30 mg).

Step 2. methyl (4S,10R)-10-(3-chlorophenyl)-6-oxo-7-propyl-4-(((R)-tetrahydro-2H-pyran-3-yl)methyl)-11-oxa-2,5,7-triazatridecan-13-ylcarbamate 2-(trimethylsilyl)ethyl (S)-2-(3-((R)-3-(2-(methoxycarbonylamino)ethoxy)-3-(3-chlorophenyl)propyl)-3-propylureido)-3-((R)-tetrahydro-2H-pyran-3-yl)propyl(methyl)carbamate (31 mg) was treated with (V/V) 20% TFA/CH$_2$Cl$_2$ (2 mL) for 1 hr. The excess reagent was evaporated and the crude material was purified via preparative HPLC to afford the desired product (25.7 mg). LC-MS (3 min) tR=1.36 m/z=527. 1H NMR (CD3OD) d 7.25-7.35 (m, 4H), 4.30 (t, 1H), 4.10 (m, 1H), 3.89 (dd, 1H), 3.83 (m, 1H), 3.63 (s, 3H), 3.36-3.42 (m, 4H), 3.27 (m, 3H), 3.05-3.17 (m, 3H), 2.97 (t, 1H), 2.71 (s, 3H), 1.82-1.92 (m, 3H), 0.91 (t, 3H).

Example 19 methyl (4S,10S)-10-(3-chlorophenyl)-7-ethyl-6-oxo-4-(((R)-tetrahydro-2H-pyran-3-yl)methyl)-11-oxa-2,5,7-triazatridecan-13-ylcarbamate The title compound was prepared following procedures analogous to those described in Example 18 using 2-(trimethylsilyl)ethyl (S)-2-(3-(3-(2-(methoxycarbonylamino)ethoxy)-3-((S)-3-chlorophenyl)propyl)-3-propylureido)-3-((R)-tetrahydro-2H-pyran-3-yl)propyl(methyl)carbamate in Step 2. LC-MS (3 min) tR=1.35 m/z=527. 1H NMR (CD3OD) d 7.25-7.35 (m, 4H), 4.32 (m, 1H), 4.06 (m, 1H), 3.88 (m, 1H), 3.8 (m, 1H), 3.62 (s, 3H), 2.70 (s, 3H), 1.90 (m, 2H), 1.81 (m, 1H), 1.38-1.66 (m, 7H), 1.28 (m, 1H), 0.91 (t, 3H).

Example 20 methyl (4S)-10-(3-chlorophenyl)-7-ethyl-6-oxo-4-(((R)-tetrahydro-2H-pyran-3-yl)methyl)-11-oxa-2,5,7-triazatridecan-13-ylcarbamate The title compound was prepared following procedures analogous to those described in Example 18 using methyl 2-(1-(3-chlorophenyl)-3-(ethylamino)propoxy)ethylcarbamate and 2-(trimethylsilyl)ethyl (S)-2-amino-3-((R)-tetrahydro-2H-pyran-3-yl)propyl(methyl)carbamate, prepared using procedures described in U.S. Prov. App. No. 06/043,920 (PCT App No. 60/736,564), in Step 1. LC-MS (3 min) tR=1.29 m/z=513. 1H NMR (CD3OD) d 7.25-7.35 (m, 8H), 4.31 (m, 2H), 4.08 (m, 2H), 3.86 (m, 4H), 3.62 (s, 6H), 2.72 (s, 3H), 2.70 (s, 3H), 1.14 (s, 6H).

Example 21

3-((S)-1-cyclohexyl-3-(methylamino)propan-2-yl)-1-(2-((S)-6-fluoro-1-(4-methoxybutyl)-3-oxoisoindolin-1-yl)ethyl)-1-methylurea

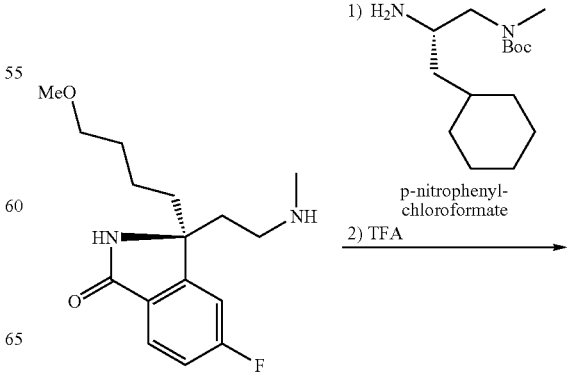

-continued

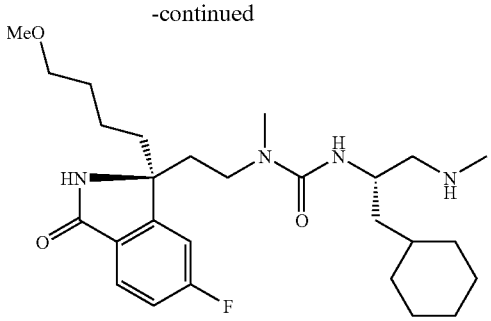

Step 1. 3-((S)-1-Cyclohexyl-3-(methylamino)propan-2-yl)-1-(2-((S)-6-fluoro-1-(4-methoxybutyl)-3-oxoisoindolin-1-yl)ethyl)-1-methylurea A mixture of (S)-tert-butyl 2-amino-3-cyclohexylpropyl (methyl)carbamate (73 mg, 0.27 mmol), 4-nitrophenylchloroformate (60 mg, 0.29 mmol) and sodium bicarbonate (227 mg, 2.7 mmol) in anhydrous acetonitrile (5 mL) was stirred for 4 h until the solution turned to green yellow color. The reaction mixture was filtered through Celite. A portion of the filtrate (0.8 mL) was added to a solution of (S)-5-fluoro-3-(4-methoxybutyl)-3-(2-(methylamino)ethyl)isoindolin-1-one (8.2 mg, 0.02 mmol) and diisopropylethylamine (0.02 mL, 0.11 mmol) in anhydrous acetonitrile (2 mL). The mixture was stirred for 1 h. The reaction mixture was purified by reverse phase HPLC to give coupling adduct (7 mg, 40%). To a solution of the coupling adduct (7 mg, 0.01 mmol) in dichloromethane (2 mL) was added trifluoroacetic acid (4 mL) and stirred for 2 h. The excess reagent and solvent was removed in vacuo. The residue was purified by preparative HPLC (C-18 column, 5 to 70% CH$_3$CN in H$_2$O containing 0.01% CF$_3$CO$_2$H over 20 min, 20 mL min$^{-1}$) HPLC to give product as TFA salt (5.5 mg, 75%). $^1$H NMR (CD$_3$OD) δ7.74 (dd, J=8.5, 5.0 Hz, 1H), 7.34 (dd, J=8.5, 2.1 Hz, 1H), 7.24 (td, J=8.5, 2.0 Hz, 1H), 3.97-4.05 (m, 1H), 3.27 (t, J=6.5 Hz, 2H), 3.24 (s, 3H), 2.85-3.12 (m, 4H), 2.79 (s, 3H), 2.70 (s, 3H), 2.17 (t, J=7.1 Hz, 2H), 1.94 (t, J=7.9 Hz, 2H), 1.62-1.78 (m, 5H), 1.42-1.52 (m, 3H), 1.14-1.34 (m, 6H), 0.74-1.04 (m, 3H). MS EI m/z 491 (M+H)$^+$.

Example 22

3-((S)-1-cyclohexyl-3-(methylamino)propan-2-yl)-1-(2-(6-fluoro-1-(4-methoxybutyl)-3-oxo-1,3-dihydroisobenzofuran-1-yl)ethyl)-1-methylurea The following compounds were prepared following procedures analogous to those described in Example 21 using 5-fluoro-3-(4-methoxybutyl)-3-(2-(methylamino)ethyl)isobenzofuran-1(3H)-one in Step 1. LC-MS (3 min) tR=m/z=492. 1H NMR (CD3OD) d 7.85-7.91 (m, 1H), 7.39-7.44 (m, 1H), 7.32-7.38 (m, 1H), 3.98-4.11 (m, 1H), 3.25-3.30 (m, 2H), 3.23 (s, 3H), 3.01-3.22 (m, 3H), 2.86-2.96 (m, 1H), 2.82 (s, 1.5H), 2.76 (s, 1.5H), 2.70 (s, 3H), 1.96-2.42 (m, 4H), 1.60-1.80 (m, 5H), 1.42-1.53 (m, 3H), 1.14-1.35 (m, 6H), 0.82-1.02 (m, 3H).

Example 23

3-((S)-1-cyclohexyl-3-(methylamino)propan-2-yl)-1-(2-((R)-6-fluoro-1-(4-methoxybutyl)-3-oxoisoindolin-1-yl)ethyl)-1-methylurea The following compounds were prepared following procedures analogous to those described in Example 21 using (R)-5-fluoro-3-(4-methoxybutyl)-3-(2-(methylamino)ethyl)isoindolin-1-one in Step 1. LC-MS (3 min) tR=m/z=491. 1H NMR (CD3OD) d 7.76 (dd, J=8.2, 4.7 Hz, 1H), 7.34 (dd, J=8.5, 2.1 Hz, 1H), 7.25 (td, J=8.5, 1.8 Hz, 1H), 4.03-4.12 (m, 1H), 3.27 (t, J=6.5 Hz, 2H), 3.23 (s, 3H), 3.19-3.22 (m, 1H), 3.04 (dd, J=12.6, 3.5 Hz, 1H), 2.79-2.91 (m, 2H), 2.72 (s, 3H), 2.70 (s, 3H), 2.16 (t, J=7.6 Hz, 2H), 1.94 (t, J=8.2 Hz, 2H), 1.62-1.81 (m, 5H), 1.41-1.50 (m, 3H), 1.14-1.34 (m, 6H), 0.74-1.04 (m, 3H).

Example 24 methyl 2-((R)-3-(3-((S)-2-amino-3-((R)-tetrahydro-2H-pyran-3-yl)propyl)-1-methylureido)-1-(3-chlorophenyl)propoxy)ethylcarbamate The following compounds were prepared following procedures analogous to those described in Example 21 using (R)-methyl 2-(1-(3-chlorophenyl)-3-(methylamino)propoxy)ethylcarbamate and tert-butyl (S)-1-amino-3-((R)-tetrahydro-2H-pyran-3-yl)propan-2-yl(methyl)carbamate in Step 1. LC-MS (3 min) tR=1.18 m/z=486. 1H NMR (CD3OD) d 7.35-7.23 (m, 4H), 4.28 (dd, J=8.8, 4.4 Hz, 1H), 3.86-3.82 (m, 2H), 3.62 (s, 3H), 3.50-3.23 (m, 10H), 3.12 (dd, J=11.2, 8.8 Hz, 1H), 2.89 (s, 3H), 1.95-1.82 (m, 3H), 1.75 (m, 1H), 1.66-1.49 (m, 3H), 1.39 (m, 1H), 1.27 (m, 1H).

Example 25 methyl 2-((R)-3-(3-((S)-2-amino-3-((R)-oxepan-3-yl)propyl)-1-methyl ureido)-1-(3-chlorophenyl)propoxy)ethylcarbamate The following compounds were prepared following procedures analogous to those described in Example 21 using (R)-methyl 2-(1-(3-chlorophenyl)-3-(methylamino)propoxy)ethylcarbamate and tert-butyl (S)-1-amino-3-((R)-oxepan-3-yl)propan-2-ylcarbamate, prepared using procedures described in U.S. Prov. App. No. 06/043,920 (PCT App No. 60/736,564), in Step 1. LC-MS (3 min) tR=1.24 m/z=500. 1H NMR (CD3OD) d 7.35-7.23 (m, 4H), 4.28 (dd, J=8.8, 4.4 Hz, 1H), 3.76-3.65 (m, 3H), 3.62 (s, 3H), 3.50-3.24 (m, 10H), 2.89 (s, 3H), 1.91-1.55 (m, 9H), 1.47-1.35 (m, 2H).

Example 26 methyl (3S,10R)-10-(3-chlorophenyl)-7-methyl-6-oxo-3-(((R)-tetrahydro-2H-pyran-3-yl)methyl)-11-oxa-2,5,7-triazatridecan-13-ylcarbamate The following compounds were prepared following procedures analogous to those described in Example 21 using (R)-methyl 2-(1-(3-chlorophenyl)-3-(methylamino)propoxy)ethylcarbamate and ten-butyl (S)-1-amino-3-((R)-oxepan-3-yl)propan-2-ylcarbamate and tert-butyl (S)-1-amino-3-((R)-tetrahydro-2H-pyran-3-yl)propan-2-yl(methyl) carbamate in Step 1. LC-MS (3 min) tR=1.2 m/z=500. 1H NMR (CD3OD) d 7.35-7.23 (m, 4H), 4.28 (dd, J=8.4, 4.4 Hz, 1H), 3.86-3.81 (m, 2H), 3.62 (s, 3H), 3.54 (br d, J=14.4 Hz, 1H), 3.50-3.23 (m, 10H), 3.14 (dd, J=11.2, 9.6 Hz, 1H), 2.90 (s, 3H), 2.74 (s, 3H), 1.95-1.43 (m, 8H), 1.26 (m, 1H).

Example 27 methyl (3S,10R)-10-(3-chlorophenyl)-7-methyl-3-((R)-oxepan-3-ylmethyl)-6-oxo-11-oxa-2,5,7-triazatridecan-13-ylcarbamate The following compounds were prepared following procedures analogous to those described in Example 21 using (R)-methyl 2-(1-(3-chlorophenyl)-3-(methylamino)propoxy)ethylcarbamate and tert-butyl (S)-1-amino-3-((R)-oxepan-3-yl)propan-2-yl(methyl)carbamate, prepared using procedures described in U.S. Prov. App. No. 06/043,920 (PCT App No. 60/736,564), in Step 1. LC-MS (3 min) tR=1.26 m/z=514. 1H NMR (CD3OD) d 7.35-7.23 (m, 4H), 4.28 (dd, J=8.8, 4.4 Hz, 1H), 3.77-3.63 (m, 3H), 3.62 (s, 3H), 3.54 (br d, J=15.2 Hz, 1H), 3.47-3.20 (m, 9H), 2.90 (s, 3H), 2.74 (s, 3H), 1.91-1.50 (m, 10H), 1.35 (m, 1H).

Example 28 methyl 3-((R)-1-(2-(3-((S)-1-cyclohexyl-3-(methylamino)propan-2-yl)-1-methylureido)ethyl)-6-fluoro-3-oxoisoindolin-1-yl)propylcarbamate The following compounds were prepared following procedures analogous to those described in Example 21 using (R)-methyl 3-(6-fluoro-1-(2-(methylamino)ethyl)-3-oxoisoindolin-1-yl)propylcarbamate in Step 1. LC-MS (3 min) tR=m/z=520. 1H NMR (CD3OD) d 7.76 (dd, J=8.5, 5.0 Hz, 1H), 7.34 (dd, J=8.5, 2.0 Hz, 1H), 7.25 (td, J=9.0, 2.0 Hz, 1H), 4.01-4.06 (m, 1H), 3.58 (s, 3H), 3.18-3.28 (m, 1H), 2.82-3.06 (m, 5H), 2.72 (s, 3H), 2.70 (s, 3H), 2.16 (t, J=7.6 Hz, 2H), 1.93 (t, J=8.2 Hz, 2H), 1.62-1.80 (m, 5H), 1.42-1.50 (m, 1H), 1.14-1.34 (m, 6H), 0.81-1.02 (m, 3H).

Example 29

1-(2-((R)-6-chloro-1-(4-methoxybutyl)-3-oxoisoindolin-1-yl)ethyl)-3-((S)-1-cyclohexyl-3-(methylamino)propan-2-yl)-1-methylurea The following compounds were prepared following procedures analogous to those described in Example 21 using 5-chloro-3-(4-methoxybutyl)-3-(2-(methylamino)ethyl)isoindolin-1-one in Step 1. LC-MS (3 min) tR=m/z=507. 1H NMR (CD3OD) d 7.70 (d, J=7.9 Hz, 1H), 7.63 (brs, 1H), 7.52 (d, J=7.9 Hz, 1H), 4.03-4.12 (m, 1H), 3.18-3.30 (m, 3H), 3.24 (s, 3H), 2.98-3.06 (m, 1H), 2.84-2.92 (m, 2H), 2.72 (s, 3H), 2.70 (s, 3H), 2.16 (t, J=7.9 Hz, 2H), 1.94 (t, J=8.2 Hz, 2H), 1.62-1.80 (m, 5H), 1.42-1.50 (m, 3H), 1.16-1.36 (m, 6H), 0.76-1.02 (m, 3H).

Example 30

1-(2-((S)-6-chloro-1-(4-methoxybutyl)-3-oxoisoindolin-1-yl)ethyl)-3-((S)-1-cyclohexyl-3-(methylamino)propan-2-yl)-1-methylurea The following compounds were prepared following procedures analogous to those described in Example 21 using 5-chloro-3-(4-methoxybutyl)-3-(2-(methylamino)ethyl)isoindolin-1-one in Step 1. LC-MS (3 min) tR=m/z=507. 1H NMR (CD3OD) d 7.68 (dd, J=8.2, 1.2 Hz, 1H), 7.63 (brs, 7.50 (1H, d, J=8.2 Hz, 1H), 3.96-4.04 (m, 1H), 3.27 (t, J=6.2 Hz, 2H), 3.23 (s, 3H), 2.83-3.12 (m, 4H), 2.79 (s, 3H), 2.70 (s, 3H), 2.17 (t, J=7.0 Hz, 2H), 1.93 (t, J=8.1 Hz, 2H), 1.62-1.78 (m, 5H), 1.40-1.50 (m, 3H), 1.14-1.34 (m, 6H), 0.72-1.02 (m, 3H).

Example 31 methyl 3-((S)-6-chloro-1-(2-(3-((S)-1-cyclohexyl-3-(methylamino)propan-2-yl)-1-methylureido)ethyl)-3-oxoisoindolin-1-yl)propylcarbamate The following compounds were prepared following procedures analogous to those described in Example 21 using (S)-methyl 3-(6-chloro-1-(2-(methylamino)ethyl)-3-oxoisoindolin-1-yl)propylcarbamate in Step 1. LC-MS (3 min) tR=m/z=536. 1H NMR (CD3OD) d 7.69 (d, J=7.9 Hz, 1H), 7.63 (d, J=1.5 Hz, 1H), 7.51 (dd, J=7.9, 1.2 Hz, 1H), 3.96-4.05 (m, 1H), 3.58 (s, 3H), 2.85-3.14 (m, 6H), 2.79 (s, 3H), 2.71 (s, 3H), 2.18 (t, J=7.0 Hz, 2H), 1.94 (t, J=8.2 Hz, 2H), 1.62-1.80 (m, 5H), 1.42-1.50 (m, 1H), 1.14-1.35 (m, 6H), 0.82-1.04 (m, 3H).

Example 32 methyl (4S,11R)-11-(3-chlorophenyl)-8-methyl-7-oxo-4-(((R)-tetrahydro-2H-pyran-3-yl)methyl)-12-oxa-3,6,8-triazatetradecan-14-ylcarbamate The following compounds were prepared following procedures analogous to those described in Example 21 using (R)-methyl 2-(1-(3-chlorophenyl)-3-(methylamino)propoxy)ethylcarbamate and tert-butyl (S)-1-amino-3-((R)-tetrahydro-2H-pyran-3-yl)propan-2-yl(ethyl)carbamate, prepared using procedures analogous to those described in Preparation Z1, Steps 1-2, U.S. Prov. App. No. 06/043,920 (PCT App No. 60/736,564), in Step 1. LC-MS (3 min) tR=1.25 m/z=513. 1H NMR (CD3OD) d 7.36-7.24 (m, 4H), 4.29 (dd, J=8.8, 4.4 Hz, 1H), 3.87-3.80 (m, 2H), 3.62 (s, 3H), 3.55 (d, J=12.4 Hz, 1H), 3.46-3.10 (m, 12H), 2.91 (s, 3H), 1.98-1.20 (m, 12H).

Example 33 methyl (4S)-10-(3-chlorophenyl)-7-methyl-4-((R)-oxepan-3-ylmethyl)-6-oxo-11-oxa-2,5,7-triazatridecan-13-ylcarbamate The following compounds were prepared following procedures analogous to those described in Example 21 using methyl 2-(1-(3-chlorophenyl)-3-(methylamino)propoxy)ethylcarbamate and 2-(trimethylsilyl)ethyl (S)-2-amino-3-((R)-oxepan-3-yl)propyl(methyl)carbamate, prepared using procedures described in U.S. Prov. App. No. 06/043,920 (PCT App No. 60/736,564), in Step 1. LC-MS (3 min) tR=1.3 m/z=514. 1H NMR (CD3OD) d 7.35-7.24 (m, 4H), 4.30 (dd, J=8.8, 4.4 Hz, 1H), 4.06 (m, 1H), 3.76-3.64 (m, 3H), 3.62 (s, 3H), 3.47-3.24 (m, 7H), 3.07 (dd, J=12.8, 3.2 Hz, 1H), 2.97 (br d, J=10.4, 1H), 2.92 (s, 3H), 2.70 (s, 3H), 1.94-1.37 (m, 11H).

Example 34

1-(3-(3-chlorophenyl)-3-(3-methoxypropoxy)propyl)-3-((S)-1-cyclohexyl-3-(methylamino)propan-2-yl)-1-isopropylurea The following compounds were prepared following procedures analogous to those described in Example 21 using 3-(3-chlorophenyl)-N-isopropyl-3-(3-methoxypropoxy)propan-1-amine and (S)-2-(trimethylsilyl)ethyl 2-amino-3-cyclohexylpropyl(methyl)carbamate, prepared using procedures described in PCT App No. 60/736,564, in Step 1. LC-MS (3 min) tR=1.75 m/z=496. 1H NMR (CD3OD) d 7.27-7.41 (m, 8H), 4.34-4.37 (m, 4H), 4.16 (br m, 2H), 3.08-3.16 (m, 2H), 2.92-2.99 (m, 2H), 2.74 (s, 3H), 2.73 (s, 3H).

Example 35 methyl (4S,10S)-10-(3-chlorophenyl)-4-(cyclohexylmethyl)-7-isopropyl-6-oxo-11-oxa-2,5,7-triazatridecan-13-ylcarbamate The following compounds were prepared following procedures analogous to those described in Example 21 using methyl 2-(1-(3-chlorophenyl)-3-(isopropylamino)propoxy)ethylcarbamate and (S)-2-(trimethylsilyl)ethyl 2-amino-3-cyclohexylpropyl(methyl)carbamate in Step 1. LC-MS (3 min) tR=1.59 m/z=525.

Example 36 methyl (4S,10R)-10-(3-chlorophenyl)-4-(cyclohexylmethyl)-7-isopropyl-6-oxo-11-oxa-2,5,7-triazatridecan-13-ylcarbamate The following compounds were prepared following procedures analogous to those described in Example 21 using methyl 2-(1-(3-chlorophenyl)-3-(isopropylamino)propoxy)ethylcarbamate and (5)-2-(trimethylsilyl)ethyl 2-amino-3-cyclohexylpropyl(methyl)carbamate in Step 1. LC-MS (3 min) tR=1.61 m/z=525.

Example 37 methyl (4S)-10-(3-chlorophenyl)-4-(cyclohexylmethyl)-6-oxo-7-propyl-11-oxa-2,5,7-triazatridecan-13-ylcarbamate The following compounds were prepared following procedures analogous to those described in Example 21 using methyl 2-(1-(3-chlorophenyl)-3-(propylamino)propoxy)ethylcarbamate and (S)-2-(trimethylsilyl)ethyl 2-amino-3-cyclohexylpropyl(methyl)carbamate in Step 1. LC-MS (3 min) tR=1.64 m/z=525. 1H NMR (CD3OD) d 7.25-7.36 (m, 8H), 4.30 (m, 2H), 3.63 (s, 6H), 2.71 (s, 3H), 2.70 (s, 3H), 0.92 (t, 6H).

Example 38

In Vitro Activity Studies

IC$_{50}$ for Renin

The compounds of the invention have enzyme-inhibiting properties. In particular, they inhibit the action of the natural enzyme renin. The latter passes from the kidneys into the blood where it effects the cleavage of angiotensinogen, releasing the decapeptide angiotensin I, which is then cleaved in the blood, lungs, the kidneys and other organs by angiotensin converting enzyme to form the octapeptide angiotensin II. The octapeptide increases blood pressure both directly by binding to its receptor, causing arterial vasoconstriction, and indirectly by liberating from the adrenal glands the sodium-ion-retaining hormone aldosterone, accompanied by an increase in extracellular fluid volume. That increase can be attributed to the action of angiotensin II. Inhibitors of the enzymatic activity of renin bring about a reduction in the formation of angiotensin I. As a result a smaller amount of angiotensin II is produced. The reduced concentration of that active peptide hormone is the direct cause of the hypotensive effect of renin inhibitors.

The action of renin inhibitors in vitro is demonstrated experimentally by means of a test that measures the increase in fluorescence of an internally quenched peptide substrate. The sequence of this peptide corresponds to the sequence of human angiotensinogen. The following test protocol is used: All reactions are carried out in a flat bottom white opaque microtiter plate. A 4 µL aliquot of 400 µM renin substrate (DABCYL-γ-Abu-Ile-His-Pro-Phe-His-Leu-Val-Ile-His-Thr-EDANS) in 192 µL assay buffer (50 mM BES, 150 mM NaCl, 0.25 mg/mL bovine serum albumin, pH7.0) is added to 4 µL of test compound in DMSO at various concentrations ranging from 10 µM to 1 nM final concentrations. Next, 100 µL of trypsin-activated recombinant human renin (final enzyme concentration of 0.2-2 nM) in assay buffer is added, and the solution is mixed by pipetting. The increase in fluorescence at 495 nm (excitation at 340 nm) is measured for 60-360 min at rt using a Perkin-Elmer Fusion microplate reader. The slope of a linear portion of the plot of fluorescence increases as a function of time is then determined, and the rate is used for calculating percent inhibition in relation to uninhibited control. The percent inhibition values are plotted as a function of inhibitor concentration, and the IC$_{50}$ is determined from a fit of this data to a four parameter equation. The IC$_{50}$ is defined as the concentration of a particular inhibitor that reduces the formation of product by 50% relative to a control sample containing no inhibitor. (Wang G. T. et al. *Anal. Biochem.* 1993, 210, 351; Nakamura, N. et al. *J. Biochem.* (*Tokyo*) 1991, 109, 741; Murakami, K. et al. *Anal Biochem.* 1981, 110, 232).

Example 39

In Vitro Activity Studies

IC$_{50}$ for Renin

All reactions are carried out in a low volume, black, 384 well microtiter plate (Greiner Bio-one). Compounds were diluted in 100% DMSO, and a 100 nL aliquot of each compound concentration was stamped into the plate using a Hummingbird (Genomic Solutions). 5 µL of 600 pM renin (trypsin-activated recombinant human renin) was then added to the plate, followed by 5 µL of 2 µM substrate (Arg-Glu-Lys(5-FAM)-Ile-His-Pro-Phe-His-Leu-Val-Ile-His-Thr-Lys (5,6-TAMRA)-Arg-CONH$_2$). Both renin and substrate were made up in buffer containing 50 mM HEPES, 125 mM NaCl, 0.1% CHAPS, with the pH adjusted to 7.4. After 2 hours of reaction at room temperature, the plates were read on a Viewlux™ (PerkinElmer) with an excitation/emission of 485/530 nm, and using a 505 nm cutoff filter. The percent inhibition values are plotted as a function of inhibitor concentration, and the IC$_{50}$ is determined from a fit of this data to a four parameter equation. The IC$_{50}$ is defined as the concentration of a particular inhibitor that reduces the formation of product by 50% relative to a control sample containing no inhibitor.

Example 40

In Vitro Activity of the Disclosed Compounds in Human Plasma

The action of renin inhibitors in vitro in human plasma is demonstrated experimentally by the decrease in plasma renin activity (PRA) levels observed in the presence of the compounds. Incubations mixtures contain in the final volume of 250 μL 95.5 mM N,N-bis(2-hydroxyethyl)-2-aminoethanesulfonic acid, pH 7.0, 8 mM EDTA, 0.1 mM neomycin sulfate, 1 mg/ml sodium azide, 1 mM phenylmethanesulfonyl fluoride, 2% DMSO and 87.3% of pooled mixed-gender human plasma stabilized with EDTA. For plasma batches with low PRA (less than 1 ng/ml/hr) ~2 pM of recombinant human renin IS added to achieve PRA of 3-4 ng/ml/hr. The cleavage of endogenous angiotensinogen in plasma is carried out at 37° C. for 90 min and the product angiotensin I is measured by competitive radioimmunoassay using DiaSorin PRA kit. Uninhibited incubations containing 2% DMSO and fully inhibited controls with 2 μM of isovaleryl-Phe-Nle-Sta-Ala-Sta-OH are used for deriving percent of inhibition for each concentration of inhibitors and fitting dose-response data into a four parametric model from which $IC_{50}$ values, defined as concentrations of inhibitors at which 50% inhibition occurs, is determined.

Example 41

$IC_{50}$ Values of the Disclosed Compounds for Renin

The $IC_{50}$ values of the disclosed compounds for renin were determined according to the protocols described in Example 38 or 39. In these in vitro systems the compounds of the invention exhibit 50% inhibition at concentrations of from approximately 5000 nM to approximately 0.01 nM. Preferred compounds of the invention exhibit 50% inhibition at concentrations of from approximately 50 nM to approximately 0.01 nM. More preferred compounds of the invention exhibit 50% inhibition at concentrations of from approximately 5 nM to approximately 0.01 nM. Highly preferred compounds of the invention exhibit 50% inhibition at concentrations of from approximately 5 nM to approximately 0.01 nM and exhibit 50% inhibition at concentrations of from approximately 10 nM to approximately 0.01 nM in the in vitro assay in the presence of human plasma described in Example 40.

Example 42

Efficacy of the Disclosed Inhibitors in a Transgenic Rat Model

The efficacy of the renin inhibitors may also be evaluated in vivo in double transgenic rats engineered to express human renin and human angiotensinogen (Bohlender J, Fukamizu A, Lippoldt A, Nomura T, Dietz R, Menard J, Murakami K, Luft F C, Ganten D. High human renin hypertension in transgenic rats. *Hypertension* 1997, 29, 428-434).

Experiments could be conducted in 5-10 week-old double transgenic rats (dTGRs). The model has been described in detail earlier. Briefly, the human renin construct that may be used to generate transgenic animals (hRen) is made up of the entire genomic human renin gene (10 exons and 9 introns), with 3.0 kB of the 5'-promoter region and 1.2 kB of 3' additional sequences. A human angiotensinogen construct containing the entire human angiotensinogen gene (5 exons and 4 introns), with 1.3 kB of 5'-flanking and 2.4 kB of 3'-flanking sequences may be used to generate rats producing human angiotensinogen (hAogen). The hRen and hAogen rats may be rederived using embryo transfer from breeding pairs obtained under license from Ascencion Gmbh (Germany). The hAogen and hRen may then be crossed to produce the double transgenic dTGR) off-spring. The dTGr rats should be maintained on irradiated rodent chow (5VO2, Purina Mills Inc) and normal water. Radio telemetry transmitters (TA11PAC40, Data Sciences International) may be surgically implanted at 5-6 weeks of age. The telemetry system can provide 24-h recordings of systolic, mean, diastolic arterial pressure (SAP, MAP, DAP, respectively) and heart rate (HR). Prior to dosing, baseline hemodynamic measures should be obtained for 24 hours. Rats may then be dosed orally with vehicle or drug and monitored up to 48 hours post-dose.

Example 43

In Vivo Activity

The cardiac and systemic hemodynamic efficacy of selective renin inhibitors can be evaluated in vivo in sodium-depleted, normotensive cynomolgus monkeys and in sodium-depleted, normotensive beagle dogs following a single oral and intravenous administration of the test compound. Arterial blood pressure is monitored by telemetry in freely moving, conscious animals.

Cynomolgus Monkey: Six male naïve cynomolgus monkeys weighing between 2.5 and 3.5 kg can be used in the studies. At least 4 weeks before the experiment, the monkeys are anesthetized with ketamine hydrochloride (15 mg/kg, i.m.) and xylazine hydrochloride (0.7 mg/kg, i.m.), and are implanted into the abdominal cavity with a transmitter (Model # TL11M2-D70-PCT, Data Sciences, St. Paul, Minn.). The pressure catheter is inserted into the lower abdominal aorta via the femoral artery. The bipotential leads are placed in Lead II configuration. The animals are housed under constant temperature (19-25° C.), humidity (>40%) and lighting conditions (12 h light and dark cycle), are fed once daily, and are allowed free access to water. The animals are sodium depleted by placing them on a low sodium diet (0.026%, Expanded Primate Diet 829552 MP-VENaCl (P), Special Diet Services, Ltd., UK) 7 days before the experiment and furosemide (3 mg/kg, intramuscularly i.m., Aventis Pharmaceuticals) is administered at −40 h and −16 h prior to administration of test compound.

For oral dosing, the renin inhibitors are formulated in 0.5% methylcellulose at dose levels of 10 and 30 mg/kg (5 mL/kg) by infant feeding tubes. For intravenous delivery, a silastic catheter is implanted into posterior vena cava via a femoral vein. The catheter is attached to the delivery pump via a tether system and a swivel joint. Test compound (dose levels of 0.1 to 10 mg/kg, formulated at 5% dextrose) is administered by continuous infusion (1.67 mL/kg/h) or by bolus injection (3.33 mL/kg in 2 min).

Arterial blood pressures (systolic, diastolic and mean) and body temperature are recorded continuously at 500 Hz and 50 Hz, respectively, using the Dataquest™ A.R.T. (Advanced Research Technology) software. Heart rate is derived from the phasic blood pressure tracing. During the recording period, the monkeys are kept in a separate room without human presence to avoid pressure changes secondary to stress. All data are expressed as mean±SEM. Effects of the renin inhibitors on blood pressure are assessed by ANOVA, taking into account the factors dose and time compared with the vehicle group.

Beagle Dogs Non-naive Beagle dogs (2 per sex) weighing between 9 and 11 kg can be used in the studies. Each animal is implanted subcutaneously with a telemetry transmitter (Data Sciences) and the blood pressure catheter is inserted into the left femoral artery. The electrocardiogram leads are also tunneled subcutaneously to the appropriate anatomical regions. The animals are housed under constant temperature and lighting conditions, are fed once daily, and are allowed free access to water. A sodium depleted state is produced by placing them on a low-sodium diet (<4 meq/day, a combination of canned Prescription Diet canine h/d, from Hill's Pet Products and dry pellets from Bio-Serv Inc., Frenchtown, N.J.) beginning 10 days before the experiment, and furosemide (3 mg/kg i.m.; Aventis Pharmaceuticals) is administered at −40 and −16 h prior to administration of test compound.

A renin inhibitor is orally administered by orogastric gavage to all overnight fasted animals at a dose level of 30 mg/kg (4 mL/kg formulated in 0.5% methylcellulose). Food is given 4 h postdose. In some experiments, the renin inhibitor is administered by bolus i.v. at increasing dose levels of 1, 3 and 6 mg/kg (2, 6 and 20 mg/mL formulated in sterile saline). Cardiovascular parameters are collected continuously at least 80 min predose and 3 h postdose, followed by every 10 min for 5 h and every 30 min for 16 h postdose. The Dataquest™ ART (version 2.2) software package from DSI (Data Sciences International) is used to collect telemetered cardiovascular data.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A compound represented by the following Structural Formula:

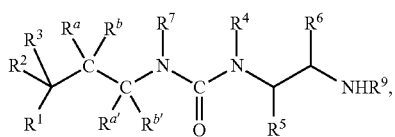

(Ie)

or an enantiomer, a diastereomer, or a pharmaceutically acceptable salt thereof, wherein:

$R^1$ is phenyl optionally substituted with 1 to 5 groups independently selected from:

1) fluorine, chlorine, bromine, iodine, cyano, nitro, amino, hydroxy, carboxy, $(C_1-C_8)$alkyl, $(C_3-C_8)$cycloalkyl, $(C_1-C_3)$alkyl$(C_3-C_8)$cycloalkyl, di$(C_1-C_3)$alkyl$(C_3-C_8)$cycloalkyl, $(C_4-C_8)$cycloalkylalkyl, $(C_2-C_6)$alkenyl, $(C_5-C_8)$cycloalkenyl, $(C_5-C_8)$cyclo-alkylalkenyl, $(C_2-C_8)$alkynyl, $(C_3-C_8)$cycloalkyl$(C_2-C_4)$alkynyl, halo$(C_1-C_8)$alkyl, halo$(C_3-C_6)$cycloalkyl, halo$(C_4-C_8)$cycloalkylalkyl, $(C_1-C_3)$alkyl$(C_4-C_8)$cycloalkylalkyl, di$(C_1-C_3)$alkyl$(C_4-C_8)$cycloalkylalkyl, halo$(C_2-C_8)$alkenyl, halo$(C_5-C_8)$cycloalkenyl, halo$(C_6-C_8)$cycloalkenylalkyl, halo$(C_3-C_8)$alkynyl, halo$(C_5-C_8)$cycloalkylalkynyl, $(C_1-C_8)$alkoxy, $(C_3-C_8)$cycloalkoxy, $(C_4-C_8)$cycloalkylalkoxy, $(C_1-C_3)$alkyl$(C_3-C_8)$cycloalkoxy, $(C_1-C_3)$alkyl$(C_4-C_8)$cycloalkylalkoxy, di$(C_1-C_3)$alkyl $(C_3-C_8)$cycloalkoxy, di$(C_1-C_3)$alkyl$(C_4-C_8)$cycloalkylalkoxy, halo$(C_1-C_6)$alkoxy, halo$(C_3-C_6)$cycloalkoxy, halo$(C_4-C_8)$-cycloalkylalkoxy, $(C_1-C_8)$alkylthio, $(C_3-C_8)$cycloalkylthio, $(C_4-C_8)$cycloalkylalkylthio, $(C_1-C_3)$alkyl$(C_3-C_8)$cycloalkylthio, $(C_1-C_3)$alkyl$(C_4-C_8)$cycloalkylalkylthio, di$(C_1-C_3)$alkyl$(C_3-C_8)$cycloalkylthio, di$(C_1-C_3)$alkyl$(C_4-C_8)$ cycloalkylalkylthio, halo$(C_1-C_8)$alkylthio, halo$(C_3-C_8)$cycloalkylthio, halo$(C_4-C_8)$-cycloalkylalkylthio, $(C_1-C_8)$alkanesulfinyl, $(C_3-C_8)$-cycloalkanesulfinyl, $(C_4-C_8)$cycloalkyl-alkanesulfinyl, $(C_1-C_3)$alkyl$(C_3-C_8)$cycloalkane-sulfinyl, $(C_1-C_3)$alkyl $(C_4-C_8)$cycloalkyl-alkanesulfinyl, di$(C_1-C_3)$alkyl$(C_3-C_8)$cycloalkanesulfinyl, di$(C_1-C_3)$alkyl $(C_4-C_8)$cycloalkylalkanesulfinyl, halo$(C_1-C_8)$alkanesulfinyl, halo$(C_3-C_8)$cycloalkanesulfinyl, halo$(C_4-C_8)$cycloalkylalkanesulfinyl, $(C_1-C_8)$alkanesulfonyl, $(C_3-C_8)$cycloalkanesulfonyl, $(C_4-C_8)$cycloalkylalkanesulfonyl, $(C_1-C_3)$alkyl$(C_3-C_8)$cycloalkanesulfonyl, $(C_1-C_3)$alkyl $(C_4-C_8)$cycloalkylalkanesulfonyl, di$(C_1-C_3)$alkyl$(C_3-C_8)$cycloalkanesulfonyl, di$(C_1-C_3)$alkyl $(C_4-C_8)$ cycloalkyl-alkanesulfonyl, halo$(C_1-C_8)$alkanesulfonyl, halo$(C_3-C_8)$cycloalkanesulfonyl, halo$(C_4-C_8)$cycloalkylalkanesulfonyl, $(C_1-C_8)$alkylamino, di$(C_1-C_8)$alkylamino, $(C_1-C_6)$alkoxy$(C_1-C_6)$alkoxy, halo$(C_1-C_6)$alkoxy$(C_1-C_6)$alkoxy, $(C_1-C_8)$alkoxycarbonyl, aminocarbonyl, $(C_1-C_8)$alkylamino-carbonyl, and di$(C_1-C_8)$alkylaminocarbonyl, piperidino, pyrrolidino, cyano$(C_1-C_6)$alkyl, hydroxy$(C_1-C_6)$alkyl, carboxy$(C_1-C_6)$alkyl, $(C_1-C_8)$alkoxy$(C_1-C_6)$alkyl, $(C_3-C_8)$cycloalkoxy$(C_1-C_6)$alkyl, $(C_4-C_8)$cycloalkylalkoxy$(C_1-C_6)$alkyl, halo$(C_1-C_6)$alkoxy$(C_1-C_6)$alkyl, halo$(C_3-C_6)$cycloalkoxy$(C_1-C_6)$alkyl, halo$(C_4-C_8)$-cycloalkylalkoxy$(C_1-C_6)$alkyl, $(C_1-C_8)$alkylthio$(C_1-C_6)$alkyl, $(C_3-C_8)$cycloalkylthio$(C_1-C_6)$alkyl, $(C_4-C_8)$ cycloalkylalkylthio$(C_1-C_6)$alkyl, halo$(C_1-C_8)$alkylthio$(C_1-C_6)$alkyl, halo$(C_3-C_8)$cycloalkylthio$(C_1-C_6)$alkyl, halo$(C_4-C_8)$-cycloalkylalkylthio$(C_1-C_6)$alkyl, $(C_1-C_8)$alkanesulfinyl$(C_1-C_6)$alkyl, $(C_3-C_8)$-cycloalkanesulfinyl$(C_1-C_6)$alkyl, $(C_4-C_8)$cycloalkyl-alkanesulfinyl$(C_1-C_6)$alkyl, halo$(C_1-C_8)$alkanesulfinyl$(C_1-C_6)$alkyl, halo$(C_3-C_8)$cycloalkanesulfinyl$(C_1-C_6)$alkyl, halo$(C_4-C_8)$ cycloalkylalkanesulfinyl$(C_1-C_6)$alkyl, $(C_1-C_8)$alkanesulfonyl$(C_1-C_6)$alkyl, $(C_3-C_8)$cycloalkanesulfonyl$(C_1-C_6)$alkyl, $(C_4-C_8)$cycloalkylalkanesulfonyl$(C_1-C_6)$ alkyl, halo$(C_1-C_8)$alkanesulfonyl$(C_1-C_6)$alkyl, halo$(C_3-C_8)$cycloalkanesulfonyl$(C_1-C_6)$alkyl, halo$(C_4-C_8)$cycloalkylalkanesulfonyl$(C_1-C_6)$alkyl, $(C_1-C_8)$alkylamino$(C_1-C_6)$alkyl, di$(C_1-C_8)$alkylamino$(C_1-C_6)$alkyl, $(C_1-C_8)$alkoxycarbonyl$(C_1-C_6)$alkyl, $(C_1-C_8)$acyloxy$(C_1-C_6)$alkyl, aminocarbonyl$(C_1-C_6)$alkyl, $(C_1-C_8)$alkylamino-carbonyl$(C_1-C_6)$alkyl, di$(C_1-C_8)$alkylaminocarbonyl$(C_1-C_6)$alkyl, $(C_1-C_8)$acylamino$(C_1-C_6)$alkyl, piperidino$(C_1-C_6)$alkyl, pyrrolidino$(C_1-C_6)$alkyl, $(C_1-C_8)$alkoxycarbonylamino, $(C_1-C_8)$alkoxycarbonylamino$(C_1-C_6)$alkyl, aminocarboxy$(C_1-C_6)$alkyl, $(C_1-C_8)$alkylamino-carboxy$(C_1-C_6)$alkyl and, di$(C_1-C_8)$alkylaminocarboxy$(C_1-C_6)$alkyl; and 2) phenyl, naphthyl, heteroaryl, bicyclic heteroaryl, phenoxy, naphthyloxy, heteroaryloxy, bicyclic heteroaryloxy, phenylthio, naphthylthio, heteroarylthio, bicyclic heteroarylthio, phenylsulfinyl, naphthylsulfinyl, heteroarylsulfinyl, bicyclic heteroarylsulfinyl, phenylsulfonyl, naphthylsulfonyl, heteroarylsulfonyl, bicyclic heteroarylsulfonyl, phenyl$(C_1-C_3)$alkyl, naphthyl$(C_1-C_3)$ alkyl, heteroaryl$(C_1-C_3)$alkyl, bicyclic heteroaryl$(C_1-C_3)$alkyl, phenyl$(C_1-C_3)$alkoxy, naphthyl$(C_1-C_3)$ alkoxy, heteroaryl$(C_1-C_3)$alkoxy, and bicyclic heteroaryl$(C_1-C_3)$alkoxy, each optionally substituted with 1 to 5 groups independently selected from: fluorine, chlorine, cyano, $(C_1-C_6)$alkyl, halo$(C_1-C_6)$alkyl, $(C_1-C_6)$alkoxy, halo$(C_1-C_6)$alkoxy, $(C_1-C_6)$alkanesulfonyl, $(C_1-C_6)$alkoxy-carbonyl, and aminocarbonyl;

R² is a (C₁-C₁₂)alkyl, (C₂-C₁₂)alkenyl, (C₂-C₁₂)alkynyl, (C₁-C₁₂)alkoxy, (C₂-C₁₂)alkenyloxy, (C₁-C₁₂)alkylthio, (C₁-C₆)alkoxy(C₁-C₆)alkyl, (C₁-C₆)alkylthio-(C₁-C₆)alkyl, (C₁-C₆)alkoxy(C₁-C₆)alkoxy, (C₁-C₆)alkoxy(C₁-C₆)alkylthio, (C₁-C₆)alkylthio (C₁-C₆)alkoxy, (C₁-C₆)alkylthio(C₁-C₆)alkylthio, (C₁-C₄)alkoxy(C₁-C₄)alkoxy(C₁-C₄)alkyl, aminocarbonylamino(C₁-C₁₂)alkyl, aminocarbonylamino(C₁-C₁₂)alkoxy, aminocarbonylamino(C₁-C₁₂)alkylthio, (C₁-C₆)alkanoylamino(C₁-C₆)alkyl, (C₁-C₆)alkanoylamino(C₁-C₆)alkoxy, (C₁-C₆)alkanoylamino(C₁-C₆)alkylthio, (C₃-C₄)cycloalkylcarbonylamino(C₁-C₆)alkyl, (C₃-C₄)cycloalkylcarbonylamino(C₁-C₆)alkoxy, (C₃-C₄)cycloalkylcarbonylamino(C₁-C₆)alkylthio, aminosulfonylamino(C₁-C₁₂)alkyl, aminosulfonylamino(C₁-C₁₂)alkoxy, aminosulfonylamino(C₁-C₂)alkylthio, (C₁-C₆)alkanesulfonylamino(C₁-C₆)alkyl, (C₁-C₆)alkanesulfonylamino(C₁-C₆)-alkoxy, (C₁-C₆)alkanesulfonylamino(C₁-C₆)alkylthio, formylamino(C₁-C₆)alkyl, formylamino(C₁-C₆)alkoxy, formylamino(C₁-C₆)alkylthio, (C₁-C₆)alkoxycarbonylamino(C₁-C₆)alkyl, (C₁-C₆)alkoxycarbonylamino(C₁-C₆)alkoxy, (C₁-C₆)alkoxycarbonylamino(C₁-C₆)alkylthio, (C₁-C₆)alkylaminocarbonylamino(C₁-C₆)alkyl, di(C₁-C₆)alkylaminocarbonylamino(C₁-C₆)alkyl, (C₁-C₆)alkylaminocarbonylamino(C₁-C₆)alkoxy, di(C₁-C₆)alkylaminocarbonylamino(C₁-C₆)alkoxy, (C₁-C₆)alkylaminocarbonylamino(C₁-C₆)alkylthio, di(C₁-C₆)alkylaminocarbonylamino (C₁-C₆)alkylthio, aminocarbonyl(C₁-C₆)alkyl, aminocarbonyl(C₁-C₆)alkoxy, aminocarbonyl(C₁-C₆)alkylthio, (C₁-C₆)alkylaminocarbonyl(C₁-C₆)alkyl, (C₁-C₆)alkylaminocarbonyl(C₁-C₆)alkoxy, (C₁-C₆)alkylaminocarbonyl(C₁-C₆)alkylthio, aminocarboxy(C₁-C₆)alkyl, aminocarboxy(C₁-C₆)alkoxy, aminocarboxy(C₁-C₆)alkylthio, (C₁-C₆)alkylaminocarboxy(C₁-C₆)alkyl, (C₁-C₆)alkylaminocarboxy(C₁-C₆)alkoxy, (C₁-C₆)alkylaminocarboxy(C₁-C₆)alkylthio, (C₁-C₁₂)alkoxycarbonylamino, (C₁-C₁₂)alkylaminocarbonylamino, (C₁-C₈)oxoalkyl, (C₁-C₁₂)alkanoylamino, (C₃-C₇)cycloalkoxycarbonylamino, aminocarbonyl, (C₁-C₆)alkylaminocarbonyl, (C₃-C₇)cycloalkylaminocarbonyl, aminocarboxy, (C₁-C₆)alkylaminocarboxy, (C₃-C₇)cycloalkylaminocarboxy, (C₁-C₆)alkylcarbonyl, (C₃-C₇)cycloalkylcarbonyl, —NHC(=NR²ᵉ)(NHR²ᵃ), or thiazolylamino, wherein R²ᵉ is H, (C₁-C₆)alkyl, phenyl, heteroaryl, cyano, nitro, —S(O)R²ᵃ, —S(O₂)R²ᵃ, —S(O₂)NHR²ᵃ, —S(O₂)NR²ᵃR²ᵃ, —C(O)R²ᵃ, —C(S)R²ᵃ, —C(O)OR²ᵃ, —C(S)OR²ᵃ, —C(O)(NH₂), —C(O)(NHR²ᵃ) and R²ᵃ is straight or branched (C₁-C₆)alkyl, straight or branched (C₁-C₆) haloalkyl, (C₃-C₇)cycloalkyl or straight or branched C₁-C₆ alkoxyalkyl; and wherein each group represented by R² is substituted by 0 to 6 groups selected from: halogen, cyano, hydroxyl, (C₁-C₃)alkoxy, (C₃-C₆)cycloalkyl, (C₃-C₆)cycloalkoxy, halo(C₁-C₃) alkoxy, halo(C₃-C₆)cycloalkyl or halo(C₃-C₆)cycloalkoxy; wherein any thio-moiety of said unsubstituted or substituted R² group is optionally and independently replaced by —S(O)— or —S(O)₂—; and wherein any carbonyl moiety of said unsubstituted or substituted R² group is optionally and independently replaced by a thiocarbonyl moiety;

R³ is 1) H, halogen, (C₁-C₆)alkyl, (C₁-C₆)alkoxy, hydroxyl, hydroxy(C₁-C₆)alkyl, hydroxy(C₁-C₆)alkoxy, (C₁-C₆)alkanoylamino, (C₁-C₆)-alkoxycarbonylamino, (C₁-C₆)alkylamino-carbonylamino, di(C₁-C₆)alkylaminocarbonylamino, (C₁-C₆)alkanesulfonylamino, (C₁-C₆)alkylaminosulfonylamino, or di(C₁-C₆)alkylaminosulfonyl-amino, or 2) phenylamino or heteroarylamino in which each phenylamino and heteroarylamino group is optionally substituted with 1 to 5 groups independently selected from:

fluorine, chlorine, bromine, iodine, cyano, nitro, amino, hydroxy, carboxy, (C₁-C₆)alkyl, (C₃-C₆)cycloalkyl, (C₄-C₇)cycloalkylalkyl, (C₂-C₆)alkynyl, (C₃-C₆)-cycloalkyl(C₂-C₄)alkynyl, halo(C₁-C₆)alkyl, halo(C₃-C₆)cycloalkyl, halo(C₄-C₇)-cycloalkylalkyl, (C₁-C₆)alkoxy, (C₃-C₆)cycloalkoxy, (C₄-C₇)cycloalkylalkoxy, halo(C₁-C₆)alkoxy, halo(C₃-C₆)cycloalkoxy, halo(C₄-C₇)cycloalkylalkoxy, (C₁-C₆)alkylthio, (C₃-C₆)cycloalkylthio, (C₄-C₇)cycloalkylalkylthio, halo(C₁-C₆)alkylthio, halo(C₃-C₆)cycloalkylthio, halo(C₄-C₇) cycloalkylalkylthio, (C₁-C₆)alkanesulfinyl, (C₃-C₆)cycloalkanesulfinyl, (C₄-C₇)cycloalkylalkanesulfinyl, halo(C₁-C₆)alkane-sulfinyl, halo(C₃-C₆)cycloalkanesulfinyl, halo(C₄-C₇)cycloalkylalkanesulfinyl, (C₁-C₆) alkanesulfonyl, (C₃-C₆)cycloalkanesulfonyl, (C₄-C₇) cycloalkylalkanesulfonyl, halo(C₁-C₆)alkanesulfonyl, halo(C₃-C₆)cycloalkanesulfonyl, halo(C₄-C₇)cycloalkylalkanesulfonyl, (C₁-C₆)alkylamino, di(C₁-C₆) alkylamine, (C₁-C₆)alkoxy(C₁-C₆)alkoxy, halo(C₁-C₆) alkoxy(C₁-C₆)alkoxy, (C₁-C₆)alkoxycarbonyl, aminocarbonyl, (C₁-C₆)alkylaminocarbonyl, and di(C₁-C₆) alkylaminocarbonyl, cyano(C₁-C₆)alkyl, hydroxy(C₁-C₆)alkyl, carboxy(C₁-C₆)alkyl, (C₁-C₆)alkoxy(C₁-C₆) alkyl, (C₃-C₈)cycloalkoxy(C₁-C₆)alkyl, (C₄-C₈) cycloalkylalkoxy(C₁-C₆)alkyl, halo(C₁-C₆)alkoxy(C₁-C₆)alkyl, halo(C₃-C₆)cycloalkoxy(C₁-C₆)alkyl, halo (C₄-C₈)-cycloalkylalkoxy(C₁-C₆)alkyl, (C₁-C₈) alkylthio(C₁-C₆)alkyl, (C₃-C₈)cycloalkylthio(C₁-C₆) alkyl, (C₄-C₈)cycloalkylalkylthio(C₁-C₆)alkyl, halo (C₁-C₈)alkylthio(C₁-C₆)alkyl, halo(C₃-C₈) cycloalkylthio(C₁-C₆)alkyl, halo(C₄-C₈)-cycloalkylalkylthio(C₁-C₆)alkyl, (C₁-C₈)alkanesulfinyl (C₁-C₆)alkyl, (C₃-C₈)-cycloalkanesulfinyl(C₁-C₆) alkyl, (C₄-C₈)cycloalkyl-alkanesulfinyl(C₁-C₆)alkyl, halo(C₁-C₈)alkanesulfinyl(C₁-C₆)alkyl, halo(C₃-C₈) cycloalkanesulfinyl(C₁-C₆)alkyl, halo(C₄-C₈)cycloalkylalkanesulfinyl(C₁-C₆)alkyl, (C₁-C₈)alkane-sulfonyl(C₁-C₆)alkyl, (C₃-C₈)cycloalkanesulfonyl(C₁-C₆) alkyl, (C₄-C₈)cycloalkylalkanesulfonyl(C₁-C₆)alkyl, halo(C₁-C₈)alkanesulfonyl(C₁-C₆)alkyl, halo(C₃-C₈) cycloalkanesulfonyl(C₁-C₆)alkyl, halo(C₄-C₈)cycloalkylalkane-sulfonyl(C₁-C₆)alkyl, (C₁-C₈)alkylamino(C₁-C₆)alkyl, di(C₁-C₈)alkylamino(C₁-C₆)alkyl, (C₁-C₈)alkoxycarbonyl(C₁-C₆)alkyl, (C₁-C₈)acyloxy (C₁-C₆)alkyl, aminocarbonyl(C₁-C₆)alkyl, (C₁-C₈) alkylamino-carbonyl(C₁-C₆)alkyl, di(C₁-C₈)alkylaminocarbonyl(C₁-C₆)alkyl (C₁-C₈)acylamino(C₁-C₆) alkyl, (C₁-C₈)alkoxycarbonylamino, (C₁-C₈) alkoxycarbonylamino(C₁-C₆)alkyl, aminocarboxy(C₁-C₆)alkyl, (C₁-C₈)alkylamino-carboxy(C₁-C₆)alkyl and di(C₁-C₈)alkylaminocarboxy(C₁-C₆)alkyl;

provided that:

1) when R³ is hydroxyl, halogen or optionally substituted phenylamino or heteroarylamino, then R² is not an optionally substituted alkoxy alkylthio or amino group as follows: a substituted or unsubstituted (C₁-

$C_{12}$)alkoxy, ($C_1$-$C_6$)alkoxy($C_1$-$C_6$)alkoxy, ($C_1$-$C_6$)alkylthio($C_1$-$C_6$)alkoxy, aminocarbonylamino($C_1$-$C_{12}$)alkoxy, ($C_1$-$C_6$)alkanoylamino($C_1$-$C_6$)alkoxy, ($C_3$-$C_4$)cycloalkylcarbonylamino($C_1$-$C_6$)alkoxy, aminosulfonylamino($C_1$-$C_{12}$)alkoxy, ($C_1$-$C_6$)alkanesulfonylamino($C_1$-$C_6$)alkoxy, formylamino($C_1$-$C_6$)alkoxy, ($C_1$-$C_6$)alkoxycarbonylamino($C_1$-$C_6$)alkoxy, ($C_1$-$C_6$)alkylaminocarbonylamino($C_1$-$C_6$)alkoxy, di($C_1$-$C_6$)alkylaminocarbonylamino($C_1$-$C_6$)alkoxy, aminocarbonyl($C_1$-$C_6$)alkoxy, ($C_1$-$C_6$)alkylaminocarbonyl($C_1$-$C_6$)alkoxy, aminocarboxy($C_1$-$C_6$)alkoxy, ($C_1$-$C_6$)alkylaminocarboxy($C_1$-$C_6$)alkoxy, ($C_1$-$C_{12}$)alkoxycarbonylamino, ($C_1$-$C_{12}$)alkylaminocarbonylamino, or ($C_1$-$C_{12}$)alkanoylamino;

2) when $R^3$ is hydroxyl, halogen or optionally substituted phenylamino or heteroarylamino, then $R^2$ is not an optionally substituted alkoxy alkylthio or amino group as follows: a unsubstituted or substituted ($C_1$-$C_{12}$)alkylthio, ($C_1$-$C_6$)alkoxy($C_1$-$C_6$)alkylthio, ($C_1$-$C_6$)alkylthio($C_1$-$C_6$)alkylthio, aminocarbonylamino($C_1$-$C_{12}$)alkylthio, ($C_1$-$C_6$)alkanoylamino($C_1$-$C_6$)alkylthio, ($C_3$-$C_4$)cycloalkylcarbonylamino($C_1$-$C_6$)alkylthio, aminosulfonylamino($C_1$-$C_{12}$)alkylthio, ($C_1$-$C_6$)alkanesulfonylamino($C_1$-$C_6$)alkylthio, formylamino($C_1$-$C_6$)alkylthio, ($C_1$-$C_6$)alkoxycarbonylamino($C_1$-$C_6$)alkylthio, ($C_1$-$C_6$)alkylaminocarbonylamino($C_1$-$C_6$)alkylthio, di($C_1$-$C_6$)alkylaminocarbonylamino($C_1$-$C_6$)alkylthio, aminocarbonyl($C_1$-$C_6$)alkylthio, ($C_1$-$C_6$)alkylaminocarbonyl($C_1$-$C_6$)alkylthio, aminocarboxy($C_1$-$C_6$)alkylthio or ($C_1$-$C_6$)alkylaminocarboxy($C_1$-$C_6$)alkylthio, wherein the thio moiety is replaced by —S(O)— or —S(O)$_2$—; and 3) when $R^3$ is hydroxyl, halogen or optionally substituted phenylamino or heteroarylamino, $R^2$ is not a unsubstituted or substituted aminocarbonylamino($C_1$-$C_{12}$)alkoxy, aminocarbonylamino($C_1$-$C_{12}$)alkylthio, ($C_1$-$C_6$)alkanoylamino($C_1$-$C_6$)alkoxy, ($C_1$-$C_6$)alkanoylamino($C_1$-$C_6$)alkylthio, ($C_3$-$C_4$)cycloalkylcarbonylamino($C_1$-$C_6$)alkoxy, ($C_3$-$C_4$)cycloalkylcarbonylamino($C_1$-$C_6$)alkylthio, formylamino($C_1$-$C_6$)alkoxy, formylamino($C_1$-$C_6$)alkylthio, ($C_1$-$C_6$)alkoxycarbonylamino($C_1$-$C_6$)alkoxy, ($C_1$-$C_6$)alkoxycarbonylamino($C_1$-$C_6$)alkylthio, ($C_1$-$C_6$)alkylaminocarbonylamino($C_1$-$C_6$)alkoxy, di($C_1$-$C_6$)alkylaminocarbonylamino($C_1$-$C_6$)alkoxy, ($C_1$-$C_6$)alkylaminocarbonylamino($C_1$-$C_6$)alkylthio, di($C_1$-$C_6$)alkylaminocarbonylamino($C_1$-$C_6$)alkylthio, aminocarbonyl($C_1$-$C_6$)alkoxy, aminocarbonyl($C_1$-$C_6$)alkylthio, ($C_1$-$C_6$)alkylaminocarbonyl-($C_1$-$C_6$)alkoxy, ($C_1$-$C_6$)alkylaminocarbonyl($C_1$-$C_6$)alkylthio, aminocarboxy($C_1$-$C_6$)alkoxy, aminocarboxy($C_1$-$C_6$)alkylthio, ($C_1$-$C_6$)alkylaminocarboxy($C_1$-$C_6$)alkoxy, ($C_1$-$C_6$)alkylaminocarboxy($C_1$-$C_6$)alkylthio, ($C_1$-$C_{12}$)alkoxycarbonylamino, ($C_1$-$C_{12}$)alkylaminocarbonylamino, or ($C_1$-$C_{12}$)alkanoylamino, wherein the carbonyl moiety is replaced by a thiocarbonyl moiety;

$R^a$, $R^b$, $R^{a'}$, $R^{b'}$ for each occurrence, are independently hydrogen, ($C_1$-$C_6$)alkyl, halo($C_1$-$C_6$)alkyl or $R^a$ and $R^b$ attached to a carbon atom taken together are an oxo or $R^{a'}$ and $R^{b'}$ attached to a carbon atom taken together are an oxo;

$R^4$ is H, ($C_1$-$C_6$)alkyl, halo($C_1$-$C_6$)alkyl; ($C_1$-$C_3$)alkoxy($C_1$-$C_3$)alkyl, or cyano($C_1$-$C_6$)alkyl;

$R^5$ and $R^6$ is each independently selected from 1) hydrogen, hydroxy, ($C_1$-$C_{12}$)alkyl, ($C_3$-$C_8$)cycloalkyl, ($C_3$-$C_8$)cycloalkyl($C_1$-$C_3$)alkyl, ($C_2$-$C_{12}$)alkenyl, ($C_5$-$C_8$)cycloalkyl($C_1$-$C_3$)alkenyl, ($C_2$-$C_{12}$)alkynyl, ($C_3$-$C_8$)cycloalkyl($C_1$-$C_3$)alkynyl, ($C_4$-$C_{12}$)bicycloalkyl($C_1$-$C_3$)alkyl, ($C_8$-$C_{14}$)tricycloalkyl($C_1$-$C_3$)alkyl, ($C_1$-$C_6$)alkoxy($C_1$-$C_6$)alkyl, ($C_3$-$C_8$)cycloalkoxy($C_1$-$C_3$)alkyl, ($C_1$-$C_6$)alkylthio($C_1$-$C_6$)alkyl, ($C_3$-$C_8$)cycloalkylthio($C_1$-$C_3$)alkyl, saturated heterocyclyl, and saturated heterocyclyl($C_1$-$C_3$)alkyl wherein (a) hydrogen atoms in these groups are optionally substituted by 1 to 6 groups independently selected from halogen, cyano, hydroxyl, ($C_1$-$C_3$)alkyl, ($C_1$-$C_3$)alkoxy, ($C_3$-$C_6$)cycloalkyl, ($C_3$-$C_6$)cycloalkoxy, halo($C_1$-$C_3$)alkyl, halo($C_1$-$C_3$)alkoxy, halo($C_3$-$C_6$)cycloalkyl, halo($C_3$-$C_6$)cycloalkoxy and wherein (b) divalent sulfur atoms are optionally oxidized to sulfoxide or sulfone; or 2) phenyl, naphthyl, heteroaryl, phenyl($C_1$-$C_3$)alkyl, naphthyl($C_1$-$C_3$)alkyl, and heteroaryl($C_1$-$C_3$)alkyl, each optionally substituted with 1 to 3 groups independently selected from: fluorine, chlorine, bromine, iodine, cyano, nitro, amino, hydroxy, carboxy, ($C_1$-$C_6$)alkyl, ($C_3$-$C_6$)cycloalkyl, ($C_4$-$C_7$)cycloalkylalkyl, ($C_2$-$C_6$)alkynyl, ($C_3$-$C_6$)cycloalkyl-($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkylthio, ($C_4$-$C_7$)cycloalkylalkylthio, halo($C_1$-$C_6$)alkylthio, halo($C_3$-$C_6$)cycloalkylthio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)-cycloalkylalkanesulfonyl, ($C_1$-$C_6$)alkylamino, di($C_1$-$C_6$)alkylamino, ($C_1$-$C_6$)-alkoxy($C_1$-$C_6$)alkoxy, halo($C_1$-$C_6$)alkoxy($C_1$-$C_6$)alkoxy, ($C_1$-$C_6$)alkoxycarbonyl, aminocarbonyl, ($C_1$-$C_6$)alkylaminocarbonyl, di($C_1$-$C_6$)alkylaminocarbonyl, cyano($C_1$-$C_6$)alkyl, hydroxy($C_1$-$C_6$)alkyl, carboxy($C_1$-$C_6$)alkyl, ($C_1$-$C_6$)alkoxy($C_1$-$C_6$)alkyl, ($C_3$-$C_8$)cycloalkoxy($C_1$-$C_6$)alkyl, ($C_4$-$C_8$)cycloalkylalkoxy($C_1$-$C_6$)alkyl, halo($C_1$-$C_6$)alkoxy($C_1$-$C_6$)alkyl, halo($C_3$-$C_6$)cycloalkoxy($C_1$-$C_6$)alkyl, halo($C_4$-$C_8$)-cycloalkylalkoxy($C_1$-$C_6$)alkyl, ($C_1$-$C_8$)alkylthio($C_1$-$C_6$)alkyl, ($C_3$-$C_8$)cycloalkylthio($C_1$-$C_6$)alkyl, ($C_4$-$C_8$)cycloalkylalkylthio($C_1$-$C_6$)alkyl, halo($C_1$-$C_8$)alkylthio($C_1$-$C_6$)alkyl, halo($C_3$-$C_8$)cycloalkylthio($C_1$-$C_6$)alkyl, halo($C_4$-$C_8$)-cycloalkylalkylthio($C_1$-$C_6$)alkyl, ($C_1$-$C_8$)alkanesulfinyl($C_1$-$C_6$)alkyl, ($C_3$-$C_8$)-cycloalkanesulfinyl($C_1$-$C_6$)alkyl, ($C_4$-$C_8$)cycloalkyl-alkanesulfinyl($C_1$-$C_6$)alkyl, halo($C_1$-$C_8$)alkanesulfinyl($C_1$-$C_6$)alkyl, halo($C_3$-$C_8$)cycloalkanesulfinyl($C_1$-$C_6$)alkyl, halo($C_4$-$C_8$)cycloalkylalkanesulfinyl($C_1$-$C_6$)alkyl, ($C_1$-$C_8$)alkane-sulfonyl($C_1$-$C_6$)alkyl, ($C_3$-$C_8$)cycloalkanesulfonyl($C_1$-$C_6$)alkyl, ($C_4$-$C_8$)cycloalkylalkanesulfonyl($C_1$-$C_6$)alkyl, halo($C_1$-$C_8$)alkanesulfonyl($C_1$-$C_6$)alkyl, halo($C_3$-$C_8$)cycloalkanesulfonyl($C_1$-$C_6$)alkyl, halo($C_4$-$C_8$)cycloalkylalkane-sulfonyl($C_1$-$C_6$)alkyl, ($C_1$-$C_8$)alkylamino($C_1$-$C_6$)alkyl, di($C_1$-$C_8$)alkylamino($C_1$-

$C_6$)alkyl, ($C_1$-$C_8$)alkoxycarbonyl($C_1$-$C_6$)alkyl, ($C_1$-$C_8$)acyloxy($C_1$-$C_6$)alkyl, aminocarbonyl($C_1$-$C_6$)alkyl, ($C_1$-$C_8$)alkylamino-carbonyl($C_1$-$C_6$)alkyl, di($C_1$-$C_8$)alkylaminocarbonyl($C_1$-$C_6$)alkyl and ($C_1$-$C_8$)acylamino($C_1$-$C_6$)alkyl, ($C_1$-$C_8$)alkoxycarbonylamino, ($C_1$-$C_8$)alkoxycarbonylamino($C_1$-$C_6$)alkyl, aminocarboxy($C_1$-$C_6$)alkyl, ($C_1$-$C_8$)alkylamino-carboxy($C_1$-$C_6$)alkyl and di($C_1$-$C_8$)alkylaminocarboxy($C_1$-$C_6$)alkyl, phenyl, naphthyl, heteroaryl, bicyclic heteroaryl, phenoxy, naphthyloxy, heteroaryloxy, bicyclic heteroaryloxy, phenylthio, naphthylthio, heteroarylthio, bicyclic heteroarylthio, phenylsulfinyl, naphthylsulfinyl, heteroarylsulfinyl, bicyclic heteroarylsulfinyl, phenylsulfonyl, naphthylsulfonyl, heteroarylsulfonyl, bicyclic heteroarylsulfonyl, phenyl($C_1$-$C_3$)alkyl, naphthyl($C_1$-$C_3$)alkyl, heteroaryl($C_1$-$C_3$)alkyl, and bicyclic heteroaryl($C_1$-$C_3$)alkyl, wherein the aromatic and heteroaromatic groups are optionally substituted with 1 to 3 groups independently selected from fluorine, chlorine, cyano, ($C_1$-$C_3$)alkyl, halo($C_1$-$C_3$)alkyl, ($C_1$-$C_3$)alkoxy, halo($C_1$-$C_3$)-alkoxy, ($C_1$-$C_3$)alkanesulfonyl, and ($C_1$-$C_3$)alkoxycarbonyl; R7 is (C1-C6)alkyl, halo(C1-C6)alkyl or (C1-C3)alkoxy(C1-C3)alkyl; and $R^9$ is a) ($C_1$-$C_{12}$)alkyl, ($C_4$-$C_{12}$)cycloalkylalkyl, halo($C_1$-$C_{12}$)alkyl, halo($C_4$-$C_{12}$)cycloalkylalkyl, ($C_2$-$C_{12}$)alkenyl, ($C_5$-$C_{12}$)cycloalkylalkenyl, halo($C_2$-$C_{12}$)alkenyl, halo($C_5$-$C_{12}$)cycloalkylalkenyl, ($C_2$-$C_{12}$)alkynyl, ($C_5$-$C_{12}$)cycloalkylalkynyl, halo($C_2$-$C_{12}$)alkynyl, halo($C_5$-$C_{12}$)cycloalkylalkynyl, ($C_1$-$C_6$)alkoxy($C_1$-$C_6$)alkyl, halo($C_1$-$C_6$)alkoxy($C_1$-$C_6$)alkyl, ($C_1$-$C_6$)alkylthio($C_1$-$C_6$)alkyl, halo($C_1$-$C_6$)alkylthio($C_1$-$C_6$)alkyl, ($C_1$-$C_6$)alkanesulfinyl($C_1$-$C_6$)alkyl, halo($C_1$-$C_6$)alkane-sulfinyl($C_1$-$C_6$)alkyl, ($C_1$-$C_6$)alkanesulfonyl($C_1$-$C_6$)alkyl, halo($C_1$-$C_6$)alkanesulfonyl($C_1$-$C_6$)alkyl, aminocarbonyl($C_1$-$C_6$)alkyl, ($C_1$-$C_6$)alkylaminocarbonyl($C_1$-$C_6$)alkyl, di($C_1$-$C_6$)alkylamino-carbonyl($C_1$-$C_6$)alkyl, cyano($C_1$-$C_6$)alkyl, carboxy($C_1$-$C_6$)alkyl, ($C_1$-$C_6$)alkoxycarbonyl($C_1$-$C_6$)alkyl, saturated heterocyclyl, or saturated heterocyclyl($C_1$-$C_6$)alkyl or b) phenyl, naphthyl, heteroaryl, phenyl($C_1$-$C_3$)alkyl, naphthyl($C_1$-$C_3$)alkyl, or heteroaryl($C_1$-$C_3$)alkyl, each optionally substituted by 1 to 3 groups independently selected from:

1) fluorine, chlorine, bromine, iodine, cyano, nitro, amino, hydroxy, carboxy, ($C_1$-$C_6$)alkyl, ($C_3$-$C_6$)cycloalkyl, ($C_4$-$C_7$)cycloalkylalkyl, ($C_2$-$C_6$)alkynyl, ($C_3$-$C_6$)cycloalkyl-($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkylthio, ($C_4$-$C_7$)cycloalkylalkylthio, halo($C_1$-$C_6$)alkylthio, halo($C_3$-$C_6$)cycloalkylthio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$)alkylamino, ($C_1$-$C_6$)alkoxy-($C_1$-$C_6$)alkoxy, halo($C_1$-$C_6$)alkoxy($C_1$-$C_6$)alkoxy, ($C_1$-$C_6$)alkoxycarbonyl, aminocarbonyl, ($C_1$-$C_6$)alkylaminocarbonyl and di($C_1$-$C_6$)alkylaminocarbonyl, cyano($C_1$-$C_6$)alkyl, hydroxy($C_1$-$C_6$)alkyl, carboxy($C_1$-$C_6$)alkyl, ($C_1$-$C_6$)alkoxy($C_1$-$C_6$)alkyl, ($C_3$-$C_8$)cycloalkoxy($C_1$-$C_6$)alkyl, ($C_4$-$C_8$)cycloalkylalkoxy($C_1$-$C_6$)alkyl, halo($C_1$-$C_6$)alkoxy($C_1$-$C_6$)alkyl, halo($C_3$-$C_6$)cycloalkoxy($C_1$-$C_6$)alkyl, halo($C_4$-$C_8$)-cycloalkylalkoxy($C_1$-$C_6$)alkyl, ($C_1$-$C_8$)alkylthio($C_1$-$C_6$)alkyl, ($C_3$-$C_8$)cycloalkylthio($C_1$-$C_6$)alkyl, ($C_4$-$C_8$)cycloalkylalkylthio($C_1$-$C_6$)alkyl, halo($C_1$-$C_8$)alkylthio($C_1$-$C_6$)alkyl, halo($C_3$-$C_8$)cycloalkylthio($C_1$-$C_6$)alkyl, halo($C_4$-$C_8$)-cycloalkylalkylthio($C_1$-$C_6$)alkyl, ($C_1$-$C_8$)alkanesulfinyl($C_1$-$C_6$)alkyl, ($C_3$-$C_8$)-cycloalkanesulfinyl($C_1$-$C_6$)alkyl, ($C_4$-$C_8$)cycloalkyl-alkanesulfinyl($C_1$-$C_6$)alkyl, halo($C_1$-$C_8$)alkanesulfinyl($C_1$-$C_6$)alkyl, halo($C_3$-$C_8$)cycloalkanesulfinyl($C_1$-$C_6$)alkyl, halo($C_4$-$C_8$)cycloalkylalkanesulfinyl($C_1$-$C_6$)alkyl, ($C_1$-$C_8$)alkane-sulfonyl($C_1$-$C_6$)alkyl, ($C_3$-$C_8$)cycloalkanesulfonyl($C_1$-$C_6$)alkyl, ($C_4$-$C_8$)cycloalkylalkanesulfonyl($C_1$-$C_6$)alkyl, halo($C_1$-$C_8$)alkanesulfonyl($C_1$-$C_6$)alkyl, halo($C_3$-$C_8$)cycloalkanesulfonyl($C_1$-$C_6$)alkyl, halo($C_4$-$C_8$)cycloalkylalkane-sulfonyl($C_1$-$C_6$)alkyl, ($C_1$-$C_8$)alkylamino($C_1$-$C_6$)alkyl, di($C_1$-$C_8$)alkylamino($C_1$-$C_6$)alkyl, ($C_1$-$C_8$)alkoxycarbonyl($C_1$-$C_6$)alkyl, ($C_1$-$C_8$)acyloxy($C_1$-$C_6$)alkyl, aminocarbonyl($C_1$-$C_6$)alkyl, ($C_1$-$C_8$)alkylamino-carbonyl($C_1$-$C_6$)alkyl, di($C_1$-$C_8$)alkylaminocarbonyl($C_1$-$C_6$)alkyl ($C_4$-$C_8$)acylamino($C_1$-$C_6$)alkyl, ($C_1$-$C_8$)alkoxycarbonylamino, ($C_1$-$C_8$)alkoxycarbonylamino(C aminocarboxy($C_1$-$C_6$)alkyl, ($C_1$-$C_8$)alkylamino-carboxy($C_1$-$C_6$)alkyl and di($C_1$-$C_8$)alkylaminocarboxy($C_1$-$C_6$)alkyl; or 2) phenyl, naphthyl, heteroaryl, bicyclic heteroaryl, phenoxy, naphthyloxy, heteroaryloxy, bicyclic heteroaryloxy, phenylthio, naphthylthio, heteroarylthio, bicyclic heteroarylthio, phenylsulfinyl, naphthylsulfinyl, heteroarylsulfinyl, bicyclic heteroarylsulfinyl, phenylsulfonyl, naphthylsulfonyl, heteroarylsulfonyl, bicyclic heteroarylsulfonyl, phenyl($C_1$-$C_3$)alkyl, naphthyl($C_1$-$C_3$)alkyl, heteroaryl($C_1$-$C_3$)alkyl, and bicyclic heteroaryl($C_1$-$C_3$)alkyl, each optionally substituted with 1 to 3 groups independently selected from fluorine, chlorine, cyano, ($C_1$-$C_3$)alkyl, halo($C_1$-$C_3$)alkyl, ($C_1$-$C_3$)alkoxy, halo($C_1$-$C_3$)alkoxy, ($C_1$-$C_3$)alkanesulfonyl, and ($C_1$-$C_3$)-alkoxycarbonyl.

2. The compound of claim 1, wherein:

$R^1$ is phenyl, optionally substituted with 1 to 5 groups independently selected from:

1) fluorine, chlorine, bromine, cyano, nitro, ($C_1$-$C_6$)alkyl, ($C_3$-$C_6$)cycloalkyl, ($C_4$-$C_7$)cycloalkylalkyl, ($C_2$-$C_6$)alkenyl, ($C_5$-$C_6$)cycloalkenyl, ($C_5$-$C_8$)cycloalkylalkenyl, ($C_2$-$C_6$)alkynyl, ($C_3$-$C_6$)cycloalkylethynyl, halo($C_1$-$C_6$)alkyl, halo($C_3$-$C_6$)cycloalkyl, halo($C_4$-$C_7$)-cycloalkylalkyl, halo($C_2$-$C_6$)alkenyl, halo($C_3$-$C_6$)alkynyl, halo($C_3$-$C_6$)cyclalkylethynyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_3$-$C_6$)alkenyloxy, and ($C_1$-$C_6$)alkanesulfonyl; or 2) phenyl, heteroaryl, phenoxy, heteroaryloxy, phenylthio, heteroarylthio, benzyl, heteroarylmethyl, benzyloxy, and heteroaryloxy, each optionally substituted with 1 to 3 groups independently selected from:

fluorine, chlorine, cyano, ($C_1$-$C_3$)alkyl, halo($C_1$-$C_3$)alkyl, ($C_1$-$C_3$)-alkoxy, halo($C_1$-$C_3$)alkoxy, and aminocarbonyl;

$R^2$ is ($C_1$-$C_8$)alkyl, ($C_3$-$C_7$)cycloalkylalkyl, fluoro($C_1$-$C_8$)alkyl, fluoro($C_3$-$C_7$)-cycloalkylalkyl, ($C_1$-$C_8$)alkoxy, ($C_3$-$C_7$)cycloalkylalkoxy, fluoro($C_1$-$C_8$)alkoxy, hydroxy($C_1$-$C_8$)alkyl, ($C_1$-$C_5$)alkoxy($C_1$-$C_5$)

alkyl, halo($C_1$-$C_5$)alkylamino($C_1$-$C_5$)alkyl, ($C_1$-$C_5$) alkoxy($C_1$-$C_5$)hydroxyalkyl, ($C_3$-$C_4$)cycloalkoxy ($C_1$-$C_5$)alkyl, fluoro($C_1$-$C_5$)alkoxy($C_1$-$C_5$)alkyl, fluoro($C_3$-$C_4$)cycloalkoxy($C_1$-$C_5$)alkyl, ($C_1$-$C_5$) alkylthio($C_1$-$C_5$)alkyl, ($C_1$-$C_5$)alkoxy($C_1$-$C_5$)alkoxy, hydroxy($C_1$-$C_8$)alkoxy, ($C_3$-$C_4$)cycloalkoxy($C_1$-$C_5$) alkoxy, fluoro($C_1$-$C_5$)alkoxy($C_1$-$C_5$)alkoxy, fluoro ($C_3$-$C_4$)cycloalkoxy($C_1$-$C_5$)alkoxy, ($C_1$-$C_3$)alkoxy ($C_1$-$C_3$)alkoxy($C_1$-$C_3$)alkyl, fluoro($C_1$-$C_3$)-alkoxy ($C_1$-$C_3$)alkoxy($C_1$-$C_3$)alkyl, aminocarbonylamino ($C_1$-$C_8$)alkyl, aminocarbonylamino($C_1$-$C_8$)alkoxy, ($C_1$-$C_5$)alkanoylamino($C_1$-$C_5$)alkyl, ($C_1$-$C_5$)alkanoylamino($C_1$-$C_5$)alkoxy, fluoro($C_1$-$C_5$)alkanoylamino($C_1$-$C_5$)alkyl, fluoro($C_1$-$C_5$)alkanoylamino ($C_1$-$C_5$)alkoxy, ($C_1$-$C_3$)alkoxy($C_1$-$C_5$) alkanoylamino($C_1$-$C_5$)alkyl, ($C_1$-$C_3$)alkoxy($C_1$-$C_5$) alkanoylamino($C_1$-$C_5$)alkoxy, ($C_3$-$C_4$)-cycloalkanecarbonylamino($C_1$-$C_5$)alkyl, ($C_3$-$C_4$) cycloalkanecarbonylamino($C_1$-$C_5$)alkoxy, aminosulfonylamino($C_1$-$C_8$)alkyl, aminosulfonylamino($C_1$-$C_8$)alkoxy, ($C_1$-$C_5$)alkanesulfonyl-amino ($C_1$-$C_5$)alkyl, ($C_1$-$C_5$)alkanesulfonylamino($C_1$-$C_5$) alkoxy, formylamino($C_1$-$C_5$)alkyl, formylamino($C_1$-$C_5$)alkoxy, ($C_1$-$C_5$)alkoxycarbonylamino($C_1$-$C_5$) alkyl, ($C_1$-$C_5$)alkoxycarbonyl-amino($C_1$-$C_5$)alkoxy, ($C_1$-$C_5$)alkylaminocarbonylamino($C_1$-$C_5$)alkyl, ($C_1$-$C_5$)alkylaminocarbonyl-amino($C_1$-$C_5$)alkyl, di($C_1$-$C_5$)alkylaminocarbonylamino($C_1$-$C_5$)alkoxy, aminocarbonyl($C_1$-$C_5$)alkyl, aminocarbonyl($C_1$-$C_5$) alkoxy, ($C_1$-$C_5$)alkylaminocarbonyl($C_1$-$C_5$)alkyl, ($C_1$-$C_5$)-alkylaminocarbonyl-($C_1$-$C_5$)alkoxy, aminocarboxy($C_1$-$C_5$)alkyl, aminocarboxy($C_1$-$C_5$) alkoxy, ($C_1$-$C_5$)alkylamino-carboxy($C_1$-$C_5$)alkyl, ($C_1$-$C_5$)alkylaminocarboxy($C_1$-$C_5$)alkoxy, ($C_1$-$C_8$)-alkoxycarbonylamino, ($C_1$-$C_8$)alkylaminocarbonylamino, ($C_1$-$C_8$)alkanoylamino, fluoro($C_1$-$C_8$) alkoxycarbonylamino, fluoro($C_1$-$C_8$) alkylaminocarbonylamino, fluoro($C_1$-$C_8$)-alkanoylamino, or ($C_1$-$C_8$)oxoalkyl;

$R^3$ is H, halogen, OH, ($C_1$-$C_4$)alkanoylamino, or ($C_1$-$C_3$)alkoxy; provided that when $R^3$ is OH or halogen, $R^2$ is not an optionally substituted alkoxy, alkylthio or amino group as follows: ($C_1$-$C_8$)alkoxy, ($C_4$-$C_8$)cycloalkylalkoxy, fluoro($C_1$-$C_8$)alkoxy, ($C_1$-$C_5$)alkoxy ($C_1$-$C_5$)alkoxy, hydroxy($C_1$-$C_8$)alkoxy, ($C_3$-$C_4$)cycloalkoxy($C_1$-$C_5$)alkoxy, fluoro($C_1$-$C_5$)alkoxy($C_1$-$C_5$)alkoxy, fluoro($C_3$-$C_4$)cycloalkoxy($C_1$-$C_5$)alkoxy, aminocarbonyl-amino($C_1$-$C_8$)alkoxy, ($C_1$-$C_5$)alkanoylamino($C_1$-$C_5$)alkoxy, fluoro($C_1$-$C_5$)alkanoylamino($C_1$-$C_5$)alkoxy, ($C_1$-$C_3$)alkoxy($C_1$-$C_5$)alkanoylamino($C_1$-$C_5$)alkoxy, ($C_3$-$C_4$)-cycloalkanecarbonylamino($C_1$-$C_5$)alkoxy, aminosulfonylamino($C_1$-$C_8$)alkoxy, ($C_1$-$C_5$)alkanesulfonylamino($C_1$-$C_5$)alkoxy, formylamino($C_1$-$C_5$) alkoxy, ($C_1$-$C_5$)alkoxy-carbonylamino($C_1$-$C_5$) alkoxy, di($C_1$-$C_5$)alkylaminocarbonylamino($C_1$-$C_5$) alkoxy, aminocarbonyl($C_1$-$C_5$)alkoxy, ($C_1$-$C_5$) alkylaminocarbonyl($C_1$-$C_5$)alkoxy, amino-carboxy ($C_1$-$C_5$)alkoxy, ($C_1$-$C_5$)alkylaminocarboxy($C_1$-$C_5$) alkoxy, ($C_1$-$C_8$)alkoxy-carbonylamino, ($C_1$-$C_8$) alkylaminocarbonylamino, ($C_1$-$C_8$)alkanoylamino, fluoro($C_1$-$C_8$)alkoxycarbonylamino, fluoro($C_1$-$C_8$) alkylaminocarbonylamino, or fluoro($C_1$-$C_8$)alkanoylamino;

$R^4$ is H or ($C_1$-$C_6$)alkyl;

$R^5$ and $R^6$, each is independently a) hydrogen; or b) ($C_1$-$C_{10}$)alkyl, ($C_3$-$C_7$)cycloalkyl($C_1$-$C_2$)alkyl, ($C_4$-$C_{10}$)bicycloalkyl($C_1$-$C_2$)alkyl, ($C_8$-$C_{12}$)tricycloalkyl ($C_1$-$C_2$)alkyl, ($C_1$-$C_6$)alkoxy($C_1$-$C_6$)alkyl, ($C_3$-$C_7$) cycloalkoxy($C_1$-$C_3$)alkyl, ($C_1$-$C_5$)alkylthio($C_1$-$C_5$) alkyl, or monocyclic or bicyclic saturated heterocyclyl($C_1$-$C_3$)alkyl wherein each of these groups are optionally substituted by 1 to 3 groups independently selected from halogen, cyano, hydroxyl, ($C_1$-$C_2$)alkyl, ($C_1$-$C_2$)alkoxy, ($C_3$-$C_6$)cycloalkyl, ($C_3$-$C_6$)cycloalkoxy, halo($C_1$-$C_2$)alkyl, halo ($C_1$-$C_2$)alkoxy, halo($C_3$-$C_6$)cycloalkyl, and halo($C_3$-$C_6$)cycloalkoxy; or c) phenyl($C_1$-$C_2$)alkyl or heteroaryl($C_1$-$C_2$)alkyl each optionally substituted with 1 to 3 groups independently selected from fluorine, chlorine, cyano, ($C_1$-$C_3$)alkyl, halo($C_1$-$C_3$)alkyl, ($C_1$-$C_3$)alkoxy, and halo($C_1$-$C_3$)alkoxy;

$R^7$ is ($C_1$-$C_6$)alkyl, halo($C_1$-$C_6$)alkyl or ($C_1$-$C_3$)alkoxy ($C_1$-$C_3$)alkyl;

$R^a$, $R^b$, $R^{a'}$, $R^{b'}$ for each occurrence, is independently hydrogen, ($C_1$-$C_6$)alkyl, halo($C_1$-$C_6$)alkyl or $R^a$ and $R^b$ attached to a carbon atom taken together is an oxo or $R^{a'}$ and $R^{b'}$ taken together is an oxo; and $R^9$ is a) hydrogen; b) ($C_1$-$C_6$)alkyl, halo($C_1$-$C_6$)alkyl, ($C_4$-$C_{10}$)cycloalkylalkyl, ($C_1$-$C_5$)alkoxy($C_1$-$C_5$) alkyl, aminocarbonyl($C_1$-$C_5$)alkyl, ($C_1$-$C_6$)alkylaminocarbonyl($C_1$-$C_6$)alkyl, or di($C_1$-$C_6$)alkyl-aminocarbonyl($C_1$-$C_6$)alkyl; or c) phenyl($C_1$-$C_2$)alkyl optionally substituted with 1 to 3 groups independently selected from fluorine, chlorine, cyano, ($C_1$-$C_3$)alkyl, halo($C_1$-$C_3$)alkyl, ($C_1$-$C_3$)alkoxy, and halo ($C_1$-$C_3$)alkoxy.

3. The compound of claim 2, wherein one of $R^5$ or $R^6$ is H and the other is a) hydrogen; or b) ($C_1$-$C_{10}$)alkyl, ($C_3$-$C_7$) cycloalkyl($C_1$-$C_2$)alkyl, ($C_4$-$C_{10}$)bicycloalkyl($C_1$-$C_2$)alkyl, ($C_8$-$C_{12}$)tricycloalkyl($C_1$-$C_2$)alkyl, ($C_1$-$C_6$)alkoxy($C_1$-$C_6$) alkyl, ($C_3$-$C_7$)cycloalkoxy($C_1$-$C_3$)alkyl, ($C_1$-$C_5$)alkylthio ($C_1$-$C_5$)alkyl, or monocyclic or bicyclic saturated heterocyclyl($C_1$-$C_3$)alkyl, wherein each of these groups are optionally substituted by 1 to 3 groups independently selected from halogen, cyano, hydroxyl, ($C_1$-$C_2$)alkyl, ($C_1$-$C_2$)alkoxy, ($C_3$-$C_6$)cycloalkyl, ($C_3$-$C_6$)cycloalkoxy, halo($C_1$-$C_2$)alkyl, halo ($C_1$-$C_2$)alkoxy, halo($C_3$-$C_6$)cycloalkyl, and halo($C_3$-$C_6$)cycloalkoxy; or c) phenyl($C_1$-$C_2$)alkyl or heteroaryl($C_1$-$C_2$) alkyl each optionally substituted with 1 to 3 groups independently selected from fluorine, chlorine, cyano, ($C_1$-$C_3$)alkyl, halo($C_1$-$C_3$)alkyl, ($C_1$-$C_3$)alkoxy, and halo($C_1$-$C_3$) alkoxy.

4. The compound of claim 2, wherein: $R^1$ is phenyl optionally substituted with 1 to 5 substituents independently selected from:

fluorine, chlorine, bromine, cyano, methyl, ethyl, isopropyl, t-butyl, isobutyl, trifluoromethyl, allyl, cyclohexyl, cyclohexen-1-yl, cyclopropylethynyl, methoxy, trifluoromethoxy, neopentyloxy, methylthio, allyloxy, cyclopropylmethoxy, 2-(cyclopropyl)ethoxy, cyclopentyloxy, cyclopentylmethoxy, benzyloxy, hydroxyl, aminocarbonyl, methoxycarbonyl, phenyl, phenoxy, benzyloxy, and heteroaryloxy, wherein the phenyl phenoxy, benzyloxy and heteroaryloxy groups are optionally substituted with 1 to 3 substituents independently selected from fluorine, chlorine, cyano, methyl, trifluoromethyl, and aminocarbonyl.

5. The compound of claim 4, wherein:
$R^2$ is ($C_1$-$C_8$)alkyl, ($C_4$-$C_8$)cycloalkylalkyl, fluoro($C_1$-$C_8$) alkyl, fluoro($C_4$-$C_8$)-cycloalkylalkyl, hydroxy($C_1$-$C_8$) alkyl, ($C_1$-$C_5$)alkoxy($C_1$-$C_5$)alkyl, halo($C_1$-$C_5$)alkylamino($C_1$-$C_5$)alkyl, ($C_1$-$C_5$)alkoxy($C_1$-$C_5$) hydroxyalkyl, ($C_3$-$C_4$)cycloalkoxy($C_1$-$C_5$)alkyl, fluoro ($C_1$-$C_5$)alkoxy($C_1$-$C_5$)alkyl, fluoro($C_3$-$C_4$)cycloalkoxy($C_1$-$C_5$)alkyl, $C_5$)alkylthio($C_1$-$C_5$)alkyl, ($C_1$-$C_5$)alkoxy($C_1$-$C_5$)alkoxy, ($C_3$-$C_4$)cycloalkoxy($C_1$-$C_5$)alkoxy, fluoro($C_1$-$C_5$)alkoxy($C_1$-$C_5$)alkoxy, fluoro($C_3$-$C_4$)cycloalkoxy($C_1$-$C_5$)alkoxy, ($C_1$-$C_3$)alkoxy($C_1$-$C_3$)alkoxy($C_1$-$C_3$)alkyl, fluoro($C_1$-$C_3$)-alkoxy($C_1$-$C_3$)alkoxy($C_1$-$C_3$)alkyl, aminocarbonylamino($C_1$-$C_8$)alkyl, ($C_1$-$C_5$)alkanoylamino($C_1$-$C_5$)alkyl, fluoro($C_1$-$C_5$)alkanoylamino($C_1$-$C_5$)alkyl, ($C_1$-$C_3$)alkoxy($C_1$-$C_5$)alkanoylamino($C_1$-$C_5$)alkyl, ($C_3$-$C_4$)-cycloalkanecarbonylamino($C_1$-$C_5$)alkyl, aminosulfonylamino($C_1$-$C_8$)alkyl, ($C_1$-$C_5$)alkanesulfonyl-amino($C_1$-$C_5$)alkyl, formylamino($C_1$-$C_5$)alkyl, ($C_1$-$C_5$)alkoxycarbonylamino(C($C_1$-$C_5$)alkoxycarbonyl-amino($C_1$-$C_5$)alkoxy, ($C_1$-$C_5$)alkylaminocarbonylamino($C_1$-$C_5$)alkyl, ($C_1$-$C_5$)alkylaminocarbonyl-amino($C_1$-$C_5$)alkyl, aminocarbonyl($C_1$-$C_5$)alkyl, ($C_1$-$C_5$)alkylaminocarbonyl($C_1$-$C_5$)alkyl, aminocarboxy($C_1$-$C_5$)alkyl, aminocarboxy($C_1$-$C_5$)alkoxy, ($C_1$-$C_5$)alkylamino-carboxy($C_1$-$C_5$)alkyl, ($C_1$-$C_5$)alkylaminocarboxy($C_1$-$C_5$)alkoxy, or ($C_1$-$C_8$)oxoalkyl, provided when $R^3$ is OH or halogen, $R^2$ is not ($C_1$-$C_5$)alkoxy($C_1$-$C_5$)alkoxy, ($C_3$-$C_4$)cycloalkoxy($C_1$-$C_5$)alkoxy, fluoro($C_1$-$C_5$)alkoxy($C_1$-$C_5$)alkoxy, fluoro($C_3$-$C_4$)cycloalkoxy($C_1$-$C_5$)alkoxy,($C_1$-$C_5$)alkoxycarbonylamino($C_1$-$C_5$)alkoxy, aminocarboxy($C_1$-$C_5$)alkoxy, or ($C_1$-$C_5$)alkylaminocarboxy($C_1$-$C_5$)alkoxy.

6. The compound of claim 5, wherein $R^1$ is phenyl, optionally substituted with 1 to 5 substituents independently selected from:
fluorine, chlorine, bromine, cyano, methyl, ethyl, isopropyl, t-butyl, isobutyl, trifluoromethyl, allyl, cyclohexyl, cyclohexen-1-yl, cyclopropylethynyl, methoxy, trifluoromethoxy, neopentyloxy, methylthio, allyloxy, cyclopropylmethoxy, 2-(cyclopropyl)ethoxy, cyclopentyloxy, cyclopentylmethoxy, benzyloxy, hydroxyl, aminocarbonyl, methoxycarbonyl, phenyl, phenoxy, benzyloxy, and heteroaryloxy, wherein the phenyl phenoxy, benzyloxy and heteroaryloxy groups are optionally substituted with 1 to 3 substituents independently selected from fluorine, chlorine, cyano, methyl, trifluoromethyl, and aminocarbonyl.

7. The compound of claim 6, wherein:
$R^2$ is methyl, ethyl, propyl, butyl, hexyl, 5-pentenyl, 3,3,3-trifluoropropyl, 4,4-difluoropentyl, 3-(cyclopropyl)propyl, 4-(cyclopropyl)butyl, 3-hydroxypropyl, 4-hydroxybutyl, 4-hydroxypentyl, 4-hydroxyhexyl, 5-hydroxyhexyl, 2-hydroxyethoxy, 5-oxohexyl, 3-ethoxypropyl, 4-methoxybutyl, 4-ethoxybutyl, 2-(ethoxy)-ethoxy, 3-methoxypropoxy, 3-ethoxypropoxy, 3-propoxypropoxy, (2-(methoxy)ethoxy)methyl, 3-(2,2,2-trifluoroethylamino)propyl, 3-(formylamino)propyl, 3-(acetylamino)propyl, 3-(propionyl-amino)propyl, 3-(butanoylamino)propyl, 3-((2-methoxypropionyl)amino)propyl, 3-(cyclopropane-carbonylamino)propyl, 3-(trifluoroacetylamino)propyl, 3-(methoxycarbonylamino)propyl, 3-(ethoxycarbonylamino)propyl, 2-(methoxycarbonylamino)ethoxy, 2-(ethoxycarbonylamino)-ethoxy, 3-(methylaminocarbonylamino)propyl, 3-(dimethylaminocarbonyl-amino)propyl, 3-(aminocarbonyl)propyl, 3-(methylaminocarbonyl)propyl, 3-(ethylamino-carbonyl)propyl, methoxymethylcarbonylaminomethyl, or 3-(aminosulfonylamino)propyl, 2-(methoxy)-ethoxy, or 4-(methoxy)-butoxy.

8. The compound of claim 7, wherein $R^3$ is H, F, OH, methoxy, acetylamino, propionylamino, (2-methylpropionyl)amino, or butanoylamino.

9. The compound of claim 8, wherein:
$R^1$ is phenyl optionally substituted with 1 to 5 substituents independently selected from the group consisting of fluorine, chlorine and methyl;
$R^5$ is hydrogen, methyl, isobutyl, t-butylmethyl, 2,2,2-trifluoroethyl, 2-(trifluoromethyl)propyl, cyclopentylmethyl, cyclohexylmethyl, (3,3-difluorocyclobutyl)methyl, 3,4-difluorocyclopentyl)methyl, 4,4-difluorocyclohexylmethyl, (4-methylcyclohexyl)methyl, tert-butoxymethyl, (4-tetrahydropyranyl)methyl, benzyl, (1-fluorocyclohexyl)methyl, (4-fluorocyclohexyl)methyl, 1-hydroxy-2-methylpropyl, (cyclopentyl)(hydroxy)methyl, (cyclohexyl)(hydroxy)methyl, (cycloheptyl)(hydroxy)methyl, (1-hydroxycyclohexyl)methyl, (4-hydroxycyclohexyl)methyl, (4-hydroxy-4-methylcyclohexyl)methyl, 1-adamantylmethyl, (3-noradamantyl)(hydroxy)methyl, 2-methoxy-2-methylpropyl, 2,2-dimethyl-3-methoxypropyl, (3-tetrahydrofuryl)methyl, (3-tetrahydropyranyl)methyl, (4-tetrahydropyranyl)methyl and $R^6$ is hydrogen; or
$R^5$ is hydrogen and $R^6$ is methyl, isobutyl, t-butylmethyl, 2,2,2-trifluoroethyl, 2-(trifluoromethyl)propyl, cyclopentylmethyl, cyclohexylmethyl, (3,3-difluorocyclobutyl)methyl, 3,4-difluorocyclopentyl)methyl, 4,4-difluoro-cyclohexylmethyl, (4-methylcyclohexyl)methyl, tert-butoxymethyl, (4-tetrahydropyranyl)methyl, benzyl, (1-fluorocyclohexyl)methyl, (4-fluorocyclohexyl)methyl, 1-hydroxy-2-methylpropyl, (cyclopentyl)(hydroxy)methyl, (cyclohexyl)(hydroxy)methyl, (cycloheptyl)(hydroxy)methyl, (1-hydroxycyclohexyl)methyl, (4-hydroxycyclohexyl)methyl, (4-hydroxy-4-methylcyclohexyl)methyl, 1-adamantylmethyl, (3-noradamantyl)(hydroxy)methyl, 2-methoxy-2-methylpropyl, 2,2-dimethyl-3-methoxypropyl, (3-tetrahydrofuryl)methyl, (3-tetrahydropyranyl)methyl, (4-tetrahydropyranyl)methyl.

10. The compound of claim 9, wherein $R^2$ is 3-methoxypropoxy, 4-methoxybutyl, 2-(methoxycarbonylamino)ethoxy or 3-(methoxycarbonylamino)propyl and $R^4$ is H.

11. The compound of claim 10, wherein:
$R^3$ is hydrogen;
$R^5$ is cyclohexylmethyl, 1-adamantylmethyl, (3-tetrahydropyranyl)methyl, (4-tetrahydropyranyl)methyl, (3-oxepanyl)methyl or 6-(4-oxaspiro[2,5]octyl)methyl and $R^6$ is H; or $R^5$ is H and $R^6$ is (3-tetrahydropyranyl)methyl or (3-oxepanyl)methyl;
$R^7$ is methyl, ethyl, propyl or isopropyl;
$R^a$, $R^b$, $R^{a'}$ and $R^{b'}$, for each occurrence, are independently hydrogen, methyl or $R^a$ and $R^b$ attached to a carbon atom taken together are oxo or $R^{a'}$ and $R^{b'}$ attached to a carbon atom taken together are oxo; and
$R^9$ is H, methyl or ethyl.

12. The compound of claim 2, wherein $R^2$ is butoxy, hexyloxy, 2-cyclopropylethoxy, 2-(acetylamino)ethoxy, 2-(propionylamino)ethoxy, aminocarbonylmethoxy, methylaminocarbonylmethoxy, ethylaminocarbonylmethoxy, propylaminocarbonylmethoxy, 2-(methylaminocarbonyl)ethoxy, 2-(ethylaminocarbonyl)ethoxy, 2-(propylaminocarbonyl)ethoxy, or (2-(methoxy)ethoxy)carbonylamino.

13. The compound of claim 12, wherein $R^1$ is phenyl, optionally substituted with 1 to 5 substituents independently selected from:
fluorine, chlorine, bromine, cyano, methyl, ethyl, isopropyl, t-butyl, isobutyl, trifluoromethyl, allyl, cyclohexyl, cyclohexen-1-yl, cyclopropylethynyl, methoxy, trifluoromethoxy, neopentyloxy, methylthio, allyloxy, cyclopropylmethoxy, 2-(cyclopropyl)ethoxy, cyclopentyloxy, cyclopentylmethoxy, benzyloxy, hydroxyl, aminocarbonyl, methoxycarbonyl, phenyl, phenoxy, benzyloxy, and heteroaryloxy, wherein the phenyl phenoxy, benzyloxy and heteroaryloxy groups are optionally substituted with 1 to 3 substituents independently selected from fluorine, chlorine, cyano, methyl, trifluoromethyl, and aminocarbonyl.

14. The compound of claim 13, wherein $R^3$ is H, F, OH, methoxy, acetylamino, propionylamino, (2-methylpropionyl)amino, or butanoylamino.

15. The compound of claim 14, wherein:
$R^1$ is phenyl optionally substituted with 1 to 5 substituents independently selected from the group consisting of fluorine, chlorine and methyl;
$R^5$ is hydrogen, methyl, isobutyl, t-butylmethyl, 2,2,2-trifluoroethyl, 2-(trifluoromethyl)propyl, cyclopentylmethyl, cyclohexylmethyl, (3,3-difluorocyclobutyl)methyl, 3,4-difluorocyclopentyl)methyl, 4,4-difluorocyclohexylmethyl, (4-methylcyclohexyl)methyl, tert-butoxymethyl, (4-tetrahydropyranyl)methyl, benzyl, (1-fluorocyclohexyl)methyl, (4-fluorocyclohexyl)methyl, 1-hydroxy-2-methylpropyl, (cyclopentyl)(hydroxy)methyl, (cyclohexyl)(hydroxy)methyl, (cycloheptyl)(hydroxy)methyl, (1-hydroxycyclohexyl)methyl, (4-hydroxycyclohexyl)methyl, (4-hydroxy-4-methylcyclohexyl)methyl, 1-adamantylmethyl, (3-noradamantyl)(hydroxy)methyl, 2-methoxy-2-methylpropyl, 2,2-dimethyl-3-methoxypropyl, (3-tetrahydrofuryl)methyl, (3-tetrahydropyranyl)methyl, (4-tetrahydropyranyl)methyl and $R^6$ is hydrogen; or
$R^5$ is hydrogen and $R^6$ is methyl, isobutyl, t-butylmethyl, 2,2,2-trifluoroethyl, 2-(trifluoromethyl)propyl, cyclopentylmethyl, cyclohexylmethyl, (3,3-difluorocyclobutyl)methyl, 3,4-difluorocyclopentyl)methyl, 4,4-difluoro-cyclohexylmethyl, (4-methylcyclohexyl)methyl, tert-butoxymethyl, (4-tetrahydropyranyl)methyl, benzyl, (1-fluorocyclohexyl)methyl, (4-fluorocyclohexyl)methyl, 1-hydroxy-2-methylpropyl, (cyclopentyl)(hydroxy)methyl, (cyclohexyl)(hydroxy)methyl, (cycloheptyl)(hydroxy)methyl, (1-hydroxycyclohexyl)methyl, (4-hydroxycyclohexyl)methyl, (4-hydroxy-4-methylcyclohexyl)methyl, 1-adamantylmethyl, (3-noradamantyl)(hydroxy)methyl, 2-methoxy-2-methylpropyl, 2,2-dimethyl-3-methoxypropyl, (3-tetrahydrofuryl)methyl, (3-tetrahydropyranyl)methyl, (4-tetrahydropyranyl)methyl.

16. The compound of claim 15, wherein
$R^3$ is hydrogen;
$R^4$ is hydrogen;
$R^5$ is cyclohexylmethyl, 1-adamantylmethyl, (3-tetrahydropyranyl)methyl, (4-tetrahydropyranyl)methyl, (3-oxepanyl)methyl or 6-(4-oxaspiro[2,5]octyl)methyl and $R^6$ is H; or $R^5$ is H and $R^6$ is (3-tetrahydropyranyl)methyl or (3-oxepanyl)methyl;
$R^7$ is methyl, ethyl, propyl or isopropyl;
$R^a$, $R^b$, $R^{a'}$ and $R^{b'}$, for each occurrence, are independently hydrogen, methyl or $R^a$ and $R^b$ attached to a carbon atom taken together are oxo or $R^{a'}$ and $R^{b'}$ attached to a carbon atom taken together are oxo; and
$R^9$ is H, methyl or ethyl.

17. The compound of claim 2, wherein the compound is represented by the following Structural Formula:

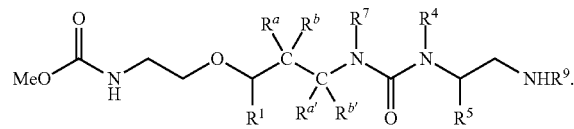

18. The compound of claim 17, wherein: $R^1$ is phenyl optionally substituted with 1 to 5 substituents independently selected from:
fluorine, chlorine, bromine, cyano, methyl, ethyl, isopropyl, t-butyl, isobutyl, trifluoromethyl, allyl, cyclohexyl, cyclohexen-1-yl, cyclopropylethynyl, methoxy, trifluoromethoxy, neopentyloxy, methylthio, allyloxy, cyclopropylmethoxy, 2-(cyclopropyl)ethoxy, cyclopentyloxy, cyclopentylmethoxy, benzyloxy, hydroxyl, aminocarbonyl, methoxycarbonyl, phenyl, phenoxy, benzyloxy, and heteroaryloxy, wherein the phenyl phenoxy, benzyloxy and heteroaryloxy groups are optionally substituted with 1 to 3 substituents independently selected from fluorine, chlorine, cyano, methyl, trifluoromethyl, and aminocarbonyl.

19. The compound of claim 18, wherein:
$R^1$ is phenyl optionally substituted with 1 to 5 substituents independently selected from the group consisting of fluorine, chlorine and methyl;
$R^5$ is methyl, isobutyl, t-butylmethyl, 2,2,2-trifluoroethyl, 2-(trifluoromethyl)propyl, cyclopentylmethyl, cyclohexylmethyl, (3,3-difluorocyclobutyl)methyl, 3,4-difluorocyclopentyl)methyl, 4,4-difluoro-cyclohexylmethyl, (4-methylcyclohexyl)methyl, tert-butoxymethyl, (4-tetrahydropyranyl)methyl, benzyl, (1-fluorocyclohexyl)methyl, (4-fluorocyclohexyl)methyl, 1-hydroxy-2-methylpropyl, (cyclopentyl)(hydroxy)methyl, (cyclohexyl)(hydroxy)methyl, (cycloheptyl)(hydroxy)methyl, (1-hydroxycyclohexyl)methyl, (4-hydroxycyclohexyl)methyl, (4-hydroxy-4-methylcyclohexyl)methyl, 1-adamantylmethyl, (3-noradamantyl)(hydroxy)methyl, 2-methoxy-2-methylpropyl, 2,2-dimethyl-3-methoxypropyl, (3-tetrahydrofuryl)methyl, (3-tetrahydropyranyl)methyl, (4-tetrahydropyranyl)methyl.

20. The compound of claim 19, wherein:
$R^4$ is H;
$R^5$ is cyclohexylmethyl, 1-adamantylmethyl, (3-tetrahydropyranyl)methyl, (4-tetrahydropyranyl)methyl, (3-oxepanyl)methyl or 6-(4-oxaspiro[2,5]octyl)methyl; and
$R^a$, $R^b$, $R^{a'}$ and $R^{b'}$, for each occurrence, are independently hydrogen, methyl or $R^a$ and $R^b$ attached to a carbon atom taken together are oxo or $R^{a'}$ and $R^{b'}$ attached to a carbon atom taken together are oxo.

21. The compound of claim 1, wherein the compound is selected from the group consisting of:
methyl (4S,10S)-10-(3-chlorophenyl)-4-(cyclohexylmethyl)-7-methyl-6-oxo-11-oxa-2,5,7-triazatridecan-13-ylcarbamate;
methyl (4S,10R)-10-(3-chlorophenyl)-4-(cyclohexylmethyl)-7-methyl-6-oxo-11-oxa-2,5,7-triazatridecan-13-ylcarbamate;
methyl (4S,9S,10S)-10-(3-chlorophenyl)-4-(cyclohexylmethyl)-7,9-dimethyl-6-oxo-11-oxa-2,5,7-triazatridecan-13-ylcarbamate;

methyl (4S,9R,10S)-10-(3-chlorophenyl)-4-(cyclohexylmethyl)-7,9-dimethyl-6-oxo-11-oxa-2,5,7-triazatridecan-13-ylcarbamate;
methyl (4S,10R)-10-(3-chlorophenyl)-4-(cyclohexylmethyl)-7,9-dimethyl-6-oxo-11-oxa-2,5,7-triazatridecan-13-ylcarbamate;
methyl (4S,9R,10R)-10-(3-chlorophenyl)-4-(cyclohexylmethyl)-7,9-dimethyl-6-oxo-11-oxa-2,5,7-triazatridecan-13-ylcarbamate;
methyl (4S,10R)-10-(3-chlorophenyl)-7-methyl-6-oxo-4-(((R)-tetrahydro-2H-pyran-3-yl)methyl)-11-oxa-2,5,7-triazatridecan-13-ylcarbamate;
methyl (4S,10S)-10-(5-chloro-2-methylphenyl)-7-methyl-6-oxo-4-(((R)-tetrahydro-2H-pyran-3-yl)methyl)-11-oxa-2,5,7-triazatridecan-13-ylcarbamate;
methyl (4S,10R)-10-(5-chloro-2-methylphenyl)-7-methyl-6-oxo-4-(((R)-tetrahydro-2H-pyran-3-yl)methyl)-11-oxa-2,5,7-triazatridecan-13-ylcarbamate;
methyl (3S)-10-(5-chloro-2-methylphenyl)-7-methyl-6-oxo-3-(((R)-tetrahydro-2H-pyran-3-yl)methyl)-11-oxa-2,5,7-triazatridecan-13-ylcarbamate;
methyl (4S,10R)-10-(3-chlorophenyl)-7-methyl-4-((R)-oxepan-3-ylmethyl)-6-oxo-11-oxa-2,5,7-triazatridecan-13-ylcarbamate;
methyl (4S,10R)-10-(3-chlorophenyl)-7-methyl-6-oxo-4-((tetrahydro-2H-pyran-4-yl)methyl)-11-oxa-2,5,7-triazatridecan-13-ylcarbamate;
methyl (4S,10R)-10-(3-chlorophenyl)-7-methyl-6-oxo-4-(((R)-4-oxaspiro[2.5]octan-6-yl)methyl)-11-oxa-2,5,7-triazatridecan-13-ylcarbamate;
methyl (4S,10R)-10-(3-chlorophenyl)-4-((2-adamantyl)methyl)-7-methyl-6-oxo-11-oxa-2,5,7-triazatridecan-13-ylcarbamate;
methyl (4S,10R)-10-(5-chloro-2-methylphenyl)-7-methyl-6-oxo-4-((tetrahydro-2H-pyran-4-yl)methyl)-11-oxa-2,5,7-triazatridecan-13-ylcarbamate;
methyl (4S,10S)-10-(5-chloro-2-methylphenyl)-7-methyl-6-oxo-4-((tetrahydro-2H-pyran-4-yl)methyl)-11-oxa-2,5,7-triazatridecan-13-ylcarbamate;
methyl (4S,10R)-10-(3-chlorophenyl)-7-ethyl-6-oxo-4-(((R)-tetrahydro-2H-pyran-3-yl)methyl)-11-oxa-2,5,7-triazatridecan-13-ylcarbamate;
methyl (4S,10S)-10-(3-chlorophenyl)-7-ethyl-6-oxo-4-(((R)-tetrahydro-2H-pyran-3-yl)methyl)-11-oxa-2,5,7-triazatridecan-13-ylcarbamate;
methyl (4S)-10-(3-chlorophenyl)-7-ethyl-6-oxo-4-(((R)-tetrahydro-2H-pyran-3-yl)methyl)-11-oxa-2,5,7-triazatridecan-13-ylcarbamate;
methyl 2-((R)-3-(3-((S)-2-amino-3-((R)-tetrahydro-2H-pyran-3-yl)propyl)-1-methylureido)-1-(3-chlorophenyl)propoxy)ethylcarbamate;
methyl 2-((R)-3-(3-((S)-2-amino-3-((R)-oxepan-3-yl)propyl)-1-methylureido)-1-(3-chlorophenyl)propoxy)ethylcarbamate;
methyl (3S,10R)-10-(3-chlorophenyl)-7-methyl-6-oxo-3-(((R)-tetrahydro-2H-pyran-3-yl)methyl)-11-oxa-2,5,7-triazatridecan-13-ylcarbamate;
methyl (3S,10R)-10-(3-chlorophenyl)-7-methyl-3-((R)-oxepan-3-ylmethyl)-6-oxo-11-oxa-2,5,7-triazatridecan-13-ylcarbamate;
methyl (4S,11R)-11-(3-chlorophenyl)-8-methyl-7-oxo-4-(((R)-tetrahydro-2H-pyran-3-yl)methyl)-12-oxa-3,6,8-triazatetradecan-14-ylcarbamate;
methyl (4S)-10-(3-chlorophenyl)-7-methyl-4-((R)-oxepan-3-ylmethyl)-6-oxo-11-oxa-2,5,7-triazatridecan-13-ylcarbamate;

1-(3-(3-chlorophenyl)-3-(3-methoxypropoxy)propyl)-3-((S)-1-cyclohexyl-3-(methylamino)propan-2-yl)-1-isopropylurea;
methyl (4S,10S)-10-(3-chlorophenyl)-4-(cyclohexylmethyl)-7-isopropyl-6-oxo-11-oxa-2,5,7-triazatridecan-13-ylcarbamate;
methyl (4S,10R)-10-(3-chlorophenyl)-4-(cyclohexylmethyl)-7-isopropyl-6-oxo-11-oxa-2,5,7-triazatridecan-13-ylcarbamate; and
methyl (4S)-10-(3-chlorophenyl)-4-(cyclohexylmethyl)-6-oxo-7-propyl-11-oxa-2,5,7-triazatridecan-13-ylcarbamate.

22. The compound of claim 1, wherein the compound is selected from the group consisting of:
methyl (4S,10R)-10-(3-chlorophenyl)-4-(cyclohexylmethyl)-7-methyl-6-oxo-11-oxa-2,5,7-triazatridecan-13-ylcarbamate;
methyl (4S,9R,10S)-10-(3-chlorophenyl)-4-(cyclohexylmethyl)-7,9-dimethyl-6-oxo-11-oxa-2,5,7-triazatridecan-13-ylcarbamate;
methyl (4S,10R)-10-(3-chlorophenyl)-4-(cyclohexylmethyl)-7,9-dimethyl-6-oxo-11-oxa-2,5,7-triazatridecan-13-ylcarbamate;
methyl (4S,9R,10R)-10-(3-chlorophenyl)-4-(cyclohexylmethyl)-7,9-dimethyl-6-oxo-11-oxa-2,5,7-triazatridecan-13-ylcarbamate;
methyl (4S,10R)-10-(3-chlorophenyl)-7-methyl-6-oxo-4-(((R)-tetrahydro-2H-pyran-3-yl)methyl)-11-oxa-2,5,7-triazatridecan-13-ylcarbamate;
methyl (4S,10R)-10-(5-chloro-2-methylphenyl)-7-methyl-6-oxo-4-(((R)-tetrahydro-2H-pyran-3-yl)methyl)-11-oxa-2,5,7-triazatridecan-13-ylcarbamate;
methyl (3S)-10-(5-chloro-2-methylphenyl)-7-methyl-6-oxo-3-(((R)-tetrahydro-2H-pyran-3-yl)methyl)-11-oxa-2,5,7-triazatridecan-13-ylcarbamate;
methyl (4S,10R)-10-(3-chlorophenyl)-7-methyl-4-((R)-oxepan-3-ylmethyl)-6-oxo-11-oxa-2,5,7-triazatridecan-13-ylcarbamate;
methyl (4S,10R)-10-(3-chlorophenyl)-7-methyl-6-oxo-4-((tetrahydro-2H-pyran-4-yl)methyl)-11-oxa-2,5,7-triazatridecan-13-ylcarbamate;
methyl (4S,10R)-10-(3-chlorophenyl)-7-methyl-6-oxo-4-(((R)-4-oxaspiro[2.5]octan-6-yl)methyl)-11-oxa-2,5,7-triazatridecan-13-ylcarbamate;
methyl (4S,10R)-10-(3-chlorophenyl)-4-((1-adamantyl)methyl)-7-methyl-6-oxo-11-oxa-2,5,7-triazatridecan-13-ylcarbamate;
methyl (4S,10S)-10-(5-chloro-2-methylphenyl)-7-methyl-6-oxo-4-((tetrahydro-2H-pyran-4-yl)methyl)-11-oxa-2,5,7-triazatridecan-13-ylcarbamate;
methyl (4S,10R)-10-(3-chlorophenyl)-7-ethyl-6-oxo-4-(((R)-tetrahydro-2H-pyran-3-yl)methyl)-11-oxa-2,5,7-triazatridecan-13-ylcarbamate;
methyl (4S)-10-(3-chlorophenyl)-7-ethyl-6-oxo-4-(((R)-tetrahydro-2H-pyran-3-yl)methyl)-11-oxa-2,5,7-triazatridecan-13-ylcarbamate;
methyl 2-((R)-3-(3-((S)-2-amino-3-((R)-tetrahydro-2H-pyran-3-yl)propyl)-1-methylureido)-1-(3-chlorophenyl)propoxy)ethylcarbamate;
methyl 2-((R)-3-(3-((S)-2-amino-3-((R)-oxepan-3-yl)propyl)-1-methylureido)-1-(3-chlorophenyl)propoxy)ethylcarbamate;
methyl (3S,10R)-10-(3-chlorophenyl)-7-methyl-6-oxo-3-(((R)-tetrahydro-2H-pyran-3-yl)methyl)-11-oxa-2,5,7-triazamidecan-13-ylcarbamate;

methyl (3S,10R)-10-(3-chlorophenyl)-7-methyl-3-((R)-oxepan-3-ylmethyl)-6-oxo-11-oxa-2,5,7-triazatridecan-13-ylcarbamate;
methyl (4S)-10-(3-chlorophenyl)-7-methyl-4-((R)-oxepan-3-ylmethyl)-6-oxo-11-oxa-2,5,7-triazatridecan-13-ylcarbamate;
methyl (4S,10R)-10-(3-chlorophenyl)-4-(cyclohexylmethyl)-7-isopropyl-6-oxo-11-oxa-2,5,7-triazatridecan-13-ylcarbamate; and
methyl (4S)-10-(3-chlorophenyl)-4-(cyclohexylmethyl)-6-oxo-7-propyl-11-oxa-2,5,7-triazatridecan-13-ylcarbamate.

23. The compound of claim 1, wherein the compound is selected from the group consisting of:
methyl (4S,10R)-10-(3-chlorophenyl)-4-(cyclohexylmethyl)-7-methyl-6-oxo-11-oxa-2,5,7-triazatridecan-13-ylcarbamate;
methyl (4S,9R,10R)-10-(3-chlorophenyl)-4-(cyclohexylmethyl)-7,9-dimethyl-6-oxo-11-oxa-2,5,7-triazatridecan-13-ylcarbamate;
methyl (4S,10R)-10-(3-chlorophenyl)-7-methyl-6-oxo-4-(((R)-tetrahydro-2H-pyran-3-yl)methyl)-11-oxa-2,5,7-triazatridecan-13-ylcarbamate;
methyl (4S,10R)-10-(5-chloro-2-methylphenyl)-7-methyl-6-oxo-4-(((R)-tetrahydro-2H-pyran-3-yl)methyl)-11-oxa-2,5,7-triazatridecan-13-ylcarbamate;
methyl (4S,10R)-10-(3-chlorophenyl)-7-methyl-4-((R)-oxepan-3-ylmethyl)-6-oxo-11-oxa-2,5,7-triazatridecan-13-ylcarbamate;
methyl (4S,10R)-10-(3-chlorophenyl)-7-methyl-6-oxo-4-(((R)-4-oxaspiro[2.5]octan-6-yl)methyl)-11-oxa-2,5,7-triazatridecan-13-ylcarbamate;
methyl (4S,10R)-10-(3-chlorophenyl)-4-((1-adamantyl)methyl)-7-methyl-6-oxo-11-oxa-2,5,7-triazatridecan-13-ylcarbamate;
methyl (4S,10R)-10-(3-chlorophenyl)-7-ethyl-6-oxo-4-(((R)-tetrahydro-2H-pyran-3-yl)methyl)-11-oxa-2,5,7-triazatridecan-13-ylcarbamate;
methyl (4S)-10-(3-chlorophenyl)-7-ethyl-6-oxo-4-(((R)-tetrahydro-2H-pyran-3-yl)methyl)-11-oxa-2,5,7-triazatridecan-13-ylcarbamate;
methyl 2-((R)-3-(3-((S)-2-amino-3-((R)-oxepan-3-yl)propyl)-1-methylureido)-1-(3-chlorophenyl)propoxy)ethylcarbamate;
methyl (3S,10R)-10-(3-chlorophenyl)-7-methyl-3-(((R)-oxepan-3-ylmethyl)-6-oxo-11-oxa-2,5,7-triazatridecan-13-ylcarbamate;
methyl (4S,10R)-10-(3-chlorophenyl)-4-(cyclohexylmethyl)-7-isopropyl-6-oxo-11-oxa-2,5,7-triazatridecan-13-ylcarbamate; and
methyl (4S)-10-(3-chlorophenyl)-4-(cyclohexylmethyl)-6-oxo-7-propyl-11-oxa-2,5,7-triazatridecan-13-ylcarbamate.

24. The compound of claim 1, wherein the compound is selected from the group consisting of:
methyl (4S,10R)-10-(3-chlorophenyl)-4-(cyclohexylmethyl)-7-methyl-6-oxo-11-oxa-2,5,7-triazatridecan-13-ylcarbamate;
methyl (4S,10R)-10-(3-chlorophenyl)-7-methyl-6-oxo-4-(((R)-tetrahydro-2H-pyran-3-yl)methyl)-11-oxa-2,5,7-triazatridecan-13-ylcarbamate;
methyl (4S,10R)-10-(5-chloro-2-methylphenyl)-7-methyl-6-oxo-4-(((R)-tetrahydro-2H-pyran-3-yl)methyl)-11-oxa-2,5,7-triazatridecan-13-ylcarbamate;
methyl (4S,10R)-10-(3-chlorophenyl)-7-methyl-4-((R)-oxepan-3-ylmethyl)-6-oxo-11-oxa-2,5,7-triazatridecan-13-ylcarbamate;
methyl (4S,10R)-10-(3-chlorophenyl)-7-methyl-6-oxo-4-(((R)-4-oxaspiro[2.5]octan-6-yl)methyl)-11-oxa-2,5,7-triazatridecan-13-ylcarbamate;
methyl (4S,10R)-10-(3-chlorophenyl)-7-ethyl-6-oxo-4-(((R)-tetrahydro-2H-pyran-3-yl)methyl)-11-oxa-2,5,7-triazatridecan-13-ylcarbamate; and
methyl (4S)-10-(3-chlorophenyl)-7-ethyl-6-oxo-4-(((R)-tetrahydro-2H-pyran-3-yl)methyl)-11-oxa-2,5,7-triazatridecan-13-ylcarbamate.

25. A pharmaceutical composition comprising a compound of claim 1, or an enantiomer, diastereomer, or salt thereof and a pharmaceutically acceptable carrier or excipient.

26. The pharmaceutical composition of claim 25, further comprising an additional agent selected from the group consisting of α-blockers, β-blockers, calcium channel blockers, diuretics, angiotensin converting enzyme (ACE) inhibitors, dual ACE and neutral endopeptidase (NEP) inhibitors, angiotensin-receptor blockers (ARBs), aldosterone synthase inhibitors, aldosterone-receptor antagonists, and endothelin receptor antagonists.

* * * * *